US010293161B2

(12) United States Patent
Charlesworth et al.

(10) Patent No.: US 10,293,161 B2
(45) Date of Patent: *May 21, 2019

(54) APPARATUSES AND METHODS FOR TRANSDERMAL ELECTRICAL STIMULATION OF NERVES TO MODIFY OR INDUCE A COGNITIVE STATE

(71) Applicant: Thync Global, Inc., Los Gatos, CA (US)

(72) Inventors: Jonathan D. Charlesworth, Menlo Park, CA (US); Sumon K. Pal, Boston, MA (US); William J. Tyler, Newton, MA (US); Daniel Z. Wetmore, Brooklyn, NY (US); Isy Goldwasser, Los Gatos, CA (US); Alyssa M. Boasso, Brookline, MA (US); Hailey M. Mortimore, Boston, MA (US); Rafal Piersiak, Los Gatos, CA (US)

(73) Assignee: Thync Global, Inc., Los Gatos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/384,249

(22) Filed: Dec. 19, 2016

(65) Prior Publication Data

US 2017/0197081 A1 Jul. 13, 2017

Related U.S. Application Data

(60) Provisional application No. 62/269,104, filed on Dec. 18, 2015, provisional application No. 62/279,992, (Continued)

(51) Int. Cl.
*A61N 1/36* (2006.01)
*A61N 1/04* (2006.01)

(52) U.S. Cl.
CPC ..... *A61N 1/36025* (2013.01); *A61N 1/36034* (2017.08); *A61N 1/0456* (2013.01); *A61N 1/0476* (2013.01); *A61N 1/0492* (2013.01)

(58) Field of Classification Search
CPC ........... A61N 1/36025; A61N 1/36034; A61N 1/0456; A61N 1/0476; A61N 1/0492
(Continued)

(56) References Cited

U.S. PATENT DOCUMENTS 3,255,753 A  6/1966 Wing
3,388,699 A  1/1968 Webb et al.
(Continued)

FOREIGN PATENT DOCUMENTS

CN  1204268 A  1/1999
CN  1607970 A  4/2005
(Continued)

OTHER PUBLICATIONS

Aston-Jones et al.; An integrative theory of locus coeruleus-norepinephrine function: adaptive gain and optimal performance; Annu. Rev, Neurosci.; 28: pp. 403-450; Jul. 21, 2005.
(Continued)

*Primary Examiner* — Carl H Layno
*Assistant Examiner* — Erin M Piateski
(74) *Attorney, Agent, or Firm* — Shay Glenn LLP

(57) ABSTRACT

Portable transdermal electrical stimulation (TES) applicators for modifying a subject's cognitive state by applying stimulation to the subject's skin. One or more electrode may be on the subject's mastoid, and/or on or near the back of the subject's neck. The portable applicators are configured and adapted to be lightweight and may be wearable, and to deliver a high-intensity TES able to evoke or enhance a predetermined cognitive effect to stimulate either the trigeminal, facial and/or cervical plexus. These TES appli-
(Continued)

cators may include a pair of electrodes and a TES control module comprising a processor, a timer and a waveform generator.

11 Claims, 58 Drawing Sheets

Related U.S. Application Data filed on Jan. 18, 2016, provisional application No. 62/281,326, filed on Jan. 21, 2016, provisional application No. 62/269,975, filed on Dec. 19, 2015.

(58) Field of Classification Search
USPC .......................................................... 607/45
See application file for complete search history.

(56) References Cited

U.S. PATENT DOCUMENTS

| | | | |
|---|---|---|---|
| 3,620,219 A | 11/1971 | Barker | |
| 3,648,708 A | 3/1972 | Haeri | |
| 3,762,396 A | 10/1973 | Ballentine et al. | |
| 4,418,687 A | 12/1983 | Matsumoto et al. | |
| 4,431,000 A | 2/1984 | Butler et al. | |
| 4,646,744 A | 3/1987 | Capel | |
| 4,664,117 A | 5/1987 | Beck | |
| 4,865,048 A | 9/1989 | Eckerson | |
| 5,144,952 A | 9/1992 | Frachet et al. | |
| 5,183,041 A | 2/1993 | Toriu et al. | |
| 5,335,657 A | 8/1994 | Terry et al. | |
| 5,342,410 A | 8/1994 | Braverman | |
| 5,397,338 A | 3/1995 | Grey et al. | |
| 5,476,481 A | 12/1995 | Schondorf | |
| 5,487,759 A | 1/1996 | Bastyr et al. | |
| 5,514,175 A | 5/1996 | Kim et al. | |
| 5,540,736 A | 7/1996 | Haimovich et al. | |
| 5,573,552 A | 11/1996 | Hansjurgens | |
| 5,578,065 A | 11/1996 | Hattori et al. | |
| 5,593,427 A | 1/1997 | Gliner et al. | |
| 5,738,647 A | 4/1998 | Bernhard et al. | |
| 5,792,067 A | 8/1998 | Karell | |
| 6,066,163 A | 5/2000 | John | |
| 6,280,454 B1 | 8/2001 | Wang | |
| 6,324,432 B1 | 11/2001 | Rigaux et al. | |
| 6,445,955 B1 | 9/2002 | Michelson et al. | |
| 6,463,328 B1 | 10/2002 | John | |
| 6,516,227 B1 | 2/2003 | Meadows et al. | |
| 6,526,318 B1 | 2/2003 | Ansarinia | |
| 6,567,702 B1 | 5/2003 | Nekhendzy et al. | |
| 6,731,987 B1 | 5/2004 | McAdams et al. | |
| 6,983,184 B2 | 1/2006 | Price | |
| 7,120,499 B2 | 10/2006 | Thrope et al. | |
| 7,146,217 B2 | 12/2006 | Firlik et al. | |
| 7,263,501 B2 | 8/2007 | Tirinato et al. | |
| 7,376,467 B2 | 5/2008 | Thrope et al. | |
| 7,422,555 B2 | 9/2008 | Zabara | |
| 7,577,481 B2 | 8/2009 | Firlik et al. | |
| 7,660,636 B2 | 2/2010 | Castel et al. | |
| 7,801,600 B1 | 9/2010 | Carbunaru et al. | |
| 7,891,615 B2 | 2/2011 | Bevirt | |
| 7,949,403 B2 | 5/2011 | Palermo et al. | |
| 8,029,431 B2 | 10/2011 | Tononi | |
| 8,034,294 B1 | 10/2011 | Goldberg | |
| 8,086,318 B2 | 12/2011 | Strother et al. | |
| 8,097,926 B2 | 1/2012 | De Graff et al. | |
| 8,116,875 B2 | 2/2012 | Osypka et al. | |
| 8,121,695 B2 | 2/2012 | Gliner et al. | |
| 8,150,537 B2 | 4/2012 | Tanaka et al. | |
| 8,190,248 B2 | 5/2012 | Besio et al. | |
| 8,197,276 B2 | 6/2012 | Egloff et al. | |
| 8,204,601 B2 | 6/2012 | Moyer et al. | |
| 8,239,030 B1 | 8/2012 | Hagedorn et al. | |
| 8,265,761 B2 | 9/2012 | Siever | |
| 8,280,502 B2 | 10/2012 | Hargrove et al. | |
| 8,346,337 B2 | 1/2013 | Heller et al. | |
| 8,380,315 B2 | 2/2013 | DeGiorgio et al. | |
| 8,428,738 B2 | 4/2013 | Valencia | |
| 8,463,383 B2 | 6/2013 | Sakai et al. | |
| 8,494,625 B2 | 7/2013 | Hargrove | |
| 8,494,627 B2 | 7/2013 | Bikson et al. | |
| 8,506,469 B2 | 8/2013 | Dietrich et al. | |
| 8,532,758 B2 | 9/2013 | Silverstone | |
| 8,560,075 B2 | 10/2013 | Covalin | |
| 8,571,651 B2 | 10/2013 | Ben-Ezra et al. | |
| 8,583,238 B1 | 11/2013 | Heldman et al. | |
| 8,583,256 B2 | 11/2013 | Tracey et al. | |
| 8,612,005 B2 | 12/2013 | Rezai et al. | |
| 8,639,343 B2 | 1/2014 | De Vos | |
| 8,660,644 B2 | 2/2014 | Jaax et al. | |
| 8,688,239 B2 | 4/2014 | Hartlep et al. | |
| 8,843,210 B2 | 9/2014 | Simon et al. | |
| 8,874,219 B2 | 10/2014 | Trier et al. | |
| 8,903,494 B2 | 12/2014 | Goldwasser et al. | |
| 8,983,621 B2 | 3/2015 | Hou et al. | |
| 9,002,458 B2 | 4/2015 | Pal et al. | |
| 9,014,811 B2 | 4/2015 | Pal et al. | |
| 9,067,054 B2 | 6/2015 | Simon et al. | |
| 9,168,374 B2 | 10/2015 | Su | |
| 9,205,258 B2 | 12/2015 | Simon et al. | |
| 9,233,244 B2 | 1/2016 | Pal et al. | |
| 9,248,292 B2 | 2/2016 | Trier et al. | |
| 9,333,334 B2 | 5/2016 | Jeffery et al. | |
| 9,364,674 B2 | 6/2016 | Cook et al. | |
| 9,393,401 B2 | 7/2016 | Goldwasser et al. | |
| 9,393,430 B2 | 7/2016 | Demers et al. | |
| 9,399,126 B2 | 7/2016 | Pal et al. | |
| 9,415,219 B2 | 8/2016 | Simon et al. | |
| 9,440,070 B2 | 9/2016 | Goldwasser et al. | |
| 9,446,242 B2 | 9/2016 | Griffith | |
| 9,474,891 B2 | 10/2016 | Demers et al. | |
| 9,474,905 B2 | 10/2016 | Doan et al. | |
| 9,517,351 B2 | 12/2016 | Charlesworth et al. | |
| 9,656,076 B2 | 5/2017 | Trier et al. | |
| 9,700,725 B2 | 7/2017 | Zhu | |
| 9,731,116 B2 | 8/2017 | Chen | |
| 9,744,347 B2 | 8/2017 | Chen et al. | |
| 9,764,133 B2 | 9/2017 | Thomas et al. | |
| 9,782,587 B2 | 10/2017 | Trier et al. | |
| 2001/0000187 A1 | 4/2001 | Peckham et al. | |
| 2002/0116036 A1 | 8/2002 | Daignault et al. | |
| 2003/0088279 A1 | 5/2003 | Rissmann et al. | |
| 2003/0134545 A1 | 7/2003 | McAdams et al. | |
| 2003/0171685 A1 | 9/2003 | Lesser et al. | |
| 2003/0225323 A1 | 12/2003 | Kiani et al. | |
| 2004/0019370 A1 | 1/2004 | Gliner et al. | |
| 2004/0098065 A1 | 5/2004 | Hagglof et al. | |
| 2004/0158305 A1 | 8/2004 | Axelgaard | |
| 2004/0267333 A1 | 12/2004 | Kronberg | |
| 2005/0165460 A1 | 7/2005 | Erfan | |
| 2005/0267388 A1 | 12/2005 | Hanna | |
| 2005/0283259 A1 | 12/2005 | Wolpow | |
| 2006/0064139 A1 | 3/2006 | Chung et al. | |
| 2006/0149119 A1 | 7/2006 | Wang | |
| 2006/0190057 A1 | 8/2006 | Reese | |
| 2006/0195159 A1 | 8/2006 | Bradley et al. | |
| 2006/0206163 A1 | 9/2006 | Wahlstrand et al. | |
| 2006/0247985 A1 | 11/2006 | Liamos et al. | |
| 2007/0053466 A1 | 3/2007 | Klostermann | |
| 2007/0088419 A1 | 4/2007 | Fiorina et al. | |
| 2007/0097593 A1 | 5/2007 | Armstrong | |
| 2007/0100275 A1 | 5/2007 | Fischer et al. | |
| 2007/0173890 A1 | 7/2007 | Armstrong | |
| 2007/0213790 A1 | 9/2007 | Nolan et al. | |
| 2007/0276451 A1 | 11/2007 | Rigaux | |
| 2008/0015641 A1 | 1/2008 | Armstrong et al. | |
| 2008/0045882 A1 | 2/2008 | Finsterwald | |
| 2008/0071626 A1 | 3/2008 | Hill | |
| 2008/0132974 A1 | 6/2008 | Strother et al. | |
| 2008/0207985 A1 | 8/2008 | Farone | |
| 2008/0208266 A1 | 8/2008 | Lesser et al. | |
| 2008/0215113 A1 | 9/2008 | Pawlowicz | |
| 2008/0275293 A1 | 11/2008 | Lattner et al. | |
| 2008/0281368 A1 | 11/2008 | Bulkes et al. | |

(56) References Cited

U.S. PATENT DOCUMENTS

| | | |
|---|---|---|
| 2008/0319505 A1 | 12/2008 | Boyden et al. |
| 2009/0048642 A1 | 2/2009 | Goroszeniuk |
| 2009/0054952 A1 | 2/2009 | Glukhovsky et al. |
| 2009/0099623 A1 | 4/2009 | Bentwich |
| 2009/0112280 A1 | 4/2009 | Wingeier et al. |
| 2009/0177243 A1 | 7/2009 | Lebedev et al. |
| 2009/0210028 A1 | 8/2009 | Rigaux et al. |
| 2009/0240303 A1 | 9/2009 | Wahlstrand et al. |
| 2009/0270947 A1 | 10/2009 | Stone et al. |
| 2009/0287108 A1 | 11/2009 | Levy |
| 2010/0057154 A1 | 3/2010 | Dietrich et al. |
| 2010/0076533 A1 | 3/2010 | Dar et al. |
| 2010/0094375 A1 | 4/2010 | Donders et al. |
| 2010/0145399 A1 | 6/2010 | Johari et al. |
| 2010/0152817 A1 | 6/2010 | Gillbe |
| 2010/0256436 A1 | 10/2010 | Partsch et al. |
| 2010/0318168 A1 | 12/2010 | Bignetti |
| 2011/0029045 A1* | 2/2011 | Cevette ............... A61N 1/323 607/62 |
| 2011/0034756 A1 | 2/2011 | Hacking et al. |
| 2011/0077660 A1 | 3/2011 | Janik et al. |
| 2011/0082326 A1 | 4/2011 | Mishelevich et al. |
| 2011/0082515 A1 | 4/2011 | Libbus et al. |
| 2011/0093033 A1 | 4/2011 | Nekhendzy |
| 2011/0112394 A1 | 5/2011 | Mishelevich |
| 2011/0112590 A1 | 5/2011 | Wu et al. |
| 2011/0114191 A1 | 5/2011 | Wheater et al. |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0172752 A1 | 7/2011 | Bingham et al. |
| 2011/0190846 A1 | 8/2011 | Ruffini et al. |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270345 A1 | 11/2011 | Johnston et al. |
| 2011/0276112 A1 | 11/2011 | Simon et al. |
| 2011/0288610 A1 | 11/2011 | Brocke |
| 2011/0301683 A1 | 12/2011 | Axelgaard |
| 2011/0307029 A1 | 12/2011 | Hargrove |
| 2011/0319950 A1 | 12/2011 | Sullivan |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0182924 A1 | 7/2012 | Gaines et al. |
| 2012/0184801 A1 | 7/2012 | Simon et al. |
| 2012/0185020 A1 | 7/2012 | Simon et al. |
| 2012/0209340 A1 | 8/2012 | Escribano |
| 2012/0209346 A1 | 8/2012 | Bikson et al. |
| 2012/0245409 A1 | 9/2012 | Liang |
| 2012/0245653 A1 | 9/2012 | Bikson et al. |
| 2012/0296390 A1 | 11/2012 | Nakashima et al. |
| 2012/0302912 A1 | 11/2012 | Moffitt et al. |
| 2012/0306628 A1 | 12/2012 | Singhal |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0096641 A1 | 4/2013 | Strother et al. |
| 2013/0131551 A1 | 5/2013 | Raghunathan et al. |
| 2013/0158627 A1 | 6/2013 | Gozani et al. |
| 2013/0184779 A1 | 7/2013 | Bikson et al. |
| 2013/0204315 A1 | 8/2013 | Wongsarnpigoon et al. |
| 2013/0226275 A1 | 8/2013 | Duncan |
| 2013/0253613 A1 | 9/2013 | Salahovic et al. |
| 2013/0267761 A1 | 10/2013 | Bentwich |
| 2013/0282095 A1 | 10/2013 | Mignolet et al. |
| 2013/0304175 A1 | 11/2013 | Voegele et al. |
| 2013/0318168 A1 | 11/2013 | Demain et al. |
| 2013/0325096 A1 | 12/2013 | Dupelle et al. |
| 2014/0031895 A1 | 1/2014 | Rahimi et al. |
| 2014/0128939 A1 | 5/2014 | Embrey et al. |
| 2014/0128944 A1 | 5/2014 | Stern et al. |
| 2014/0163645 A1 | 6/2014 | Dinsmoor et al. |
| 2014/0182350 A1 | 7/2014 | Bhavaraju et al. |
| 2014/0222102 A1 | 8/2014 | Lemus et al. |
| 2014/0257449 A1 | 9/2014 | Helmer |
| 2014/0275933 A1 | 9/2014 | Meyer et al. |
| 2014/0277324 A1 | 9/2014 | DiUbaldi et al. |
| 2014/0309709 A1 | 10/2014 | Gozani et al. |
| 2014/0336728 A1 | 11/2014 | Franke et al. |
| 2014/0371814 A1 | 12/2014 | Spizzirri et al. |
| 2015/0005841 A1* | 1/2015 | Pal ................. A61N 1/0476 607/45 |
| 2015/0066104 A1 | 3/2015 | Wingeier et al. |
| 2015/0224310 A1 | 8/2015 | Sharma et al. |
| 2015/0230863 A1 | 8/2015 | Youngquist et al. |
| 2015/0257970 A1 | 9/2015 | Mucke et al. |
| 2015/0335877 A1 | 11/2015 | Jeffery et al. |
| 2016/0008632 A1 | 1/2016 | Wetmore et al. |
| 2016/0074657 A1 | 3/2016 | Kwan et al. |
| 2016/0279435 A1 | 9/2016 | Hyde et al. |
| 2016/0317809 A1 | 11/2016 | Pal et al. |
| 2016/0346530 A1 | 12/2016 | Jeffery et al. |
| 2016/0346545 A1 | 12/2016 | Pal et al. |

FOREIGN PATENT DOCUMENTS

| | | |
|---|---|---|
| CN | 1704131 A | 12/2005 |
| CN | 1842356 A | 10/2006 |
| CN | 101234233 A | 8/2008 |
| CN | 101244314 A | 8/2008 |
| CN | 201353374 Y | 12/2009 |
| CN | 102245253 A | 11/2011 |
| CN | 102725021 A | 10/2012 |
| CN | 102906752 A | 1/2013 |
| CN | 103517732 A | 1/2014 |
| EP | 502919 B1 | 11/1993 |
| EP | 801957 A1 | 10/1997 |
| EP | 09965358 A2 | 12/1999 |
| EP | 1529550 A1 | 5/2005 |
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| JP | 49061984 A | 6/1974 |
| JP | 05031197 A | 2/1993 |
| JP | 10108913 A | 4/1998 |
| JP | 2001129100 A | 5/2001 |
| JP | 2001293097 A | 10/2001 |
| JP | 2002306604 A | 10/2002 |
| JP | 200310230 A | 1/2003 |
| JP | 2006192302 A | 7/2006 |
| JP | 3129187 U | 1/2007 |
| JP | 200985901 A | 4/2009 |
| JP | 2011118293 A | 6/2011 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO01/08071 A1 | 2/2001 |
| WO | WO01/78834 A1 | 10/2001 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2009/147599 A1 | 12/2009 |
| WO | WO2010/047834 A1 | 4/2010 |
| WO | WO2010/067145 A1 | 6/2010 |
| WO | WO2010/120823 A2 | 10/2010 |
| WO | WO2011/044176 A1 | 4/2011 |
| WO | WO2011/147546 A1 | 12/2011 |
| WO | WO2012/082960 A2 | 6/2012 |
| WO | WO2012/089588 A1 | 7/2012 |
| WO | WO2012/116407 A1 | 9/2012 |

(56) References Cited

FOREIGN PATENT DOCUMENTS

| | | |
|---|---|---|
| WO | WO2012/129574 A2 | 9/2012 |
| WO | WO2012/150600 A2 | 11/2012 |
| WO | WO2012/156051 A1 | 11/2012 |
| WO | WO2012/156052 A2 | 11/2012 |
| WO | WO2013/071307 A1 | 5/2013 |
| WO | WO2013/192582 A1 | 12/2013 |
| WO | WO2014/107624 A1 | 7/2014 |
| WO | WO2014/195516 A1 | 12/2014 |
| WO | WO2015/036420 A1 | 3/2015 |
| WO | WO2015/061663 A1 | 4/2015 |
| WO | WO2015/143053 A1 | 9/2015 |
| WO | WO2017/201525 A1 | 11/2017 |

OTHER PUBLICATIONS

Aston-Jones et al.; Role of locus coeruleus in attention and behavioral flexibility; Biological Psychiatry; 46(9); pp. 1309-1320; Nov. 1, 1999.

Backhaus et al.; Sleep disturbances are correlated with decreased morning awakening salivary cortisol; Psychoneuroendocrinology; 29(9): pp. 1184-1191; Oct. 31, 2004.

Basta et al.; Chronic Insomnia and the Stress System; Sleep Medicine Clinics; 2(2): pp. 279-291; (Author Manuscript, 20 pages); Jun. 30, 2007.

Berlad et al.; Power spectrum analysis and heart rate variability in Stage 4 and REM sleep: evidence for state-specific changes in autonomic dominance; Journal of Sleep Research; 2(2): pp. 88-90; Jun. 1, 1993.

Berridge et al.; The locus coeruleus-noradrenergic system: modulation of behavioral state and state-dependent cognitive processes; Brain Research Reviews; 42(1); pp. 33-84; Apr. 30, 2003.

Brown et al.; Control of sleep and wakefulness; Physiological reviews; 92(3); pp. 1087-1187; Jul. 1, 2012.

Brown et al.;Locus ceruleus activation suppresses feedforward interneurons and reduces beta-gamma electroencephalogram frequencies while it enhances theta frequencies in rat dentate gyrus; Journals of Neuroscience; 25(8): pp. 1985-1991; Feb. 23, 2005.

Buchanan et al.; Salivary alpha-amylase levels as a biomarker of experienced fear; Communicative and Integrative Biology; 3(6); pp. 525-527; Nov. 1, 2010.

Buckley et al.; On the Interactions of the Hypothalamic-Pituitary-Adrenal (HPA) Axis and Sleep: Normal HPA Axis Activity and Circadian Rhythm, Exemplary Sleep Disorders; The Journal of Clinical Endocrinology and Metabolism; 90(5); pp. 3106-3114; May 1, 2005.

Buysse et al.; The Pittsburgh Sleep Quality Index: a new instrument for psychiatric practice and research; Psychiatric Research; 28(2); pp. 193-213; May 31, 1989.

Carter et al.; Tuning arousal with optogenetic modulation of locus coeruleus neurons; Nature Neuroscience; 13(12); pp. 1526-1533; Dec. 1, 2010.

Cook et al.; Trigeminal nerve stimulation in major depressive disorder: acute outcomes in an open pilot study; Epilepsy and Behavior; 28(2): pp. 221-226; Aug. 31, 2013.

Degiorgio et al., Trigeminal nerve stimulation for epilepsy: long-term feasibility and efficacy; Neurology; 72(10): pp. 936-938; Mar. 10, 2009.

Degiorgio et al.; Randomized controlled trial of trigeminal nerve stimulation for drug-resistant epilepsy; Neurology; 80(9): pp. 786-791; Feb. 26, 2013.

Elder et al.; The cortisol awakening response—applications and implications for sleep medicine; Sleep Medicine Reviews; 18(3): pp. 215-224; Jun. 30, 2014.

Eschenko et al.; Noradrenergic neurons of the locus coeruleus are phase locked to cortical up-down states during sleep; Cerebral Cortex; 22(2): pp. 426-435; Feb. 1, 2012.

Franowicz et al.; Treatment with the noradrenergic alpha-2 agonist clonidine, but not diazepam, improves spatial working memory in normal young rhesus monkeys; Neuropsychopharmacology; 21(5): pp. 611-621; Nov. 1, 1999.

Garraway et al.; Modulatory actions of serotonin, norepinephrine, dopamine, and acetylcholine in spinal cord deep dorsal horn neurons; Journal of Neurophysiology; 86(5); pp. 2183-2194; Nov. 1, 2001.

Granger et al.; Salivary alpha-amylase in biobehavioral research: recent developments and applications; Annals of the New York Academy of Sciences; 1098(1); pp. 122-144; Mar. 1, 2007.

Gummadavelli et al.; Neurostimulation to improve level of consciousness in patients with epilepsy. Neurosurgical Focus; 38(6); pp. E10; (manuscript version, 14 pages); Jun. 2015.

Hajos et al.; Norepinephrine but not serotonin reuptake inhibitors enhance theta and gamma activity of the septo-hippocampal system; Neuropsychopharmacology; 28(5); pp. 857-864; May 1, 2003.

Hass et al.; Waking with the hypothalamus. Pflugers Arch R Eur. J. Physiol.; 463(1): pp. 31-42; Jan. 1, 2012.

Herwig et al.; Intracortical excitability is modulated by a norepinephrine-reuptake inhibitor as measured with paired-pulse transcranial magnetic stimulation; Psychopharmacology (Berl); 164(2): pp. 228-232; Nov. 18, 2002.

Hirotsu et al.; Interactions between sleep, stress, and metabolism; From physiological to pathological conditions; Sleep Science; 8(3); pp. 143-152; Nov. 2015.

Horvath et al.; Evidence that transcranial direct current stimulation (tDCS) generates little-to-no reliable neurophysiologic effect beyond MEP amplitude modulation in healthy human subjects: A systematic review; Neuropsychologia; 66: pp. 213-236; Jan. 31, 2015.

Just et al.; Bold responses to trigeminal nerve stimulation; Magnetic Resonance Imaging; 28(8): pp. 1143-1151; Oct. 31, 2010.

Kubota et al.; Role of the brain stem in cardiovascular changes induced by stimulation of the trigeminal nerve; Anesthesia Progress; 36(4-5); pp. 236-237; Jul. 1989.

Lee et al.; Neuromodulation of Brain States; Neuron; 76(1): pp. 209-222. Oct. 4, 2012.

Leproult et al.; Sleep loss results in an elevation of cortisol levels the next evening; Sleep; 20(10): pp. 865-870; Oct. 1997.

Lovibond et al.; The structure of negative emotional states: Comparison of the Depression Anxiety Stress Scales (DASS) with the Beck Depression and Anxiety Inventories; Behaviour Research and Therapy; 33(3); pp. 335-343; Mar. 31, 1995.

Lu et al.; A putative flip-flop switch for control of REM sleep; Nature; 441(7093): pp. 589-594; Jun. 1, 2006.

Magis et al.; Safety and patients' satisfaction of transcutaneous supraorbital neurostimulation (tSNS) with the Cefaly(R) device in headache treatment: a survey of 2,313 headache sufferers in the general population; The Journal of Headache and Pain, 14(1); pp. 95; (manuscript version, 8 pages) Dec. 1, 2013.

McGough et al.; An eight-week, open-trial, pilot feasibility study of trigeminal nerve stimulation in youth with attention-deficit/hyperactivity disorder; Brain Stimulation; 8(2); pp. 299-304; Apr. 30, 2015.

Meltzer et al; Direct comparison of two new actigraphs and polysomnography in children and adolescents; Sleep; 35(1); pp. 159-166; Jan. 1, 2012.

Nash et al.; Differential activation of the human trigeminal nuclear complex by noxious and non-noxious orofacial stimulation; Human Brain Mapping; 30(11); pp. 3772-3782; Nov. 1, 2009.

Nieuwenhuis et al.; Decision making, the P3, and the locus coeruleus-norepinephrine system; Psychological Bulletin; 131(4); pp. 510-532; Jul. 2005.

Parvizi et al.; Consciousness and the brainstem; Cognition; 79(1): pp. 135-160; Apr. 30, 2001.

Penzel et al.; Dynamics of Heart Rate and Sleep Stages in Normals and Patients with Sleep Apnea; Neuropsychopharmacology; 28(S1); pp. S48-S53; Jul. 1, 2003.

Piquet et al.; Supraorbital transcutaneous neurostimulation has sedative effects in healthy subjects; BMC Neurology; 11(1); p. 135; (manual transcript, 8 pages); Oct. 28, 2011.

Plewina et al.; Enhancement of human cortico-motoneuronal excitability by the selective norepinephrine reuptake inhibitor reboxetine; Neuroscience Letters; 330(3); pp. 231-234; Sep. 27, 2002.

Pusch et al.; Electrical stimulation of the vestibular system prevents postoperative nausea and vomiting; Acta Annesthesiol Scand.; 44(9); pp. 1145-1148; Oct. 2000.

(56) References Cited

OTHER PUBLICATIONS

Riemann et al.; The hyperarousal model of insomnia: A review of the concept and its evidence; Sleep Medicine Reviews; 14(1); pp. 19-31; Feb. 28, 2010.
Rill et al.; Pedunculopontine arousal system physiology—implications for insomnia; Sleep Science; 8(2); pp. 92-99; Jun. 30, 2015.
Rohleder et al.; Psychosocial stress-induced activation of salivary alpha-amylase: an indicator of sympathetic activity; Annals of the New York Academy of Sciences; 1032(1); pp. 258-263; Dec. 1, 2004.
Sara; The locus coeruleus and noradrenergic modulation of cognition; Nature Reviews Neuroscience; 10(3): pp. 211-223. Mar. 1, 2009.
Schmidt et al.; Adrenaline rush: the role of adrenergic receptors in stimulant-induced behaviors; Molecular Pharmacology; 85(4): pp. 640-650; Apr. 1, 2014.
Seugnet et al.; Identification of a biomarker for sleep drive in flies and humans; Proceedings of the National Academy of Sciences; 103(52); pp. 19913-19918; Dec. 26, 2006.
Shiozawa et al.; Transcutaneous vagus and trigeminal nerve stimulation for neuropsychiatric disorders: a systematic review; Arquivos de neuro-psiquiatria; 72(7): pp. 542-547; Jul. 2014.
Siegel; Brain mechanisms that control sleep and waking. Naturwissenschaften; 91(8); pp. 355-365; Aug. 1, 2004.
Somana et al.; Cerebellar afferents from the trigeminal sensory nuclei in the cat. Brain Res.; 38(1); pp. 57-64; Jan. 1980.
Strassman et al; Response of brainstem trigeminal neurons to electrical stimulation of the dura; Brain Research; 379(2): pp. 242-250; Aug. 6, 1986.
Tanaka et al.; Salivary alpha-amylase and cortisol responsiveness following electrically stimulated physical stress in bipolar disorder patients; Neuropsychiatric Disease and Treatment; 8; pp. 1899-1905; Jan. 1, 2013.
Thoma et al.; Acute stress responses in salivary alpha-amylase predict increases of plasma norepinephrine; Biological Psychology; 91(3): pp. 342-348; Dec. 31, 2012.
Tremblay et al.; Uncertain Outcome of Prefrontal tDCS; Brain Stimulation; 7(6): pp. 773-783; Dec. 31, 2014.
Trevizol et al.; Trigeminal Nerve Stimulation (TNS) for Generalized Anxiety Disorder: A Case Study; Brain Stimulation; 8(3): pp. 659-660; Jan. 1, 2015.
Trevizol et al.; Trigeminal Nerve Stimulation (TNS) for Post-traumatic Stress Disorder: A Case Study; Brain Stimulation; 8(3): pp. 676-678; Jan. 1, 2015.
Tyler et al.; Transdermal neuromodulation of noradrenergic activity suppresses psychophysiological and biochemical stress responses in humans; Scientific Reports; 5; (manual transcript, 22 pages); Feb. 8, 2015.
Upadhyay et al.; Noninvasive mapping of human trigeminal brainstem pathways; Magnetic Resonance in Medicine; 60(5): pp. 1037-1046; Nov. 1, 2008.
Van Stegeren et al.; Salivary alpha amylase as marker for adrenergic activity during stress: effect of betablockade; Psychoneuroendocrinology; 31(1); pp. 137-141; Jan. 31, 2006.
Voisin et al.; Nociceptive stimulation activates locus coeruleus neurones projecting to the somatosensory thalamus in the rat; The Journal of Physiology; 566( 3); pp. 929-937; Aug. 1, 2005.
Voss et al.; Induction of self awareness in dreams through frontal low current stimulation of gamma activity; Nature Neuroscience; 17(6); pp. 810-812; Jun. 1, 2014.
Watson et al.; Development and validation of brief measures of positive and negative affect: the PANAS scales; Jouranl of Personality and Social Psychology; 54(6); pp. 1063-1070; Jun. 1988.
Weiss et al; Validity of Activity-Based Devices to Estimate Sleep; Journal of Clinical Sleep Medicine : 6(4); pp. 336-342; Aug. 2010.
Tyler et al.; U.S. Appl. No. 15/460,138 entitled "Systems and methods for transdermal electrical stimulation to improve sleep," filed Mar. 15, 2017.
Goldwasser et al.; U.S. Appl. No. 15/601,394 entitled "Transdermal electrical stimulation at the neck to induce neuromodulation," filed May 22, 2017.
Axelgaard Manufacturing Co. Ltd.; Little PALS® (product information); 2 pgs.; printed Feb. 11, 2013 from http://www.axelgaard.com/prod_little-pals.html.
Axelgaard Manufacturing Co. Ltd.; PALS® Platinum Blue (product information); 2 pgs.; printed Feb. 11, 2013 from http://www.axelgaard.com/prod_pals-platinum-blue.html.
Chaieb et al.; Transcranial alternating current stimulation in the low kHz range increases motor cortex excitability; Restor Neurol Neurosci; 29(3); pp. 167-175; Mar. 2011.
Coutinho et al.; Musical emotions: predicting second-by-second subjective feelings of emotion from low-level psychoacoustic features and physiological measurements; Emotion; 11(4); pp. 921-937; Aug. 2011.
DaSilva et al.; Electrode positioning and montage in transcranial direct current stimulation; J Vis Exp; 51; e2744; 11 pgs.; May 2011.
Digitimer Ltd.; DS2 and DS3 Isolated Stimulator (product information); 2 pgs.; downloaded from http://www.digitimer.com/research/stimulators/index.htm on Feb. 10, 2014.
Electozyme; Company and Product Information; 3 pgs.; printed Feb. 11, 2014 from http://electrozyme.com/applications/.
Feurra et al.; Frequency specific modulation of human somatosensory cortex; Front Psychol; 2(13); 6 pgs.; Feb. 2011.
GoFLOW; tDCS Kit; product information; 9 pgs..; printed Feb. 10, 2014 (http://flowstateengaged.com/).
Golestanirad et al; Analysis of fractal electrodes for efficient neural stimulation; Frontiers in Neurengineering; 6(3); 10 pages; Jul. 2013.
Gracenote; Timeline-metadata-api; 3 pages; retrieved from the Internet Jul. 7, 2015; (https://github.com/gracenote/timeline-metadata-api/blob/master/README.md).
Grindhouse Wetware; Thinking Cap; product information; 1 pg.; printed Feb. 10, 2014 (http://www.grindhousewetware.com/thinkingcap.html).
Kanai et al.; Frequency-dependent electrical stimulatioin of the visual cortex; Curr. Biol.; 18(23); pp. 1839-1843; Dec. 9, 2008.
Paulus, W.; Transcranial electrical stimulation (tES-tDCS; tRNS, tACS) methods; Neuropsychol Rehabil.; 21(5); pp. 602-617; Oct. 2011.
Prausnitz; The effects of electric current applied to skin: a review for transdermal drug delivery; Advanced Drug Delivery Reviews; vol. 18; pp. 395-425; Feb. 8, 1996.
Saiote et al.; High-frequency TRNS reduces BOLD activity during visuomotor learning; PLOS one; 8(3); e59669; 8 pgs.; Mar. 2013.
Schutter et al.; Brain oscillations and frequency-dependent modulation of cortical excitability; Brain Stimulation; 4(2); pp. 97-103; Apr. 2011.
STD Pharmaceutical Products; Idrostar intophoresis machine (product and use information); 9 pgs.; Dec. 2011 (printed Feb. 11, 2014 from http://www.iontophoresis.info/instructions/).
Terney et al.; Increasing human brain excitability by transcranial high-frequency random noise stimulation; The Journal of Neuroscience; 28(52); pp. 14127-14155; Dec. 2008.
Turi et al.; Both the cutaneous sensation and phosphene perception are modulated in a frequency-specific manner during transcranial alternating current stimulation; Restor. Neurol. Neurosci.; 31(3); pp. 275-285; Jan. 2013.
Tyler et at; U.S. App. No. 61/550,334 entitled "Improvement of Direct Communication," filed Oct. 21, 2011.
Tyler et al.; U.S. App. No. 61/663,409 entitled "Device and Methods for Noninvasive Neuromodulation Using Targeted Transcranial Electrical Stimulation," filed Jun. 22, 2012.
Tyler et al.; U.S. App. No. 62/166,674 entitled "Systems and Methods for Suppression of Stress Responses by Transdermal Electrical Neuromodulation," filed May 26, 2015.
Goldwasser et al.; U.S. Appl. No. 15/264,224 entitled "Apparatuses and methods for neuromodulation," filed Sep. 13, 2016.
Egnal et al.; U.S. Appl. No. 15/265,633 entitled "Apparatuses and methods for auto-replenishment of electrodes for transdermal electrical stimulation," filed Sep. 14, 2016.
Jeffery; U.S. Appl. No. 15/380,028 entitled "Electrodes having surface exclusions," filed Dec. 15, 2017.

(56) References Cited

OTHER PUBLICATIONS

Pal et al.; U.S. Appl. No. 14/956,193 entitled "Transdermal electrical stimulation devices for modifying or inducing cognitive state," filed Dec. 1, 2015.
Tyler et al.; U.S. Appl. No. 15/536,148 entitled "Methods and apparatuses for transdermal stimulation of the outer ear," filed Jun. 15, 2017.
Tyler et al.; U.S. Appl. No. 15/536,151 entitled "Systems and methods for transdermal electrical stimulation to improve sleep," filed Jun. 15, 2017.
Goldwasser et al.; U.S. Appl. No. 15/967,576 entitled "Transdermal electrical stimulation at the neck," filed Apr. 30, 2018.

* cited by examiner

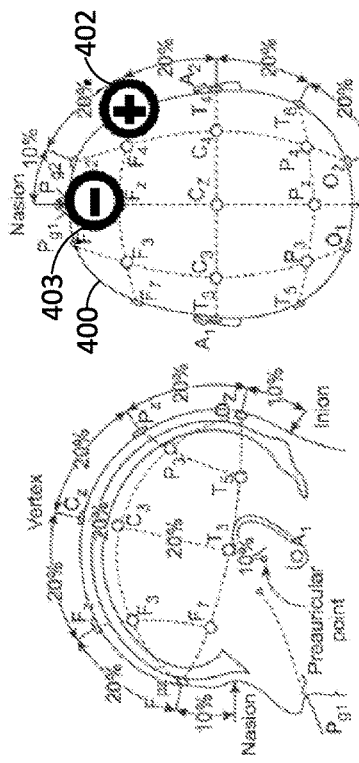
FIG.4A
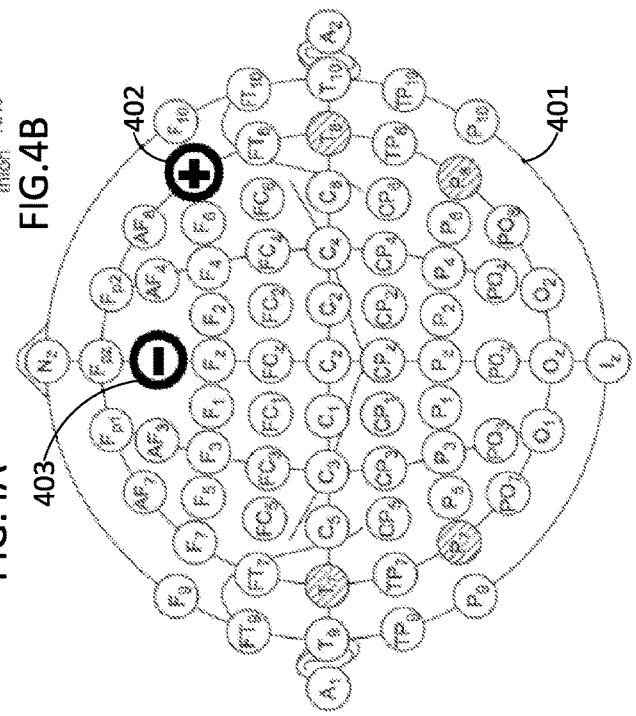
FIG.4B
FIG.4C
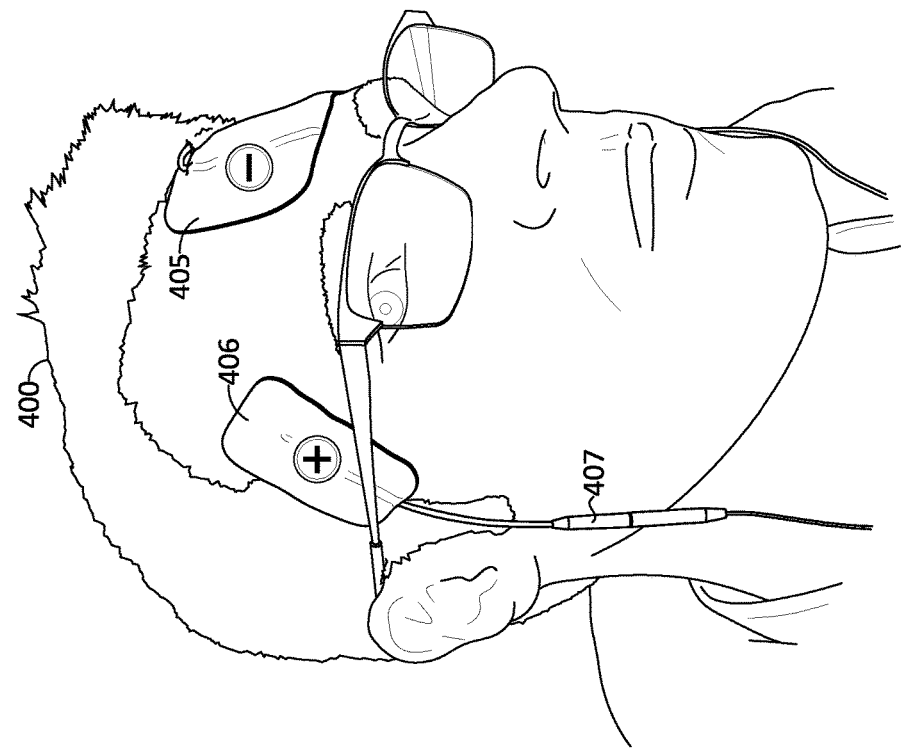
FIG.4D

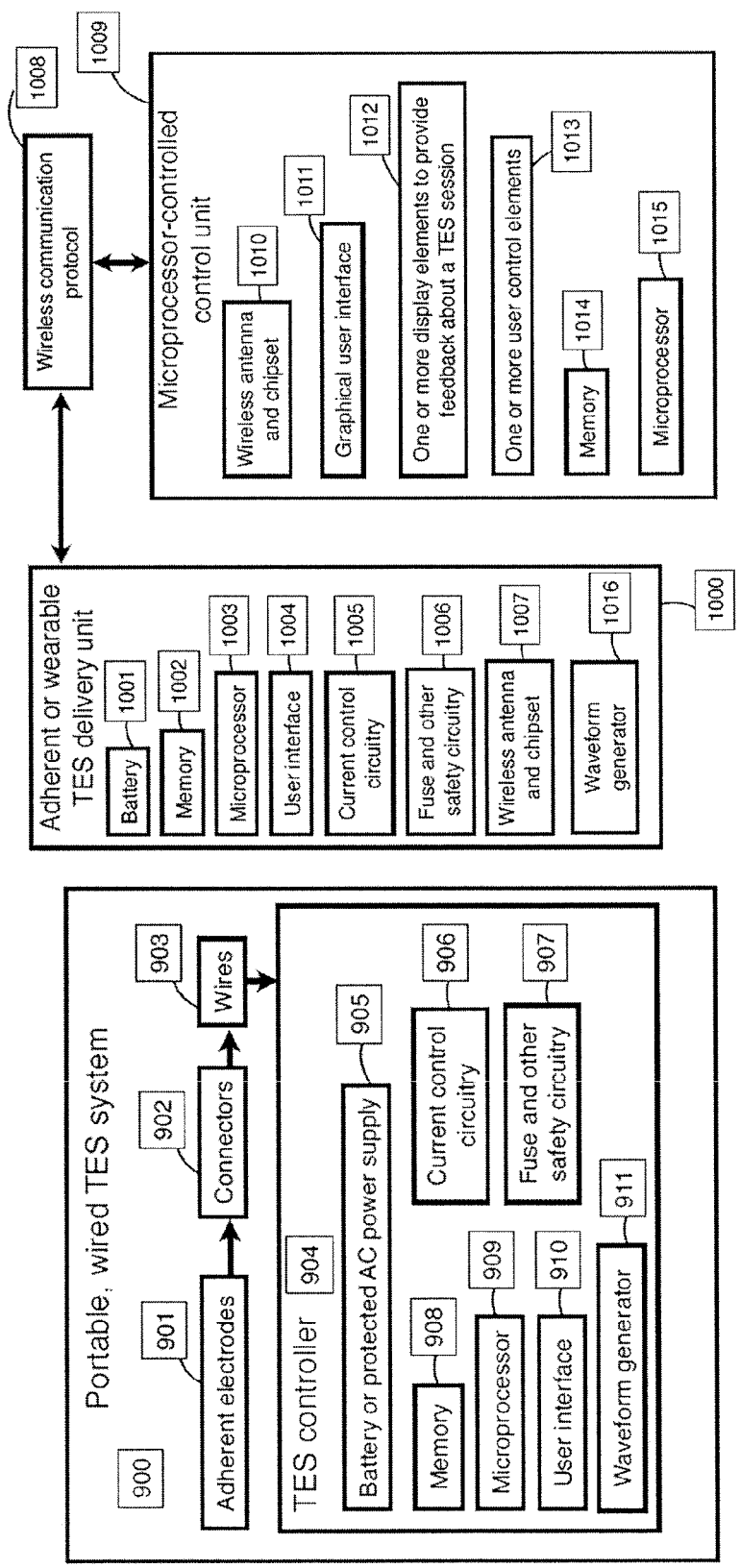

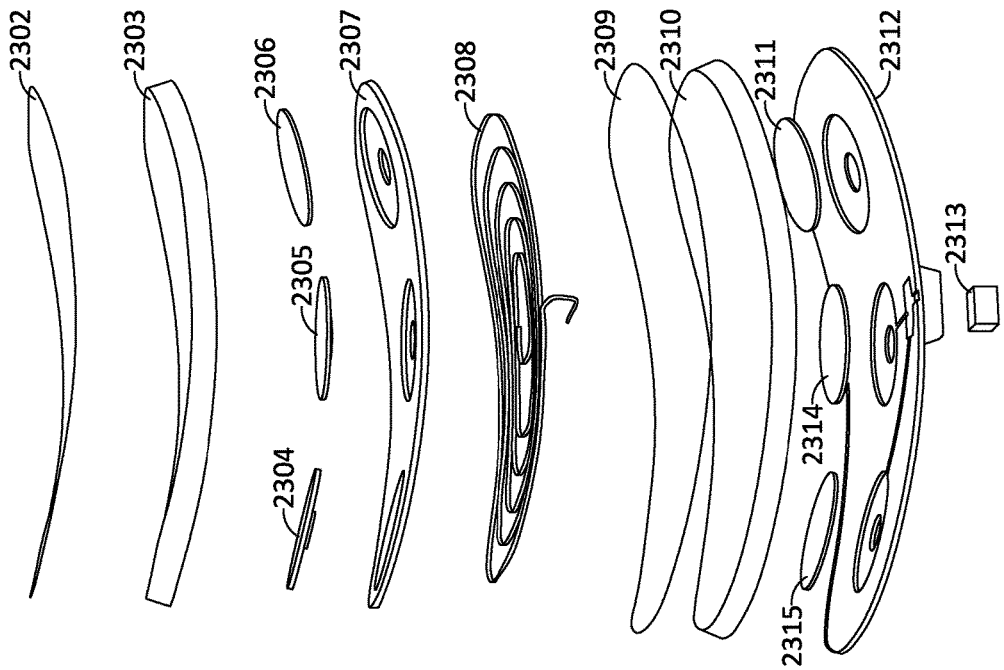
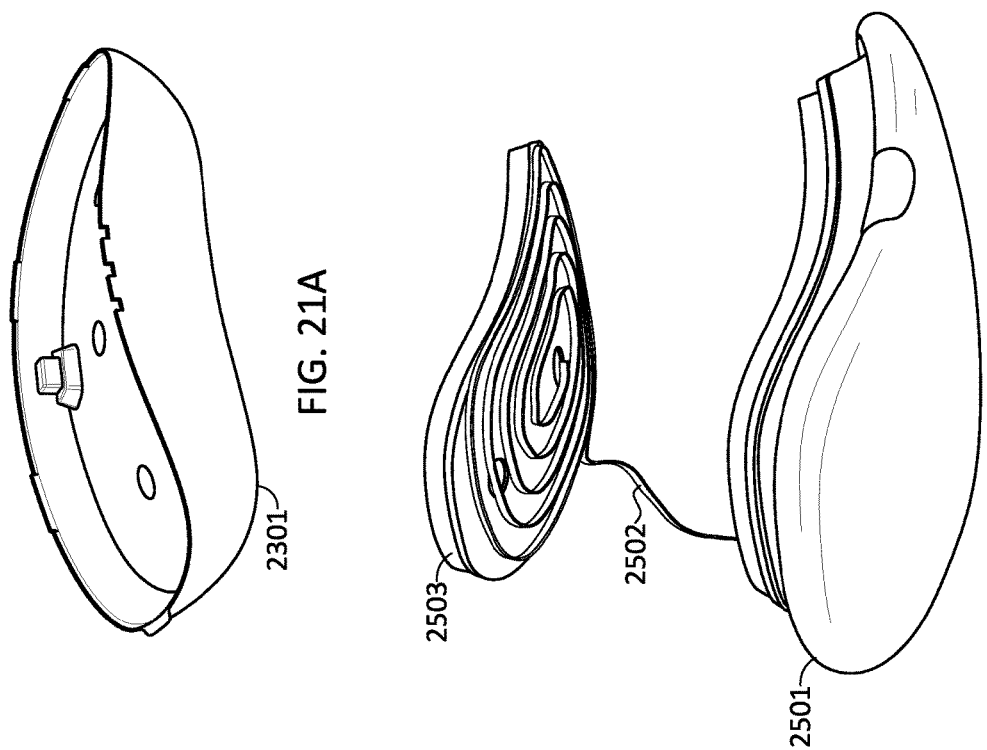
FIG. 21A
FIG. 21B
FIG. 22

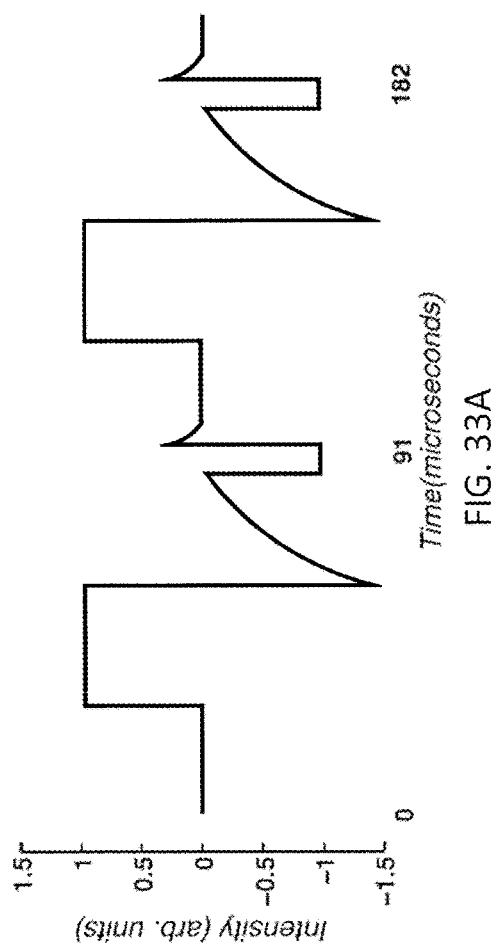
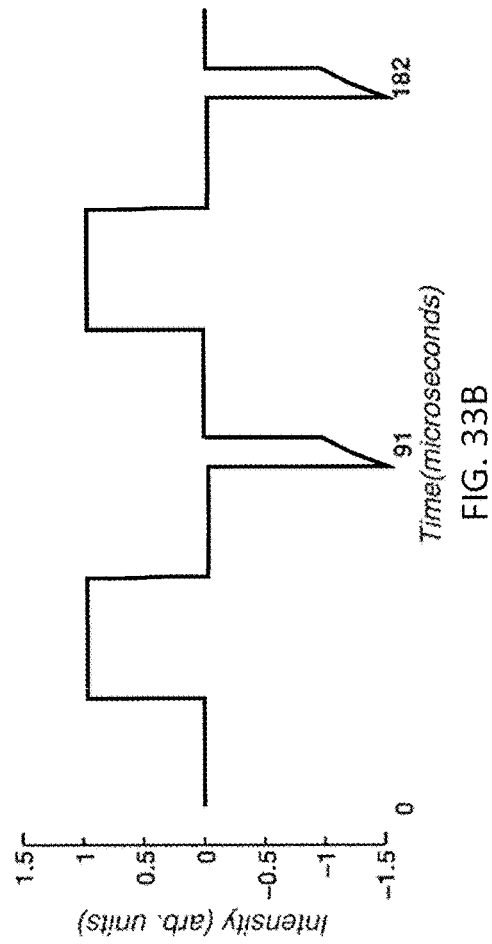

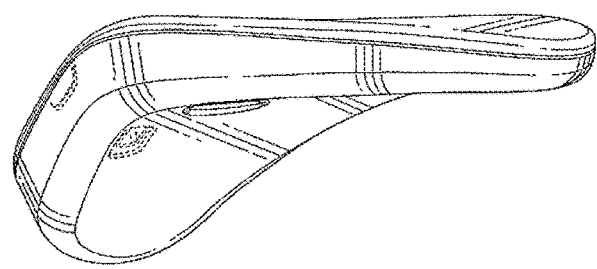
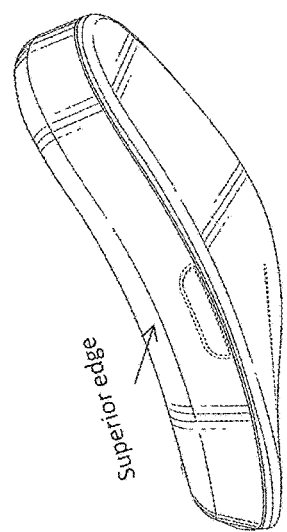
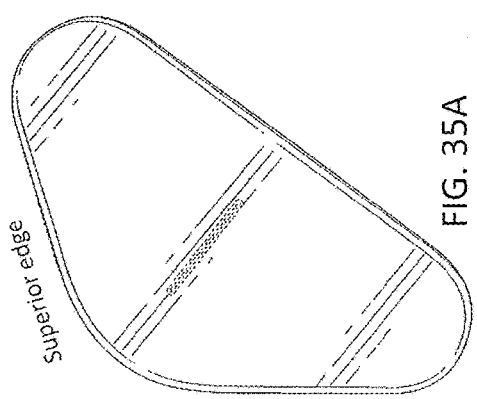
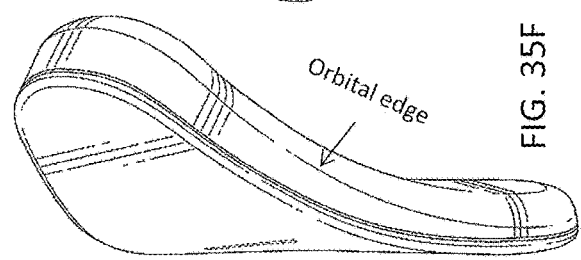
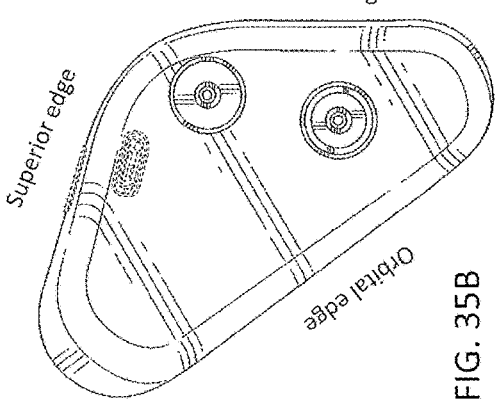
FIG. 35A
FIG. 35B
FIG. 35C
FIG. 35D
FIG. 35E
FIG. 35F

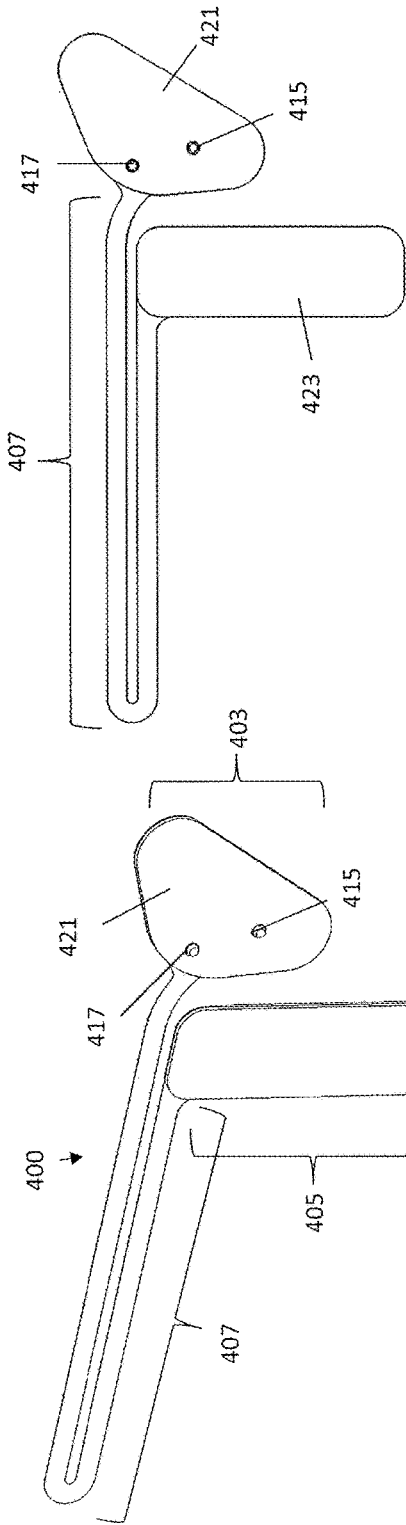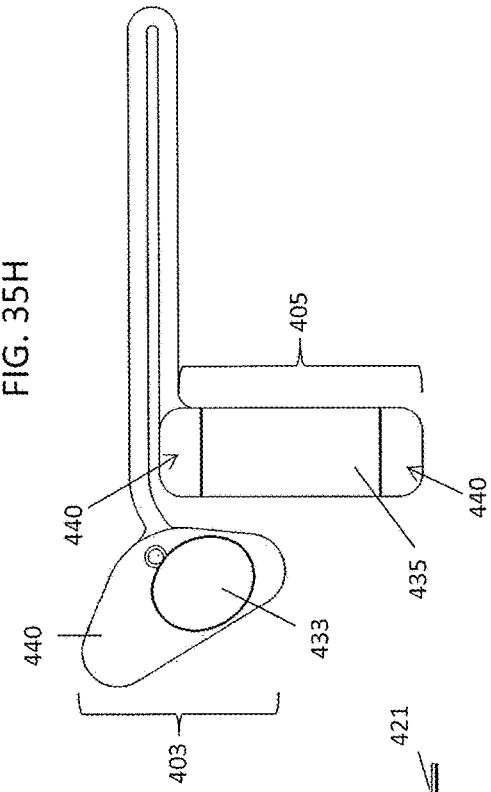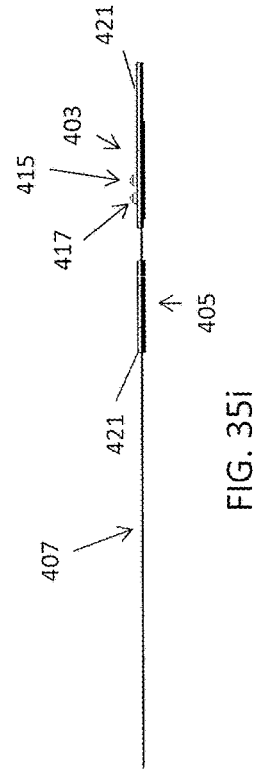
FIG. 35H
FIG. 35J
FIG. 35G
FIG. 35i

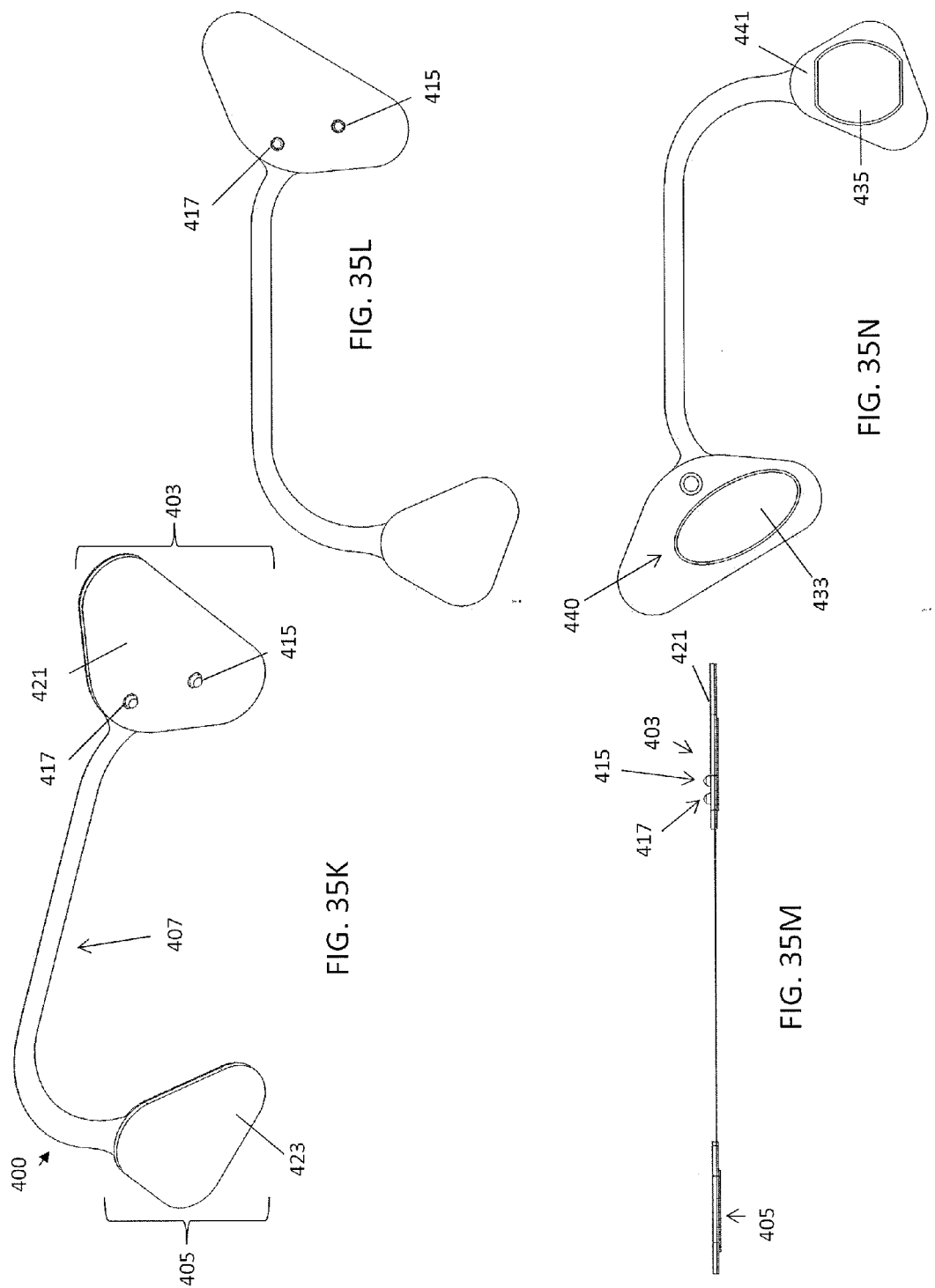

APPARATUSES AND METHODS FOR TRANSDERMAL ELECTRICAL STIMULATION OF NERVES TO MODIFY OR INDUCE A COGNITIVE STATE

CROSS REFERENCE TO RELATED APPLICATIONS

This application claims priority to U.S. Provisional Patent Application No. 62/269,104, filed Dec. 18, 2015, titled "TRANSDERMAL ELECTRICAL STIMULATION OF NERVES TO MODIFY OR INDUCE A COGNITIVE STATE"; U.S. Provisional Patent Application No. 62/279,992, filed Jan. 18, 2016, titled "TRANSDERMAL ELECTRICAL STIMULATION OF NERVES TO MODIFY OR INDUCE A COGNITIVE STATE"; U.S. Provisional Patent Application No. 62/281,326, filed Jan. 21, 2016, titled "TRANSDERMAL ELECTRICAL STIMULATION OF NERVES TO MODIFY OR INDUCE A COGNITIVE STATE"; and U.S. Provisional Patent Application No. 62/269,975, filed Dec. 19, 2015, titled "METHODS AND APPARATUSES FOR IMPROVED TRANSDERMAL NEUROSTIMULATION TO INDUCE COGNITIVE STATES"; each of which are herein incorporated by reference in its entirety.

This application may be related to one or more of: U.S. patent application Ser. No. 14/639,015, filed Mar. 4, 2015, titled "TRANSDERMAL ELECTRICAL STIMULATION DEVICES FOR MODIFYING OR INDUCING COGNITIVE STATE", now U.S. Pat. No. 9,233,244, which is a continuation of U.S. patent application Ser. No. 14/320,461, filed Jun. 30, 2014, titled "TRANSDERMAL ELECTRICAL STIMULATION DEVICES FOR MODIFYING OR INDUCING COGNITIVE STATE," filed Jun. 30, 2014, now U.S. Pat. No. 9,002,458, which also claims priority to each of the following U.S. provisional patent applications: U.S. Provisional Application No. 61/845,845, filed Jul. 12, 2013, titled "TRANSCRANIAL ELECTRICAL STIMULATION SYSTEMS AND METHODS"; U.S. Provisional Application No. 61/875,424, filed Sep. 9, 2013, titled "TRANSCRANIAL ELECTRICAL STIMULATION SYSTEMS AND METHODS"; U.S. Provisional Application No. 61/841,308, filed Jun. 29, 2013, titled "TRANSCRANIAL ELECTRICAL STIMULATION SYSTEMS"; U.S. Provisional Application No. 61/907,394, filed Nov. 22, 2013, titled "TRANSCRANIAL ELECTRICAL STIMULATION SYSTEMS AND METHODS"; U.S. Provisional Application No. 61/888,910, filed Oct. 9, 2013, titled "TRANSCRANIAL ELECTRICAL STIMULATION SYSTEMS AND METHODS"; U.S. Provisional Application No. 61/975,118, filed Apr. 4, 2014, titled "TRANSDERMAL ELECTRICAL STIMULATION SYSTEMS"; U.S. Provisional Application No. 62/002,860, filed May 25, 2014, titled "TRANSDERMAL ELECTRICAL STIMULATION SYSTEMS FOR INDUCING COGNITIVE EFFECTS AND METHODS OF USING THEM"; U.S. Provisional Application No. 62/002,909, filed May 25, 2014, titled "TRANSDERMAL ELECTRICAL STIMULATION SYSTEMS AND METHODS OF USING THEM"; U.S. Provisional Application No. 62/002,910, filed May 25, 2014, titled "TRANSDERMAL ELECTRICAL STIMULATION ELECTRODE DEGRADATION DETECTION SYSTEMS AND METHODS OF USING THEM"; U.S. Provisional Application No. 62/166,674, filed May 26, 2015, titled "SYSTEMS AND METHODS FOR SUPPRESSION OF STRESS RESPONSES BY TRANSDERMAL ELECTRICAL NEUROMODULATION", each of which are herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are transdermal electrical stimulation (TES) methods, apparatuses and systems, including applicators, for inducing cognitive effects. For example, described herein are methods and apparatuses for noninvasive neuromodulation, and more specifically to components, features, and methods of placing electrodes of transdermal electrical stimulation systems adapted to evoke a particular cognitive effect.

BACKGROUND

The brain is composed of neurons and other cell types in connected networks that process sensory input, generate motor commands, and control all other behavioral and cognitive functions. Neurons communicate primarily through electrochemical pulses that transmit signals between connected cells within and between brain areas. Noninvasive neuromodulation technologies that affect neuronal activity can modulate the pattern of neural activity and may cause altered behavior, cognitive states, perception, and motor output without requiring an invasive procedure.

Non-invasive neuromodulation includes the broad category of "transdermal electrical stimulation," which generally refers to electrical stimulation of the nervous system (brain, cranial nerves, peripheral nerves, etc.) through a subject's skin. Specific examples of transdermal electric stimulation (hereinafter "TES") may include transcranial stimulation, for example, through scalp electrodes and have been used to affect brain function in humans in the form of transcranial alternating current stimulation (hereinafter "tACS"), transcranial direct current stimulation (hereinafter "tDCS"), cranial electrotherapy stimulation (hereinafter "CES"), and transcranial random noise stimulation (hereinafter "tRNS"). Systems and methods for TES have been disclosed (see for example, Capel U.S. Pat. No. 4,646,744; Haimovich et al. U.S. Pat. No. 5,540,736; Besio et al. U.S. Pat. No. 8,190,248; Hagedorn and Thompson U.S. Pat. No. 8,239,030; Bikson et al. U.S. Patent Application Publication No. 2011/0144716; and Lebedev et al. U.S. Patent Application Publication No. 2009/0177243). tDCS systems with numerous electrodes and a high level of configurability have been disclosed (see for example Bikson et al. U.S. Patent Application Publication Nos. 2012/0209346, 2012/0265261, and 2012/0245653), as have portable TES systems for auto-stimulation (Brocke U.S. Pat. No. 8,554,324).

In general, TES has been shown to improve motor control and motor learning, improve memory consolidation during slow-wave sleep, regulate decision-making and risk assessment, affect sensory perception, and cause movements. TES has been used therapeutically in various clinical applications, including treatment of pain, depression, epilepsy, and tinnitus. In at least some cases of TES (e.g., tDCS) therapeutic use, more data concerning the efficacy of tDCS in treatment is needed.

Despite research done on TES neuromodulation, existing systems and methods for TES are lacking in at least some cases in their capacity to safely and robustly affect cognitive function and induce cognitive states in human subjects. The development of new TES methods, TES stimulation protocols, TES systems, and TES electrode configurations that induce substantial changes in cognitive function and/or cognitive state comfortably would be advantageous. Existing systems and methods can cause skin irritation or pain and are lacking with regard to the reliability and amount of change in cognitive state that can be achieved.

Electrotherapy for muscles and other peripheral nervous system applications (e.g. TENS and transdermal drug delivery) have used strategies to reduce pain, irritation, and tissue damage, including (1) higher frequencies of alternating current stimulation and (2) a beat frequency generally between 1 Hz and 200 Hz created from a difference frequency of two channels (anode-cathode pairs) of electrodes. Reduced side-effects (e.g. pain and irritation) are approximately linear across a wide range from ~1 kHz to 100 kHz. Skin impedance is frequency dependent, with lower impedances at higher electrical stimulation frequencies. For interferential stimulation, a beat frequency of between 1 and 200 Hz is an advantageous frequency to avoid activating pain and muscle fibers that are perceived as irritating or painful. Power density also affects skin resistivity, with lower resistivity occurring at higher power densities. However, systems and methods for TES are lacking in terms of mitigation of pain, irritation, and tissue damage.

Typical transcranial alternating current stimulation protocols are also typically below 150 Hz (see Paulus 2011), consistent with frequencies of brain rhythms or below 640 Hz as used in tRNS protocols. Recently, Chaieb et al. used 1 kHz, 2 kHz, and 5 kHz tACS to induce neuromodulation (Chaieb L, Antal A, Paulus W. "Transcranial alternating current stimulation in the low kHz range increases motor cortex excitability." Restor Neurol Neurosci. 2011; 29(3): 167-75, incorporated fully herein by reference). International Publication No. WO 2012/089588 by inventors Paulus and Warschewske describes systems and methods of tACS at frequencies between 1 Hz and 50 kHz, including interferential tACS from two anode-cathode electrode pairs and pulsed tACS. However, existing tACS systems for neuromodulation are less than ideal for inducing cognitive effects robustly and comfortably.

One advantage of transcranial alternating current stimulation relative to transcranial direct current stimulation is reduced pain and irritation. However, existing tACS systems for neuromodulation are less than ideal in at least some instances, because alternating currents affect nervous system function (i.e., brain function) differently than direct currents. One advantage of pulsed transcranial direct current stimulation relative to unpulsed transcranial direct current stimulation is reduced pain and irritation. Pulsed transcranial direct current stimulation has been previously reported for peripheral use in patients but has not been used for targeting the brain transcranially. The Idrostar Iontophoresis Machine (STD Pharmaceutical Products Ltd, Hereford, England) delivers pulsed direct current stimulation (7 kHz, about 42% duty cycle) to address hyperhidrosis (excess sweating). Alternative transcranial electrical stimulation protocols that achieve desired effects on the nervous system with manageable amounts of pain and/or irritation would be advantageous.

It would generally be advantageous to provide devices and methods that allow transdermal electrical stimulation in a manner that overcomes the problems with pain and efficacy discussed above. In particular, it would be beneficial to provide TES devices and methods for modulating (e.g., inducing, enhancing, reversing, or otherwise increasing or changing) a cognitive effect and/or mental state. For example, TES stimulation protocols and electrode configurations that induce a relaxing, calming, anxiolytic, dissociated, high mental clarity, or worry-free state of mind in a subject would be advantageous for improving the subject's experiences and state of mind, as well as addressing insomnia and mitigating negative responses to stress. Similarly TES stimulation protocols and apparatuses that increase a subject's motivation, subjective (and/or physiological) energy level, or focus would be advantageous for improving a subject's productivity and providing beneficial states of mind.

Systems and methods for inducing these states via transdermal electrical stimulation targeting peripheral nerves at any (or multiple) locations would be a beneficial improvement by permitting targeting more broadly (i.e. for wearable systems on users with varying anatomy of bones (which may restrict conformity of a wearable system) and hair (which limits low-impedance, uniform contact to skin for stimulation). The anatomy of various peripheral nerves, including cranial and cervical spinal nerves (among others) are well-known and generally conserved across individuals. Moreover, electrophysiological or other mapping may be used to more accurately identify the location of branches of a targeted peripheral nerve.

Personalizing or optimizing TES for a subject (electrode position and waveform parameters) would be beneficial given inherent variability between individuals. Existing systems are less than ideal, because they lack physiological measurements from sensor systems of a TES apparatus to provide feedback to a TES controller and/or TES user.

In some instances, being able to place electrodes and/or a wearable neurostimulator module of a TES system on a part of the body other than the head or neck may be advantageous for comfortably inducing a cognitive effect in a less obtrusive way (relative to having a neurostimulator on the temple area).

Sympathetic nervous system activity can only be directly assessed through neurophysiological recordings from sympathetic nerve fibers or from plasma measurements of norepinephrine spillover. Of the two, recording of muscle sympathetic nerve activity has higher temporal resolution and is both easier technically and provides real-time data. Accordingly, direct microneurographic recordings of muscle sympathetic nerve activity (MSNA) are considered the gold standard for assaying sympathetic outflow or tone. Previous TES systems are lacking in part because they have not incorporated methods for MSNA to assess effects on sympathetic nervous system activity.

Many TES systems described to date use fixed waveform parameters, limiting the adaptability and effectiveness of TES systems. TES systems and methods for using them that apply more general principles of TES waveform design would be beneficial for improved consistency, effectiveness, and comfort of TES for inducing a change in cognitive state. The systems and methods described herein address this deficiency.

Described herein are methods and apparatuses (including devices and systems) and methods that may address the problems and opportunities discussed above.

SUMMARY OF THE DISCLOSURE

Described herein are apparatuses (including devices and systems) and methods for transdermal electrical stimulation (hereinafter "TES"), including transcranial electrical stimulation, to induce neuromodulation. In particular, described herein are methods and apparatuses for targeting one or more nerves (including a nerve plexus) for inducing a specific and intentional cognitive effect. For example, described herein are methods and apparatuses for inducing a relaxed or calm mental state or an enhanced focus, attention and/or alertness mental state by specifically targeting one or more of the trigeminal cranial nerve (the fifth cranial nerve), nerves of the facial nerve (the seventh cranial nerve), nerves of the cervical plexus (ventral rami of the first four cervical spinal nerves), and nerves of the brachial plexus (anterior rami of the lower four cervical nerves and first thoracic nerve).

In general, the devices described herein include a pair of electrodes that may be connected to different, predefined regions of a subject's head and/or neck overlying one of the target nerves (trigeminal nerve, facial nerve, nerves of the cervical plexus, and/or nerves of the brachial plexus), and a TES control module that is configured specifically to deliver stimulation within a range of parameters, including intensity and frequency, determined to be effective for inducing, enhancing, or promoting (collectively, "modifying") a desired cognitive state and/or effect while minimizing pain and discomfort due to the relatively large magnitude stimulation provided.

For example, an apparatus (such as an applicator) may include a control module having circuitry (e.g., hardware), software and/or firmware that allows the apparatus to apply signals within an effective range, including, for example, one or more processors, timers and waveform generators. In general, the TES control module may be specifically adapted to deliver a biphasic electrical stimulation signal of 10 seconds or longer between the first and second electrodes, where the signal has a frequency of 100 Hz or greater (e.g., 200 Hz or greater, 400 Hz or greater, 450 Hz or greater, 500 Hz or greater, 600 Hz or greater, 700 Hz or greater, etc.) and an intensity of 2 mA or greater (e.g., 3 mA or greater, 4 mA or greater, 5 mA or greater, etc.). The control module may also be configured to reduce pain when applying the stimulation by controlling the duty cycle (e.g., the percent of time that the current applied is non-zero, and/or greater than zero), e.g. so that the duty cycle of the applied energy is greater than 10 percent (e.g., greater than 15 percent, greater than 20 percent, greater than 30 percent). In addition, the control module may be configured so that the applied current is biphasic and/or is not charge balanced (e.g., has a DC offset, also referred to as DC bias, so that the mean amplitude of the applied waveform is non-zero). Alternatively or in addition, the control module (TES control module) may be configured to discharge capacitance built up on the electrodes, e.g., by occasionally or periodically "shorting" the electrodes, and/or by applying an opposite current(s). In general, a control module may be configured to generate stimulation that includes these parameters, and may be configured to prevent stimulation outside of these parameters, in order to avoid inducing pain.

These parameters, which are described in greater detail below, are generally adapted to cause a cognitive effect. The devices and methods described herein allow the reproducible evoking of cognitive effects, as are described herein. The nature of the cognitive effect resulting from the methods and devices described may depend, at least in part, on the positioning of the electrodes on the subject's body (e.g., head, neck, etc.), and particularly over, immediately adjacent to, or spanning (i.e. with an anode and a cathode on either side of) the target nerve or nerves (trigeminal nerve, facial nerve, nerves of the cervical plexus, and/or nerves of the brachial plexus). For example, a class of cognitive effects generally results in the subject experiencing an increased mental focus and may include: enhanced focus and attention; enhanced alertness; increased focus and/or attention; enhanced wakefulness; increased subjective feeling of energy; increased objective (i.e. physiological) energy levels; higher levels of motivation (e.g. to work, exercise, complete chores, etc.); increased energy (e.g., physiological arousal, increased subjective feelings of energy); and a physical sensation of warmth in the chest. This class of cognitive effects may be referred to collectively as enhancing (or enhanced) attention, alertness, or mental focus. Placing at least one of a pair of transdermal electrodes (or arrays of electrodes) over or adjacent the trigeminal nerve and facial nerve may induce these effects; the other electrode may be positioned elsewhere so that the target nerve is between the first and second electrodes (or electrode arrays).

Another example of a class of cognitive effects includes those associated with relaxation and a calm mental state, for example: a state of calm, including states of calm that can be rapidly induced (i.e. within about 5 minutes of starting a TES session); a care-free state of mind; a mental state free of worry; induction of sleep; a slowing of the passage of time; enhanced physiological, emotional, or and/or muscular relaxation; enhanced concentration; inhibition of distractions; increased cognitive and/or sensory clarity; a dissociated state; a state akin to mild intoxication by a psychoactive compound (i.e. alcohol); a state akin to mild euphoria induced by a psychoactive compound (i.e. a morphine); the induction of a state of mind described as relaxed and pleasurable; enhanced enjoyment of auditory and visual experiences (i.e., multimedia); reduced physiological arousal; increased capacity to handle emotional or other stressors; a reduction in psychophysiological arousal as associated with changes in the activity of the hypothalamic-pituitary-adrenal axis (HPA axis) generally associated with a reduction in biomarkers of stress, anxiety, and mental dysfunction; anxiolysis; a state of high mental clarity; enhanced physical performance; promotion of resilience to the deleterious consequences of stress; a physical sensation of relaxation in the periphery (i.e., arms and/or legs); a physical sensation of being able to hear your heart beating, and the like. This class of cognitive effects may be referred to collectively as "a calm or relaxed mental state". Placing at least one of a pair of transdermal electrodes (or arrays of electrodes) over or adjacent the nerves of the cervical plexus may induce these effects; the other electrode may be positioned elsewhere so that the target nerve(s) is/are between the first and second electrodes (or electrode arrays).

The methods described herein include methods of positioning the electrodes on the subject to evoke a particular cognitive effect when applying stimulation. Devices (e.g., applicators) may be particularly adapted or configured for a particular positioning configuration. For example, an applicator may include the surface of an electrode (or electrodes) that is adapted to fit into a particular location on the subject's body to evoke a predetermined cognitive effect. Also, although the majority of the examples described herein refer to a single electrode (anode/cathode) positioned at a first location and a single (counter, e.g., cathode/anode) electrode positioned at a second location, multiple electrodes (including multiple anodes and/or multiple cathodes) may be positioned at each location. In general, the electrode positioning relative to a particular body site refers to the positioning the electrode so that the peak density of the applied current from the electrode(s) is at the target location; thus the electrodes may be smaller or larger than the target region. Proper electrode positioning, as described in greater detail herein, may also prevent pain and discomfort. In general, the electrodes referred to herein form pairs that are separated on the subject's body; although one end of a pair may be made up of multiple electrodes. For example, a first electrode (or collection of electrodes) may be positioned on a first location on the subject's head or neck, e.g., over or near nerves of the cervical plexus, trigeminal and/or facial nerves. A second electrode (or collection of electrodes) may be positioned at a second location on the subject, including the head or neck. A target nerve may be positioned between these nerves, or the source (e.g., catheter) electrode may be positioned over, immediately adjacent to, or spanning (i.e. with an anode and a cathode on either side of) the target nerve. This first electrode may be an anode and the second electrode may be a cathode; or conversely the first electrode may be a cathode and the second electrode an anode. TES current is typically applied between the two electrodes (or two groups/arrays of electrodes).

For example, in one configuration (referred to herein for convenience as "configuration A" or "configuration 2") a first electrode may be applied to the subject near the temple/lateral eyebrow area (e.g., laterally to the eye, such as slightly above and to the right of the right eye or the left eye) and at least one second electrode may be positioned behind the right ear in the mastoid region (e.g., on or near the mastoid), over or adjacent the trigeminal and/or facial nerve. The electrode may be any appropriate size (e.g. area), for example, an electrode may have an area at least about 10 $cm^2$ (e.g., at least about 20 $cm^2$) near the right temple and a smaller mastoid electrode between about 3 $cm^2$ and about 10 $cm^2$. TES stimulation of this region may result in enhanced attention, alertness, or mental focus.

Another configuration (referred to herein for convenience as "configuration B" or "configuration 3") may include an electrode positioned on the subject's skin near the subject's temple area (e.g., above and to the right of the right eye) and a second electrode on the subject's neck (e.g., on a superior portion of the neck centered to the right of the midline and, optionally, partially overlapping the spinal cord, e.g., over or adjacent a cervical plexus nerve). Beneficial embodiments comprise electrodes for the neck having an area of at least about 20 $cm^2$ and an electrode having area at least about 10 $cm^2$ (optimally at least about 20 $cm^2$) near the right temple. TES stimulation of this region may result in enhancing a calm or relaxed mental state.

Another configuration (referred to herein for convenience as "configuration 7") may include two electrodes positioned on the back of a subject's neck. Peripheral nerves in this area that may be targeted by TES include cervical spinal nerves and branches of the vagus nerve. The two electrodes may be positioned on inferior and superior portions of the back of neck; on medial and lateral portions of the back of the neck; or otherwise positioned so that both electrodes are on the back of the neck (or nearby portions of the back or shoulders).

For these exemplary configurations, waveforms of transdermal electrical stimulation as provided herein may induce a strong and reliable cognitive effect while mitigating skin irritation, pain, and tissue damage. Waveforms may be defined according to one or more of: frequency, peak intensity, duty cycle, the proportion of non-zero current flow that is positive-going (i.e. 'percent direct current'), whether the waveform is biphasic or only transmits current in one direction, and whether the electrical stimulation system shorts the electrical paths between the anode and cathode between pulses. In some embodiments, ramping of parameters (i.e. frequency, peak intensity, duty cycle) between two values occurs during a waveform or portion of a waveform.

Any of the waveforms described herein may be applied continuously or intermittently, including with variations such as transitions states (e.g., ramps) from outside of these ranges into these ranges or within the ranges of current and frequency (and in some variations, DC offset and/or duty cycle). In general, ramping and other waveform features can be incorporated in order to shift a waveform between different effective ranges of parameters for inducing a particular cognitive effect and thus achieve a more intense, longer lasting cognitive effect. Shifting between effective waveforms may be iterative (i.e. one parameter changes, than another changes) and may be repetitive (i.e. change from one waveform to a second waveform, then back to the first waveform, etc.; or toggling between three or more effective waveforms). In some embodiments, rapidly shifting one or more waveform parameters within an effective range induces a stronger cognitive effect, wherein rapid generally refers to less than 15 seconds and may be as short as one second or less.

As mentioned, the devices described herein may include a controller having components operating at high voltage so that sufficiently high peak currents can be achieved (i.e. greater than 10 V, greater than 15 V, greater than 20 V, greater than 25 V, greater than 30 V, greater than 35 V, greater than 40 V, greater than 45 V, greater than 50 V, greater than 55 V, greater than 60 V, greater than 65 V, and greater than 75V). Impedances of a subject's tissue (mostly due to skin impedance) and hardware components of the system including electrodes are generally between 1 kOhm and 20 kOhm (though occasionally up to 30 kOhm or higher), so high voltage current sources above 50 V are beneficial for delivering higher peak currents required for inducing a cognitive effect.

In general, described herein are methods of modifying a subject's cognitive state. For example, a method of modifying a subject's cognitive state may typically include: placing a first electrode of a transdermal electrical stimulation (TES) applicator on the subject's skin on a temple region on a first side of the subject's body; placing a second electrode on the subject's skin on either the mastoid region of the first side of the subject's body or on the subject's neck above the vertebra prominens; activating the TES applicator to deliver a transdermal electrical stimulation having a frequency of 100 Hz or greater and an intensity of 2 mA or greater; and modifying the subject's cognitive state by applying the transdermal electrical stimulation between the first and second electrodes for 10 seconds or longer.

For example, described herein are methods of modifying a subject's cognitive state, the method comprising: placing a first electrode of a portable transdermal electrical stimulation (TES) applicator on the subject's skin on a temple region on a first side of the subject's body; placing a second electrode on the subject's skin on either the mastoid region of the first side of the subject's body or on the subject's neck; activating the TES applicator to deliver a biphasic transdermal electrical stimulation having a frequency of 400 Hz or greater and an intensity of 3 mA or greater, wherein the biphasic transdermal electrical stimulation has a DC offset; and modifying the subject's cognitive state by applying the biphasic transdermal electrical stimulation between the first and second electrodes for 10 seconds or longer. Activating the portable TES applicator may include activating the TES applicator to deliver the biphasic transdermal electrical stimulation having a duty cycle of greater than 10 percent.

These methods may be specific to methods for enhancing attention, alertness, or mental focus or for enhancing a calm or relaxed mental state. For example, modifying the subject's cognitive state may comprise enhancing attention, alertness, or mental focus, and placing the second electrode may comprise placing the second electrode on the mastoid region of the first side of the subject's body. Similarly, modifying the subject's cognitive state may comprise enhancing a calm or relaxed mental state, and placing the second electrode may comprise placing the second electrode on the back of the subject's neck.

Any of the methods described herein may be performed by the subject wearing the device. This is possible because the devices described herein are configured to be relatively lightweight and easy to work with so that an untrained user may be able to operate them. For example the subject may place the first electrode and the second electrode on his/her head and/or neck, without the need for a physician or third party to participate.

Once applied, the application of TES may be triggered automatically (e.g., after sensing attachment), or manually and either locally (e.g., operating a switch on the device) or remotely, e.g., using a device that wirelessly communicates with the device once applied to the subject's head. The subject may activate and/or modify operation of the TES himself or herself. For example, activating the portable TES applicator may include wirelessly triggering activation of the portable TES applicator. Activating the portable TES applicator comprises triggering activation of the portable TES applicator from a handheld device.

As mentioned, during the application of the TES, the applied TES does not need to be constant, but may preferably be variable and/or intermittent. For example, application of TES may include varying the applied biphasic transdermal electrical stimulation while the biphasic transdermal stimulation is applied. The applied biphasic transdermal electrical stimulation may be varied while keeping the biphasic transdermal electrical stimulation within a duty cycle of greater than 10 percent, a frequency of 400 Hz or greater, and an intensity of 3 mA or greater (and with a DC offset).

In general, to provide effective and comfortable TES, the parameters of intensity and frequency may be held within the specified ranges. For example, intensity (current) may be high, e.g. greater than about 2 mA, greater than 3 mA, or preferably greater than 4 mA or greater than 5 mA (e.g., between 5 mA and 20 mA). The frequency of the stimulation may be generally relatively high, for example, greater than 100 Hz, greater than 200 Hz, greater than 400 Hz or more particularly greater than 450 Hz or greater than 500 Hz. Operation of these parameters may typically be done with a biphasic stimulation (e.g., having a periodic rise and fall, typically having two phases), and may also include a DC offset so that the signal is not charge balanced. As mentioned, in general a direct current (DC) offset (also referred to as a DC component, DC bias, or DC coefficient) is the mean value of the waveform. If the mean amplitude is zero, there is no DC offset. Thus, the applied TES may typically be pulsed, biphasic and asymmetric. Similarly, the TES stimulation may also have a duty cycle that is between 10% and 100% (e.g., less than 100% and greater than 10%), including greater than 20% or greater than 30%.

In any of these TES protocols, the electrodes may be 'shorted' during the stimulation (within the application of the TES periodically or occasionally) to discharge capacitive build up on the electrodes. Similarly, any of the devices (e.g., TES applicators) described herein may include short-circuiting features. For example, a short-circuit for the electrodes may be made with a fixed current source similar to the main current source, but the 'shorting' source may be saturating at 0V and then can just discharge the accumulated charges. In some variations the nominal (or maximal) short-circuit current may be preset (e.g., 40 mA) and/or may be changed by changing a resistor. Alternatively, discharging can be made by the regular current source with an adjustable current inside the range. For example, the range may be up to 20 mA, and turning on rectified switches may avoid reverse charging.

In general, ramping the biphasic transdermal electrical stimulation during the application may be achieved by decreasing one or more of the intensity, duty cycle or DC offset and then increasing one or more of the intensity, duty cycle or DC offset (similarly, frequency may be ramped by increasing then decreasing the frequency).

When placing the electrode on the temple, placement may be made to optimize the effect while avoiding pain. For example, placement on the temple may comprise placing the electrode lateral to the subject's eye and above the subject's cheekbone; for example, slightly above and to the right of the right eye, or to the left of the left eye. Placing the electrode on the temple may exclude placing the electrode on or near the subject's orbital region (to avoid pain and/or distracting muscle twitches around the eye) or below the cheekbone (to avoid reduced efficacy and/or muscle twitch).

In some variations, an electrode may be placed on the subject's forehead. In particular, the electrode may be placed so that the region of peak current is delivered on the skin over the subject's nasion, between the eyebrows and immediately above the nose (e.g., directly between the eyes, just superior to the bridge of the nose). For example, a first electrode may be placed on the nasion region and a second electrode on the temple, or the second electrode may be placed on the neck, or the second electrode may be placed behind the ear, as described, and TES applied as generally described herein. The use of the nasion electrode placement, particularly with the temple placement for the second electrode, may be used to for evoking, enhancing or improving a cognitive state such for enhancing attention, alertness, or mental focus.

In general, the electrodes may be placed on the same side of the subject's body (e.g., both on the right side or both on the left side).

In any of the methods described, the TES applicator may be self-contained, and may be lightweight. In particular, the applicator may be wearable. For example, the applicator may be adhesively secured to the subject's body (e.g., face, head, neck, etc.). Wearable devices (including applicators) are described in greater detail below, and are generally low-profile, e.g. projecting from the skin by less than about 2 cm, less than 1.5 cm, less than 1 cm, less than 0.5 cm, etc., and lightweight, e.g., less than 60 grams, less than 50 grams, less than 40 grams, less than 30 grams, etc.

The overall duration of the applied TES is generally longer than 10 seconds (though may be shorter in some variations) but may be more robustly applied for longer, including longer than 15 seconds, longer than 20 seconds, longer than 30 seconds, longer than 1 minute, longer than 5 minutes, etc. For example, modifying the subject's cognitive state may comprise applying the biphasic transdermal electrical stimulation between the first and second electrodes for 5 minutes or longer.

When placing the second electrode on the neck, an appropriate region of the neck may be the region of the neck above the vertebra prominens. The placement may be laterally offset from the midline of the neck, e.g., towards the side of the subject that the first electrode (the temple electrode) is positioned on.

As mentioned, any of the methods for modifying a subject's cognitive state may be performed by the subject. For example, described herein are methods of modifying a subject's cognitive state (including a calm or relaxed cognitive state or a cognitive state of attention, alertness, or mental focus), and may include the steps of: instructing a subject to place a first electrode of a portable transdermal electrical stimulation (TES) applicator on the subject's skin on a temple region on a first side of the subject's body; instructing the subject to place a second electrode on the subject's skin on the subject's head or neck on the first side of the subject's body; instructing the subject to modify their cognitive state by activating the portable TES applicator, wherein the portable TES applicator is configured to deliver a biphasic transdermal electrical stimulation between the first and second electrodes, the biphasic transdermal electric stimulation having a duty cycle of greater than 10 percent, a frequency of 400 Hz or greater, an intensity of 3 mA or greater, and a DC offset.

For example, a method of enhancing attention, alertness, or mental focus may include: placing a first electrode of a wearable transdermal electrical stimulation (TES) applicator on the subject's skin on a temple region on a first side of the subject's body; placing a second electrode on the subject's skin in the mastoid region of the first side of the subject's body; activating the wearable TES applicator to deliver a biphasic transdermal electrical stimulation having a duty cycle of greater than 10 percent, a frequency of 400 Hz or greater, and an intensity of 3 mA or greater, wherein the biphasic transdermal electrical stimulation has a DC offset; and enhancing attention, alertness or mental focus by applying the biphasic transdermal electrical stimulation between the first and second electrodes for 10 seconds or longer. As mentioned, the subject may place the first electrode and the second electrode, and/or may trigger or activate the wearable TES applicator, e.g., by wirelessly triggering activation of the wearable TES applicator. As described in more detail below, the subject may operate a remote controller (e.g., mobile phone/smart phone, laptop computer, pad, tablet, etc.).

Similarly, a method of enhancing a calm or relaxed mental state may include: placing a first electrode of a wearable transdermal electrical stimulation (TES) applicator on the subject's skin on a temple region on a first side of the subject's body; placing the second electrode on the back of the subject's neck above the vertebra prominens; activating the wearable TES applicator to deliver a biphasic transdermal electrical stimulation having a duty cycle of greater than 10 percent, a frequency of 400 Hz or greater, and an intensity of 3 mA or greater, wherein the biphasic transdermal electrical stimulation has a DC offset; and enhancing a calm or relaxed mental state by applying the biphasic transdermal electrical stimulation between the first and second electrodes for 10 seconds or longer. As mentioned, the subject may place the first electrode and the second electrode, and/or may trigger or activate the wearable TES applicator.

Also described herein are portable transdermal electrical stimulation (TES) applicators for modifying a subject's cognitive state. In general, these applicators may be lightweight (e.g., less than 60 grams, less than 50 grams, less than 40 grams, less than 30 grams, less than 25 grams, less than 20 grams, etc.) and may be wearable, including self-contained wearable devices that can be secured directly to the subject (e.g., by an adhesive).

For example, portable TES device (applicator) may include: a body (which may include a housing); a first electrode that is configured to be secured to the subject's skin; a second electrode that is configured to be secured to a second portion of the subject's skin, and is connected to the rest of the device by a cable, cord, etc.; and a TES control module at least partially within the body and comprising a processor, a timer and a waveform generator, wherein the TES control module is adapted to deliver a biphasic electrical stimulation signal of 10 seconds or longer between the first and second electrodes having a frequency of 400 Hz or greater, a duty cycle of greater than 10 percent, an intensity of 3 mA or greater, with a DC offset. The device may also include a wireless receiver coupled to the TES control module, a battery, and additional electronic components, including memory and the like.

A wearable transdermal electrical stimulation (TES) applicator for modifying a subject's cognitive state may include: a body adapted to be worn by the subject; a first electrode; a second electrode; a TES control module at least partially within the body, the TES control module including a power source, a processor, a timer, and a waveform generator, wherein the TES control module is adapted to deliver a biphasic electrical stimulation signal of 10 seconds or longer between the first and second electrodes having a frequency of 400 Hz or greater, a duty cycle of greater than 10 percent, an intensity of 3 mA or greater, with a DC offset; and a wireless receiver connected to the TES control module; wherein the wearable TES applicator weighs less than 50 grams.

A wearable transdermal electrical stimulation (TES) applicator for modifying a subject's cognitive state may include: a body adapted to be worn against the subject's skin; a first electrode on the body; a second electrode coupled to the body by a cord; and a TES control module at least partially within the body and comprising a processor, a timer and a waveform generator, wherein the TES control module is adapted to deliver a biphasic electrical stimulation signal of 10 seconds or longer between the first and second electrodes having a frequency of 400 Hz or greater, a duty cycle of greater than 10 percent, an intensity of 3 mA or greater, with a DC offset; further wherein the wearable TES applicator weighs less than 50 grams.

As mentioned above, any of the devices described herein may be configured to discharge capacitance built up on the electrodes during operation of the device. For example, any of these devices may include a capacitive discharge circuit. A capacitive discharge circuit may be controlled by the TES control module and may remove the discharge occasionally, periodically, or regularly during the application of stimulation by the device. Thus, a TES control module may be configured to occasionally or periodically trigger the capacitive discharge circuit to discharge capacitance on the electrodes during the delivery of the biphasic electrical stimulation.

Another example of the portable transdermal electrical stimulation (TES) applicators for modifying a subject's cognitive state described herein may include TES devices having the capacitive discharging features ('short circuiting' applicator) described. For example, a portable TES device for modifying a subject's cognitive state may include: a body; a first electrode; a second electrode; a TES control module at least partially within the body and comprising a processor, a timer and a waveform generator, wherein the TES control module is adapted to deliver a biphasic electrical stimulation signal of 10 seconds or longer between the first and second electrodes having a frequency of 400 Hz or greater, a duty cycle of greater than 10 percent, an intensity of 3 mA or greater, with a DC offset; and a capacitive discharge circuit, wherein the TES control module is configured to occasionally trigger the capacitive discharge circuit to discharge capacitance on the electrodes during the delivery of the biphasic electrical stimulation. The device may include a switch on the capacitive discharge circuit, wherein the switch is coupled to the TES control module.

Any of the methods described herein may include discharging the capacitance on the electrodes (e.g., short circuiting them) briefly during the application of the TES. For example, a method of modifying a subject's cognitive state may include: placing a first electrode of a transdermal electrical stimulation (TES) applicator on the subject's skin; placing a second electrode of the TES applicator on the subject's skin; activating the TES applicator to deliver a biphasic transdermal electrical stimulation having a frequency of 400 Hz or greater and an intensity of 3 mA or greater, wherein the biphasic transdermal electrical stimulation has a DC offset; modifying the subject's cognitive state by applying the biphasic transdermal electrical stimulation between the first and second electrodes for a treatment period of 10 seconds or longer; and triggering a capacitive discharge circuit for a sufficiently long enough time to discharge capacitance occasionally during the treatment period.

In general, the body region of any of the applicators described herein may include a housing to at least partially enclose some or all of the electronics. In general, the housing may be adapted to protect the electronics and the circuitry (such as the power supply, e.g., batteries, capacitors, etc., and the TES control module, etc.). In wearable variations the housing may be low-profile (e.g., thinner than 30 mm, thinner than 25 mm, thinner than 20 mm, thinner than 18 mm, thinner than 15 mm, etc.), and/or may be adapted to conform to a particular region of the head, such as the temple region. For example, the body may be elongate and curved, so that it can fit to the head and not overlap with the eye orbit region, which may interfere with vision. In some embodiments of the devices described herein the first electrode may be positioned on an outer surface of the body, and the second electrode may be connected to the body (e.g., to the TES control module) by a cord (wire, conductor, cable, etc.). The device may also include an adhesive (e.g. a biocompatible and/or conductive adhesive). In some variations both the first electrode and the second electrode are coupled to the body by a cord (either the same cord or two separate cords). In some variations the device is not held on the body, but is positioned nearby (e.g., by being worn on the subject's clothes, etc., or positioned near the subject (e.g., on a desk, in a pocket, etc.)).

Any of the devices described herein may include an input, and particularly a manual input, for entering control commands to regulate action/activity of the device. For example, the device may include a manual control on the body of the device that is coupled to the control module. A manual control may be a button, switch, touch screen, etc.

The TES controller may generally include one or more circuits specifically adapted to drive stimulation in the range of parameters that is relatively high-intensity (to effectively induce a cognitive state) but configured to prevent discomfort and/or pain. For example, the waveform generator of the TES module may include an oscillator (oscillator circuit) that can drive between 100 Hz and 30 KHz) as well as filters and rectifiers, as illustrated herein. In particular the devices described herein may generally include safety features such as current limiters, which may act as a fuse, to prevent harming the subject wearing the device. The TES controller may include or may be connected to a memory (e.g., a volatile memory such a one or more registers, flash memory, etc.) adapted to store information on the operation of the TES applicator.

Also described herein are methods and devices for TES modulation of a subject's cognitive state that provide or include TES with fast transitions during a TES treatment regime. Fast transitions may be referred to as ramps or as excursions, since they typically include a transition or excursion from a cognitive state-modifying simulation level to a stimulation level that is sub-threshold for inducing the cognitive effect, and then quickly back to the suprathreshold level for inducing the cognitive effect. The excursion stimulation ("ramping") is typically within the TES protocol, and enhances the cognitive effect and/or perception of the cognitive effect. While more gradual transition (or ramps) may be useful for reducing habituation, rapid (as described below) transitions may be particularly useful for enhancing the subject's experience of the induced cognitive state.

In general, a method of enhancing transdermal electrical stimulation (TES) for modifying a subject's cognitive state may include changing at least one of intensity, frequency, duty cycle and/or DC offset to change the stimulation being applied from the suprathreshold level for inducing the cognitive effect into a sub-threshold level for inducing the cognitive effect. The TES typically remains in the sub-threshold range only briefly (e.g., for less than 15 seconds, less than 10 seconds, less than 5 seconds, less than 2 seconds, etc.), before the stimulation is changed back to a suprathreshold level for inducing the cognitive effect. The change in the parameter level may occur relatively slowly compared to the time to restore the parameter to the suprathreshold level for inducing the cognitive effect, which typically occurs on the order of a few seconds.

For example a method of enhancing transdermal electrical stimulation (TES) for modifying a subject's cognitive state may include delivering a TES stimulation having an intensity, frequency, duty cycle and DC offset to the subject to evoke a cognitive state, the TES stimulation comprising a biphasic electrical stimulation having a target frequency of 400 Hz or greater, a target intensity of 3 mA or greater, a target duty cycle of greater than 10 percent, and a target DC offset of greater than 10 percent; and enhancing the subject's cognitive state during the application of the TES stimulation by performing one or more of: reducing the intensity by more than 20% of the target intensity, and, after a delay of less than 15 seconds, restoring the intensity to the target intensity at a rate of greater than a 5% change in intensity per second, increasing the frequency by more than 10% of the stimulation frequency, and, after a delay of less than 15 seconds, restoring the frequency to the target frequency at a rate of greater than 5% change in frequency per second, decreasing the duty cycle by 2% or more from the target duty cycle, and after a delay of less than 15 seconds, restoring the duty cycle to the target duty cycle at a rate of greater than 0.5% per second, or modifying the DC offset to +/−5% from the target DC offset, and after a delay of less than 15 seconds, restoring the DC offset to the target DC offset at a rate of greater than 1% per second.

Any of these methods may include placing a first electrode of a TES applicator on the subject's skin and placing a second electrode of the TES applicator on the subject's skin, wherein delivering TES stimulation comprises applying the TES stimulation between the first and second electrodes. In any of the methods described herein, delivering a TES stimulation may include delivering the TES stimulation for more than 10 seconds (e.g., for more than 30 seconds, for more than 1 minute, for more than 2 minutes, for more than 5 minutes, for more than 10 minutes, for more than 12 minutes, for more than 15 minutes, for more than 20 minutes, for more than 25 minutes, for more than 30 minutes, etc.). Also, any of the methods described herein may be useful to modify any appropriate cognitive state, including, for example, a calm or relaxed mental state or an alert or focused metal state.

As mentioned, any of these methods may also be driven by the subject himself or herself triggering the enhanced cognitive state. For example, enhancing the subject's cognitive state may comprise the subject triggering the start, triggering ramping (to enhance the stimulation), the subject modifying the waveform, etc. For example, the subject may trigger the ramping (excursion) described above to enhance the experience of the induced cognitive effect, or the ramping may be triggered automatically. Triggering the ramping described above may be referred to as boosting the induced cognitive effect.

For example, in one variation a boost to the induced cognitive effect may be triggered (e.g. by a subject), wherein the apparatus reduces the intensity by more than 50% of the target intensity (suprathreshold stimulation parameters) and, restores the intensity comprises restoring the intensity to the target intensity at a rate of greater than a 50% change in intensity per 500 ms.

In general, although precise supra threshold stimulation parameters may be subject-dependent, and may be empirically determined, described herein are generic suprathreshold parameters that can be generally applied, and may be referred to as target stimulation parameters, including a target intensity of about 3 mA or greater, a target frequency of about 400 Hz or greater, a target duty cycle of 10% or greater, and a target DC offset of greater than about 10%.

For example, increasing the frequency and restoring the frequency may include restoring the frequency to the target frequency at a rate of greater than 50% change in frequency per 500 ms. Decreasing the duty cycle and restoring the duty cycle may comprise restoring the duty cycle to the target duty cycle at a rate of greater than 15% per 500 ms. Modifying the DC offset and restoring the DC offset may comprise restoring the DC offset to the target DC offset at a rate of greater than 15% per 500 ms.

Also described herein are methods and apparatuses for modifying a subject's cognitive state by transdermal electrical stimulation (TES).

In general, a neurostimulator for TES may include one or more sensors for monitoring subject physiology before, during, and/or after a TES session, including a temperature sensor (i.e. a thermistor) for detecting changes in facial blood flow and a heart beat sensor (i.e. optical heart beat sensor for measuring heart rate and heart rate variability). Physiological monitoring may be beneficial for optimizing the positioning of TES electrodes and for optimizing one or more waveform parameter (i.e. intensity, frequency, bursting duty cycle, etc.).

Described herein are TES electrode configurations for modulating autonomic nervous system activity (i.e. suppressing or enhancing sympathetic nervous system activity) for which at least one electrode is not on the head or neck.

Direct microneurographic recordings of muscle sympathetic nerve activity (MSNA) are considered the gold standard for assaying sympathetic outflow or tone. The method of performing intra-nerve bundle recordings of sympathetic nerve activity is well-established and has been used for decades to study autonomic function. In general, a TES system may incorporate an MSNA recording to assess the effectiveness of neuromodulation. In general, methods for assessing TES for modulating sympathetic nervous system activity are also described herein.

Although the methods and apparatuses described herein are generally directed to methods and apparatuses for delivery to a subject's head or head and neck, any of the methods and apparatuses described herein may also be useful for other regions of the body. For example, the methods and apparatuses may be used with other electrode locations, including electrode locations that are only on the body below the neck (e.g., arms, legs, torso, etc.). In particular, the ensemble waveforms described herein may generally be useful when electrically stimulating regions of the body other than the head and neck. In addition the ensemble waveforms described herein for neurostimulation to change cognitive states may be used for other electrical stimulation methods (such as TENS, etc.).

In general, the TES systems and methods described herein may incorporate pulsing parameters for TES waveforms based on general principles of effective and comfortable waveform design.

Waveforms with a pulsing frequency between 150 Hz and 750 Hz may be effective for inducing cognitive effects in at least some instances. Described herein are systems and methods for using TES waveforms with a pulsing frequency of 150 to 750 Hz to induce a shift in cognitive state, including TES waveforms as described herein that modulate the activity of the autonomic nervous system.

In some variations, the set of waveform parameters (or waveform properties) may generally comprises a peak intensity of between about 5 mA and 25 mA, a frequency between about 150 Hz and 30 kHz (e.g., having a lower bound of greater than 150, 200, 250, 300, 350, 400, 450, 500, 550, 600, 650, 700, 750, etc. Hz), a duty cycle of between about 20 and 80%, and a percent charge imbalance of between about 10% and 100%.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4A-4C illustrate exemplary electrode placement positions on a subject's head (shown in the context of a 10/20 system of positions) for another configuration ("configuration 1" for enhanced attention, alertness, or mental focus.

FIG. 4D illustrates one example of the configuration shown in FIGS. 4A-4C.

FIG. 5H is an example of an ensemble waveform, graphically depicted to show the current amplitude and frequency waveform components (but not percent charge imbalance or duty cycle).

FIG. 7A is also an example of a neurostimulator that may be configured for use with (and may deliver) the ensemble waveforms described herein.

FIG. 9 schematically illustrates components of a portable, wired TES system.

FIG. 10 schematically illustrates components of a TES system that connects wirelessly to a control unit comprising a microprocessor.

FIG. 21A shows one variation of TES applicator.

FIG. 21B shows the applicator of FIG. 21A in an exploded view.

FIG. 22 is a perspective view of the applicator of FIGS. 21A and 21B.

FIG. 33A illustrates one variation of a pair of base waveforms including a first variation of a capacitive discharge.

FIG. 33B illustrates a second variation of a pair of base waveforms including a second variation of capacitive discharge.

FIGS. 35A-35F illustrate another example of a neurostimulator as described herein.

FIGS. 35G-35J illustrates a first example of one variation of an electrode assembly, configured as a "calm" electrode assembly.

FIGS. 35K-35N illustrate a second example of one variation of an electrode assembly, configured as an "energy" electrode assembly.

DETAILED DESCRIPTION

Figure 1A:
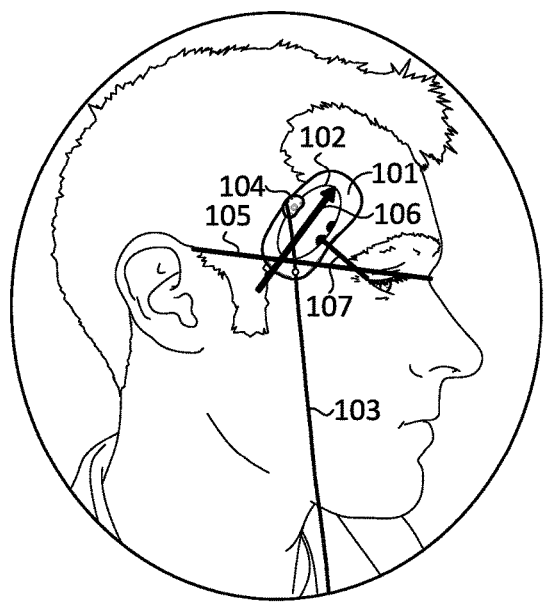
FIGS. 1A and 1B illustrate placement of first electrode in the temple region of a subject's head.

Described herein are transdermal electrical stimulation (TES) methods and apparatuses, including devices and systems, such as TES applicators for modifying a subject's cognitive state. In general, these applicators and methods for TES may induce neuromodulation with electrical stimulation delivered to a human subject to induce a beneficial or desired change in cognitive function and/or cognitive state. Other examples of devices and methods for transdermal electrical stimulation (including transcranial electrical stimulation) are described in U.S. patent application Ser. No. 14/091,121, now U.S. Pat. No. 8,903,494, by named inventors of this application titled "WEARABLE TRANSDERMAL ELECTRICAL STIMULATION DEVICES AND METHODS OF USING THEM" and is herein incorporated by reference in its entirely herein.

In general, described herein are general TES waveforms parameters that may be used to invoke, enhance, or modify a variety of cognitive states. Although the apparatuses and methods described herein may be used to provide TES to induce and/or modify a variety of cognitive states, two particular examples are described in detail herein, including inducing enhancing attention, alertness, or mental focus and inducing a calm or relaxed mental state. Configurations of apparatuses and methods specific to enhancing attention, alertness, or mental focus and inducing a calm or relaxed mental state, including specific configurations for causing neuromodulation that achieves one of these particular cognitive effects in a subject are described in particular detail.

A generic TES applicator (device or system) for modifying a cognitive state may include a pair of two electrodes (or two sets of electrodes), one anode and one cathode, that can be applied to specific regions of the subject's body and used to provide TES stimulation within the relatively high-intensity, high-frequency ranges described as effective herein. Current is typically applied between the anode and cathode electrodes (or groups of anodes and cathode electrodes); without being bound by a particular theory of operating, the current may be passed through the body between the anode and cathode, potentially applying energy in an appropriate treatment regime to underlying neural tissue (cranial nerves, brain, etc.) in a particular neural pathway to result in the desired target effect (e.g., attention, alertness, or mental focus and inducing a calm or relaxed mental state). Thus, the placement locations of the electrodes on the subject's body are important to provide the desired cognitive effect. The placement positions for the pairs of electrodes (anodal and cathodal electrodes) specific to a desired cognitive effect may be referred to as a placement regime or configuration, and may generally be selected to target one or more peripheral nerves (i.e. cranial nerve, nerve of the cervical spinal plexus, nerve of the brachial plexus, etc.). For example, a first placement configuration for inducing a cognitive state of attention, alertness, or mental focus, which may be referred to as "configuration A" or "configuration 2" includes a first electrode applied to the subject near the temple area (e.g., laterally to the eye, such as slightly above and to the right of the right eye or above and to the left of the left eye) and a second electrode positioned behind the ear on the same side as the first electrode in the mastoid region (e.g., on or near the mastoid). High-intensity TES stimulation (as described in greater detail below) of this region may result in enhanced attention, alertness, or mental focus. A second configuration (referred to for convenience herein as "configuration C" or "configuration 1") for enhanced attention, alertness, or mental focus may include placement of a first electrode on the temple area (e.g., laterally to the eye, such as slightly above and to the right of the right eye or above and to the left of the left eye) and a second electrode positioned on the forehead, e.g., near or above the nasion). A third configuration (referred to for convenience herein as "configuration 8") for enhanced attention, alertness, or mental focus may include placement of a first electrode on the back of the neck and a second electrode positioned behind the ear on the same side as the first electrode in the mastoid region (e.g., on or near the mastoid). Configuration 8 is illustrated in FIGS. 32A-32F.

For example, TES using configuration A, configuration C, or configuration 8 to enhance attention, alertness, or mental focus may result in: enhanced focus and attention; enhanced alertness; increased focus and/or attention; enhanced wakefulness; increased subjective feeling of energy; increased objective (i.e. physiological) energy levels; higher levels of motivation (e.g. to work, exercise, complete chores, etc.); increased energy (e.g., physiological arousal, increased subjective feelings of energy); and a physical sensation of warmth in the chest.

Figure 32A:
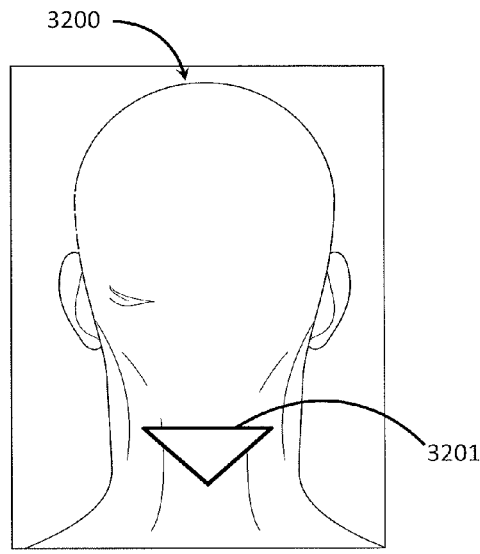
FIGS. 32A-32F illustrate subjects with electrodes positioned per configuration 8.
Figure 32B:
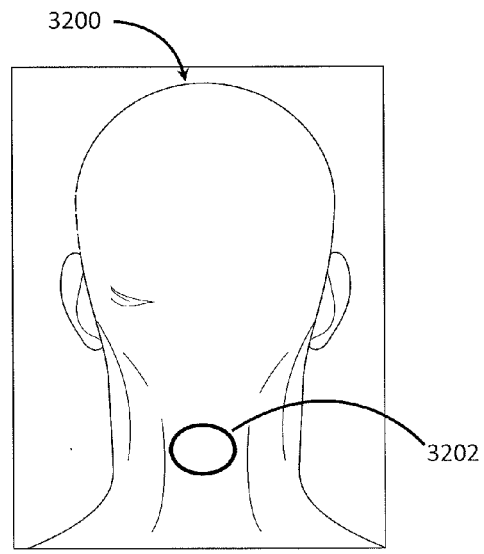
Figure 32C:
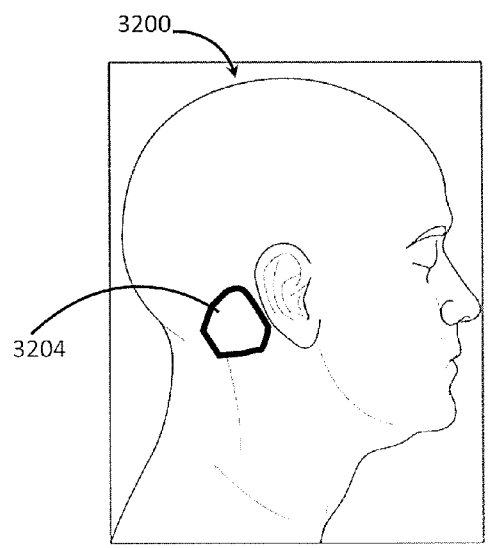
Figure 32D:
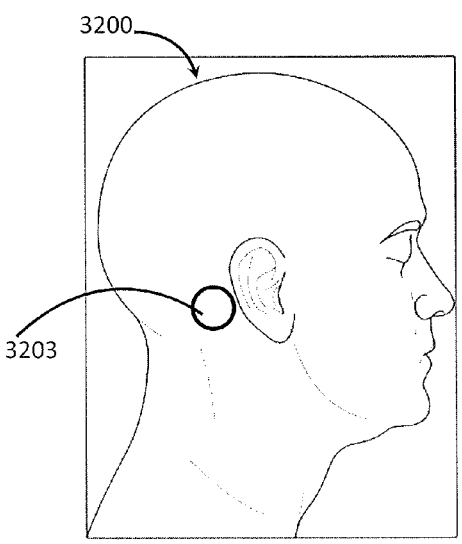
Figure 32E:
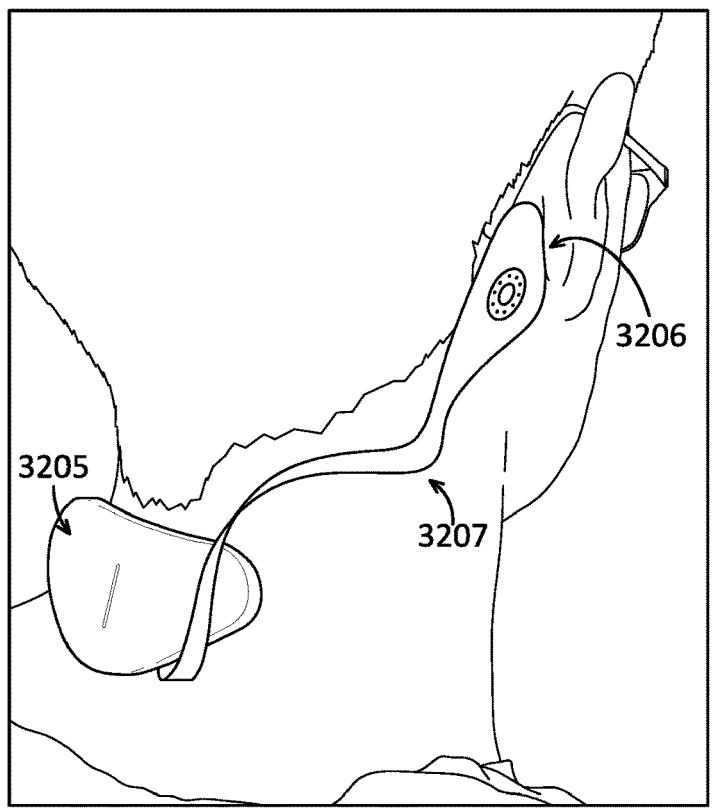
Figure 32F:
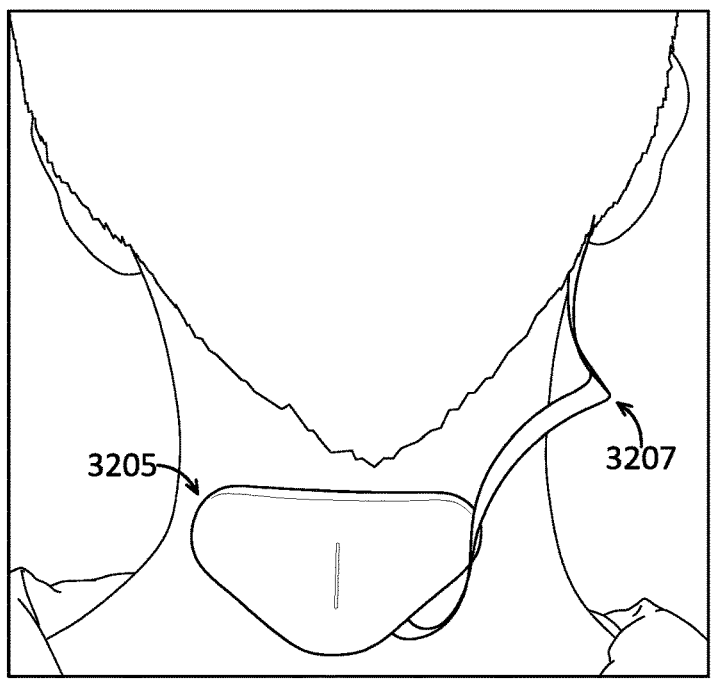

FIGS. 32A-32F show different variations of electrodes placed according to configuration 8 on subjects 3200. FIGS. 32A and 32B illustrate two electrodes positioned near the midline of the back of the neck having a triangular (FIG. 32A, 3201) or oval (FIG. 32B, 3202) shape. The second (mastoid, near the ear) electrode is not shown in FIGS. 32A and 32B—but is illustrated in FIGS. 32C-32D as having a round (FIG. 32D, 3203) or irregular shape (FIG. 32C, 3204) targeting the generally hairless area over the mastoid bone behind the ear. The electrodes in FIGS. 32C-32D are shown on the right side, though placement on the left side is also effective for inducing increased physiological arousal and related effects as described above. FIGS. 32E-32F show an adherent flexible electrode array positioned according to configuration 8 on a subject, including mastoid electrode area 3206, conductive connector cable 3207 and TES module 3205 overlying a neck electrode area (not visible, beneath the white module). For any of the variations of configuration 8 shown in FIGS. 32A-32F, different electrode sizes and shapes may be used with similar positioning and the outlines of electrode positions shown in FIGS. 32A-32F may have active electrode areas comprising all or a part of the indicated area (i.e. part of the area may be non-active and incorporate an adhesive on the dermal-facing surface). The electrode locations in FIGS. 32A-32F are exemplary and other variations of these locations may be used to induce or enhance a state of increased physiological arousal and related cognitive effects.

Another configuration (referred to herein for convenience as "configuration B" or "configuration 3") may include an electrode positioned on the subject's skin near the subject's temple area (e.g., above and to the right of the right eye) and a second electrode on the subject's neck (e.g., on a superior portion of the neck centered to the right (or left) of the midline and partially overlapping the spinal cord). TES stimulation of this region may result in enhancing a calm or relaxed mental state.

Another configuration (referred to herein for convenience as "configuration 7") may include two electrodes positioned on the back of a subject's neck. Peripheral nerves in this area that may be targeted by TES include cervical spinal nerves and branches of the vagus nerve. The two electrodes may be positioned on inferior and superior portions of the back of neck; on medial and lateral portions of the back of the neck; or otherwise positioned so that both electrodes are on the back of the neck (or nearby portions of the back or shoulders). TES stimulation of this region may result in enhancing or inducing a calm or relaxed mental state.

Figure 31A:
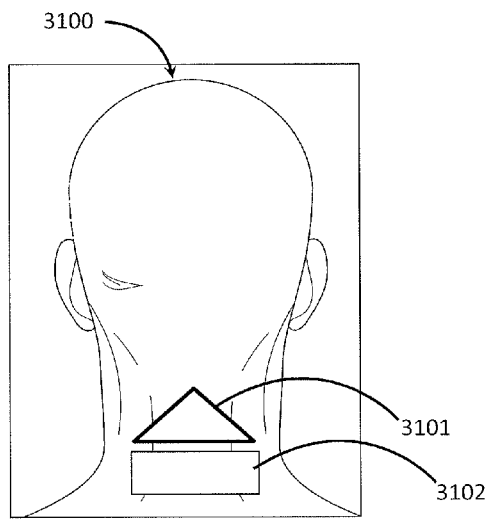
FIGS. 31A-31D illustrate a subject with electrodes positioned per configuration 7.
Figure 31B:
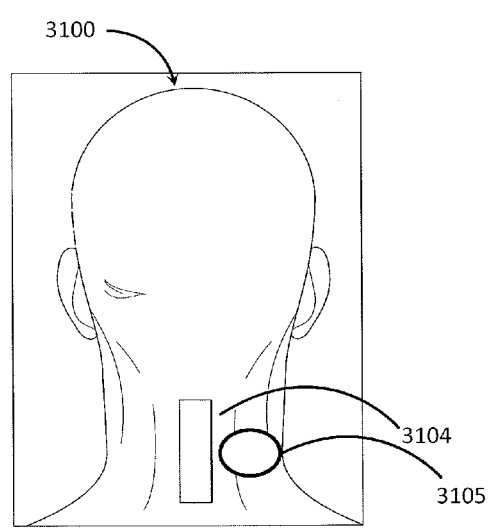
Figure 31C:
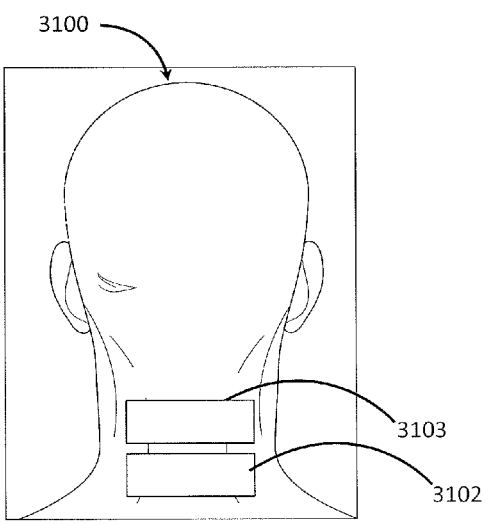
Figure 31D:
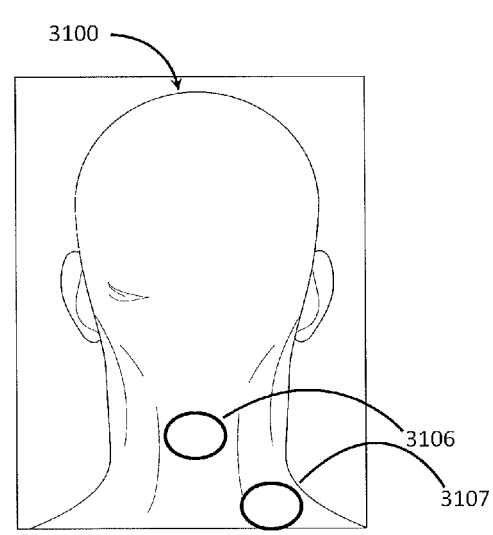

FIGS. 31A-31D show different variations of electrodes placed according to configuration 7 on subject 3100. FIGS. 31A and 31C illustrate two electrodes positioned near the midline of the inferior (3102) and superior (3101, 3103) portions of the neck. In FIG. 31A the superior electrode 3101 is triangular and inferior electrode 3102 is rectangular. In FIG. 31C both electrodes 3102, 3103 are rectangular. FIG. 31B illustrates two electrodes positioned on the back of the neck wherein one electrode 3104 is rectangular and vertically oriented along the midline and a second electrode 3105 is oval and positioned laterally. FIG. 31D illustrates one oval electrode 3106 positioned medially on the back of the neck and second electrode 3107 positioned at the edge of the neck and shoulder/back area. For any of the variations of configuration 7 shown in FIGS. 31A-31D, different electrode sizes and shapes may be used with similar positioning and the outlines of electrode positions shown in FIGS. 31A-31D may have active electrode areas comprising all or a part of the indicated area (i.e. part of the area may be non-active and incorporate an adhesive on the dermal-facing surface). The electrode locations in FIGS. 31A-31D are exemplary and other locations on the neck for two electrodes may be used to induce or enhance a calm or relaxed state.

TES using Configuration B or configuration 7 may result in cognitive effects including, but not limited to: a state of calm, including states of calm that can be rapidly induced (i.e. within about 5 minutes of starting a TES session); a care-free state of mind; a mental state free of worry; induction of sleep; a slowing of the passage of time; enhanced physiological, emotional, or and/or muscular relaxation; enhanced concentration; inhibition of distractions; increased cognitive and/or sensory clarity; a dissociated state; a state akin to mild intoxication by a psychoactive compound (i.e. alcohol); a state akin to mild euphoria induced by a psychoactive compound (i.e. a morphine); the induction of a state of mind described as relaxed and pleasurable; enhanced enjoyment of auditory and visual experiences (i.e. multimedia); reduced physiological arousal; increased capacity to handle emotional or other stressors; a reduction in psychophysiological arousal as associated with changes in the activity of the hypothalamic-pituitary-adrenal axis (HPA axis) generally associated with a reduction in biomarkers of stress, anxiety, and mental dysfunction; anxiolysis; a state of high mental clarity; enhanced physical performance; promotion of resilience to the deleterious consequences of stress; a physical sensation of relaxation in the periphery (i.e. arms and/or legs); and a physical sensation of being able to hear your heart beating.

In general, cognitive effects may be stereotypical across a population (though with individual variation and degree) and may be demonstrated by any appropriate means. For example, the effect of neuromodulation according to configuration A or configuration B (or any other Configuration) may be detected by one or more method chosen from the group including, but not limited to: subjectively by the recipient as a perception, movement, concept, instruction, other symbolic communication by modifying the recipient's cognitive, emotional, physiological, attentional, motivational, or other cognitive state; (ii) through physiological measurement of brain activity by one or a plurality of: electroencephalography (EEG), magnetoencephalography (MEG), functional magnetic resonance imaging (fMRI), functional near-infrared spectroscopy (fNIRS), positron emission tomography (PET), single-photon emission computed tomography (SPECT), computed tomography (CT), functional tissue pulsatility imaging (fTPI), xenon 133 imaging, magnetic resonance spectroscopy (MRS), or other techniques for measuring brain activity known to one skilled in the art; and (iii) by making a physiological measurement of the body such as by electromyogram (EMG), galvanic skin response (GSR), electrocardiogram (EKG), pulse oximetry (e.g. photoplethysmography), heart rate, blood pressure, respiration rate, pupil dilation, eye movement, gaze direction, measurement of circulating hormone (e.g. cortisol or testosterone), protein (e.g. amylase), or gene transcript (i.e. mRNA); and other physiological measurement.

Figure 1B:
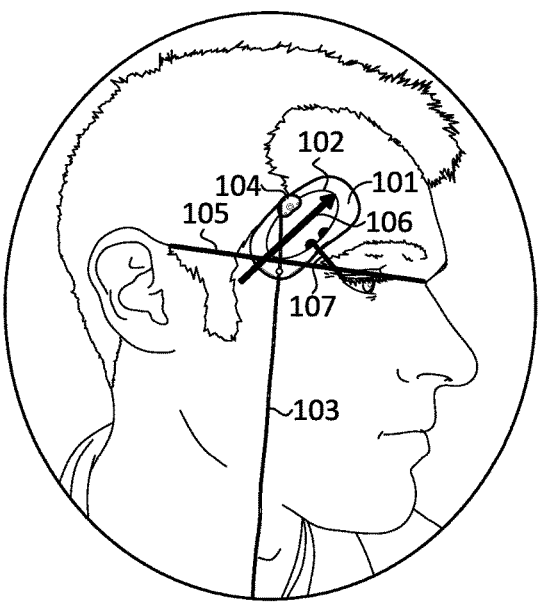
Figure 1C:
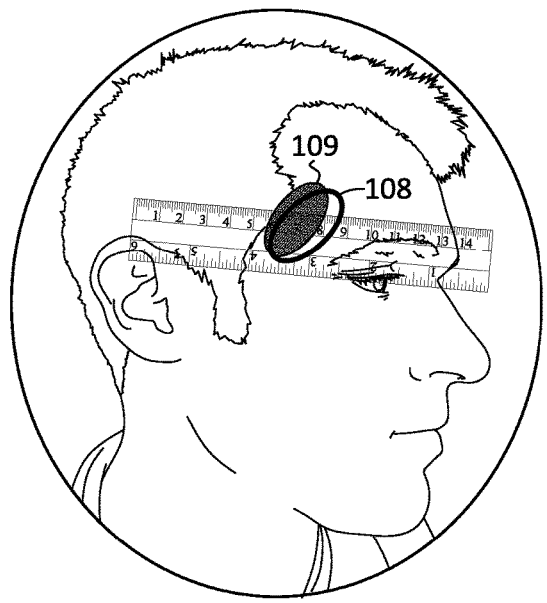
FIG. 1C shows alternative variations of the temple electrode placement.
Figure 1D:
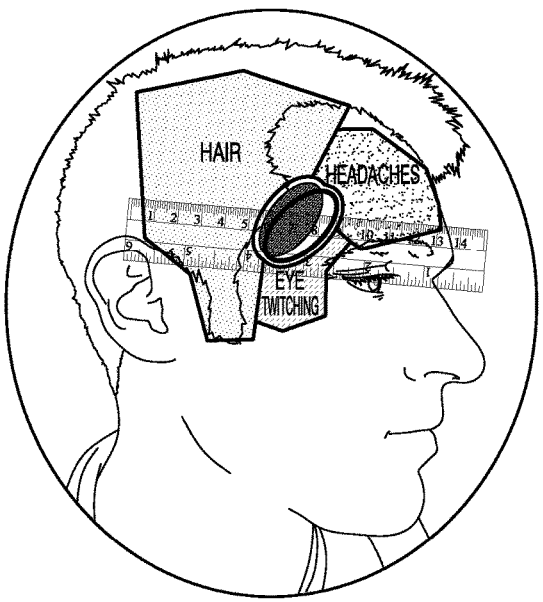
FIG. 1D illustrates a schematic representation of exemplar electrode placement for a temple electrode. The temple electrode placement shown may be used with another electrode placed in another part of the subject's body for TES modulation of cognitive state.

For both Configuration A and Configuration B, the first electrode may be either an anode or a cathode. For convenience, the first (temple) electrode may be referred to as the anode. The anode (or set of isoelectric anodes) in all of configurations A, B and C may be positioned at the right temple, above and to the right of the right eye, between the eyebrow and hairline. Two exemplary electrode placements are shown in FIGS. 1A and 1B for an electrode assembly having connector between TES apparatus and an anode-cathode pair 104, wire to second electrode 103 (second electrode not shown), plastic backing 101 (top, away from skin), active electrode region 102 (i.e. for conducting current transdermally), and adhesive hydrocolloid region (bottom, adherent to skin). In this example, the bottom edge of active electrode region 102 is approximately aligned with a line running between the nasion and top of the ear 105. The nearest edge of the active electrode region may be at least about 0.5 cm from the eye (and optimally at least about 1 cm from the eye) to prevent distracting and uncomfortable eye muscle twitching caused by TES waveforms delivered (see FIG. 1D). Line running between eye and edge of active electrode region 107 indicates a beneficial distance between the edge of the electrode and the eye. FIG. 1A show a first effective orientation rotated counter-clockwise relative to a second effective orientation in FIG. 1B. The electrode angles are represented schematically by arrows 106. For subjects with a low hairline, the positioning of FIG. 1B may be preferred to avoid placing adhesive or electrode overlaying hair. The approximate location of the active electrode region is shown schematically in FIG. 1C for the position of FIG. 1A (109) and FIG. 1B (108).

For configurations A, B, and C, the anode electrode area may generally be greater than about 5 cm$^2$ and may be somewhat larger (i.e. greater than about 7 cm$^2$; greater than about 10 cm$^2$; or greater than about 15 cm$^2$. Larger electrode areas than 20 cm$^2$ (e.g., composed of a single anode or set of anodes) may be less effective for inducing the cognitive effects associated with configurations A, B, and C than smaller electrodes due to less precise targeting of electric fields delivered transdermally. Effective electrode shapes for these configurations may be generally longer than wide, including but not limited to rectangles, ovals, and irregular oblong shapes.

Figure 2A:
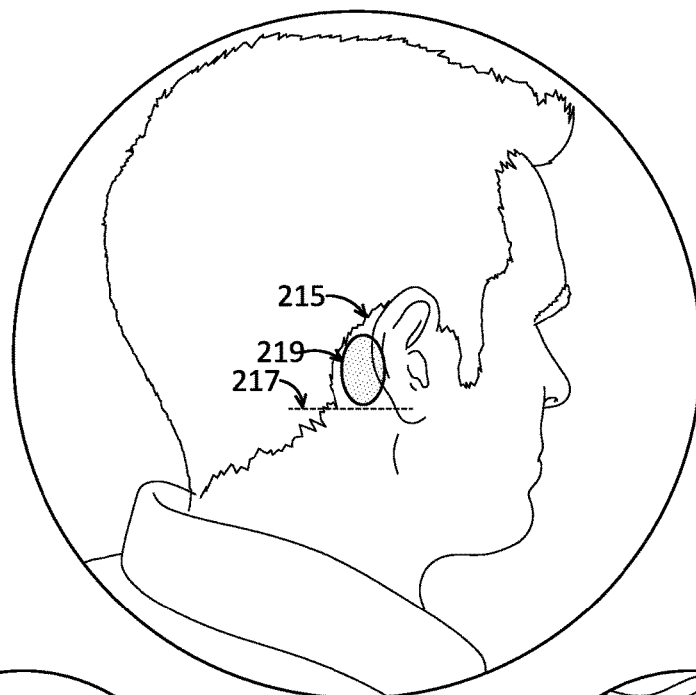
FIG. 2A illustrates the mastoid region for behind-the-ear placement of an electrode, which may be used in conjunction with a second electrode such as the temple electrode shown in FIGS. 1A-1D.
Figure 2B:
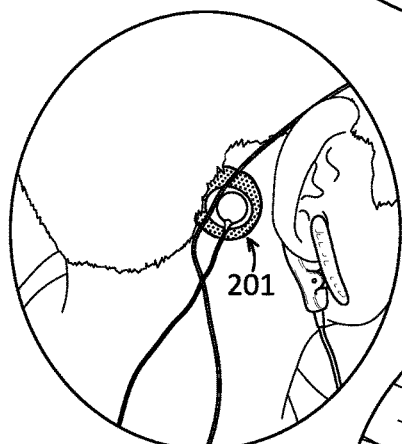
FIGS. 2B-2D show other variations of mastoid electrode placement for TES modulation of cognitive state.
Figure 2C:
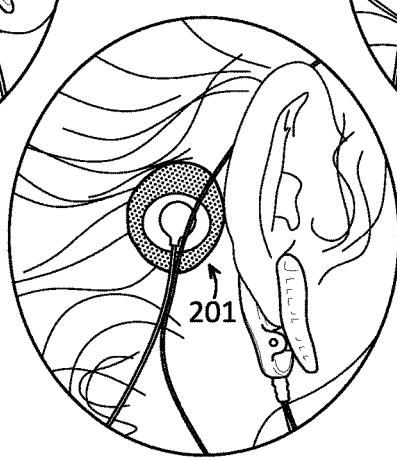
Figure 2D:
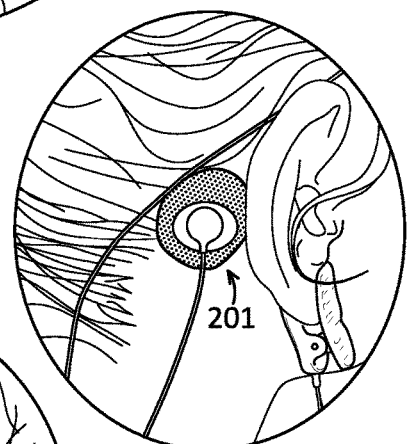

The second electrode position for configuration A may (for convenience) be referred to as a cathode (or set of isoelectric cathodes) covering most of the right mastoid process, behind the right ear (FIG. 2A). Preferably, the second electrode for configuration A should not touch the back of the ear. An effective electrode shape for the cathode (or set of cathodes) of configuration A may be round or oval with a diameter between about 0.5" to 1"—or may have an irregular shape to fit the mastoid area more effectively (i.e. a crescent shape). Conformable electrodes are preferred for making uniform (or near uniform) contact with the skin over the mastoid. In some cases the transdermally contacting portion of the cathode may be somewhat larger, particularly in the vertical dimension but is generally limited in size by the presence of hair above and behind the mastoid process. In FIG. 2A, the electrode may extend from the upper region of the mastoid region 215 to a lower region 217 (see oval region 219). The center of this electrode may be aligned with the ear canal, or it may be shifted up or down by about 5 mm, depending on the hairline and mastoid bone location of the subject. As with the first electrode, the hair may be avoided. FIGS. 2B-2D illustrate other positioning variations within acceptable ranges.

Figure 2E:
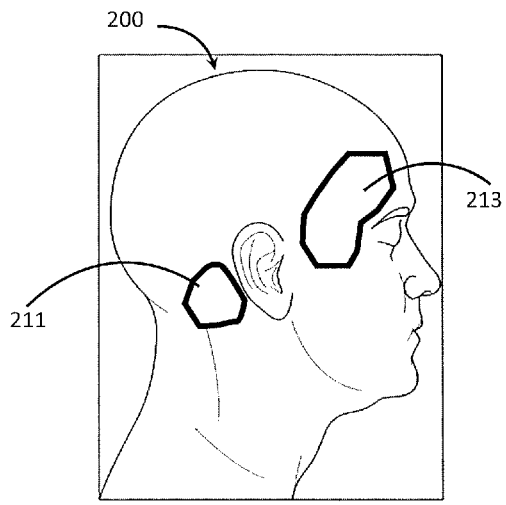
FIG. 2E illustrates the electrode placement regions for a configuration (configuration 2) to evoke a cognitive state of attention, alertness, or mental focus.
Figure 2F:
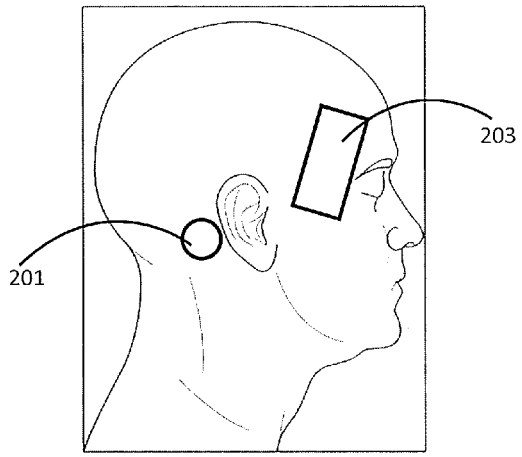
FIGS. 2F-2H schematically illustrate electrodes placed per this configuration.
Figure 2G:
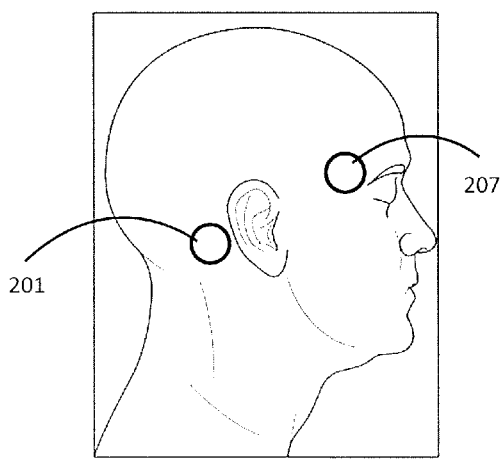
Figure 2H:
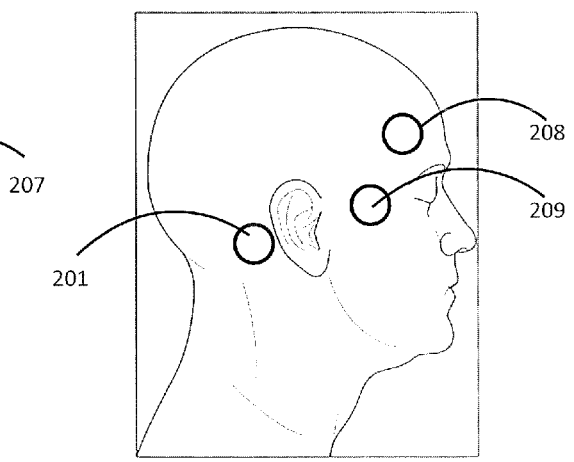

FIGS. 2E-2H illustrate other examples of electrodes and electrode placement for configuration A. In FIG. 2E a subject's head 200 is shown with the regions for temple electrode placement 213 and mastoid region electrode placement 211 outlined. FIG. 2F illustrates an example of a rectangular electrode at the temple 203 and a circular electrode 201 at the mastoid region. Similarly, in FIG. 2G, the temple electrode 207 is circular. FIG. 2H illustrates an example having two circular electrodes 208, 209 that may be configured as anodes (or both as cathodes).

Figure 3A:
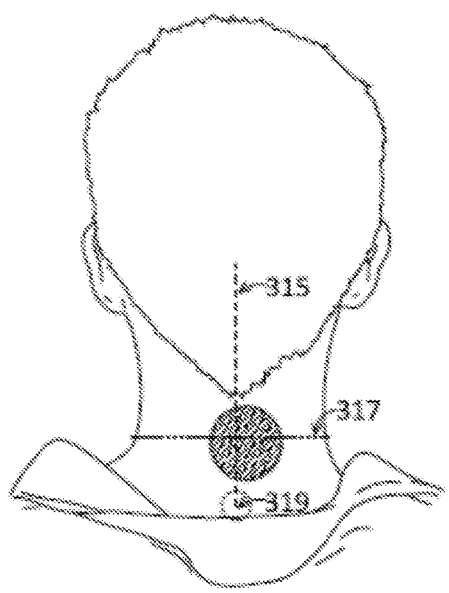
FIG. 3A illustrates the back of the neck region for placement of an electrode, which may be used in conjunction with a second electrode such as the temple electrode shown in FIGS. 1A-1D.
Figure 3B:
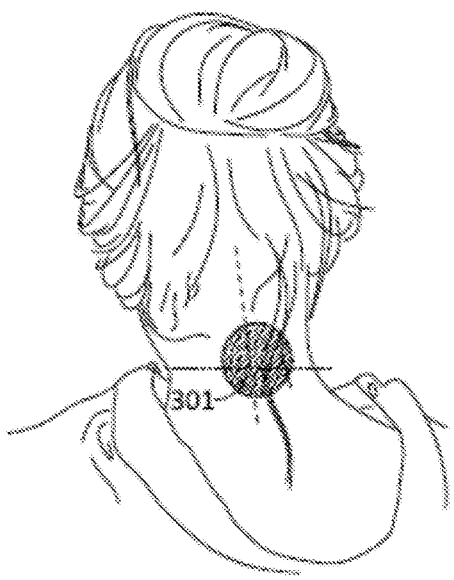
FIGS. 3B and 3C illustrate examples of this electrode placement showing an electrode positioned off-center on the back of the neck.
Figure 3C:
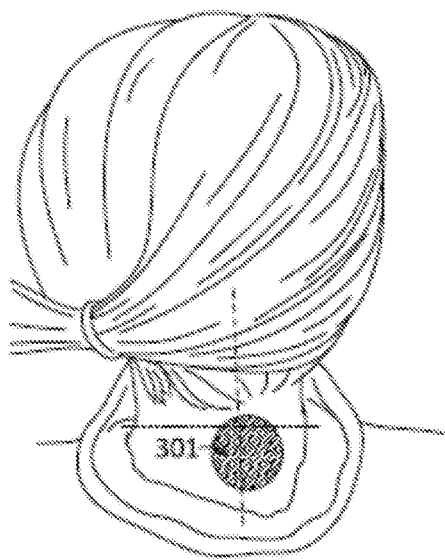
Figure 3D:
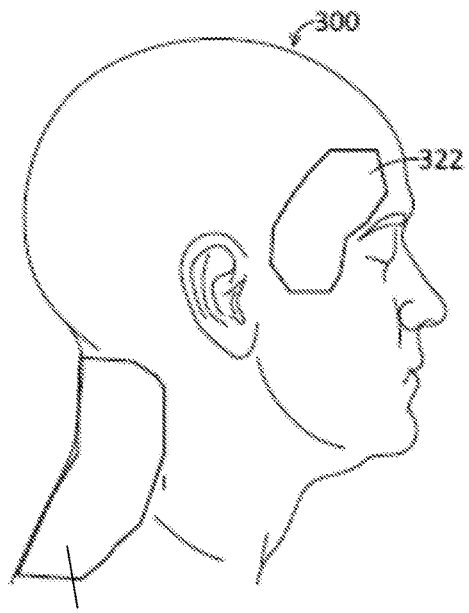
FIG. 3D shows electrode placement regions for a configuration (configuration 3) for enhancing a calm or relaxed mental state, including placing the TES electrodes on the back of the subject's neck and at the temple region.

In addition to the first, temple-positioned electrode, configuration B uses a second electrode (or set of isoelectric electrodes, e.g., for convenience referred to as cathodes) 301 placed on the superior portion of a subject's neck (i.e. with the superior edge of the electrode at or near the edge of a user's hairline) at the midline or, optimally, shifted to the subject's right by up to about 2 cm as shown in FIGS. 3A-3C. The electrode size for the cathode (or set of cathodes) of configuration B preferably has an area greater than about 10 cm$^2$; or optimally greater than about 15 cm$^2$; or optimally greater than about 20 cm$^2$. Electrodes for configuration B greater than about 40 cm$^2$ may be less effective for inducing the desired cognitive effect from neuromodulation due to less precise targeting of electrode fields into the body. The cathode (or set of cathodes) for configuration B may be round, oval, square, rectangular, or another regular or irregular shape. The second electrode position 301 in FIGS. 3A-3C are shown shifted to the right; in general, the second electrode may be off-centered from the neck midline (dashed vertical line 315 in the same direction as the side of the subject that the temple electrode is placed (e.g., right or left). Thus, the position of the second electrode is slightly to the right or to the left of off-center. Vertically on the subject's neck, the electrode may be positioned between the base of the hairline and the upper extent of the vertebra prominens 319 (e.g., closer to the hairline, such as above the region where the neck starts to curve into the shoulders 317). FIGS. 3B and 3C show alternative examples of position of the electrode 301 on the neck, each for a subject wearing the temple electrode on their right side. FIG. 3D illustrates the approximate regions for electrode placement of configuration B. In FIG. 3D, the electrodes may be placed in the temple region 322 of the subject 300 as well as on the back of the neck 311.

Electrode positioning for the anodes and cathodes of both configurations may be beneficially selected to be in areas that have minimal or no hair so that low impedance and uniform electrical contact can be made to the skin without requiring messy gel or saline. For example, beneficial electrode configurations may comprise electrodes sized such that the current density is less than 2 mA/cm$^2$.

FIGS. 4A-4D illustrate electrode positions for configuration 1 (configuration C). Electrodes placed on the head according to configuration 1 can be used as part of a TES system for delivering electrical stimulation to increase attention and/or alertness. The default mode network (a distributed functional network in the cerebral cortex) exhibits reduced activity during sustained attention and increased activity during mind-wandering and daydreaming. The right anterior insula and frontal operculum (along the inferior frontal gyrus) have been identified in functional magnetic resonance imaging (fMRI) studies as brain regions activated during sustained attention. The placement of electrodes in this configuration may increase the activity of areas near the right inferior frontal gyrus (including the right insula) and reduce activity in the default mode network, but other brain regions may be activated, inhibited, or modulated in at least some instances. A first electrode may be placed over the right inferior frontal gyms near position F8 on the 10/20 standard and a second electrode near position AFz. FIGS. 4A-4C shows exemplar placements of anode and cathode electrodes according to configuration 1 on schematics showing 10/20 electrode locations 401. The approximate center of anode 402 is shown with a plus sign in a circle and the approximate center of cathode 403 is shown with a minus sign in a circle. An exemplar electrode location is shown on subject's head 400. Rectangular anode electrode 406 is indicated with a plus sign and cathode electrode 405 is indicated with a minus sign. Note anode wire 407 that connects the electrode to a portable handheld tDCS unit. In a preferred embodiment, larger electrodes (about 1" by about 2" or larger) are effective in configuration 1. In some embodiments, a single larger anode is replaced by two or more smaller anodes placed near 10/20 position F8. In at least some instances a larger anode electrode is used that extends from just below eye-level upwards laterally of the right eye (ranging from F10 to F6 on the 10/20 system). The placement of the cathode is approximately over the midline at the center of a user's forehead.

Figure 4E:
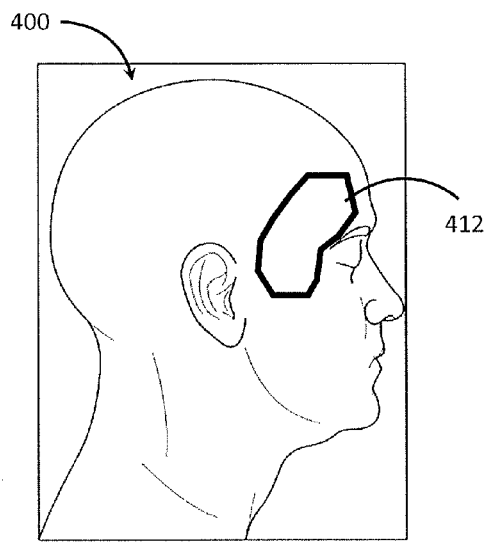
FIGS. 4E and 4F show the temple and forehead, respectively, of one example of electrode placement regions for configuration 1.
Figure 4F:
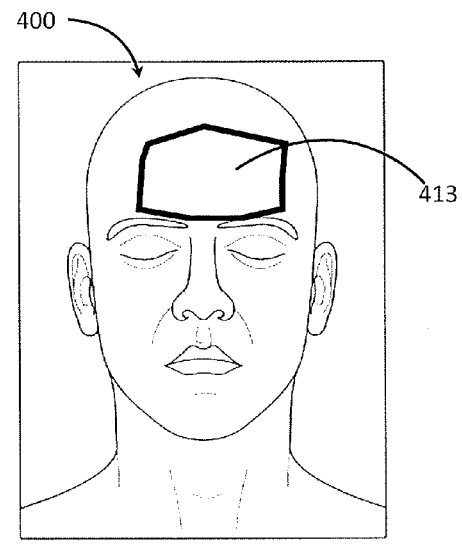
Figure 4G:
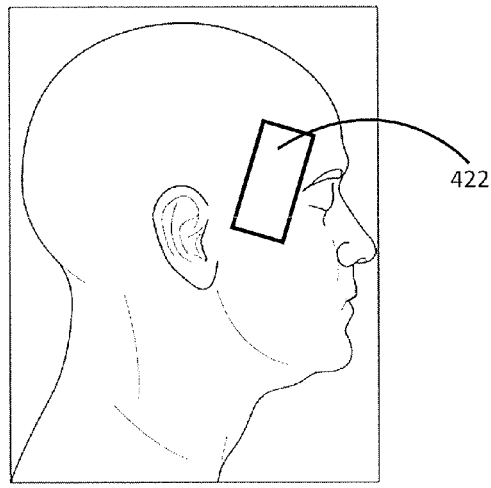
FIGS. 4G and 4H illustrate a subject with electrodes positioned per this configuration.
Figure 4H:
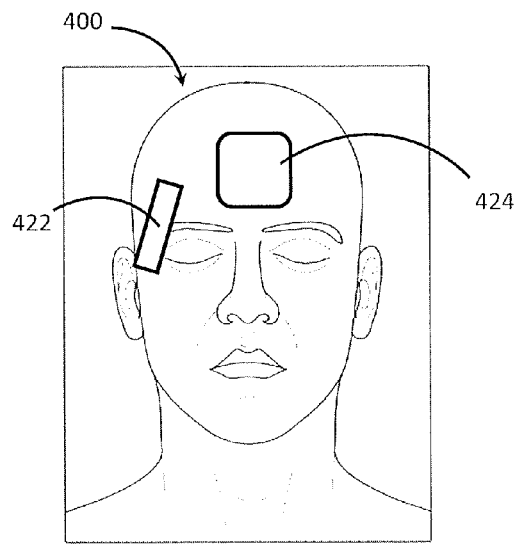

FIGS. 4E-4H show different variations of electrodes placed according to configuration C. FIGS. 4E and 4F illustrate approximate regions on a subject's head 400 where electrodes may be placed. In FIG. 4E the temple region 412 is illustrated, while in FIG. 4F the forehead region 413 is shown. FIG. 4G shows an approximately rectangular electrode 422 positioned at the temple location and FIG. 4H shows both the temple electrode 422 and a rounded square forehead electrode 424.

Any of the electrode configurations described herein can be achieved with adherent electrodes placed on the skin of a subject; non-adherent electrodes (e.g. saline-soaked sponges) held in low impedance contact with the skin of a subject by a wearable assembly (e.g. hat, headband, armband, or other wearable attachment system, which itself may be adherent, even if an electrode of the system is non-adherent); or a combination of adherent and non-adherent electrodes whereby a first set of electrodes are adherently attached to a subject and a second set of electrodes are non-adherently attached to the subject. Adherent electrodes are convenient because they can be configured to be removed while leaving minimal residue on the skin of the subject and to deliver TES to the subject without addition saline or gel. Non-adherent electrodes (e.g. saline-soaked sponges or gel-based electrode systems) are useful on hairy areas of the head, face, and body because a low impedance contact can be made through the hair with the conductive liquid or gel. The TES electrodes are electrically coupled to TES control circuitry that supplies appropriate electrical stimulation waveforms to the at least two electrodes. In embodiments using adherent electrodes, the TES control circuitry can be a component of the adherent assembly that contains the at least one electrode. In alternative embodiments using adherent electrodes, the TES control circuitry is contained in a separate assembly from the electrodes and connected by wires to the power and control circuitry.

In some embodiments, a single anode or cathode electrode can be replaced by a larger number of electrically continuous electrodes (i.e. replacing a single large anode electrode with two smaller anode electrodes placed in proximity to each other). The size and shape of each electrode used is a parameter that allows control over the area of stimulation delivered and the level of pain or irritation perceived by a subject. In some embodiments, each electrode position for a given configuration can be one electrode or more than one electrode positioned in a target area and conductively connected to each other (optionally at least 2 electrodes, optionally at least 3 electrodes, optionally at least 4 electrodes, optionally at least 5 electrodes, optionally at least 10 electrodes, optionally at least 25 electrodes, optionally at least 50 electrodes, optionally at least 100 electrodes, or optionally at least 1000 electrodes).

In general, peak stimulation intensities above at least 3 mA may be advantageous for transdermal electrical stimulation that causes neuromodulation by targeting the brain, nerves (e.g., cranial nerves, vagal nerve, peripheral nerves), and/or spinal cord. To achieve these peak intensities without causing pain, irritation, or discomfort in a subject may require appropriate electrodes and TES waveforms. Beneficial electrodes may have pH buffering properties and may contain components for uniformly (or more uniformly) delivering current across the dermal-facing portion of the electrode.

Functional lateralization is present in the human brain. The degree and side of functional lateralization can vary between individuals. For instance, left-handed people and women may have a lower degree of lateralization than right-handed men. For each of the configurations described above for the right side of the head and neck, electrodes placed at similar locations on the left side of the head and neck or both sides of the head may be as effective or more effective for some subjects.

In some users, improved efficacy may occur for electrodes placed on the left side of the user's head and neck; for two sets of electrodes placed bilaterally and connected so that anode-cathode pairs are unilateral; or for two pairs of electrodes placed bilaterally and connected so that anode-cathode pairs are transhemispheric. In embodiments with two sets of electrodes positioned bilaterally, the laterality of stimulation can be configured to be: constant for a particular session (e.g. only right side, only left side, or bilateral); selected automatically according to a measurement of a user's physiology or cognitive state; user-selected; switched between unilateral anode-cathode pairing and transhemispheric anode-cathode pairing; or varying over time. In some embodiments wherein the laterality of stimulation is time varying, stimulation alternates between one configuration of stimulation and another (e.g. right side stimulation for a period of time, then left side stimulation for a period of time—or unilateral stimulation through bilateral sets of electrode for a period of time followed by transhemispheric stimulation through bilateral sets of electrode for a period of time).

Multiple anode-cathode electrodes pairs positioned according to one of the configurations described herein may use identical stimulation protocols. Multiple anode-cathode electrodes pairs positioned according to one of the configurations described herein may use a stimulation protocol that differs in at least one parameter selected from the list including but not limited to: current intensity, waveform, duration, and other stimulation parameter. One of ordinary skill in the art would appreciate there are many positions in which the electrodes could be functionally arranged, and embodiments of the present invention are contemplated for use with any such functional arrangement.

In general, the TES waveforms for use with any of the configurations described herein may be a pattern of currents delivered into tissue of a subject (e.g. transdermally). Although there may be variations (optimizations) of these waveforms and electrical protocols for each configuration (electrode placement) and each target cognitive state, in general, the patterns may be within the same range of values to provide high-intensity, high frequency, high-duty cycle and not charge balanced (e.g., DC offset) signals that are applied to robustly evoke a response in most individuals while causing at most a low level (e.g. minimal or none) of discomfort and/or pain.

The time varying pattern of electrical stimulation delivered transcranially to induce neuromodulation may be referred to as a transdermal electrical stimulation waveform ('TES waveform'). A stimulation protocol may define the temporal pattern of current delivered to an anode-cathode set and can incorporate one or more waveform components including but not limited to: direct current, alternating current, pulsed current, linear current ramp, nonlinear current ramp, exponential current ramp, modulation of current (e.g. amplitude modulation at one or more frequencies), and more complex (including repeated, random, pseudo-random, and chaotic patterns). In operation, the device may provide current flow at target areas (e.g., in the brain, facial nerves, vagal nerve, or other neuronal targets) to induce neuromodulation when appropriate electrode configurations and stimulation protocols are delivered.

In general, a TES waveform may be defined by a duration, direction, peak current, and frequency. In some embodiments, a TES waveform is further defined by a percent duty cycle (FIG. 5A), percent direct current (FIG. 5A), ramping or other amplitude modulation, one or multiple frequency components, phase relationship of biphasic current, flat or structured noise, wave shapes (i.e. sawtooth, triangular, sine wave, square wave, exponential, or other wave shape), capacitance compensation features, or other parameters as discussed in U.S. patent application Ser. No. 14/091,121, now U.S. Pat. No. 8,903,494, titled "WEARABLE TRANSDERMAL ELECTRICAL STIMULATION DEVICES AND METHODS OF USING THEM", filed Nov. 26, 2013, which is herein incorporated by reference in its entirety. As used herein, 'percent duty cycle' may refer to the proportion of a cycle of a waveform that causes non-zero (or nominally non-zero) current to be delivered transdermally (see equation, FIG. 5A). Further, 'percent direct current' may refer to the non-zero portion of a waveform cycle that is positive-going (see equation, FIG. 5A).

Inducing significant, robust, and/or reliable cognitive effects typically requires an appropriate TES waveform defined by a set of parameters. A stimulation protocol ('TES waveform') may define the temporal pattern of current delivered to an anode-cathode set and can incorporate one or more waveform components including but not limited to: direct current, alternating current, pulsed current, linear current ramp, nonlinear current ramp, exponential current ramp, modulation of current, and more complex (including repeated, random, pseudo-random, and chaotic patterns). In operation, the device may provide current flow at target areas (e.g., in the brain) to induce neuromodulation when appropriate electrode configurations and stimulation protocols are delivered.

A set of waveform parameters may be selected based on the desired cognitive effect (e.g., configuration A, configuration B, etc.) and the number of electrodes, positions of electrodes, sizes of electrode, shapes of electrode, composition of electrodes, and anode-cathode pairing of electrodes (i.e., whether a set of electrodes is electrically coupled as an anode or cathode; also whether multiple independent channels of stimulation are present via current sources driving independent anode-cathode sets). Changing any of the features in the preceding list may require adapting a TES waveform by changing one or more parameters in order to achieve a desired cognitive effect.

Figure 5A:
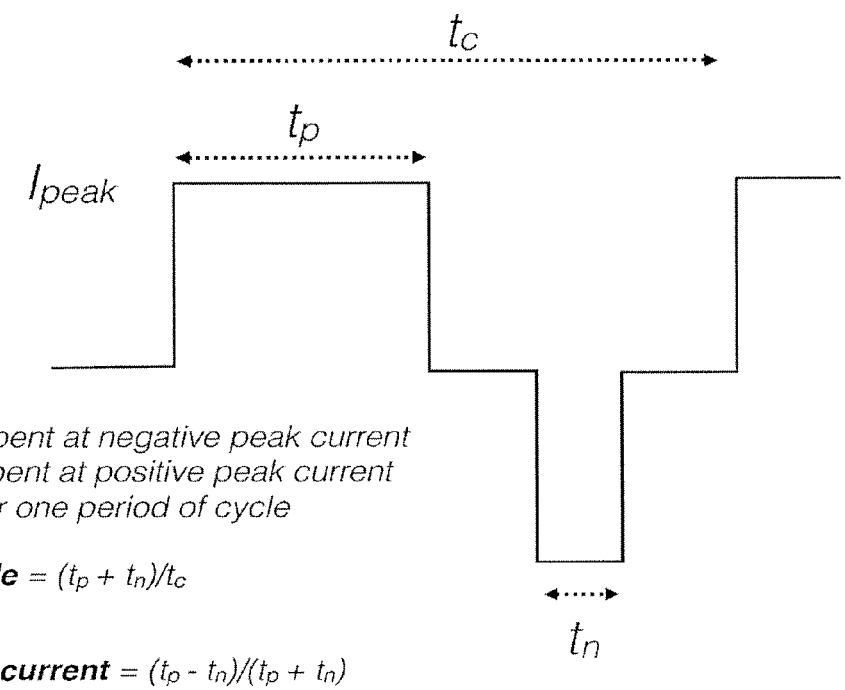
FIG. 5A schematically illustrates one example of a cycle of a transdermal electrical stimulation waveform and illustrates duty cycle percentage and percent direct current parameters of the TES waveform.
Figure 5C:
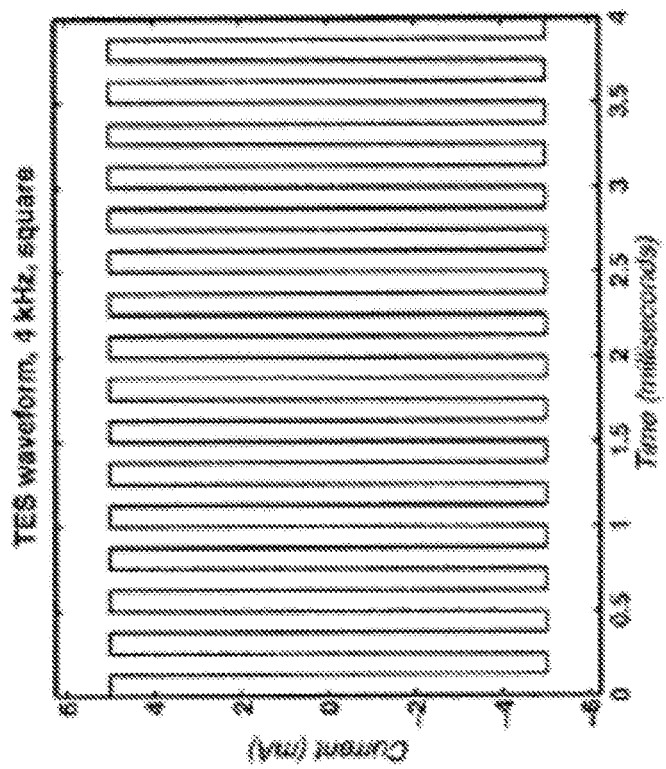
FIGS. 5B and 5C show exemplary biphasic waveforms for TES using a sine wave pattern or a square wave pattern, respectively.
Figure 5B:
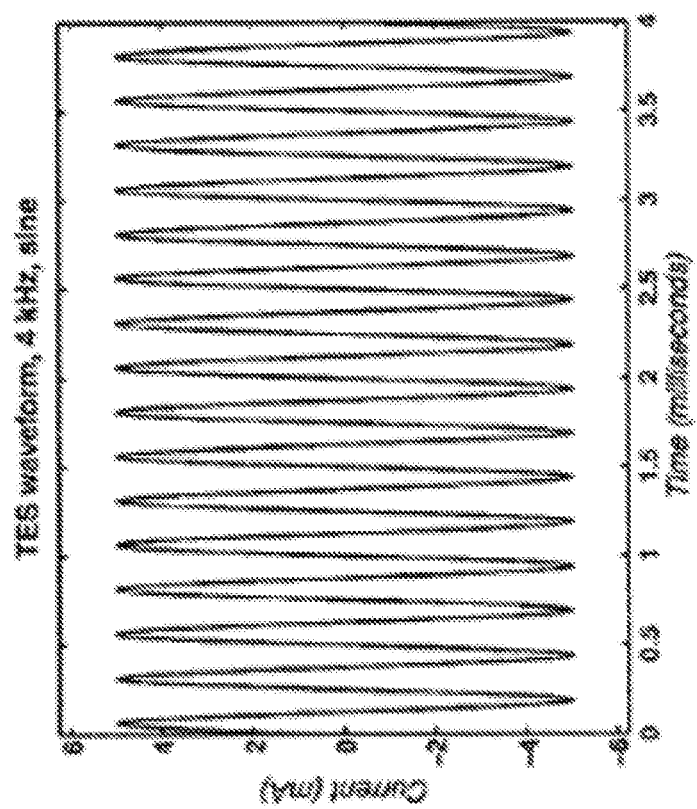
Figure 5E:
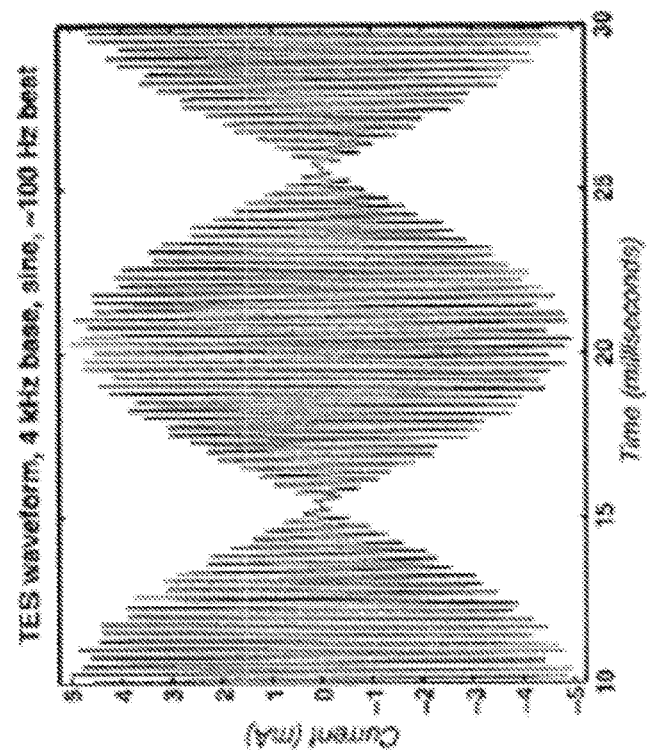
FIGS. 5D and 5E show two different temporal scales of a biphasic waveform for interferential transcranial alternating current stimulation.
Figure 5D:
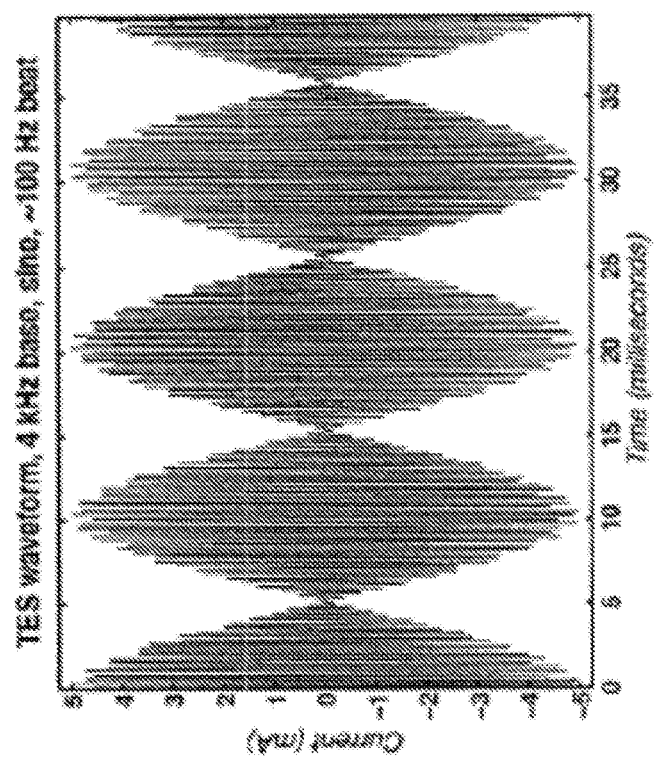
Figure 5F:
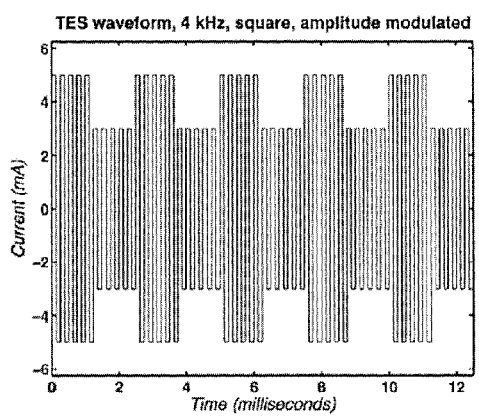
FIGS. 5F and 5G show TES stimulation waveforms for high frequency biphasic alternating current stimulation (square wave, amplitude modulated).
Figure 5G:
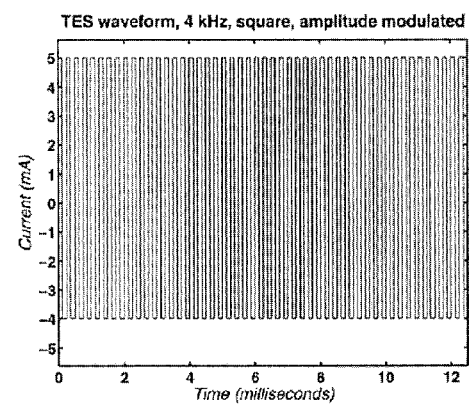

FIGS. 5B and 5C show an example of a sine wave (FIG. 5B) and square wave (FIG. 5C) at 4 kHz that maybe used to form the waveforms described herein. For example, FIGS. 5F and 5G show an example of a 4 kHz square wave with amplitude modulation (shown in FIG. 5F). FIG. 5G shows an example of a 4 kHz square wave with a direct current shift of 1 mA. Note that advantageous pulsing regimes can include amplitude modulation, frequency modulation, and other linear and nonlinear techniques for modulating an alternating current. For example, sine wave and square wave (e.g., 4 kHz waveforms) may be useful for TES stimulation as described herein. One example of an effective pulsing regime is 4 ms on, 16 ms off. Moreover, pulsing can be used to stimulate neural circuits at biologically relevant frequencies less than about 200 Hz.

Figure 5I:
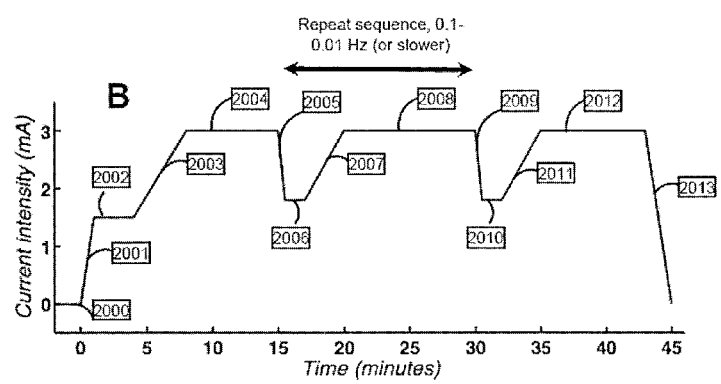
FIG. 5i shows an exemplary schematic of a treatment waveform protocol including multiple excursion stimulations (ramps) which may enhance the TES stimulation to modify a cognitive state.
Figure 5H:
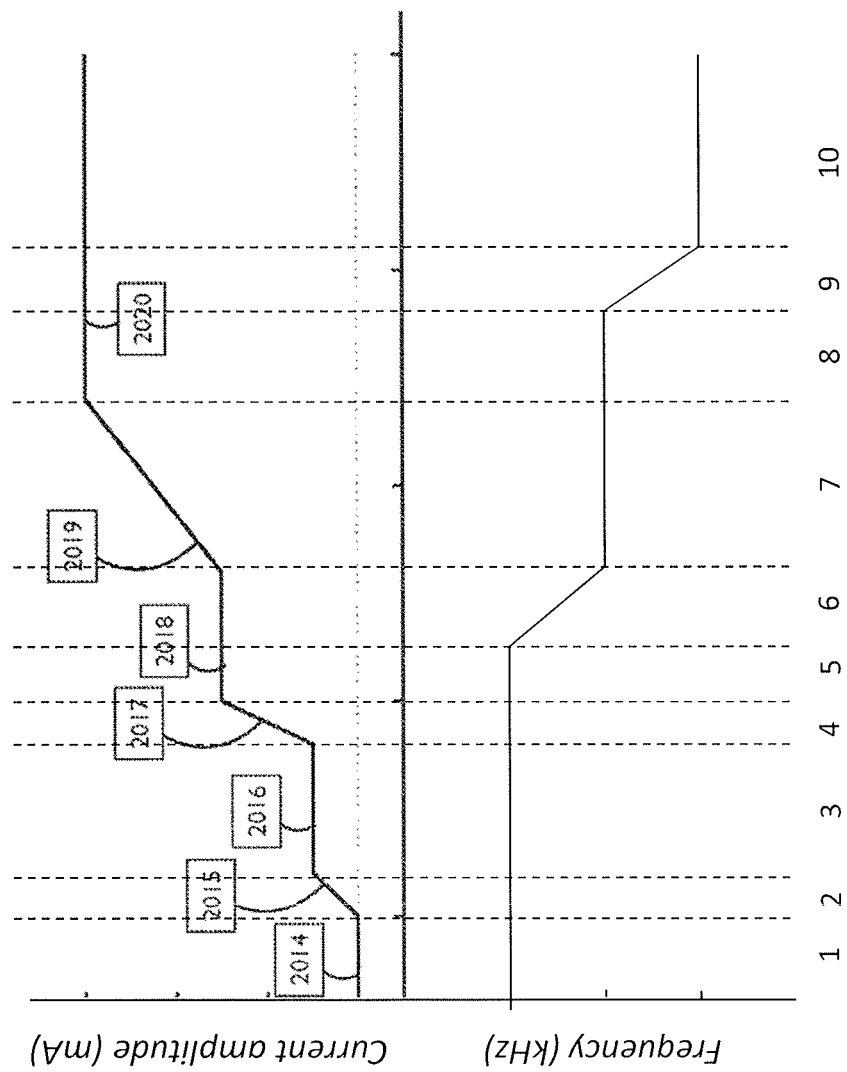
FIG. 5H shows an exemplary schematic of a ramp for gradually increasing the current intensity for TES as described herein.
Figure 5J:
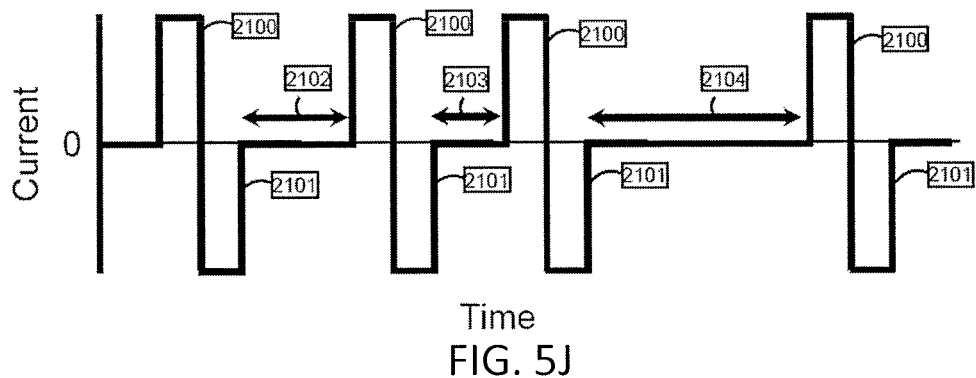
FIGS. 5J and 5K illustrate exemplary biphasic waveforms for TES (e.g., transcranial alternating current stimulation) to modify a cognitive state.
Figure 5K:
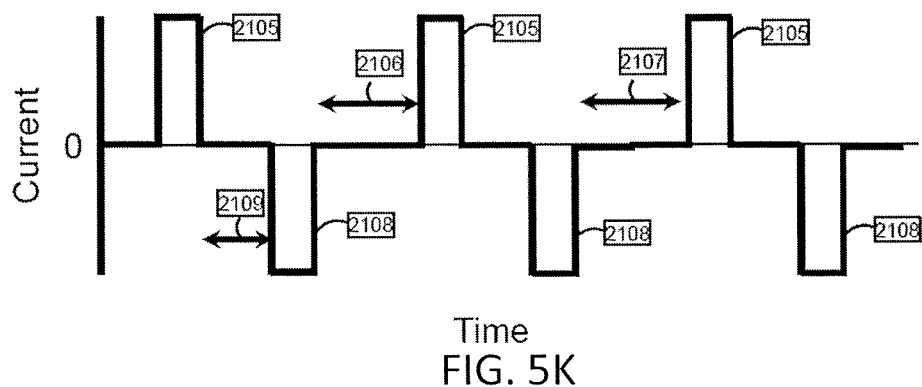
Figure 5L:
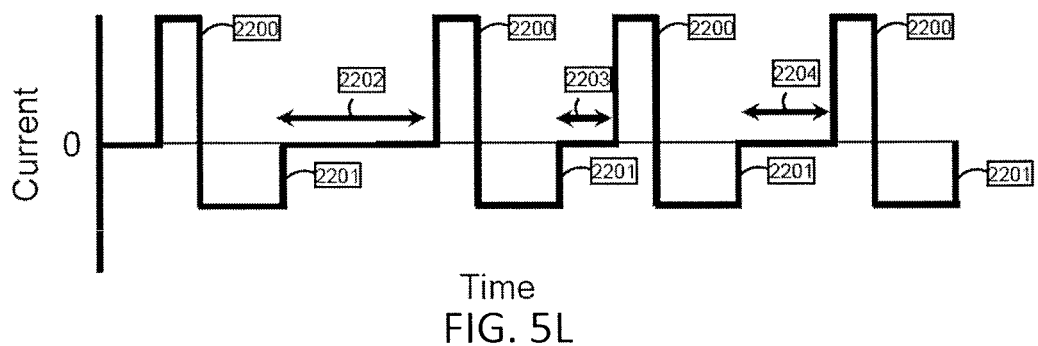
FIGS. 5L and 5M illustrate exemplary biphasic waveforms for TES to modify a cognitive state as described herein.
Figure 5M:
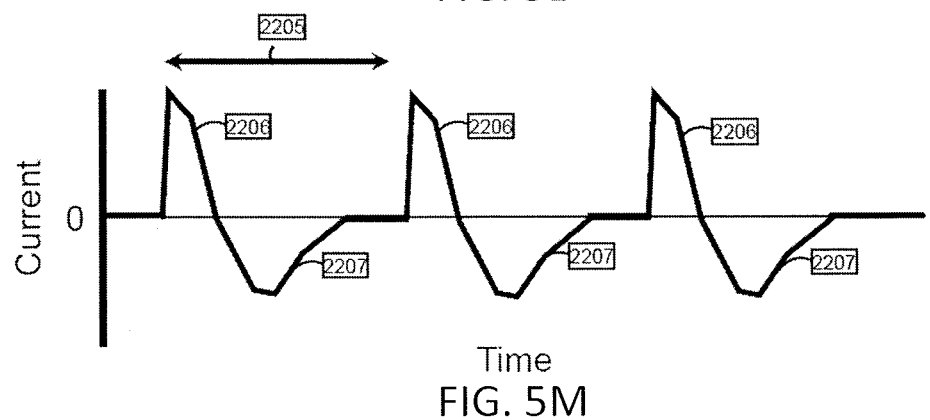

FIGS. 5J and 5K illustrate two pulsing strategies with zero net current. One pulsing strategy has negative-going phases 2101 that follow immediately after positive-going phases 2100 with variable inter-pulse intervals 2102, 2103, 2104 consistent with frequency modulation. In alternative embodiments, a constant inter-pulse interval is used. Another pulsing strategy separates positive-going pulse phase 2105 from negative-going pulse phase 2108 by intervals 2106, 2107, 2109. FIGS. 5L and 5M show two additional pulsing strategies with zero net current. One pulsing strategy has brief, high-current positive-going phase 2200 followed by longer, lower-current negative-going phase 2201 and variable inter-pulse intervals 2202, 2203, 2204. Another pulsing strategy delivers non-square waveforms with positive going phase 2206, negative-going phase 2207, and interval between the start of pulses 2205.

For high frequency biphasic stimulation, current intensity can be ramped up very quickly without discomfort relative to direct current stimulation. This feature is advantageous for being able to induce beneficial cognitive effects quickly without painful, irritating, or distracting side effects. Accordingly, changes in cognitive state are more immediate for high frequency biphasic alternating current stimulation as described here than for tDCS.

An alternative strategy for pain relief may include the use of interferential stimulation. Interferential stimulation uses two anode-cathode pairs, for example, one pair at a constant 4 kHz and one pair at a variable frequency between about 4001 kHz and 4200 Hz. This produces a 'beat frequency' between 1 and 200 Hz in the tissue beneath the electrodes, which is intended to reduce pain transmission. The advantage of this method over stimulation via one anode-cathode pair at 1-200 Hz is that uncomfortable sensory side effects of stimulation may be minimized. For interferential stimulation, the 'beat frequency' of between 1 and 200 Hz is the important frequency for modulating pain and muscle fibers. The 'carrier frequency' of about 4 kHz reduces discomfort typically associated with applying high intensity stimulation between 1 and 200 Hz. In order to deliver a beat frequency to the brain of a subject, two channels (i.e. anode-cathode sets) are required (e.g. one channel delivering stimulation at 4000 Hz and a second channel delivering stimulation at 4100 Hz). FIGS. 5D and 5E shows two views of an interferential tACS waveform comprised of a 4000 Hz sine wave and a 4100 Hz sine wave.

The current threshold for inducing changes in mental state with a high-frequency biphasic stimulation protocol is between 3 and 10 mA or higher (higher than for tDCS in at least some cases), but using the stimulation protocols described herein, at these higher currents there may be much less tingling, itching, and burning than expected. In some variations, a net zero current waveform of the biphasic stimulation may reduce or eliminate skin irritation. However, as described herein, it may also be (surprisingly) beneficial to have biphasic current with a DC offset that would otherwise result in a charge imbalance; as described below, one or more techniques for reducing irritation (including removing capacitive charge by short-circuiting the electrodes) may be used. One possible side effect is muscle contractions, which can be noticeable at high currents (>6 mA) and which may be distracting for some users but are not painful. Up to 11 mA has been used without too much discomfort from muscle contractions, but muscle contractions typically become noticeable between 5 and 10 mA. Even higher frequencies (e.g. up to 50 kHz) can be used to prevent muscle contractions. Smaller electrodes (e.g. 1 square inch) may result in a lower threshold for muscle contractions and lower threshold for changes in mental state (presumably both effects are related to current density).

In some variations, low or zero net current may be an advantageous feature of biphasic high frequency TES, because skin irritation is directly related to pH changes under the electrodes, which is proportional to current density under the electrodes, and low net current may be similarly effective for reducing pain and irritation from pH changes in the skin. For instance, a DC offset similar to the threshold current density for getting skin irritation with DC (about 0.5 mA/cm$^2$ with Little PALS electrodes and about 0.2 mA/cm$^2$ with regular adherent skin electrodes) could be used together with high frequency alternating current stimulation (FIG. 5G) to provide TES with minimal irritation, pain, and tissue damage. However, as described above, in some variations, having a charge imbalance (e.g., a DC offset) is particularly effective, particularly in combination with 'short-circuiting' during stimulation to remove capacitive charge.

Preliminary data suggests a different 'rule' with pulsed stimulation than with DC stimulation. With DC stimulation in at least some instances, cognitive effects last throughout stimulation. With biphasic pulsed stimulation in at least some instances, the effects are much greater when you are raising and lowering the max amplitude current around a certain threshold value. With this protocol habituation does not occur in at least some instances. In at least some instances, the current can be increased and decreased repeatedly to induce desirable cognitive effects with each increase, but when you leave the amplitude at a certain value (even if that value is at threshold), the effects may subside. This finding inspired an additional embodiment wherein a secondary (slower) frequency modulates the amplitude of the high-frequency biphasic tACS (FIG. 5F). This slower modulation would sustain the effect by having frequent rises and dips above and below the threshold for sensations. In the example shown in FIG. 5F, the amplitude of the biphasic high frequency TES signal alternates between +/−5 mA (above threshold for a cognitive effect) and +/−3 mA (below threshold for a cognitive effect). Note that other patterns of amplitude modulation between suprathreshold and subthreshold current intensities can be used (e.g. linear or nonlinear ramping, sawtooth pattern, sine wave, or other amplitude modulation waveform).

In another alternative embodiment, high-frequency biphasic TES (e.g., tACS) may be applied to a subject to induce a desired cognitive effect, then the system switches to a DC mode of operation to sustain a cognitive effect. High-frequency biphasic TES may be applied concurrently with a DC offset or DC bias (of for example 0.5 mA or 1 mA) to induce large cognitive effects while at the same time reducing painful or irritating sensations (FIG. 5G).

Adherent, self-contained TES systems that apply one or more of the above pulsing, TES, and interferential stimulation strategies may be advantageous for achieving a desirable form of neuromodulation with minimal pain, irritation, and tissue damage.

TES systems that incorporate "short-circuiting" (e.g., discharging the capacitance on the electrodes) may be useful for pulsed stimulation regimes, and may help reduce or prevent pain and discomfort. In some variations the apparatus includes short circuiting (or capacitance discharging) circuitry in connection with the electrodes. For example, capacitance discharging circuitry may include electronic components and firmware features that short the anode-cathode path with a low ohm resistor (e.g. 50 Ohms) to permit discharge of capacitance that builds up during a pulse (e.g. in the subject's skin). In some instances, short-circuiting is beneficial for reducing discomfort and accordingly increasing the cognitive effects induced by TES (due to one or both of: reducing the distraction of discomfort so that other cognitive effects can be experienced by a subject and permitting higher peak current intensities to be delivered that induce more significant cognitive effects). Other systems and methods for rapidly discharging capacitive current to minimize side-effects that are irritating and thus distract from desired cognitive effects or mental states—or limited with regard to peak intensity delivered—may be used as an alternative to a short-circuiting mode and system as described. For example, a capacitive discharging circuitry may include a fixed current source similar to the main current source in the device, but saturating at 0V and allowing discharge of the accumulated charges. The discharge time may be fixed or may depend on the voltage and electrode capacitance. In one example a nominal short-circuit current may be adjustable (e.g., to 40 mA), which could be changed by changing a resistor. The discharge could be made by the regular current source with an adjustable current inside the range, e.g., up to 20 mA; turning on the two rectified bottom switches may avoid reverse charging in this case. In general, a short circuiting discharge can be very quick (e.g. on the microsecond timescale) and could use a very high current, e.g., tens of mA to 100 mA.

For both configuration A and configuration B described above, within a range of acceptable TES waveforms, changing one or more parameters may vary the modification of the cognitive state, e.g., changing the subjective experience of an induced cognitive effect. Some stimulation parameters may be more effective in one subject as opposed to another.

In general, ramping and other waveform features can be incorporated in order to shift a waveform between different effective ranges of parameters for inducing a particular cognitive effect and thus achieve a more intense, longer lasting cognitive effect. Shifting between effective waveforms may be iterative (i.e. one parameter changes, than another changes) and it may be repetitive (i.e. change from one waveform to a second waveform, then back to the first waveform, etc.; or toggling between three or more effective waveforms). In some embodiments, rapidly shifting one or more waveform parameters within an effective range induces a stronger cognitive effect, wherein rapid generally refers to less than 15 seconds and may be as short as one second or less.

In both configuration A and configuration B, biphasic TES waveforms (direct current <100%) for neuromodulation may have the center of the positive-going and negative-going pulses separated by 180 degrees in phase or may have a smaller phase offset so long as the positive-going and negative-going pulses are non-overlapping. In general, a TES waveform for any of the configuration described herein may be added, subtracted, convolved, or otherwise amplitude modulated. Moreover, in embodiments, a TES waveform for either configuration described herein may have its amplitude ramped using linear, exponential, or another ramp shape. Pulses of a TES waveform can comprise square waves, sine waves, sawtooth waves, triangular waves, rectified (uniphasic) waves, pulse-width modulated, amplitude-modulated, frequency-modulated, or other pattern of alternating current waveform.

Figure 6:
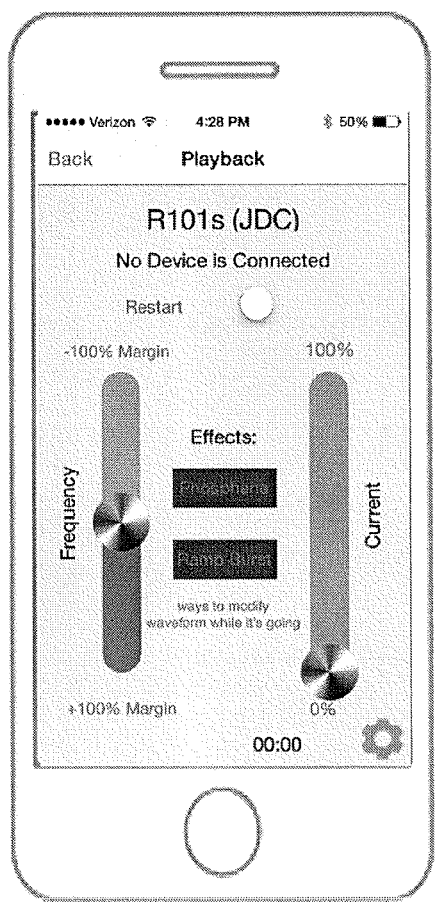
FIG. 6 illustrates one example of a handheld apparatus having a processor configured (e.g., containing a non-transitory computer-readable storage medium storing a set of instructions capable of being executed by the remote processor such as a smartphone or the like) to display user interface controls of TES waveform parameters.

The delivery of the waveform may start, pause, stop, or be modulated (e.g. a parameter of a TES waveform be changed) when a subject activates a user interface (a physical button, switch, or the like; or a non-transitory computer-readable storage medium storing a set of instructions capable of being executed by a remote processor (and particularly a smartphone or the like), when executed by the computing device containing the remote processor causes a user interface for commencing a TES waveform to be displayed on the screen of a TES apparatus or a computing device communicably connected to the TES apparatus). See, for example, FIG. 6, illustrating one example of remote processor that may be used to trigger stimulation of a wearable device worn by a subject. The remote processor may be a smartphone, and may communicate (two-way or one-way) with the device, for selecting the stimulation parameters, etc.).

Changes in cognitive state induced by TES can be difficult for a user to recognize subjectively and assign causally to the electrical stimulation. By incorporating intermittent, transient periods of reduced current intensity (increased frequency, reduced duty cycle, reduced DC offset, etc.), the cognitive change that occurred moments earlier is made apparent, improving the user experience and positive reaction to the system. In short, transiently (and quickly) decreasing and then increasing current intensity to create a stark subjective contrast for the subject may provide an induced cognitive effect at higher current level more obvious to a user. Accordingly, methods and systems that guide a user's perception of induced change in cognitive state by a TES session are beneficial. For example, after maintaining a current intensity above a threshold for inducing neuromodulation, suprathreshold level for inducing the cognitive effect, the current intensity may be rapidly (e.g. over less than 5 seconds; optionally over less than 10 seconds; optionally over less than 15 seconds) decreased below a threshold value for inducing a cognitive effect (subthreshold for inducing the cognitive effect), thereby causing a subject to more readily recognize an induced cognitive effect at the preceding higher current intensity.

An exemplary sequence can be described by the following four-steps: (1) rapid ramp down to an intermediate current intensity below that is below that required for an induced cognitive effect, (2) maintenance at the intermediate level for a period of time sufficient for the subject to recognize the absence of the previously induced change in cognitive state, (3) gradual increase in current intensity at a rate sufficiently slow such that the increasing current intensity is minimally irritating and/or painful for the subject, and (4) maintenance of a current intensity for TES that is sufficient to induce a cognitive effect of interest. The four-step sequence can be delivered a single time to a subject or repeated at a fixed or variable frequency chosen to be between about 0.001 Hz and 0.1 Hz.

For example, FIGS. 5H and 5*i* show exemplary patterns including both slow ramps (ramp on) and rapid ramps (transient excursions) to improve TES efficacy. In the example of FIG. 5*i*, current intensity starts at level of 0 mA 2000, increases linearly 2001 to intermediate sub-threshold (for neuromodulation to induce an intended cognitive effect in a subject) current 2002, then ramps up again 2003 to current 2004 that is above threshold for neuromodulation to induce an intended cognitive effect in a subject. Next, rapid decrease in TES current 2005 delivered occurs over a brief time period down to level of current intensity below the minimum for inducing the change in cognitive state 2006 that is maintained for a minute or two minutes before gradual increase in current intensity 2007 back to higher current level 2008 that is above threshold for neuromodulation to induce an intended cognitive effect in a subject. In this example, transient decrease in current intensity 2009, 2010, 2011, 2012 is repeated once before the current level is reduced back to 0 mA 2013. In some variations it has been found to be even more effective if the intensity is ramped down (subthreshold) either quickly or slowly, but the time to ramp back up to suprathreshold is much faster (e.g., less than a few seconds, etc.).

Sets of waveforms intended for use with the same electrode configuration may be used to induce cognitive effects that are sustained, more intense, or that provide a related but subjectively distinct experience (e.g. a first TES stimulation waveform may cause increased motivation while a second, related TES stimulation waveform induces an increase in mental clarity and focus). An apparatus (including the applicator and/or remote processor paired with the applicator) may include these various waveform sets and may be selected (and in some cases modified) by the subject.

One way to cause a sustained, longer-lasting cognitive effect in a subject is to deliver a first TES waveform that causes the induction of a desired cognitive effect, then delivering a second TES waveform following a pause after the first TES waveform. When the first TES waveform ends, the induced cognitive effect may endure for some period of time but gradually degrades in intensity or quality. A second TES waveform can then be presented that causes a boost or re-induction of the degrading cognitive effect caused by the first TES waveform. Generally, an induction protocol may be longer (i.e., one minute or longer; beneficially 3 minutes or longer; or 5 minutes or longer; or 10 minutes or longer) relative to the second TES waveform that will generally last seconds to minutes. This arrangement may be beneficial relative to simply re-triggering the first, longer TES waveform because it is more comfortable, more power efficient (so that the batteries on a TES system are longer lasting), and safer because it induces a similar cognitive effect while introducing less energy into the body.

For example, an 8 minute induction TES waveform configured for electrodes placed according to configuration A may be delivered transdermally to a subject, then some minutes to tens of minutes (or hours) after the end of the 'induction' TES waveform, a second TES waveform is selected to 'recharge' or 're-induce' the effect through a more brief (i.e., less than two minutes; or less than five minutes) TES waveform. The re-induction TES waveform is intended to be reused as needed by a user. In an embodiment for which a smartphone app is used by a subject to select an effect, a user interface element may be presented to the subject automatically at a particular time after the end of the first session so that the user may trigger a 're-induction' (or 'recharge') TES waveform matched to the first induction TES waveform.

Some methods for inducing 're-induction' or 'recharge' TES waveforms may permit a user to remove electrodes between the induction session and the recharge session (or between multiple recharge sessions) and optionally remind them to place the electrodes when it is time for recharge session. The timing of a recharge session may be determined purely based on time (i.e. open loop) or may be triggered automatically based on physiological, behavioral, cognitive, and/or other data and an appropriate algorithm that determines when an induced cognitive effect has worn off thus requiring a 'recharge' TES waveform.

Examples of effective TES waveforms to induce cognitive effects associated with configuration A may use pulsed biphasic stimulation waveforms (i.e. with stimulation in both directions during a cycle), though pulsed monophasic stimulation waveforms and alternating current stimulation waveforms may also be effective for inducing similar cognitive effects in at least some instances.

Pulsed biphasic stimulation may be effective for inducing the cognitive effects associated with Configuration A with a duty cycle between 30% and 50%. For example, a direct current percentage between 30% and 50%; a dominant frequency between 750 Hz and 6 kHz; and a minimum peak current intensity that is frequency-dependent and in the range of 3 mA to 16 mA. Peak intensity useful to induce the cognitive effects of configuration A may be approximately linearly proportional to the dominant frequency of the TES waveform. For example, to induce the cognitive effects of configuration A reliably across individuals the required peak currents may be: at least 3 mA at 750 Hz; at least 7 mA at 4 kHz; and at least 16 mA at 10 kHz. In general, a peak current of at least 3 mA is useful to robustly induce cognitive effects of configuration A. In general, as frequency increases, current to experience the effect may increase. However, the effective range for duty cycle and percentage direct current may not change as a function of stimulation frequency.

For devices with high voltage (e.g., at least 50V) and high power (e.g. at least 700 mW), there are also comfortable and effective waveforms with a dominant frequency component above 6 kHz. However, since frequency and current needed for the effect are approximately proportional, only a small percentage of the population with relatively low skin impedance (e.g., 10 kOhm or less)—estimated to be less than 20%—can achieve these effects with lower powered devices. When feasible, TES waveforms comprised of a dominant frequency above 6 kHz (i.e., between 6 kHz and 25 kHz; or between 6 kHz and 15 kHz; or between 10 kHz and 15 kHz) are also effective for inducing effects of configuration A. Since higher current intensities are required with increasing frequency, peak currents above about 7 mA (and preferably above about 10 mA) are required to induce effects of configuration A in this higher frequency range.

For devices configured with short-circuiting between pulses (which reduces capacitive charge buildup and thus increases comfort and reduces side effects), TES waveforms comprised of a dominant frequency in a lower frequency range in the traditional range of nerve stimulation (i.e. between about 80 Hz and about 150 Hz) can yield effective cognitive effects associated with Configuration A, possibly due to stimulation of the facial nerve. For TES waveforms comprised of a dominant frequency in this lower range, duty cycle and percentage direct current are optimally below about 30 percent.

As mentioned, in general, rapid ramps of stimulation frequency (e.g. occurring over less than 10 seconds and optimally over less than 3 seconds) within effective frequency ranges can induce stronger cognitive effects associated with configuration A. To improve comfort, it is generally preferred to use a peak current intensity at or near the lower end of the frequency range that is comfortable for a subject while shifting frequency. Repeated shifts in frequency may also be beneficial for inducing strong cognitive effects. For example, a shift from 2 kHz to 6 kHz then back to 6 kHz occurring over 3 seconds or less may be an effective TES waveform feature for improving the strength of cognitive effects associated with configuration A.

An exemplar effective TES waveform for inducing effects associated with configuration A lasts between five and 15 minutes with a 40% duty cycle, 38% direct current, a 10 mA peak intensity (which optionally increases gradually over the course of a waveform, e.g. from 8 mA to 10 mA), and a dominant frequency that shifts between 4 kHz and 6 kHz.

In general, a short-term increase in the level of cognitive effects associated with Configuration A can be achieved by transiently and rapidly modulating one or more parameters of stimulation, including increasing peak current; increasing duty cycle; and reducing stimulation frequency. However, modulating the percentage direct current is not a reliable way to increase the intensity of cognitive effects induced by configuration A. To achieve the desired short-term increase in cognitive effect requires modulating a TES waveform parameter that ideally occurs within 1 second, but up to 5 seconds can be somewhat effective. In general, a preceding (optionally occurring more gradually; i.e. overs 10 or more seconds up to minutes or longer) modulation of the TES waveform parameter in the opposite direction is required in order to deliver the modulation that causes the short-term increase in cognitive effect while remaining within an effective range for the modulated parameter. In general, rapid increases in current or duty cycle require a responsive TES current control circuit that can quickly recruit the needed higher power.

Effective TES waveforms to induce the 'relaxation' cognitive effects associated with configuration B may use pulsed biphasic stimulation waveforms (e.g., with stimulation in both directions during a cycle) or pulsed monophasic stimulation waveforms, though alternating current stimulation waveforms may also be effective for inducing similar cognitive effects in at least some instances. Pulsed biphasic stimulation may be effective for inducing the cognitive effects associated with configuration B with a duty cycle between 30% and 60%; a direct current percentage between 85% and 100% (where 100% direct current corresponds to a monophasic pulsed stimulation waveform); a dominant frequency between 5 kHz and 50 kHz (e.g., 5 kHz and 25 25 kHz; up to 50 kHz, etc.); and a peak current intensity between 1 mA and 20 mA (though in some instances higher peak intensities above 20 mA may also be effective if comfortable for the user).

TES waveforms that include cycles of lowering and increasing peak current may be beneficial for inducing cognitive effects associated with configuration B. For example, such a cycle may comprise 3 to 4 minutes at a high peak intensity (e.g. 15 mA) followed by a transient reduction to a lower peak intensity (e.g. 4 mA or lower) for a period between 10 seconds and 1 minute. For example, TES waveforms that have at least 3 cycles of reducing then increasing current intensity over a period of about 10 minutes are effective for inducing cognitive effects associated with configuration B. In general, shifts or ramps of a dominant stimulation frequency of about +/−1000 Hz while at peak current is another strategy for inducing strong cognitive effects associated with configuration B.

TES waveforms that incorporate gradual increases in effective intensity may be beneficial for enhancing cognitive effects associated with configuration B. Effective intensity can be increased by increasing peak current, lowering stimulation frequency, increasing duty cycle, increasing direct current percentage, or any combination thereof.

As mentioned above, TES waveforms delivered by a TES system with short-circuiting enabled (including capacitive discharging of the electrodes) may be a beneficial feature due to the high direct current percentages required to induce effects associated with configuration B. High direct current typically means more charge imbalance of stimulation and thus a higher capacitive load to discharge via a short-circuiting mode. However, in some instances, cognitive effects associated with configuration B may be induced without short-circuiting (e.g. with a TES waveform having parameters of: 2-4 kHz, 7-8 mA, 80% duty cycle, and 15% direct current).

An exemplar effective TES waveform for inducing effects associated with configuration B uses a 38% duty cycle, 100% direct current (monophasic pulses), a 16 mA peak intensity (which optionally increases gradually over the course of minutes of a waveform, e.g., from 14 mA to 16 mA), a dominant frequency of 7 kHz (that optionally shifts up and/or down by up to about 1 kHz during the waveform), and ramps down to and back up from 11 mA intermittently during the waveform.

Another exemplar effective TES waveform for inducing effects associated with configuration B uses a 44% duty cycle, 95% direct current, a 13 mA peak intensity (which optionally increases gradually over the course of minutes of a waveform, e.g. from 10 mA to 13 mA), a dominant frequency that modulates within a range of 7.5 kHz to 8.5 kHz, and intensity ramps down to and back up from 4 mA intermittently during the waveform.

In general, TES waveforms for inducing effects associated with configurations A and B are at least three minutes in duration (though 'recharge' waveforms as described herein may be shorter, e.g., tens of seconds or longer).

In general, the comfort of TES waveforms for inducing effects associated with Configurations A and B may be increased by having a gradual ramp from zero (or near zero) current to an effective current intensity so that the subject may habituate to the current.

In general, TES waveforms for inducing effects associated with configuration A or B may include shifts or ramps between parameter values within effective ranges. Gradual increases in intensity over minutes of a TES waveform for configuration A or configuration B (e.g., from 8 mA to 10 mA over 10 min) are beneficial for inducing robust and/or long-lasting effects since subjects tend to initially be very sensitive to the side-effects but later adapt to the side-effects.

Applicators

The methods of modifying a subject's cognitive state described above may be implemented by a variety of different devices, such as TES applicators. In general, a TES applicator may include hardware and software system for TES such as: a battery or power supply safely isolated from mains power; control hardware, firmware, and/or software for triggering a TES event and controlling the waveform, duration, intensity, and other parameters of stimulation of each electrode; and one or more pairs of electrodes with gel, saline, or another material for electrical coupling to the scalp. The hardware, firmware, and software for TES may include additional or fewer components. Hardware, firmware, and software for TES may include a variety of components.

Embodiments of the TES applicators described herein may be adherent and self-contained transdermal electrical stimulation (TES) systems. In at least some embodiments, an adherent and self-contained TES system is battery powered, communicates wirelessly with a controller unit, and can detach into two independent assemblies, a master assembly and a slave assembly, coupled only by an electrically conductive wire. The master incorporates a microcontroller for managing the current delivery, a battery, a microcontroller, a wireless communication module, other electronic circuitry, and an adherent electrode assembly. The slave assembly contains an adherent electrode assembly, is tethered to the master assembly (only) by a multicore wire, and fits in the case of the master assembly until a subject is ready for a TES session. To begin a TES session a subject separates the slave assembly from the master assembly housing and places both adherent electrodes on his/her head. The electrode assemblies are replaceable and/or disposable.

Figure 7A:
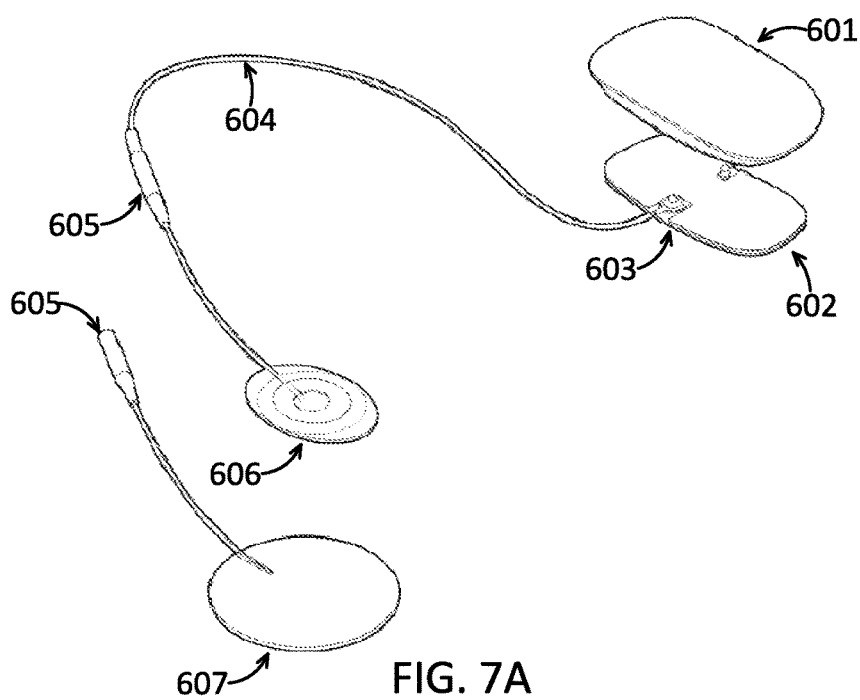
FIG. 7A is one example of a TES applicator in a kit including a reusable transdermal electrical stimulation controller and multiple electrodes that may be connected thereto.

FIG. 7A illustrates one example of a TES applicator as described herein. In FIG. 7A, the TES applicator includes a pair of electrodes, a first electrode 601 that is coupled directly to the body 603 of the TES applicator 602, and a second electrode 606 that is connected 605 by a cable or wire 604 to the body 603 of the applicator. The electrodes may be replaceable/disposable. Different shaped electrodes 607 may be used with the same re-usable TES applicator device. This apparatus is compact (low-profile) and extremely lightweight and may be worn by the subject, e.g., on the subject's head or face.

Figure 7B:
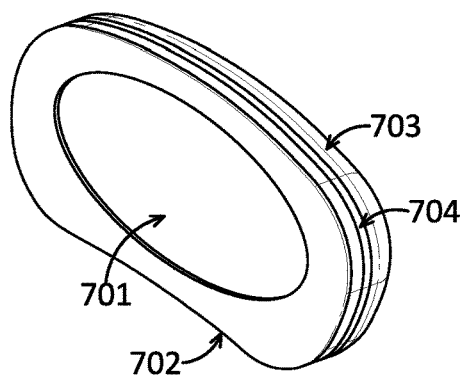
FIG. 7B shows one example of an electrode and housing (body) for a TES applicator.
Figure 7C:
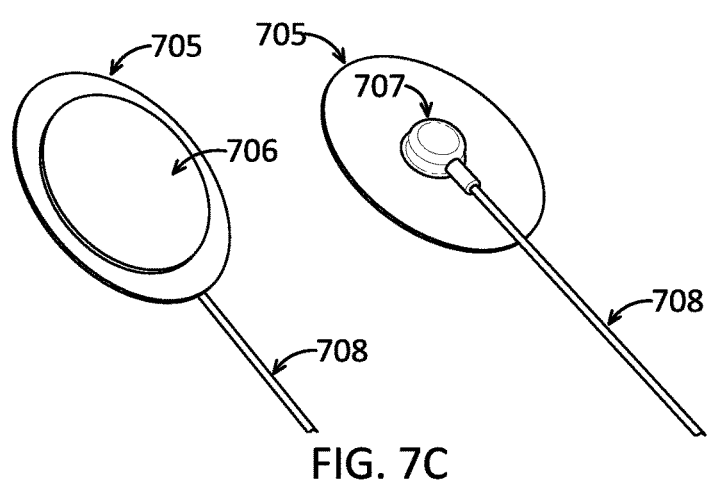
FIG. 7C shows one example of a TES electrode that may be used (e.g., to attach to the neck, behind the ear, etc.) as described herein.

FIG. 7B is another example of an applicator including a first electrode 701 attached to the body 703 of the device including plastic backer 704. The electrode may be removably attached 702 to the body 703. A second electrode (shown in FIG. 7C in front and back views) may also be connected to the body 703 of the device and includes an electrode contact portion 706 and an adhesive portion 705. The second electrode includes a cord or wire 708 electrically connecting it 707 to the body of the device.

Figure 7D:
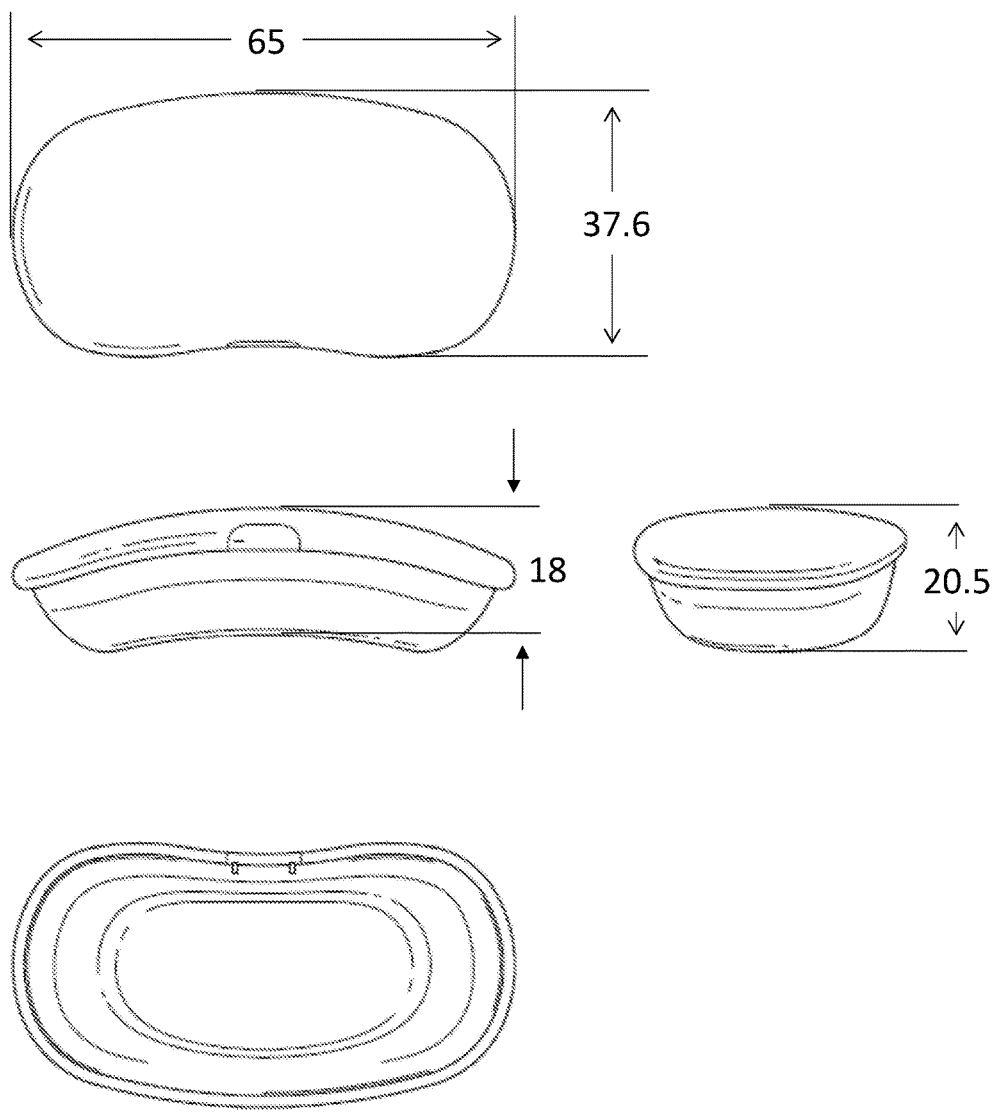
FIG. 7D schematically illustrates one variation of an applicator (showing top, side bottom and front views) of a device (including exemplary dimensions in mm) including a body of a TES applicator that may be wearably attached to the subject.

FIG. 7D shows different views (top, bottom, side, and front) of a body portion of another variation of a lightweight, wearable applicator in which an electrode may be attached to the device. In this example, which is particularly useful for connecting to the temple region of the subject, the applicator housing is thin and encloses much of the electronic components of the device.

TES methods and the various configurations described herein may be used with any TES system capable of delivering an appropriate TES waveform transdermally. In general, a TES system may use adherent electrodes and/or electrodes held in place by a wearable apparatus (i.e. cap, headband, necklace, eyeglass frame, or other form factor that enables an electrode to be in physical contact with the subject's skin). In general, the composition of transdermal electrodes of a TES system may have one or more features selected from the group including but not limited to: a hydrogel that contacts the skin, an $Ag/AgCl_2$ component for efficiently transforming an electrical current to an electrochemical one (i.e. carried by charged ions); a layer or other structure for improving the uniformity of current across the face of the electrode; an adhesive (e.g. hydrocolloid) for more securely holding the electrode in consistent contact with the skin; a saline soaked sponge component for delivering current transdermally; or other transdermal electrode technology known to one skilled in the art of transdermal electrical stimulation. In general, the power supply, current controller, and other electronic circuitry (e.g. safety circuitry and, optionally, wireless communication chip sets) of a TES controller may be in a handheld, tabletop, or other portable controller system; wearable components that connect directly to one or both electrodes or connect to the electrodes by wire and are otherwise wearable by a user (or placed within another worn structure (e.g. a headband or armband; a pocket; a necklace, earing, or eyeglass frame)); or completely disposable and integrated with one or more transdermal electrodes of the system.

For example, embodiments of the invention include methods for using electrodes according to configuration A and/or configuration B to induce a cognitive effect as described above by delivering an appropriate TES waveform from a transdermal electrical stimulation system to a subject. Generally, embodiments of the invention also include systems whereby a TES apparatus includes a power supply (e.g. battery), current control and safety circuitry, processor (i.e. microprocessor, microcontroller or the like), electrically conductive connectors and/or cables connecting to the anode(s) and cathode(s), and, optionally, a wireless communication module, in addition to a non-transitory computer-readable storage medium storing a set of instructions capable of being executed by the processor that, when executed by the processor causes a TES waveform to be delivered transdermally between the anode (or set of isoelectric anodes) and cathode (or set of isoelectric cathodes).

Stimulation intensities above 10 mA may be used for inducing a beneficial cognitive effect. However, electrodes for TES need to be small in at least some instances (e.g. to achieve improved localization of an electrode field to a target portion of the nervous system; or because an electrode location is near an area that is covered with hair and thus less than optimal for electrode placement; or because an area of skin sensitivity is nearby, such as the mastoid area behind the ear; or because an area of sensitivity to muscle twitching is nearby, such as the area around the eye). Relative to larger electrodes, embodiments of the TES system that use smaller electrodes have higher impedance due to reduced surface area of contact with the subject. Moreover, electrodes comprised of hydrogels (including adhesive hydrogels) or other compositions for coupling electrically to the body without leaving a significant residue (or wetness, as occurs for saline-soaked sponge electrodes) may be limited in terms of how low electrode impedance can be while maintaining other required properties (e.g. capacity to buffer pH changes from charge imbalanced stimulation).

Despite the known reduction of tissue impedance at increasing frequencies (e.g. from 100 s of Hz to low 10 s of kHz)—and the effect of other waveform features on impedance, the system impedance of a TES apparatus and electrode configuration as described herein for inducing a beneficial cognitive effect is generally between 1 kOhm and 25 kOhm. Impedance values above 10 kOhm are not uncommon. Accordingly, high supply voltages are required to deliver peak currents above 3 mA (or up to and above 15 mA in some instances) according to Ohm's law.

Thus, TES systems described herein incorporate electronic circuitry to achieve high voltage electrical stimulation, where high voltage corresponds to a circuit supply voltage generally greater than 10 V and optionally greater than 15 V, greater than 20 V, greater than 30 V, greater than 40 V, greater than 50 V, greater than 55 V, greater than 60 V, greater than 65 V, or greater than 75 V. An apparatus for delivering high current stimulation comprises a power source (generally a battery) with rapid discharge properties (generally 1 C or higher; preferably 3 C or higher; 5 C or higher; or 10 C or higher) so that peak currents can be delivered; a transformer (buck boost or other) to take lower voltage output of a battery or other power source and provide high voltage levels needed to provide specified power level; and other electronic circuit components designed to operate predictably and reliably at high voltage.

Previous systems for transdermal electrical stimulation targeting the nervous system have generally used direct current stimulation for which currents above 2 mA (and especially for currents above 3 mA) often cause irritation, pain, or tissue damage. Thus, high voltage transdermal electrical stimulation systems for inducing neuromodulation have not previously been considered.

Special care must be taken to ensure that the high voltage TES systems described herein operate safely and do not shock, burn, irritate, or otherwise induce discomfort in or tissue damage to a user. In general, safety elements can be incorporated in electrical circuit and firmware components of a TES system, including but not limited to: maximum instantaneous power output; maximum instantaneous current output; maximum temporal average power output; maximum temporal average current output; maximum controller operating temperature; maximum battery operating temperature; minimum battery supply voltage and/or capacity); and other features to ensure that stimulation delivered meets specifications for safety.

In embodiments of the invention, a wearable assembly constrains the position of electrodes so that when a user wears the assembly, the electrode positions are at or near the locations required for a configuration. Alternatively, the shape or other features (e.g. tactile features) can guide a user to place an electrode in an appropriate location for a particular Configuration. The wearable assembly can take a variety of forms, including, but not limited to, a hat, headband, necklace, around-the-ear form factor, or another wearable system that constrains electrode positions. Optionally, a wearable assembly that constrains electrode positions according to Configuration A or Configuration B also contains a battery or other power source and programmable controller that delivers a TES waveform to electrodes. One of ordinary skill in the art would appreciate there are many usable forms for a wearable assembly, and embodiments of the present invention are contemplated for use with any such wearable assembly.

Generally, the apparatuses described herein may include two electrodes (e.g., cathodes or sets of cathodes) placed at appropriate locations for both Configuration A and Configuration B on a subject and further comprising a switch (electrical, mechanical, optical, or the like) that alternatively connects the single anode (or set of isoeletric anode electrodes) to the cathode for configuration A or configuration B and is further configured to deliver an appropriate TES waveform to induce the cognitive effect associated with the cathode configuration.

Figure 8:
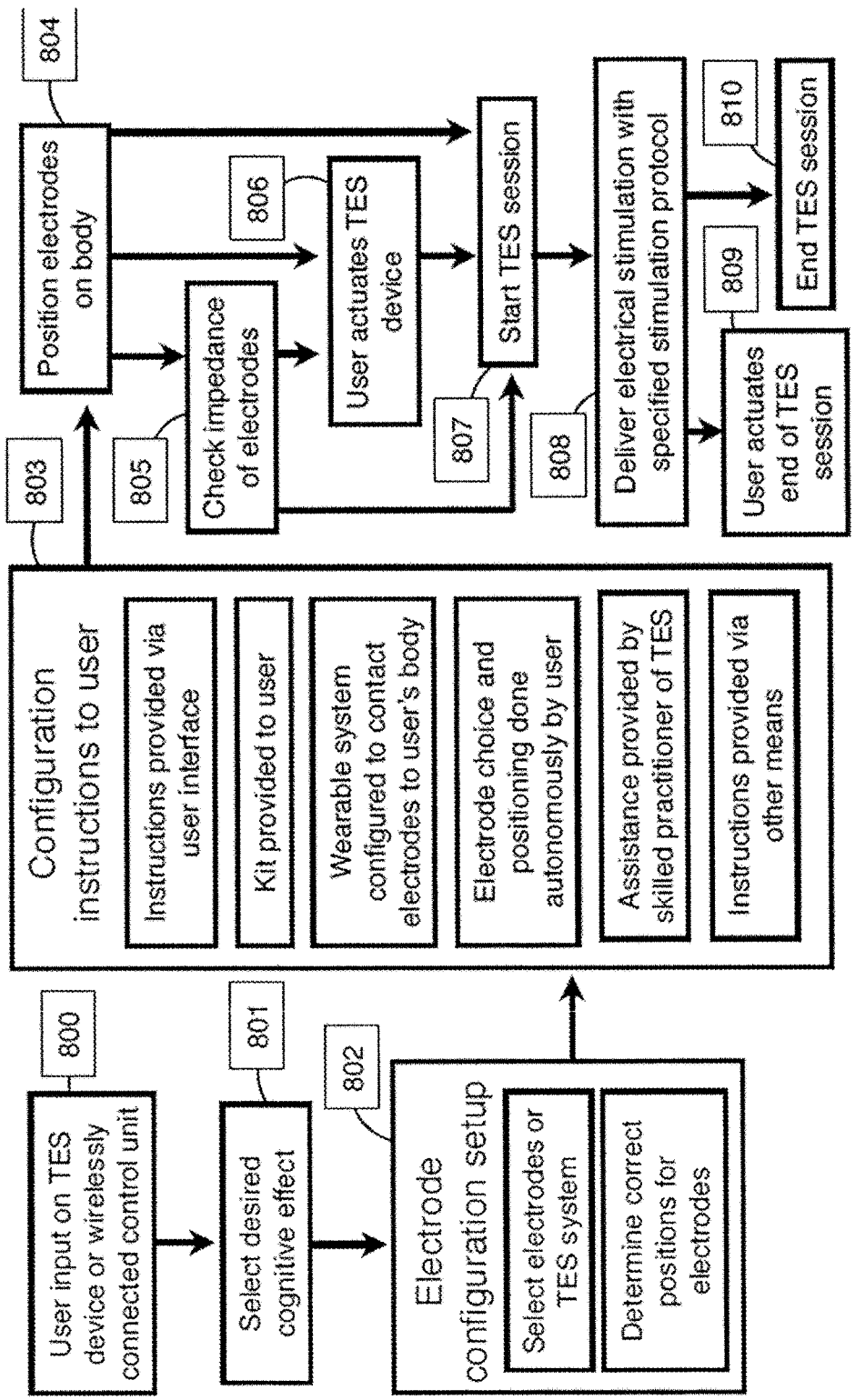
FIG. 8 illustrates one variation of a workflow for configuring, actuating, and ending a TES session.

FIG. 8 illustrates one variation of a schematic diagram showing the composition and use of TES systems. FIG. 8 shows an exemplary workflow for configuring, actuating, and ending a TES session. User input on TES device or wirelessly connected control unit 800 may be used to select desired cognitive effect 801 which determines electrode configuration setup 802 to achieve the desired cognitive effect, including selection of electrodes or a TES system that contains electrodes and determination of correct positions for electrodes. In an embodiment, configuration instructions to user 803 are provided by one or more ways selected from the list including but not limited to: instructions provided via user interface; kit provided to user; wearable system configured to contact TES electrodes to appropriate portions of a user's body; electrode choice and positioning done autonomously by user (e.g. due to previous experience with TES); assistance provided by skilled practitioner of TES; and instructions provided via other means.

Based on these instructions or knowledge, a user or other individual or system positions electrodes on body 804. In some embodiments, the TES session starts 807 automatically after electrodes are positioned on the body. In other embodiments, the impedance of the electrodes 805 is checked by a TES system before the TES session starts 807. In some embodiments, after impedance of the electrodes 805 is checked by a TES system, user actuates TES device 806 before the TES session starts 807. In other embodiments, after positioning electrodes on the body 804 the user actuates the TES device 806 to start the TES session 807. Once the TES session starts, the next step is to deliver electrical stimulation with specified stimulation protocol 808. In some embodiments, a user actuates end of TES session 809. In other embodiments, the TES session ends automatically when the stimulation protocol completes 810.

FIG. 9 shows components of portable, wired TES system 900. Adherent electrodes 901 may be connected to TES controller 904 via connectors 902 and wires 903. TES controller 904 has several components including battery or protected AC power supply 905, fuse and other safety circuitry 907, memory 908, microprocessor 909, user interface 910, current control circuitry 906, and waveform generator 911. The neuroConn DC-stimulator (neuroConn GmbH, Ilmenau, Germany) and Activadose II (Activatek Inc. Salt Lake City, Utah) are commercially available portable systems that connect to electrodes by wires that can be used for tDCS. The inTENSity™ product line (Current Solutions LLC, Austin, Tex.) are commercially available portable systems that connect to electrodes by wires and can be configured for constant and interferential tACS. Other commercial or custom systems can be used as a portable, wired TES system to deliver tACS, tDCS, tRNS, or another form of TES.

FIG. 10 shows a TES system comprising adherent or wearable TES delivery unit 1000 that communicates wirelessly with microprocessor-controlled control unit 1009 (e.g. a smartphone running an Android or iOS operating system such as an iPhone or Samsung Galaxy, a tablet such as an iPad, a personal computer including, but not limited to, laptops and desktop computers, or any other suitable computing device). In this exemplar embodiment, adherent or wearable TES delivery unit 1000 holds two or more electrodes in dermal contact with a subject with one or more of: an adhesive, a shaped form factor that fits on or is worn on a portion of a user's body (e.g. a headband or around-the-ear 'eyeglass' style form factor). In an exemplar embodiment, adherent or wearable TES delivery 1000 comprises components: battery 1001, memory 1002, microprocessor 1003, user interface 1004, current control circuitry 1005, fuse and other safety circuitry 1006, wireless antenna and chipset 1007, and waveform generator 1016. Microprocessor-controlled control unit 1009 includes components: wireless antenna and chipset 1015, graphical user interface 1011, one or more display elements to provide feedback about a TES session 1012, one or more user control elements 1013, memory 1014, and microprocessor 1015. In an alternate embodiment the TES delivery unit 1000 may include additional or fewer components. One of ordinary skill in the art would appreciate that a TES delivery unit could be comprised of a variety of components, and embodiments of the present invention are contemplated for use any such component.

Adherent or wearable TES delivery 1000 may be configured to communicate bidirectionally with wireless communication protocol 1008 to microprocessor-controlled system 1009. The system can be configured to communicate various forms of data wirelessly, including, but not limited to, trigger signals, control signals, safety alert signals, stimulation timing, stimulation duration, stimulation intensity, other aspects of stimulation protocol, electrode quality, electrode impedance, and battery levels. Communication may be made with devices and controllers using methods known in the art, including but not limited to, RF, WIFI, WiMax, Bluetooth, BLE, UHF, NHF, GSM, CDMA, LAN, WAN, or another wireless protocol. Pulsed infrared light as transmitted for instance by a remote control is an additional wireless form of communication. Near Field Communication (NFC) is another useful technique for communicating with a neuromodulation system or neuromodulation puck. One of ordinary skill in the art would appreciate that there are numerous wireless communication protocols that could be utilized with embodiments of the present invention, and embodiments of the present invention are contemplated for use with any wireless communication protocol.

Adherent or wearable TES delivery unit 1009 may not include user interface 1004 and is controlled exclusively through wireless communication protocol 1008 to control unit 1009. In an alternate embodiment, adherent or wearable TES delivery unit 1009 does not include wireless antenna and chipset 1007 and is controlled exclusively through user interface 1004. One skilled in the art will recognize that alternative TES systems can be designed with multiple configurations while still being capable of delivering electrical stimulation transcranially and transdermally into a subject.

FIGS. 21A to 27 illustrate one variation of a TES applicator apparatus as described herein. In this example, the TES applicator is configured as an adherent and self-contained TES system that is battery powered, communicates wirelessly with a remote controller unit and includes a master assembly (body with control module therein and an attached electrode) and a slave assembly (second electrode), coupled only by an electrically conductive wire. The master incorporates a microcontroller (control module) for managing the current delivery, a battery, a wireless communication module, other electronic circuitry, and an adherent electrode assembly. The slave assembly contains an adherent electrode assembly, is tethered to the master assembly (only) by a multicore wire, and fits in the case of the master assembly until a subject is ready for a TES session. To begin a TES session a subject may (in some variations) separate the slave assembly from the master assembly housing and places both adherent electrodes on his/her body in the appropriate locations, consistent with the instructions for a particular configuration as described herein. The electrode assemblies may be replaceable and/or disposable. For example, FIGS. 21A and 21B show renderings of one variation of a TES system 2301 (FIG. 21A) and 'exploded' view of the TES system (FIG. 21B). The system includes components of an electrode assembly of a slave assembly: peel and stick adhesive film 2302; electrically conductive adhesive electrode 2303; Ag/AgCl current spreaders (and pH buffering units) 2304, 2305, 2306; and tethered electrode base (e.g. made of molded styrene or pressure formed PET) 2307. The slave assembly is connected to the master assembly by flexible conductive wire 2308. The master assembly also has an electrode assembly comprising: peel and stick adhesive film 2309; electrically conductive adhesive electrode 2310; Ag/AgCl current spreaders (and pH buffering units) 2311, 2314, 2315; tethered electrode base (e.g. made of molded styrene or pressure formed PET) 2312; and connector 2313 for attaching to and delivering current from a control module of the master assembly. FIG. 22 shows a view of a TES applicator ("puck") with slave electrode 2503 assembly separate from master assembly 2501 and tethered by wire 2502 connecting the two.

The body of the TES applicator may be made of any appropriate material, for example, pressure formed PET or injection molded styrene, and may be a reusable control module enclosure ('keeper') of master assembly that contains: power, wireless communication, programmable processor, and other electrical components.

Figure 27:
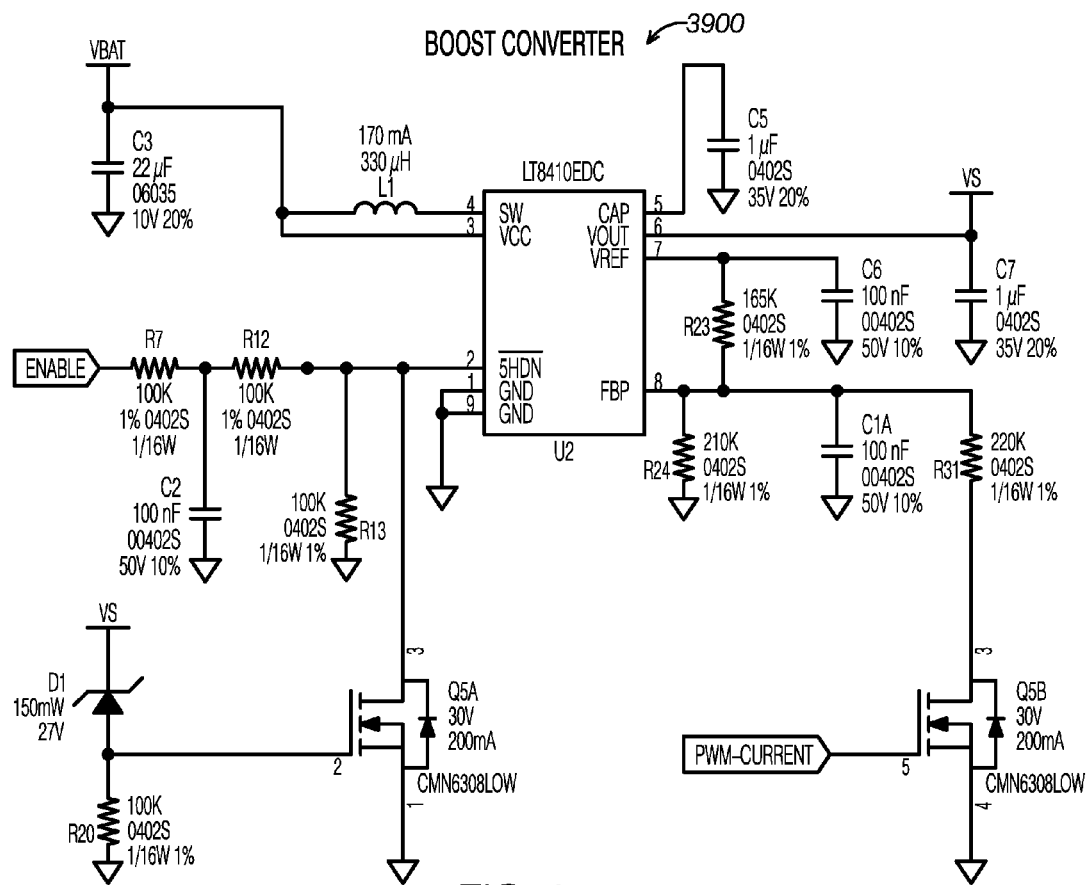
FIG. 27 is a schematic of a burst converter for a TES applicator as described herein.

Circuit diagrams of certain components for a TES system are shown in FIGS. 23 to 27 including the wireless Bluetooth module 3902 (FIG. 23), smart power switch 3901 (FIG. 24), current sources 3904 (FIG. 25), buck convertor 3903 (FIG. 26) and burst converter 3900 (FIG. 27). Circuitry for LED, battery voltage monitoring, programming interface, power supply access, current sources connector and the like are not shown.

An advantageous feature of a TES applicator having a master assembly and a slave assembly may be that the TES system can be detached and connected only by a flexible, electrically conductive tethering wire. In some embodiments, the electrically conductive tethering wire can be a ribbon cable or a multi-core wire. The electrode assemblies on both the master and slave units are thus electrically coupled to the reusable control module of the master assembly. The electrically conductive tethering wire may be part of the disposable electrode assembly. A subject (user) may unfurl the electrically conductive tethering wire as needed so that the master and slave electrode assemblies can be adhered to appropriate parts of the head to deliver TES neuromodulation to a brain region of interest. This embodiment is advantageous because the relative position of the two assemblies is only constrained by the length of an electrically conductive flexible wire connecting the two assemblies. This embodiment provides flexibility for electrode positioning, because the electrode assemblies are adherent, small, and not part of a larger assembly that constrains the relative position where a plurality of electrodes is in contact with the head or body.

A small battery or supercapacitor may be sufficient to supply the power for a TES session. The primary power drain for a TES system is the current delivered to the body of a subject. Even a relatively high tDCS current of 6 mA delivered for 30 minutes only requires 3 mA-hours (mAh), easily attainable from a portable battery (e.g. a commercially available rechargeable 3.7V 150 mAh lithium ion polymer battery weighs less than 5 grams). Pulsed stimulation protocols are even more efficient in terms of power requirements. Embodiments that incorporate one or more capacitors and/or supercapacitors are useful for shorter or lower current TES sessions (e.g. a 3.6 F supercapacitor provides 1 mAh, sufficient for 6 mA direct current to be delivered for 5 minutes and even longer pulsed stimulation sessions). Additional power may be required for other electrical components of a battery-powered TES system, informing battery and capacitor choices for a given TES duration and protocol.

An audio port or charging connector for a smartphone or tablet may be used to supply power and/or control signals to a TES system. In advantageous embodiments, the audio port or charging connector for a smartphone or tablet is used to charge a battery or capacitor of a TES system so that electrical stimulation can be delivered at a later time when the smartphone or tablet is no longer connected to the TES system. In some embodiments, power is supplied to a TES system by a manually-operated crank charging system or one or more solar cells.

The systems and methods described herein may permit users to 'bookmark' a transdermal electrical stimulation waveform to provide commentary, tagging, feedback, and/or social sharing. The experience of receiving transdermal electrical stimulation extends in time and waveforms may be designed so that the experience changes over the course of seconds to minutes. For instance, a phosphene may be delivered at a particular time point; or a parameter of stimulation may be changed (e.g. a peak intensity, stimulation frequency, pulse width, or other parameter may be ramped over a period of time) that induces a variation in the neuromodulation delivered to the subject and thus may modify in quality or intensity a cognitive effect induced in the subject. A user interface may permit a subject to associate a point in time during a waveform with a comment, rating, tag, highlight, or other information that communicates something about the experience of that transdermal electrical stimulation by the user.

Also described herein are non-transitory computer-readable storage medium storing a set of instructions capable of being executed by a remote processor (and particularly a smartphone or the like), when executed by the computing device containing the remote processor causes a user interface to be presented that enables a user to generate a comment, rating, tag, highlight, or other information that communicates something about the experience of that transdermal electrical stimulation by the user and automatically associates that information with a transdermal electrical stimulation waveform. In one embodiment, a database entry is made for the comment that includes a ranking and a tag, as well as a unique ID for the user, the waveform, and the time during the waveform at which the comment is made. For instance, a user interface may include a data entry field (e.g. text field that incorporates 'auto-complete' functionality based on previously entered tags), button, pull-down menu, or ranking system (select 1 or more stars) on a touchscreen display such that a user can generate a comment about stimulation that is automatically associated with the waveform and time during the waveform.

One beneficial feature of this embodiment is that comments, tags, rankings, etc. can be compiled across users (all users; sets of users defined demographically, psychographically, socially (e.g. composed of friends on Facebook), or otherwise) and across sessions so that a particular user can compare experiences between sessions using the same transdermal electrical stimulation waveform. In an embodiment, a non-transitory computer-readable storage medium storing a set of instructions capable of being executed by a remote processor (and particularly a smartphone or the like), when executed by the computing device containing the remote processor causes a display on the computing device (or communicably connected to the computing device, i.e. via screen sharing or Apple TV) to show a user commentary across users and/or sessions for a selected waveform, including commentary associated with portions of the waveform that the user has not yet experienced during a TES session. Thus, a user will form an expectation of highly salient or otherwise interesting (or uninteresting) portions of a waveform (i.e. 'watch out for phosphenes' or 'turn up the intensity here'). The display of commentary and feedback can be quantitative (e.g. a heat map showing the average ranking across sections of the waveform as a function of time or the density of feedback during a particular portion of a TES waveform). Different metadata may be displayed automatically depending on the amount of feedback available and/or the temporal scale of the waveform being displayed.

Similarly, metadata from sensors worn by or otherwise interrogating a TES user such as physiological sensors (e.g. measuring galvanic skin response, temperature, heart rate, heart rate variability, breathing rate, pupil dilation, movements, cortisol levels, amylase levels) can be aligned temporally with a waveform.

Any of the systems and methods for adapting a TES waveform described herein may account for impedance and/or capacitance during use.

In general, TES waveforms may account for expected changes in electrode and/or skin impedance during a session (or across sessions). Degrading electrodes generally exhibit increased impedance and may deliver current non-uniformly across the electrode-dermal surface (thereby causing increased skin discomfort at current intensity boundaries). In contrast, during a TES session extending minutes, tissue (skin) impedance generally decreases. Impedance of tissue (skin) is known to be frequency-dependent. Generally, higher frequencies of alternating or pulsed stimulation exhibit lower impedance relative to lower frequencies. Frequency dependence of a user's tissue can be estimated or tested empirically.

In general, TES waveforms for configurations described herein may compensate for changing electrical properties of electrode(s) and tissue by altering the frequency, intensity, duty cycle, waveform shape, or other waveform parameter.

Impedance checks or estimates (e.g. from historical data from the user or other users) can be used ahead of time to select a waveform or electrode configuration (e.g. including composition, size, and/or positioning) so that effective and comfortable transdermal electrical stimulation can be delivered for neuromodulation that induces a desired cognitive effect.

In an embodiment, the electrical properties of a user (e.g. frequency-dependent skin impedance) can be used to automatically change the properties of a TES waveform. Both initial (pre-stimulation) and stimulation-induced changes in electrical properties of a user's tissue can help guide waveform selection and/or adjustment for comfort and efficacy.

The system can measure impedance and/or capacitance data from a user once or repeatedly. Repeated measurements can occur at regular intervals, in response to a selection by a user or third party via a user interface on a wearable TES system or controller communicably connected to a wearable TES system (e.g. a smartphone or tablet wirelessly communicating with a TES system). Measured impedance and/or capacitance data is beneficially stored to improve future device function. Impedance and/or capacitance data stored locally on a machine-readable computer memory component of a wearable TES may be beneficial as diagnostic information for improving the function of that unit. Measured impedance and/or capacitance data may also be transferred from a wearable TES system via wired or wireless communication protocols for storage on a machine-readable computer memory component of a computer, smartphone, tablet, dedicated computing unit, or other computerized system. Impedance and/or capacitance data transmitted in real-time or asynchronously via the Internet to a remote server is advantageous because it permits automated storage and integration of data from many users and TES systems for improved device comfort and function.

Beneficial embodiments of TES systems comprise electrical circuitry for measuring impedance and/or capacitance that transmit these data to a machine-readable hardware external to the wearable TES system (including remote servers connected via the Internet) associate metadata with the measurements, including the user, and hardware component versions (e.g. electrodes). Metadata may also include geographical data (i.e. collected from a GPS system contained within the TES system or a separate hardware controller of the TES system such as a smartphone or tablet computer). Geographical data can be used to associate impedance and/or capacitance values with temperature, humidity, and other ambient factors that can affect the electrical properties of electrodes and/or human tissue.

Examples of TES applicators and systems operating as described herein to modify a subject's cognitive state are provided in FIGS. 11-15B.

Figure 11:
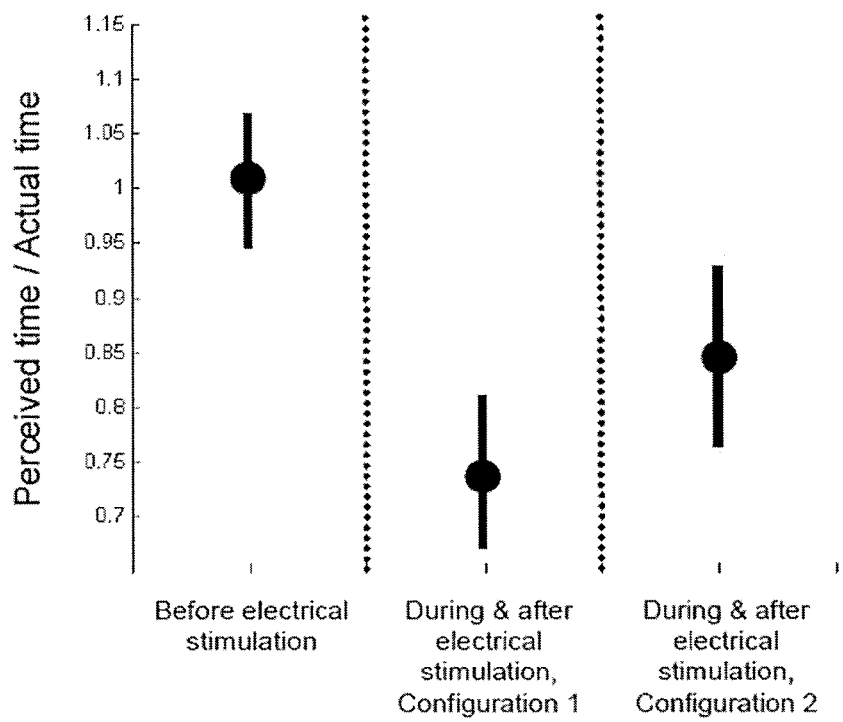
FIG. 11 illustrates the changes in perceived passage of time during and after a TES stimulation session using configuration 1 as described herein.

For example, FIG. 11 illustrates the ratio of perceived time divided by actual time averaged across subjects receiving TES stimulation as described herein. Before electrical stimulation (left data point in FIG. 11), the ratio is about 1, consistent with subjects accurately estimating the passage of time. During stimulation, subjects received transcranial direct current stimulation at a maximum current intensity of 1.0 mA delivered through electrodes positioned according to configuration 1 with the lateral electrode placed on the subject's right side. A rectangular 1.3"×2.1" PALS® Platinum electrode (Axelgaard Manufacturing Co., LTD, part number 891200) served as the anode (106) and a square 2"×2" electrode (Axelgaard Manufacturing Co., LTD, part number UF2020) served as the cathode (105). As a result, during and after stimulation, subjects estimated that time passed slowly: the average time estimate from subjects was about 75% of the actual amount of time that had passed (center data point in FIG. 11). Similarly, subjects receiving stimulation using configuration 2 (TES at 1.5 mA delivered through electrodes positioned according to configuration 2 with both electrodes placed on the subject's right side; a rectangular 1.3"×2.1" PALS® Platinum electrode (Axelgaard Manufacturing Co., LTD, part number 891200) served as the anode and a round (about 1" diameter) Little PALS® ECG electrode (Axelgaard Manufacturing Co., LTD, part number SEN5001) served as the cathode), gave an average estimate of time passage during and after stimulation that was about 85% of the actual amount of time that had passed (right data point in FIG. 11). These results show that TES stimulation for configurations 1 and 2 induces a subjective perception of time passing quickly, a perceptual quality corresponding to cognitive states of focus, attention, and flow.

Figure 12:
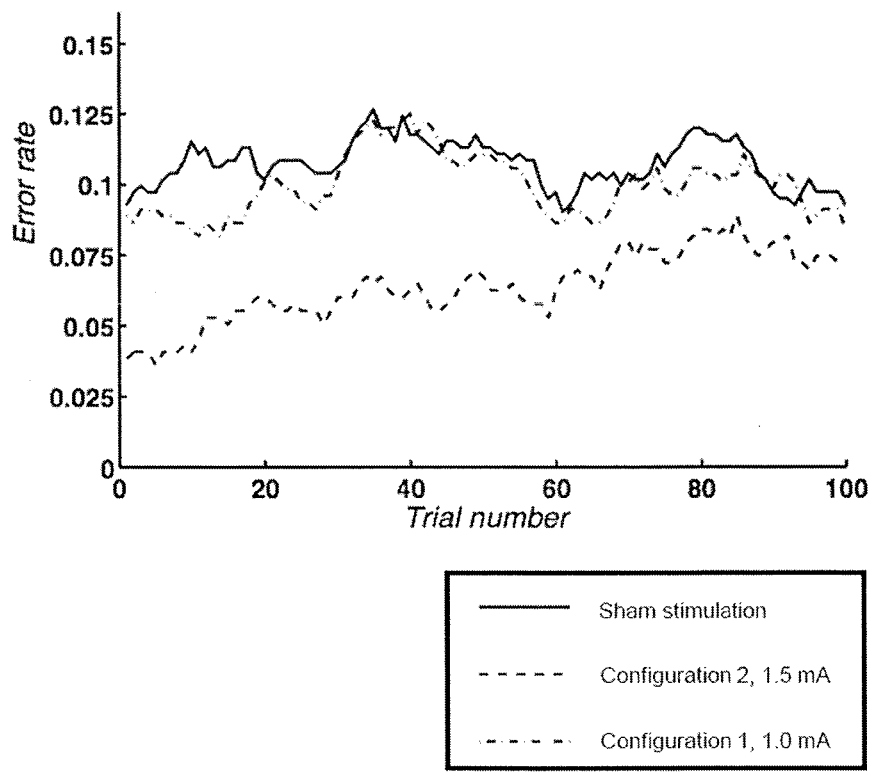
FIG. 12 shows data from subjects performing the 'n-back' task during TES (e.g., tDCS) and sham stimulation.

As shown in FIG. 12, direct current TES using configuration 2 at 1.5 mA also resulted in a significant improvement in performance on a working memory task. In separate sessions on three different days, subjects performed the 'n-back' (where n=2) task while receiving TES or sham stimulation. The n-back task probes working memory, an executive function system closely linked to intellectual function, attention, literacy, and educational success. Working memory is not easily improved with training, suggesting that TES systems and methods for improving working memory could lead to improved intellectual abilities in subjects. In repeated trials, more robust effects were found across subject's using a higher (e.g., 3 mA) intensity.

Figure 13:
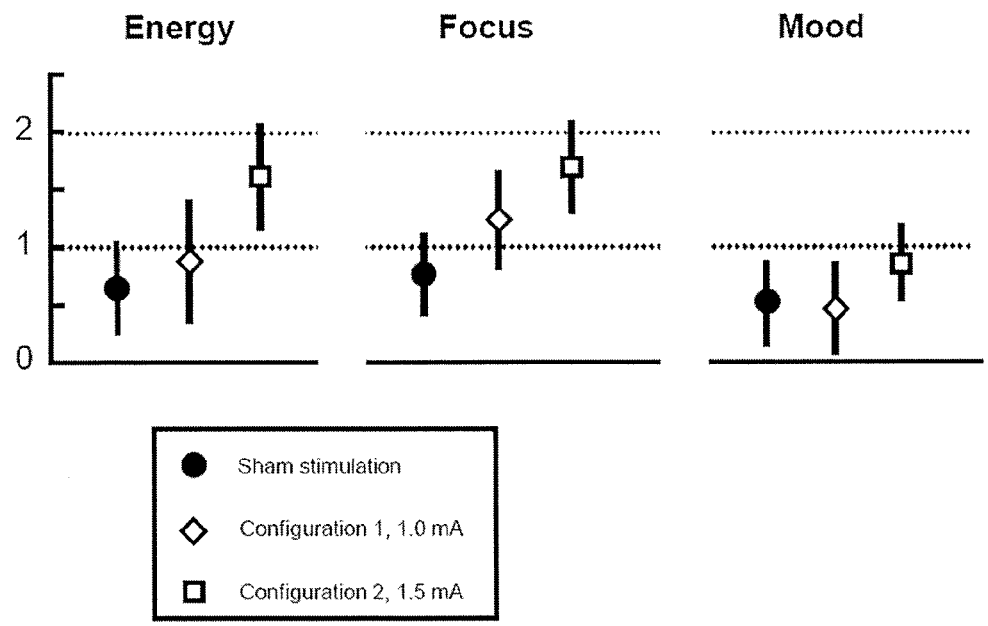
FIG. 13 illustrates subjects' self-reported energy, focus, and mood during TES (e.g., tDCS) and sham stimulation.

FIG. 13 shows average error rates across subjects as a function of trial number in a 100-trial n-back session. Subjects receiving TES using configuration 1 performed at the same baseline level of about 10% error rate as subjects receiving sham "S1" stimulation. In contrast, subjects receiving stimulation using configuration 2 TES had significantly fewer errors, particularly for the first about 50 trials of the n-back session. These results show that a direct current TES stimulation using >1.5 (and more robustly, greater than 3 mA) intensity significantly improves performance on the n-back task, consistent with an enhancement in working memory during stimulation. In contrast, a lower (1 mA) intensity session had no effect on n-back performance relative to sham "S1" stimulation.

This was also seen, for example, when configuration 3 (at an intensity of between 3 and 3.5 mA) was used. In this example, TES increased energy, focus, and mood. Higher energy levels, increased focus, and improved mood are highly desirable changes in cognitive state for enhanced productivity, activity, and happiness. In separate sessions on three different days, subjects completed a survey that assessed subjective perceptions of energy, focus, and mood after receiving TES (configuration 1) stimulation, TES (configuration 2) stimulation, TES (configuration 3) stimulation, sham "S1" stimulation, or sham "S2" stimulation.

Figure 14:
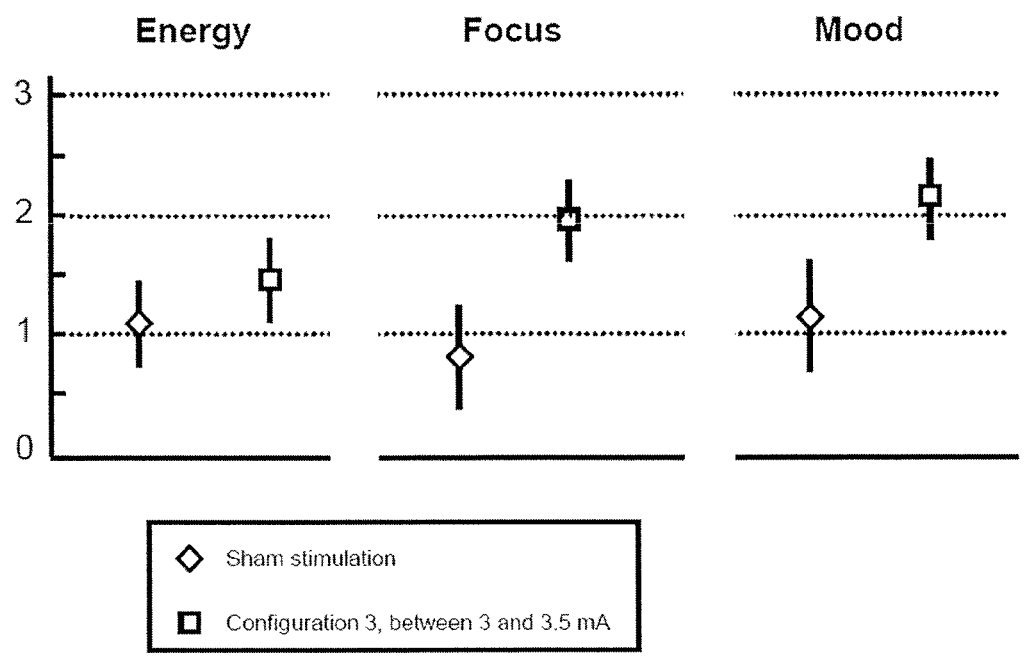
FIG. 14 illustrates subjects' self-reported energy, focus, and mood during TES (e.g., tDCS) and sham stimulation.

FIGS. 12 and 13 show average (+/−SEM) survey results for energy, focus, and mood, normalized to a pre-stimulation baseline survey where higher scores correspond to higher levels of energy, improved focus, and a better mood. Note that sham stimulation survey results greater than 0 likely correspond to a placebo effect. Relative to sham "S1" stimulation, configuration 1 TES induced a moderate improvement in focus, but did not significantly affect energy or mood (FIG. 12). Relative to sham "S1" stimulation, configuration 2 TES induced a substantial improvement in energy and focus in subjects, but did not significantly affect mood (FIG. 12). Relative to sham "S2" stimulation, configuration 3 TES led to subjective reports of improved focus and mood, but did not significantly affect subjective reports about energy levels (FIG. 14). These results show that: a configuration 1 session improves subjects' focus by a small amount, but does not affect their focus or mood; a TES configuration 2 session improves subjects' energy and focus, but does not affect their mood; and a TES configuration 3 session improves subjects' focus and mood, but does not affect their energy. Increasing the intensity, and controlling the frequency (and DC offset and duty cycle as described above) provided substantially more robust effects.

Figures 15A, 15B:
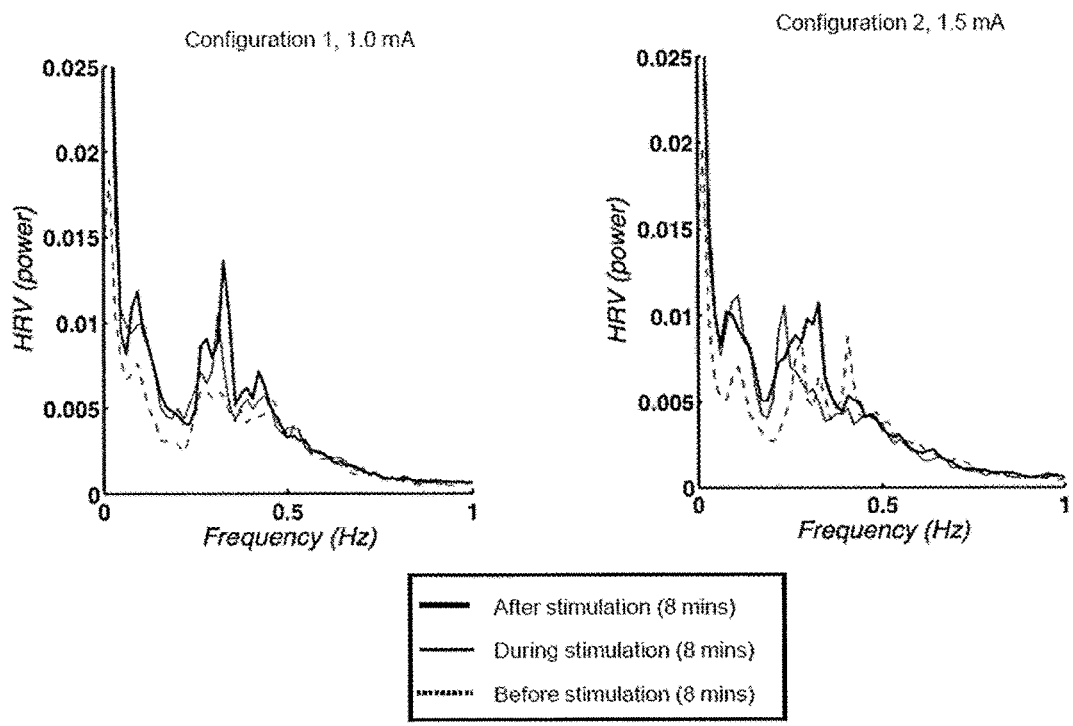
FIGS. 15A and 15B are Fourier transform plots of heart rate variability data collected before, during, and after TES (tDCS) stimulation as described herein for configuration 1 and 2 respectively.

FIGS. 15A and 15B examine the effect of TES on heart rate variability. Heart rate variability (HRV) measures the variability of inter-heartbeat intervals and is considered to be a sensitive assay of autonomic nervous system function. In separate sessions on two different days, subjects wore a pulse sensor system before, during, and after a configuration 1 or configuration 2 TES session. FIGS. 15A and 15B show an average Fourier transform of HRV across subjects receiving a configuration 1 (FIG. 15A) or configuration 2 (FIG. 15B) TES session. Either form of TES stimulation induced increased HRV that was not frequency specific. These results show that a configuration 1 or configuration 2 TES session induces increased heart rate variability and suggests that these forms of transcranial electrical stimulation are effective for controlling the autonomic nervous system and thus a wide range of physiological functions within and outside of the brain.

Figure 16:
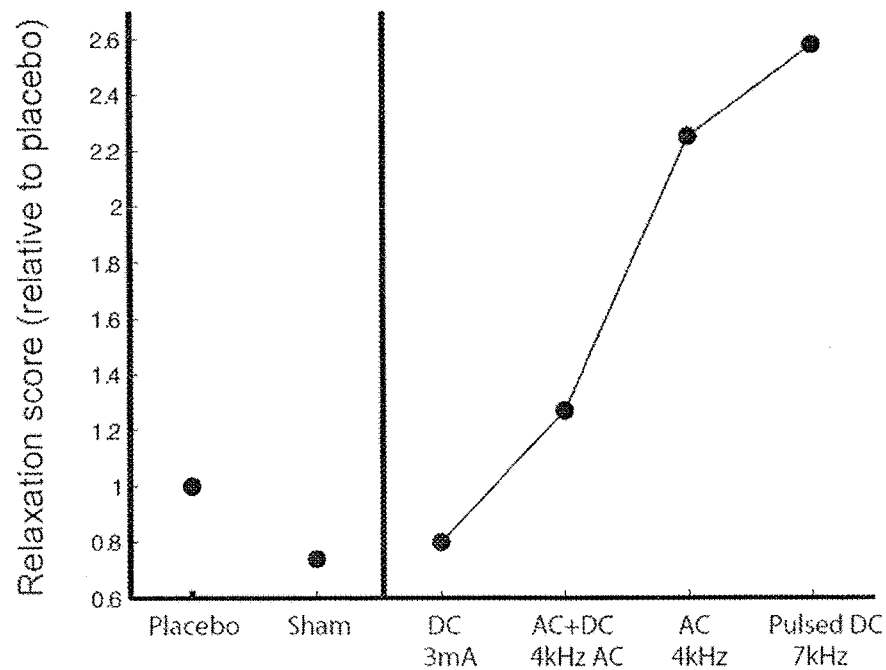
FIG. 16 illustrates subjects' level of relaxation during TES using placebo condition, sham stimulation, and various forms alternating and direct current TES using configuration 3 described herein.

FIG. 16 illustrates high-intensity TES stimulation on subjects' level of relaxation with electrodes positioned according to Configuration 3. In this example, subjects received TES, placebo, or sham stimulation and were assessed for subjective feelings of relaxation with electrodes positioned according to configuration 3. Scores are shown in FIG. 16 and were normalized so that the placebo condition was equivalent to a relaxation score of 1. Sham stimulation caused a slight decrease in average relaxation scores among subjects. Direct current stimulation at 3 mA also did not cause an increase in relaxation. In contrast, alternating current stimulation (4 kHz square wave biphasic; inTENSity unit, Current Solutions LLC, Austin Tex.; current intensity was controlled by subjects up to a maximum of 10 mA) in isolation or combined with direct current caused increased relaxation. Pulsed direct current stimulation induced the largest increases in relaxation (Idrostar system, STD Pharmaceuticals, Inc, Hereford England; 7 kHz pulsing, about 42% duty cycle, current intensity was controlled by subjects up to a maximum of 10 mA). A TES system with electrodes positioned according to configuration 3 provides feelings of enhanced relaxation in subjects when configured with appropriate TES protocols.

Figure 17:
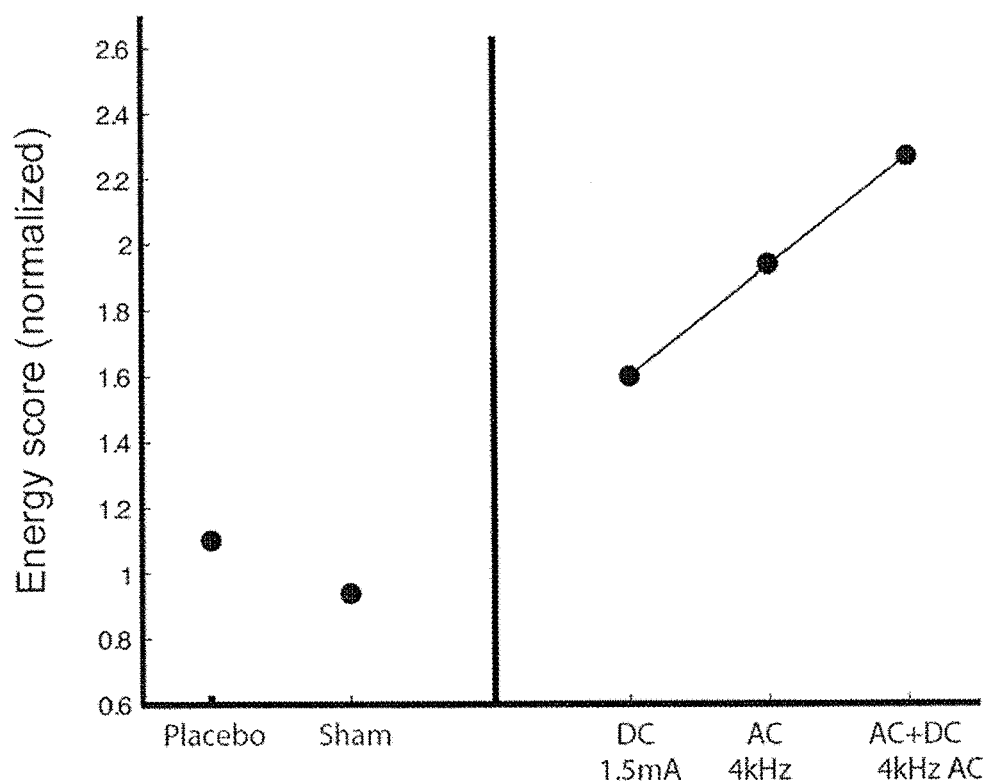
FIG. 17 illustrates subjects' level of relaxation during TES using placebo condition, sham stimulation, and various forms alternating and direct current TES using configuration 3, described herein.

FIG. 17 illustrates the effects of a TES protocol in configuration 2 on subjects' feelings of energy. In this example, subjects received TES, placebo, or sham stimulation and were assessed for subjective feelings of energy with electrodes positioned according to configuration 2. Scores are shown in FIG. 17. Sham stimulation caused a slight decrease in average relaxation scores among subjects relative to placebo. Direct current stimulation at 1.5 mA caused a moderate increase in feelings of energy. Alternating current stimulation (4 kHz square wave biphasic; inTENSity unit, Current Solutions LLC, Austin Tex.; current intensity was controlled by subjects up to a maximum of 10 mA) in isolation or combined with direct current (1.5 mA) caused larger enhancements in subjects' feelings of energy. A TES system with electrodes positioned according to configuration 2 provides feelings of enhanced energy in subjects when configured with appropriate TES protocols.

Figures 18A, 18B:
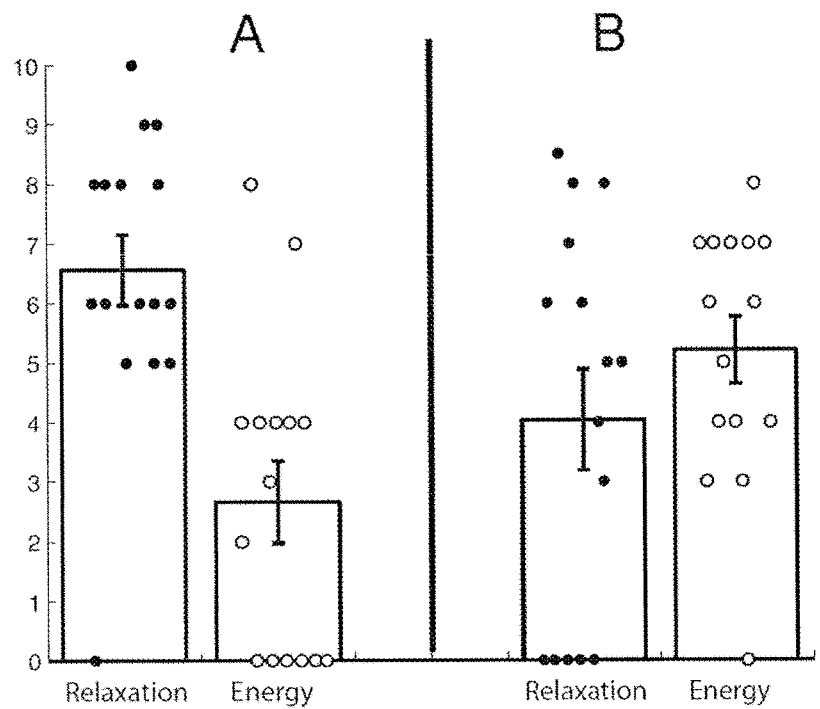
FIGS. 18A and 18B illustrate subjects' energy during TES using placebo condition, sham stimulation, and various forms alternating and direct current TES using configuration 2, described herein.

FIGS. 18A and 18B illustrate the effects of configuration 2 and configuration 3 on a subject's feelings of relaxation and energy. In this example, subjects received pulsed direct current stimulation from an Idrostar system STD Pharmaceuticals, Inc, Hereford England; 7 kHz pulsing, about 42% duty cycle, current intensity was controlled by subjects up to a maximum of 10 mA). In a first session, subjects had electrodes positioned according to configuration 3 and reported subjective feelings of relaxation and energy after 10 minutes of electrical stimulation. Subjects reported high levels of relaxation but low levels of energy on a customized 10-point scale (FIG. 18A). After a 10 minute "washout" period, subjects' electrodes were shifted to positions for configuration 2 and pulsed direct current stimulation began again. After this second 10 minute electrical stimulation session, subjects reported increased energy and lower relaxation scores. These results indicate a robust and reversible neuromodulatory effects from configuration 2 for increasing energy and configuration 3 for increasing relaxation.

Based on experiments such as this one and others, numerous other (negative) experiments using other electrode positions (configurations), position has been found to be extremely important to evoking a particular cognitive effect.

Figure 19A:
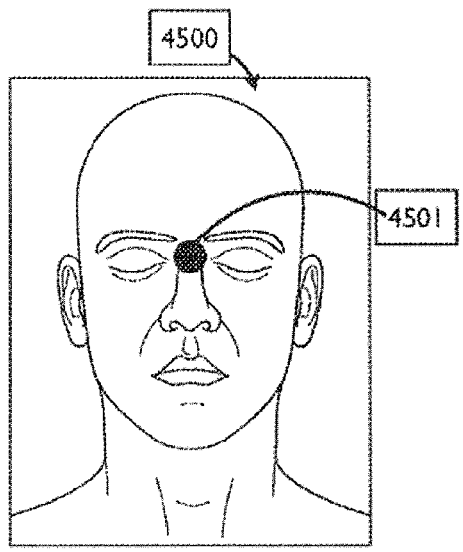
FIGS. 19A and 19B show exemplary electrode positions for a configuration 4; the first electrode position is shown in FIG. 19A and the second electrode position in 19B.
Figure 19B:
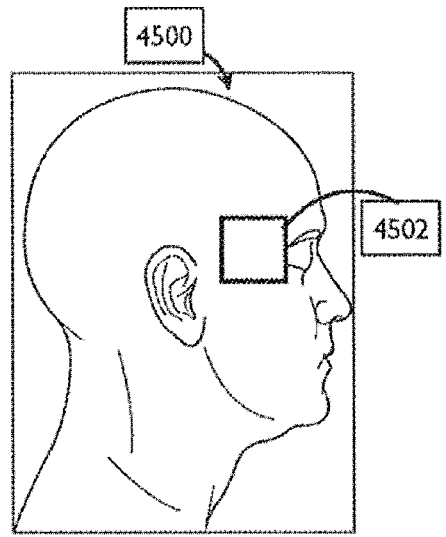

Other configurations (e.g., placement locations) of electrodes may have different effects, and have been exampled. For example FIGS. 19A and 19B illustrate one example of a configuration ("configuration 4") in which an electrode is positioned on the bridge of the subject's nose and a second electrode is positioned on the head greater than a few inches from the first electrode (e.g., on the subject's forehead or temple. Configuration 4 electrode placement is relatively easy for a user to do themselves. Systems and methods for TES using configuration 4 electrically couple a first electrode (e.g., anode) to the subject between the eyes at the bridge of the nose. FIG. 19A shows model subject 4500 with a round anode electrode placed between the eyes on the bridge of the nose. In a preferred embodiment, the anode electrode is less than 1" across and flexible in order to conform to the curvature of the area near the bridge of the nose of a subject. The anode electrode may be round, elliptical, square, rectangular, or an irregular shape configured for ease of placement on the curved areas of the nose. In a preferred embodiment, a second electrode (e.g., cathode) is located at a site selected from the list including, but not limited to: temple 4502 (as shown in FIG. 19B), forehead, neck, mastoid, shoulder, arm, or elsewhere on the face, head, neck, or body below the neck. A second electrode can be placed on either side of the body. In some embodiments, multiple cathode electrodes can be used.

The forehead electrode can be easily affixed using a mirrored surface or smartphone (or tablet) camera, and the neck cathode positioning does not need to be precise. In at least some instances, Configuration 4 requires relatively high currents, e.g. TES (tDCS) of at least about 3 mA, to achieve desired cognitive effects. Electrodes placed on the head according to configuration 4 can be used as part of a TES system for delivering electrical stimulation to induce a change in cognitive state for enhancing a state of calm in a subject, enhancing drowsiness so that it is easier to fall asleep, or inducing sleep. Configuration 4 may be used as part of a TES system configured to deliver one or more of: direct currents with maximum intensity greater than 3 mA; pulsed direct currents with maximum intensity greater than 5 mA; or alternating currents with maximum intensity greater than +/−5 mA.

Figure 20A:
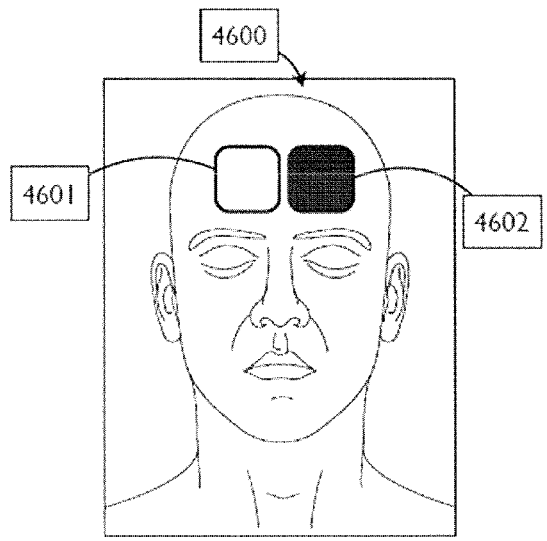
FIG. 20A shows an example of a configuration 5.

FIG. 20A illustrates another configuration, referred to herein (for convenience) as "configuration 5". In this example, the use of configuration 5 for TES as described herein may result in an induced cognitive effect including, but not limited to: increased energy; enhanced focus; improved mood; and feelings of pleasantness. Configuration 5 may cause neuromodulation by targeting one or more of: the brain; one or more cranial nerves; one or more nerves; and one or more nerve ganglia. As shown in FIG. 20A, configuration 5 electrode placement is relatively easy for a user to do themselves, by attaching both the first and second electrodes to the subject's forehead. FIG. 20A shows model subject 4600 with rounded square electrodes placed adjoining each other or within 2 cm of each other on the forehead. A first electrode (e.g., anode) 4602 is positioned above the subject's left eye and a second electrode (e.g., cathode) 4601 is positioned above the subject's right eye. In some embodiments, multiple isoelectric electrodes can replace a single anode or cathode. Interestingly, a similar placement nearby these regions is ineffective; positioning with a small electrode more superior and lateral on the subject's left forehead and second electrode (e.g., oval shaped electrode) above the subject's right eyebrow does not result in this induced cognitive effect, showing the importance of configuration (placement) of electrodes. The forehead electrodes in configuration 5 can be affixed by the subject himself or herself using a mirrored surface or camera (e.g., smartphone or tablet camera) to guide them. Configuration 5 may be robustly result in modification of a cognitive state by using high currents (e.g. TES stimulation of at least about 3 mA) as described herein to achieve desired cognitive effects, requiring electrodes and/or stimulation protocols to be selected for reduced pain and irritation in a user.

Figure 20B:
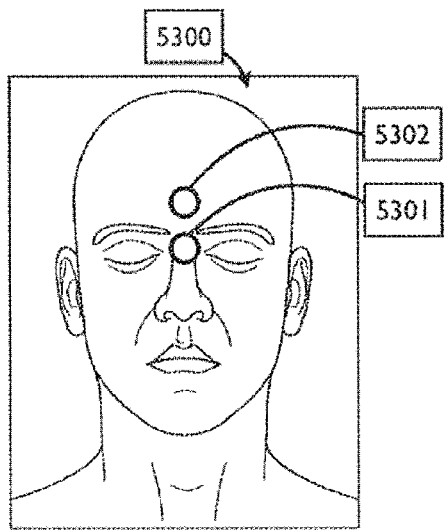
FIG. 20B shows an example of a configuration 6.
Figure 23:
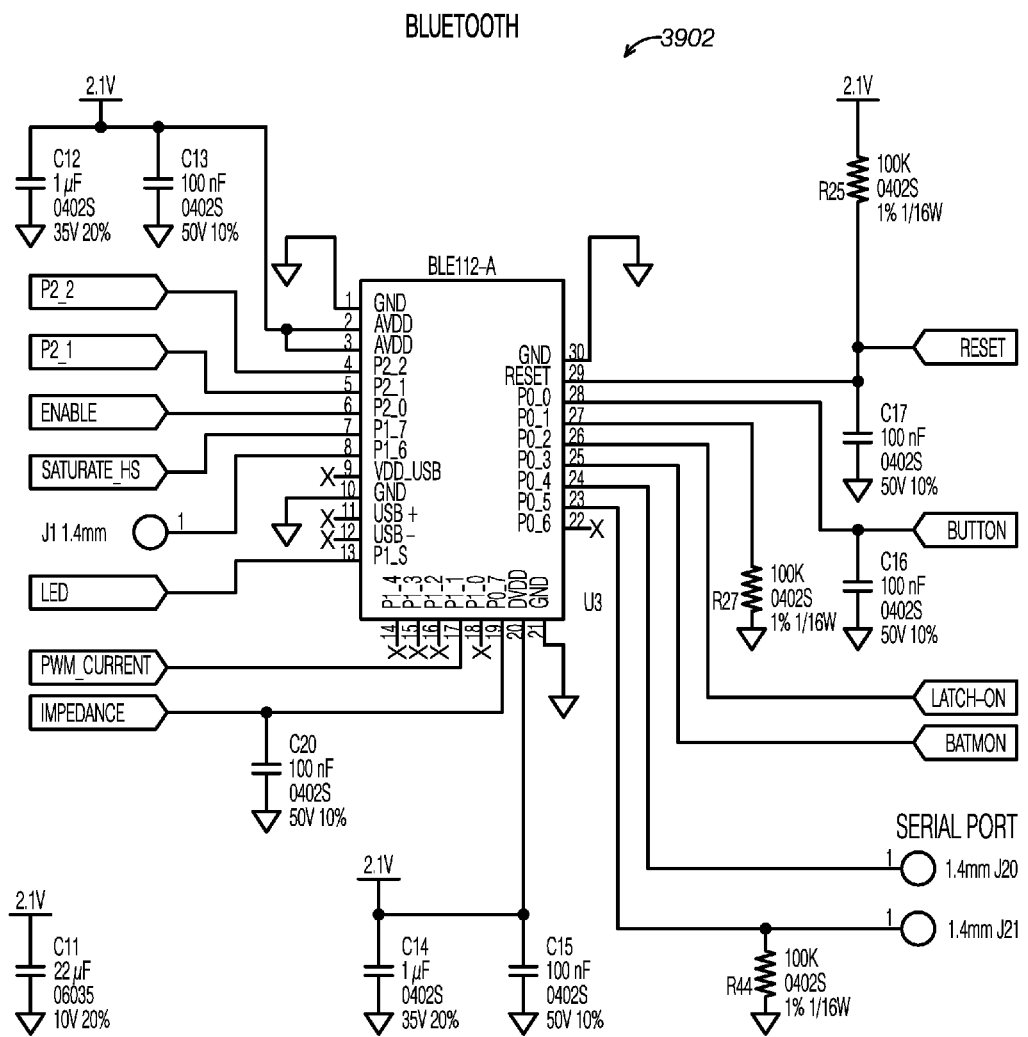
FIG. 23 is a schematic illustrating one variation of a wireless communications module (e.g., Bluetooth module) that may be used as part of a TES applicator.
Figure 24:
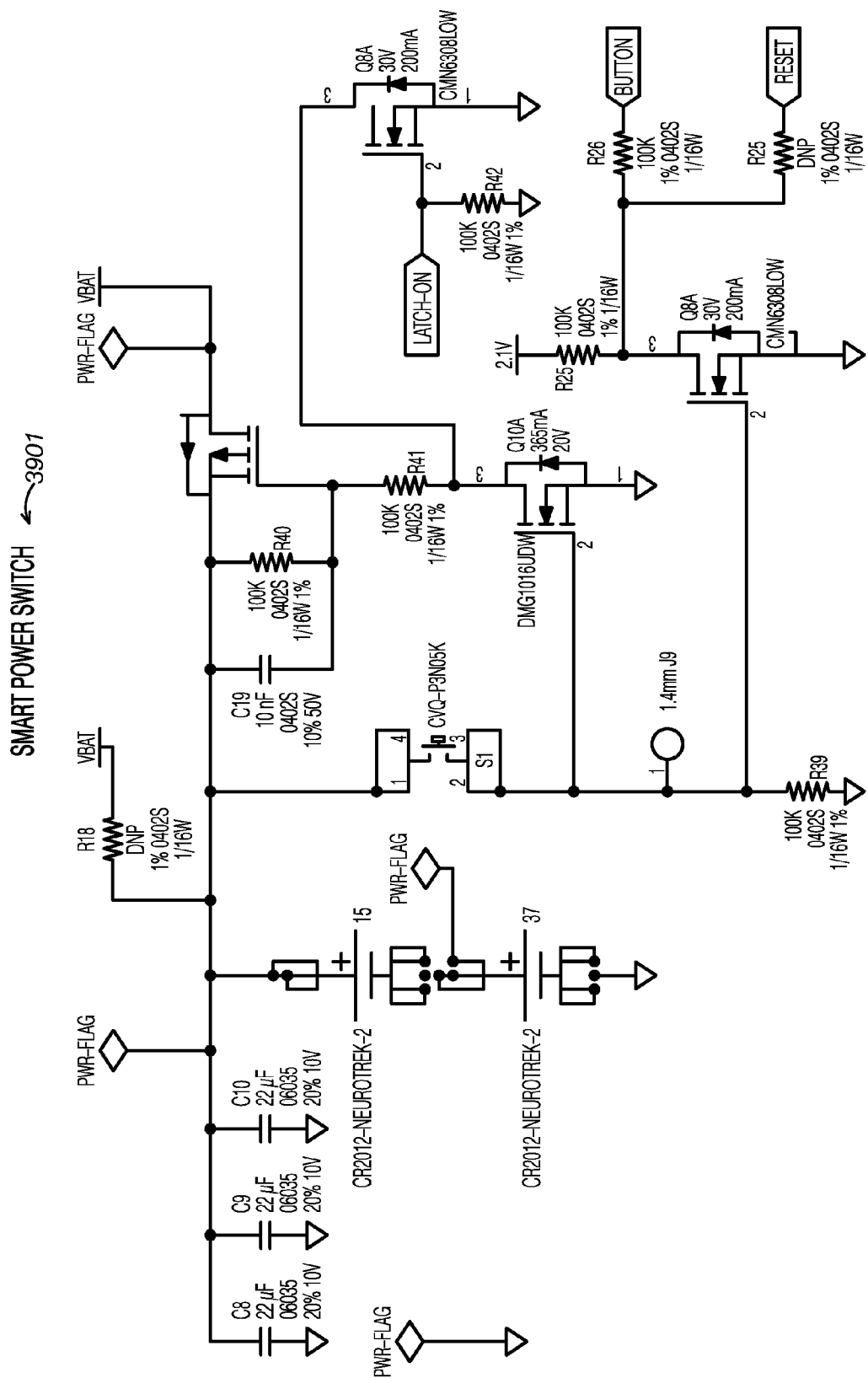
FIG. 24 is a schematic illustrating one variation of a smart power switch that may be used as part of a TES applicator.
Figure 25:
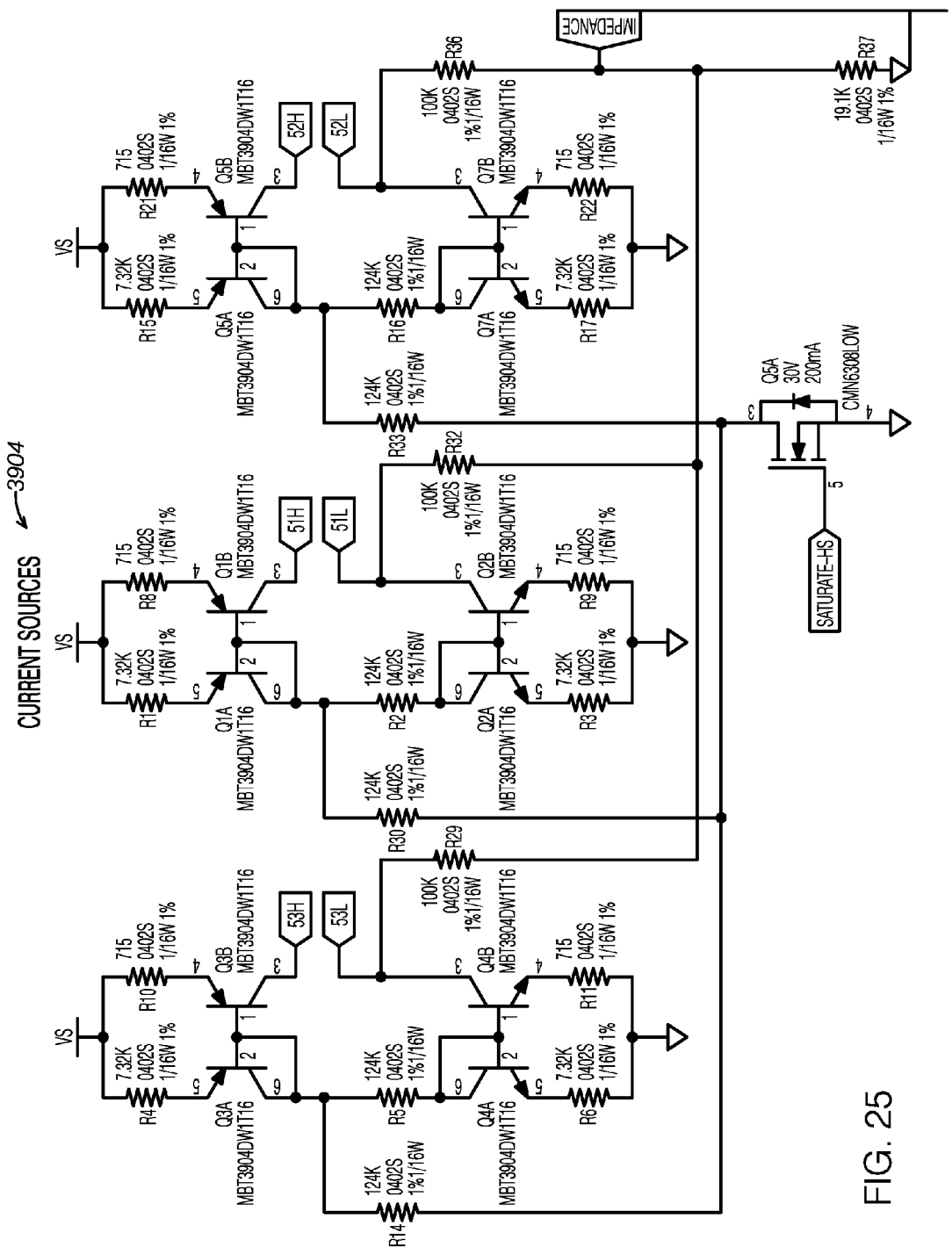
FIG. 25 is a schematic of current sources that may be part of a TES applicator as described herein.
Figure 26:
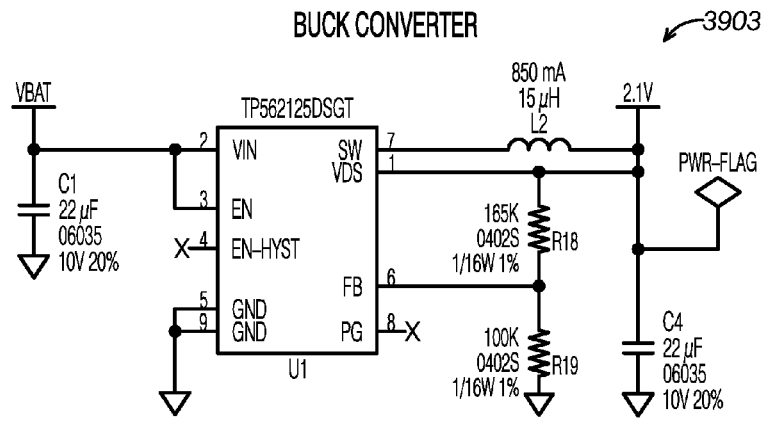
FIG. 26 is a schematic of a buck converter for a TES applicator.

FIG. 20B illustrates another example of a configuration, referred to herein as configuration 6. In configuration 6, the first electrode (e.g., anode) is placed over the bridge of the nose (e.g., the nasion region) and a second electrode (e.g., a small, round cathode) is positioned right above it, e.g., nearby within a few cm. The cognitive effects evoked using this configuration may be bimodal in terms of energy and sleepiness depending on waveform delivered.

Subjects treated with TES using configuration 6 may experience different forms of neuromodulation with distinct cognitive effects depending on the waveform and intensity delivered. Configuration 6 electrically couples an electrode to a subject between the eyes at the bridge of the nose ('nasal' electrode) and a second electrode near the midline on the forehead ('forehead' electrode), superior to the nasal electrode. The nasal electrode may be about 1" or less across and flexible in order to conform to the curvature of the area near the bridge of the nose of a subject (e.g. 1" diameter PALS platinum electrodes from Axelgaard Manufacturing Co., Ltd.; Fallbrook, Calif.). The forehead electrode may be close to (i.e. about 1 cm) and directly above (superior to) the nasal electrode. The forehead electrode may also be a 1" flexible round electrode or may be selected to have a different size, shape, and/or composition. Generally, electrodes less than about 2" in diameter are preferable to be used as the forehead electrode in configuration 6 in order to avoid side effects. A forehead electrode may be positioned slightly lateral to the left or right of the midline on the forehead and/or further superior on the forehead.

FIG. 20B shows model subject 5300 with electrodes placed according to configuration 6. Either of the electrodes can be configured as the anode or cathode. However, preferred embodiments are configured with round nasal electrode 5301 as the anode and round forehead electrode 5302 affixed to the lower medial forehead area directly above nasal electrode 5301. In some embodiments, multiple isoelectric electrodes can replace a single anode or cathode. In FIG. 20B, the nasal electrode is an anode and the forehead electrode is a cathode.

Systems and methods with this electrode configuration deliver different electrical stimulation waveforms to achieve distinct cognitive effects, as described below. For example, a first waveform delivers TES using an alternating transcranial electrical stimulation current at a frequency between 3 kHz and 5 kHz (100% duty cycle, no direct current offset) at an intensity greater than 2 mA (preferably greater than 5 mA) and induces neuromodulation in a subject with cognitive effects including, but not limited to: increased drowsiness; increased desire to sleep: induction of sleep; induction of a relaxed state of mind; and induction of a calm state of mind. In alternative embodiments, shorter duty cycles and a DC offset less than about 2 mA is used to enhance the cognitive effects achieved from this waveform. One side effect reported for TES using this type of waveform is mild sinus pressure.

A second waveform delivers TES using an alternating transcranial electrical stimulation current at a frequency less than 3 kHz (100% duty cycle, no direct current offset; preferably between 300 Hz and 1 kHz) at an intensity greater than 1 mA (preferably greater than 2 mA) induces neuromodulation with cognitive effects including, but not limited to: increased energy and enhanced wakefulness. One side effect reported for TES using this type of waveform is tingliness or itching in the skin of the face and scalp, presumably due to trigeminal nerve stimulation. Lower frequencies of alternating current stimulation are associated with higher skin impedance and more substantial side effects that can be disruptive to the experience of the induced cognitive effect in the user.

By alternating, interleaving, and/or combining the first and second alternating current transcranial electrical stimulation waveforms described above, a subject can achieve titrated levels of energy and relaxation, as well as beneficial and enjoyable experiences wherein a subject's levels of energy and relaxation vary over time. Electrode positioning for configuration 6 is important to get both effects with minimal undesirable side effects. Embodiments wherein the electrodes are in close proximity (i.e. nearest electrode edges about 1 cm or less from each other) minimize resistance in the stimulation circuit, improving energy efficiency of a TES system. Energy efficiency is a beneficial quality of portable and battery-powered TES systems. Another benefit of placing the electrodes on the nasal region and directly above on the lower medial portion of the forehead is to reduce undesirable side effects. If one of the electrodes is more lateral and near the eyelid area (e.g. temples), irritating eye twitchiness can occur with the 400 Hz alternating current stimulation protocol and a calming/sleepiness effect can be mitigated by facial tingling (presumably due to trigeminal nerve activation) with the 4000 Hz alternating current stimulation protocol.

Another beneficial optional feature using configuration 6 is to ramp the current intensity up and/or down quickly for waveforms to enhance either form of neuromodulation due to the pleasurability and interesting sensory quality of the neuromodulatory effects and sensory side effects, as described in greater detail above.

A system for TES using configurations such as configuration 6 may include a set of eyeglasses or other worn band, assembly, or cap that holds the electrodes in place. For instance, sunglasses or 'shutter shades' can be used to hold a nasal electrode and forehead electrode firmly in place.

Electrode Placement and Nerve Stimulation

As mentioned above, in any of the methods described herein, one or more of the electrodes (or arrays of electrodes) may drive stimulation as described herein specifically of one or more of the subject's trigeminal nerve (cranial nerve V), facial nerve (cranial nerve VII), or a nerve (or nerves) of the subject's cervical plexus. Thus, in some variations, these electrode(s) may be positioned on the subject's skin over, immediately adjacent to, or spanning (i.e. with an anode and a cathode on either side of) one or more of these nerves. In addition, the temple/forehead, mastoid region and back of the neck placements described herein may correspond to the facial, trigeminal and/or cervical plexus regions, although other regions on the head and/or neck may also be used to drive simulation of the trigeminal, facial and/or cervical plexus.

Figure 28:
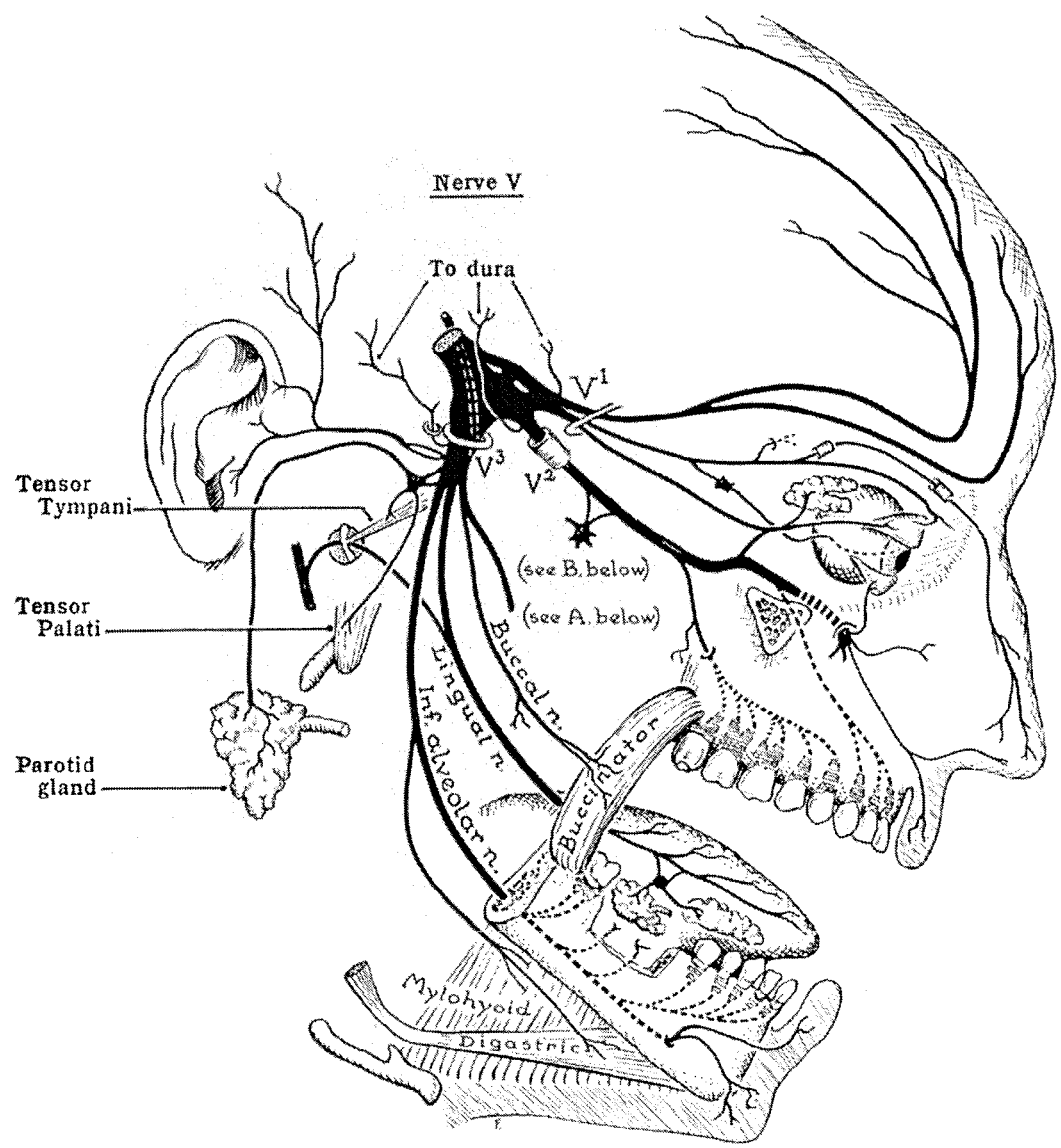
FIG. 28 illustrates an exemplary course of a trigeminal nerve of an adult male (image adapted from "Grant 1962 654" by Grant, John Charles Boileu, "An atlas of anatomy", 1962).
Figure 29:
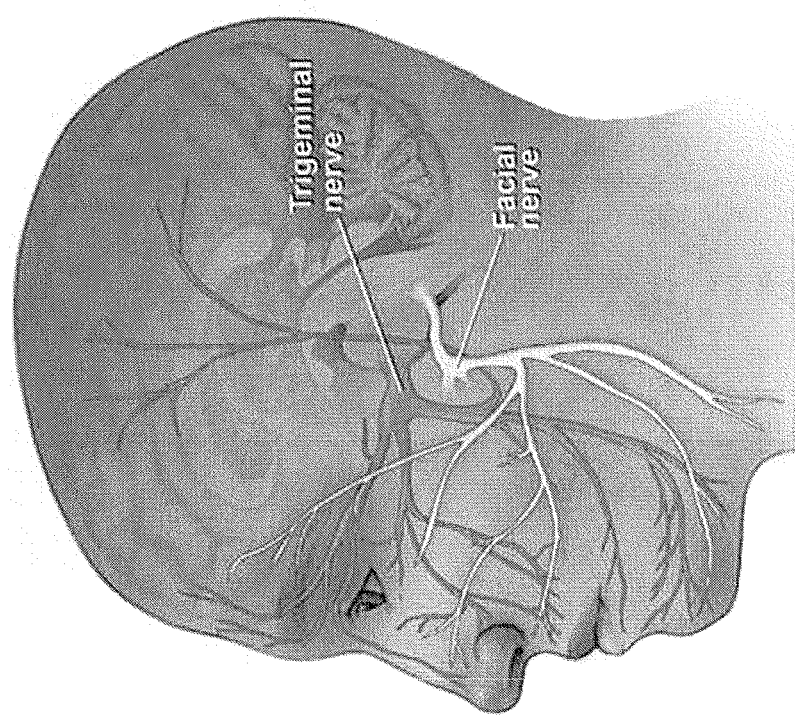
FIG. 29 illustrates an exemplary course of the trigeminal and facial nerves of an adult male (image adapted from Mayo Clinic, https://12cranialnerves.wordpress.com/cranial-nerve-7-facial-nerve/, last visited Aug. 9, 2015).
Figure 30:
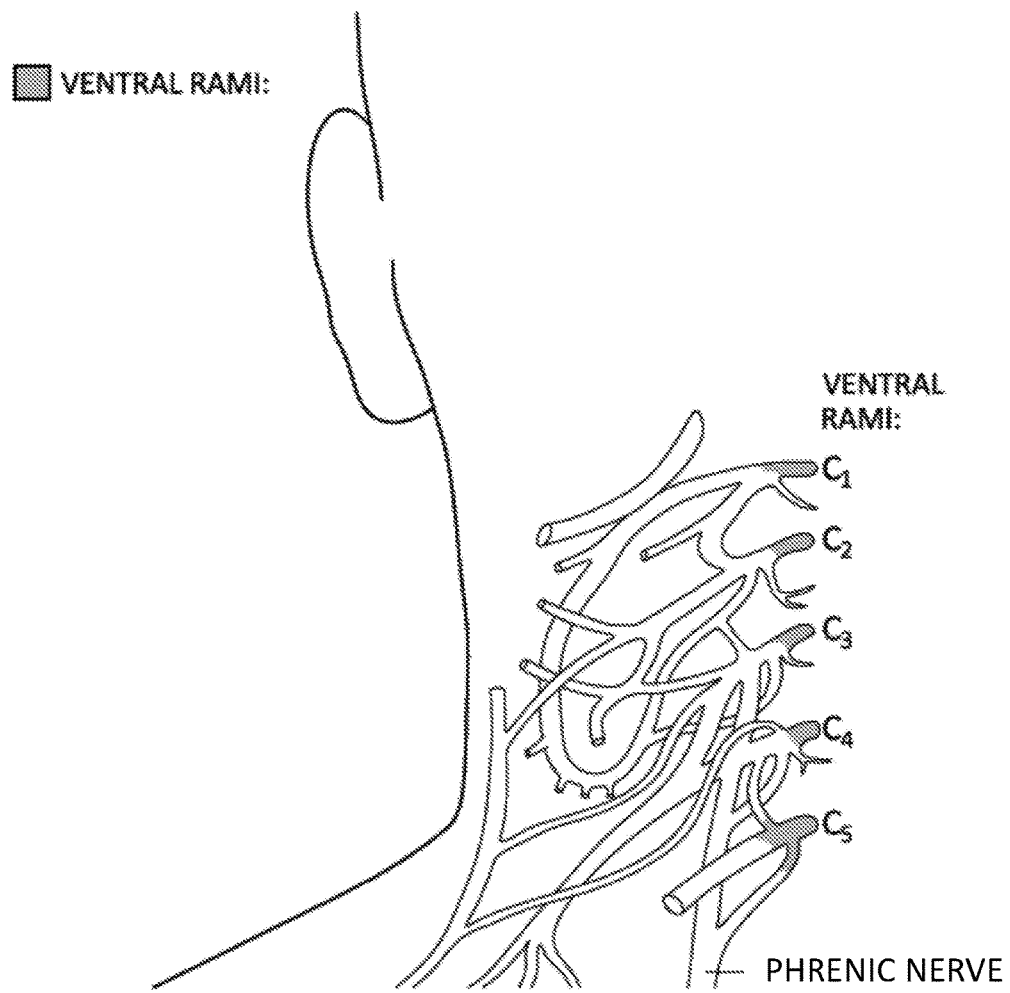
FIG. 30 illustrates an exemplary course of the cervical plexus of an adult male (image adapted from Netter, 1984).

FIGS. 28-30 illustrate general putative locations of the trigeminal nerve (FIGS. 28 and 29), facial nerve (FIG. 29) and cervical plexus (FIG. 30).

For example, the trigeminal nerve (the fifth cranial nerve, or simply CN V) is responsible for sensation in the face and motor functions such as biting and chewing. The largest of the cranial nerves, it has three major branches: the ophthalmic nerve (V1), the maxillary nerve (V2), and the mandibular nerve (V3). The ophthalmic and maxillary nerves are purely sensory, and the mandibular nerve has sensory (or "cutaneous") and motor functions. Sensory information from the face and body is processed by parallel pathways in the central nervous system. The three major branches of the trigeminal nerve—the ophthalmic nerve (V1), the maxillary nerve (V2) and the mandibular nerve (V3), converge on the trigeminal ganglion (also called the semilunar ganglion or gas serian ganglion), located within Meckel's cave and containing the cell bodies of incoming sensory-nerve fibers. The trigeminal ganglion is analogous to the dorsal root ganglia of the spinal cord, which contain the cell bodies of incoming sensory fibers from the rest of the body. FIG. 28 illustrates the trigeminal nerve, including all three branches, in an exemplary adult.

From the trigeminal ganglion a single, large sensory root enters the brainstem at the level of the pons. Immediately adjacent to the sensory root, a smaller motor root emerges from the pons at the same level. Motor fibers pass through the trigeminal ganglion on their way to peripheral muscles, but their cell bodies are located in the nucleus of the fifth nerve, deep within the pons.

The areas of cutaneous distribution (dermatomes) of the three branches of the trigeminal nerve may have relatively sharp borders with relatively little overlap (unlike dermatomes in the rest of the body, which have considerable overlap).

Nerves on the left side of the jaw slightly outnumber the nerves on the right side of the jaw. The ophthalmic, maxillary and mandibular branches leave the skull through three separate foramina: the superior orbital fissure, the foramen rotundum and the foramen ovale, respectively. The ophthalmic nerve (V1) carries sensory information from the scalp and forehead, the upper eyelid, the conjunctiva and cornea of the eye, the nose (including the tip of the nose, except alae nasi), the nasal mucosa, the frontal sinuses and parts of the meninges (the dura and blood vessels). The maxillary nerve (V2) carries sensory information from the lower eyelid and cheek, the nares and upper lip, the upper teeth and gums, the nasal mucosa, the palate and roof of the pharynx, the maxillary, ethmoid and sphenoid sinuses and parts of the meninges. The mandibular nerve (V3) carries sensory information from the lower lip, the lower teeth and gums, the chin and jaw (except the angle of the jaw, which is supplied by C2-C3), parts of the external ear and parts of the meninges. The mandibular nerve carries touch-position and pain-temperature sensations from the mouth. Although it does not carry taste sensation (the chorda tympani is responsible for taste), one of its branches, the lingual nerve, carries sensation from the tongue.

FIG. 29 illustrates both putative locations of the trigeminal nerve and the facial nerve.

The facial nerve is the seventh cranial nerve, or simply cranial nerve VII. It emerges from the brainstem between the pons and the medulla, controls the muscles of facial expression, and functions in the conveyance of taste sensations from the anterior two-thirds of the tongue and oral cavity. It also supplies preganglionic parasympathetic fibers to several head and neck ganglia. The path of the facial nerve can be divided into six segments: intracranial (cisternal) segment; meatal segment (brainstem to internal auditory canal); labyrinthine segment (internal auditory canal to geniculate ganglion); tympanic segment (from geniculate ganglion to pyramidal eminence); mastoid segment (from pyramidal eminence to stylomastoid foramen); and extratemporal segment (from stylomastoid foramen to post parotid branches).

The motor part of the facial nerve arises from the facial nerve nucleus in the pons while the sensory and parasympathetic parts of the facial nerve arise from the intermediate nerve. From the brain stem, the motor and sensory parts of the facial nerve join together and traverse the posterior cranial fossa before entering the petrous temporal bone via the internal auditory meatus. Upon exiting the internal auditory meatus, the nerve then runs a tortuous course through the facial canal, which is divided into the labyrinthine, tympanic, and mastoid segments. The labyrinthine segment is very short, and ends where the facial nerve forms a bend known as the geniculum of the facial nerve ("genu" meaning knee), which contains the geniculate ganglion for sensory nerve bodies. The first branch of the facial nerve, the greater superficial petrosal nerve, arises here from the geniculate ganglion. The greater petrosal nerve runs through the pterygoid canal and synapses at the pterygopalatine ganglion. Post synaptic fibers of the greater petrosal nerve innervate the lacrimal gland.

In the tympanic segment, the facial nerve runs through the tympanic cavity, medial to the incus. The pyramidal eminence is the second bend in the facial nerve, where the nerve runs downward as the mastoid segment. In the temporal part of the facial canal, the nerve gives to the stapedius and chorda tympani. The chorda tympani supplies taste fibers to the anterior two thirds of the tongue, and also synapses with the submandibular ganglion. Postsynaptic fibers from the submandibular ganglion supply the sublingual and submandibular glands. Upon emerging from the stylomastoid foramen, the facial nerve gives rise to the posterior auricular branch. The facial nerve then passes through the parotid gland, which it does not innervate, to form the parotid plexus, which splits into five branches innervating the muscles of facial expression (temporal, zygomatic, buccal, marginal mandibular, cervical).

The facial nerve also includes intracranial branches, such as the greater petrosal nerve, which provides parasympathetic innervation to several glands, including the nasal gland, palatine gland, lacrimal gland, and pharyngeal gland. It also provides parasympathetic innervation to the sphenoid sinus, frontal sinus, maxillary sinus, ethmoid sinus and nasal cavity. This nerve also includes taste fibers for palate via lesser palatine nerve and greater palatine nerve. The facial nerve also includes the nerve to stapedius, which may provide motor innervation for stapedius muscle in middle ear. Another intercranial branch includes the chorda tympani, which may innervate the submandibular gland, sublingual gland and special sensory taste fibers for the anterior ⅔ of the tongue.

The facial nerve may also include extracranial branches (e.g., distal to stylomastoid foramen), and may include nerves branch off the facial nerve such as the posterior auricular nerve (controlling movements of some of the scalp muscles around the ear), a branch to the posterior belly of digastric muscle as well as the stylohyoid muscle, and five major facial branches (temporal, zygomatic, buccal, marginal mandibular and cervical branches).

The facial nerves may be recognized at three landmarks: at the tip of tragal cartilage where the nerve is 1 cm deep and inferior, at the posterior belly of digastric by tracing this backwards to the tympanic plate the nerve can be found between these two structures; and by locating the posterior facial vein at the inferior aspect of the gland where the marginal branch would be seen crossing it.

As illustrated in FIG. 30, the cervical plexus is a plexus of the ventral rami of the first four cervical spinal nerves which are located from C1 to C4 cervical segment in the neck. They are typically located laterally to the transverse processes between prevertebral muscles from the medial side and vertebral (m. scalenus, m. levator scapulae, m. splenius cervicis) from lateral side. There is anastomosis with accessory nerve, hypoglossal nerve and sympathetic trunk. Thus, the cervical plexus may be located in the neck, deep to sternocleidomastoid. Nerves formed from the cervical plexus also innervate the back of the head, as well as some neck muscles. The branches of the cervical plexus emerge from the posterior triangle at the nerve point, a point which lies midway on the posterior border of the sternocleidomastoid.

The cervical plexus may have two types of branches: cutaneous and muscular. Cutaneous branches may include the great auricular nerve (which innervates skin near concha auricle and external acoustic meatus, C2 and C3), the transverse cervical nerve (which innervates anterior region of neck, C2 and C3), the lesser occipital (which innervates the skin and the scalp posterosuperior to the auricle, C2 and C3), and the supraclavicular nerves (which innervate regions of supraspinatus, shoulder, and upper thoracic region, C3,C4). The cervical plexus also includes nerve extending in the musculature, including the ansa cervicalis, phrenic, and segmental branches. Additionally there are two branches formed by roots of spinal nerves: preauricular nerve, and postauricular nerve.

In practice, either or both electrodes (or electrode arrays) may be placed over one or more nerves of the trigeminal, facial and/or cervical plexus, including the locations described above in FIGS. 1A-4H, and 19A-20B, or other locations over, immediately adjacent to, or spanning (i.e. with an anode and a cathode on either side of) these nerves in order to produce the cognitive effects described using any of the stimulation parameters described herein.

Also described herein are methods and apparatuses for transdermal electrical stimulation (e.g., neurostimulation) of a subject. In general, the methods and apparatuses may allow effective neuromodulation with electrical stimulation to induce a beneficial or desired change in cognitive function and/or cognitive state.

TES Apparatuses with Physiological Measurements from a User

TES stimulation is known to modulate autonomic nervous system activity (i.e. see U.S. Provisional Patent Application No. 62/166,674 by named inventors of this invention, filed May 26, 2015, titled "SYSTEMS AND METHODS FOR SUPPRESSION OF STRESS RESPONSES BY TRANSDERMAL ELECTRICAL NEUROMODULATION"). Physiological monitoring that incorporates one or more sensor to measure an aspect of a user's physiology, behavior, etc. that correlates with autonomic nervous system modulation may be beneficial for optimizing the positioning of TES electrodes and for optimizing one or more waveform parameter (i.e. intensity, frequency, bursting duty cycle, etc.), as well as for providing feedback to a user (i.e. to encourage their continued use of the system, prove to themselves and others that TES is in fact modifying their cognitive state and physiology, etc.).

Figure 36A:
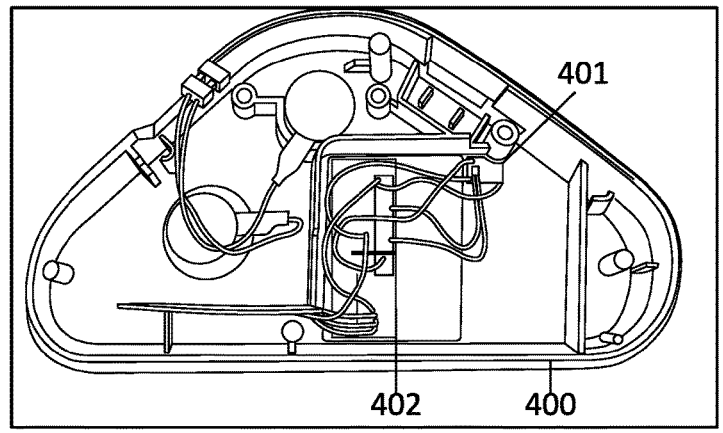
FIGS. 36A-36C show images of a prototype neurostimulator system adapted for optical monitoring of a user's heart rate.
Figure 36B:
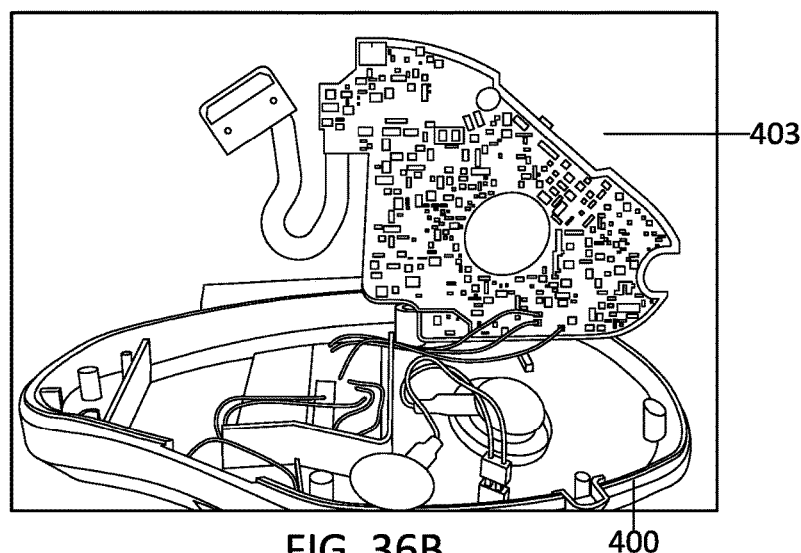
Figure 36C:
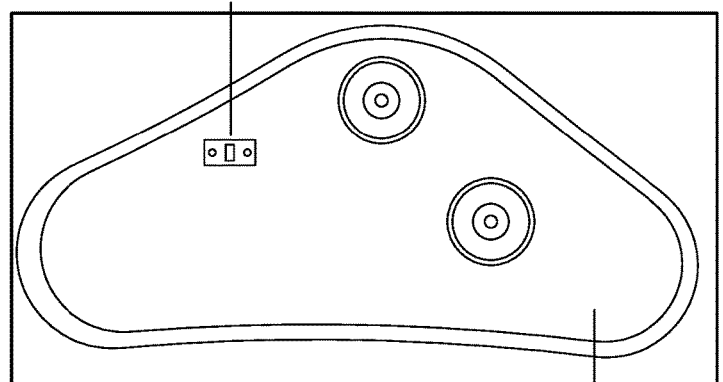

FIGS. 36A-36C show images of a prototype neurostimulator system adapted for optical monitoring of a user's heart beats. Appropriately matched LED emitter-diode pair 401 is mounted through neurostimulator enclosure 400 (or optionally through a portion of the enclosure sufficiently transparent for the transmitted and reflected light wavelengths) as shown in FIG. 36C. Wires, cables, or another conductive path connects the emitter-diode pair to a power source (i.e. battery, not shown in FIGS. 36A-36C) and control circuitry 402 for detecting heart beats based on changes in reflection of the transmitted wavelength (according to the well-known techniques of plethsymography). FIG. 36A is an image showing an internal view of enclosure 400 and LED emitter-diode pair 401. FIG. 4B is another image of an internal view of enclosure 400 and LED emitter-diode pair 401 further showing TES control circuitry (including communication components for wireless control by a user computing device (i.e. via BTLE)) 403.

Facial temperature changes with relatively high signal-to-noise and short latency (generally 10 s of seconds to minutes) can be detected by infrared thermography or by a thermistor component in, on, or coupled near a neurostimulator, electrode apparatus, or other wearable component of a TES system. In an embodiment, a thermistor component at or near the enclosure of a wearable neurostimulator may be used to detect facial temperature changes caused by modulation of smooth muscle on blood vessels and alterations in blood flow. For example, dilation of blood vessels (and increased facial temperature) occurs when sympathetic nervous system activity is suppressed by TES that enhances calmness and related cognitive states as described herein. Conversely, constriction of blood vessels (and reduced facial temperature) occurs for TES that increases sympathetic nervous system activity (including those that enhance states of physiological arousal and related cognitive states as described herein).

Heart rate variability may change after TES that modulates autonomic nervous system activity in a subject. Heart rate may decrease in response to a TES session to enhance physiological arousal that increases sympathetic nervous system activity.

A thermistor for detecting facial temperature or a heart rate sensor (which may measure heart beats optically or electrically) may provide feedback to a user about the effect of a TES session and/or may be used to optimize usage of a TES system (positioning of electrode(s), waveform parameter(s)) in an automated (i.e. closed-loop) fashion by a neurostimulator controller (403) or in a user-actuated manner based on physiological data being displayed on a screen or other user interface.

Electrode Configurations with at Least One Electrode not on the Head or Neck for TES for Modifying a Cognitive State of a User by Suppressing Sympathetic Nervous System Activity Configuration 7

Figure 37A:
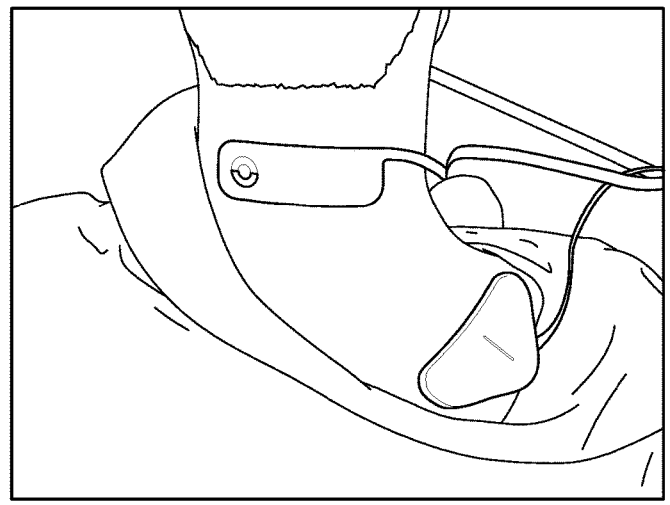
FIGS. 37A-37C and 38A-38D show variations of neck and upper back/shoulder configurations.
Figure 37B:
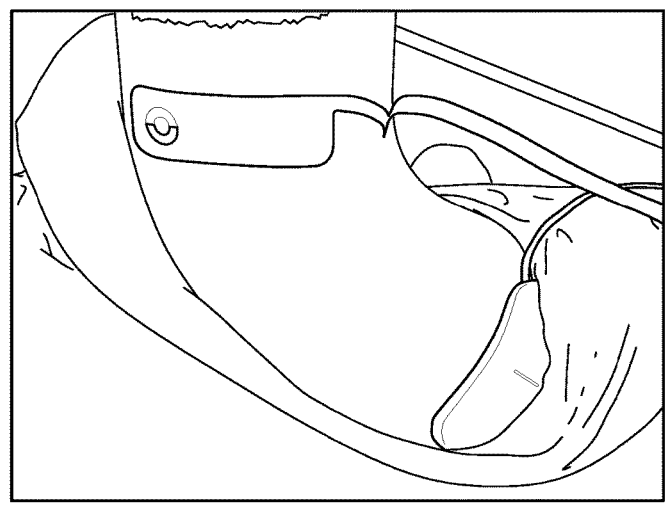
Figure 37C:
Figure 38A:
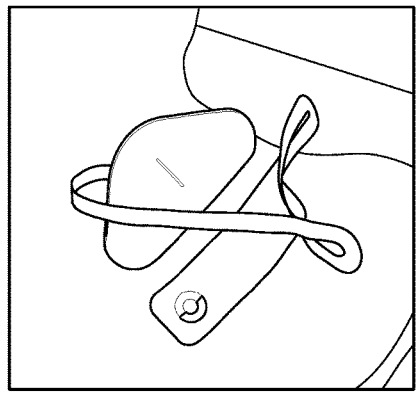
Figure 38B:
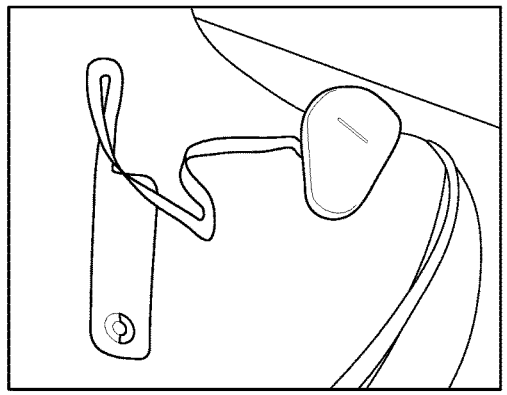
Figure 38C:
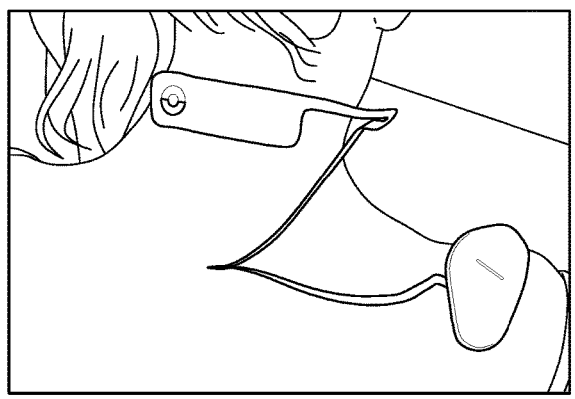
Figure 38D:
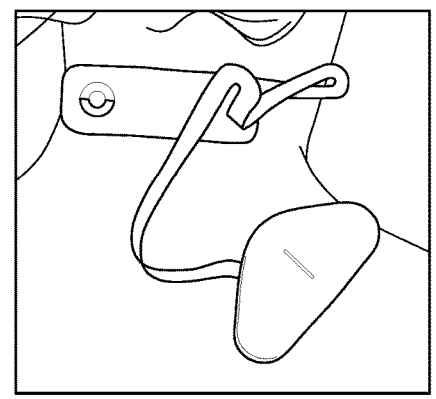
Figure 39A:
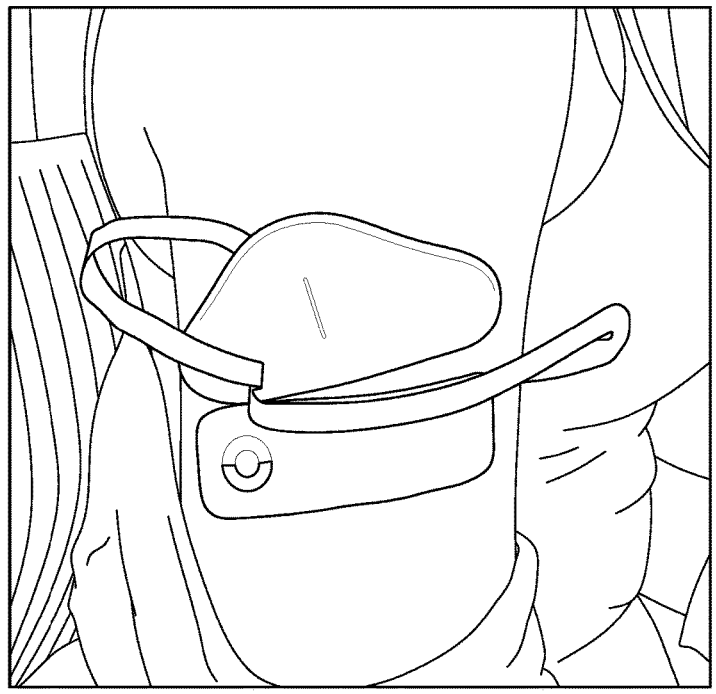
FIGS. 39A and 39B show variations of configurations targeting the arm.
Figure 39B:
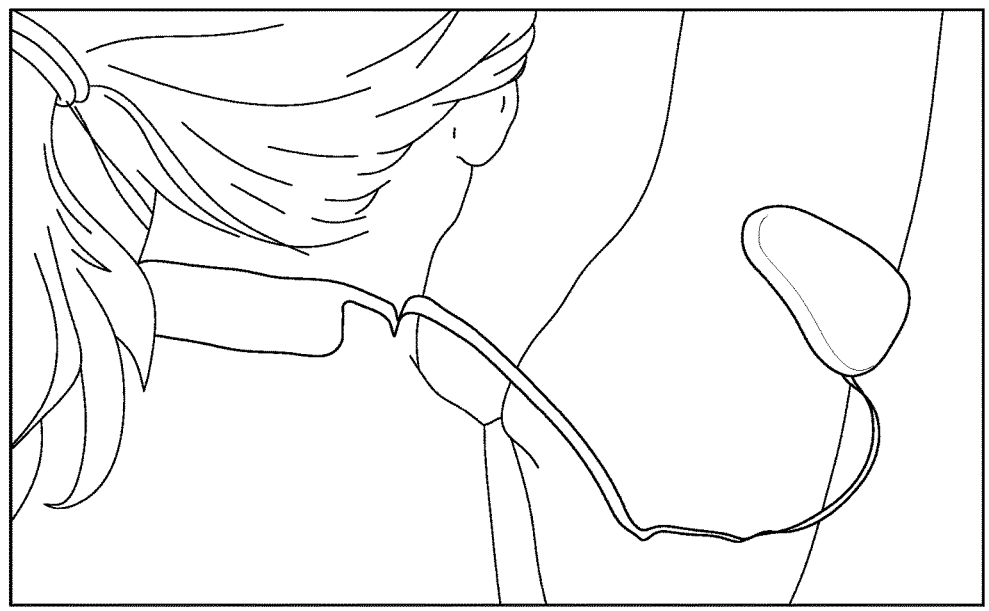
Figure 40A:
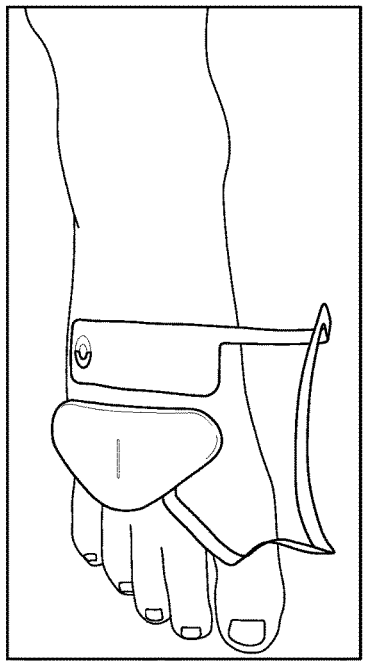
FIGS. 40A-40D show variations of foot configurations.
Figure 40B:
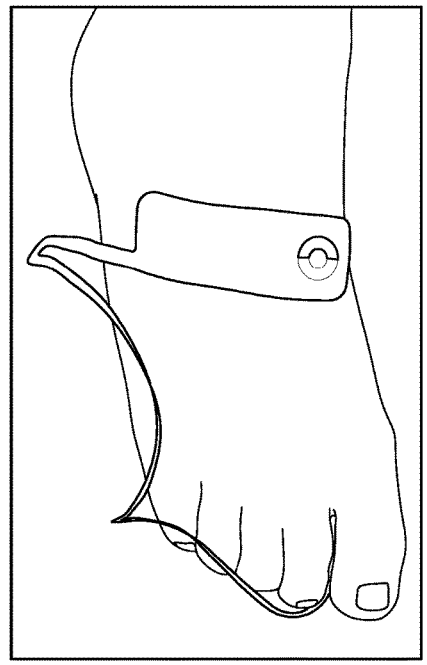
Figure 40C:
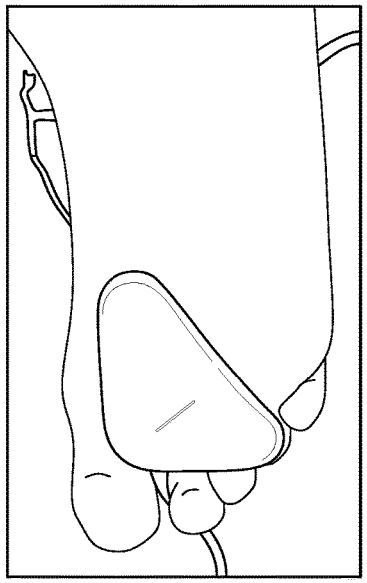
Figure 40D:
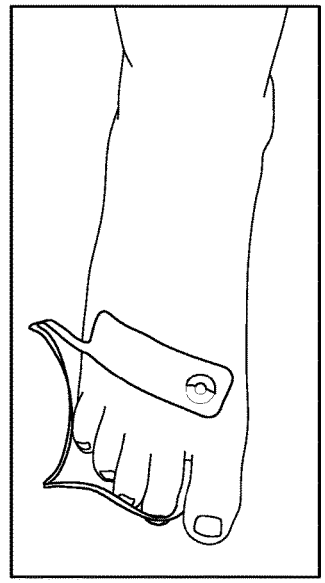
Figure 41:
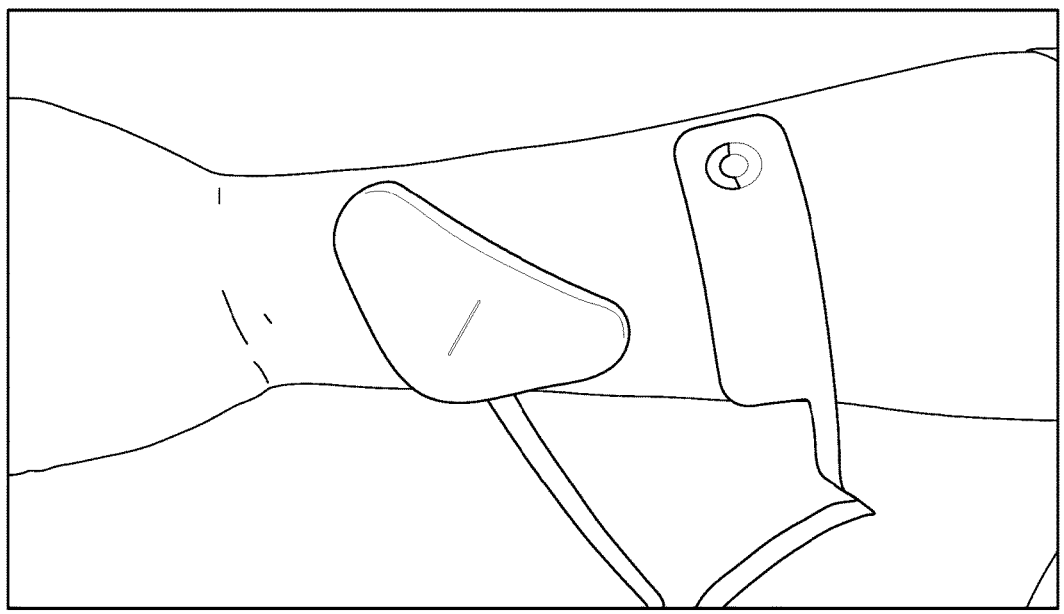
FIG. 41 shows a configuration for targeting the median nerve on the wrist.

For the TES electrode configuration shown in images of FIGS. 37A-37C, the cathode is placed on a subject's the neck, and an anode (with white attached neurostimulator module) is positioned on the subject's shoulder (trapezious (FIGS. 37A and 37B) or front of shoulder (FIG. 37C, rear electrode on back of shoulder not shown)). This positioning targets stimulation to the brachial plexus and other peripheral nerves nearby.

FIGS. 37A and 37B are two effective locations with the anode (and white neurostimulator module) at varying distances from the neck cathode. FIG. 37C is an effective alternative location with the anode (and white neurostimulator module) on the front aspect of the shoulder.

A benefit to configuration 7 relative to configurations for which the anode is placed on the temple or forehead is that by removing the temple/forehead electrode (which can induce a headache or cause periocular muscle contractions and eye twitches for higher current intensities), a higher comfortable peak current can be reached, leading to stronger calming effects (presumably due to greater reductions in sympathetic nervous system activity).

For example, an effective waveform with this montage used the following parameters with an intensity guided by the presence of strong tingling sensations in the trapezious muscle: no capacitive discharge (For at least some subjects, more muscle contraction on neck/shoulder occur with capacitive discharge waveforms. These sensations may be distracting and uncomfortable and thus less effective for inducing calm effect); 2-5 mA peak intensity; 400 Hz pulsing; 30-40% duty cycle; 30% charge imbalance; 40 Hz bursting (AKA amplitude modulation); and 75% bursting duty cycle (AKA amplitude modulation duty cycle). Searching within a range between 50-90% bursting duty cycle can be useful for identifying an optimal waveform for a particular individual. Moreover, shifting back and forth within the range of 50-90% bursting duty cycle may lead to stronger effects in at least some cases.

Various 'Off-the-Head' Electrode Configurations

States of enhanced calm may be induced by stimulating known acupressure points off of the head. Effective waveforms use pulsing at 400-750 Hz or at 5-12 kHz.

FIGS. 34A-34D show variations of neck and upper back/shoulder configurations. The neurostimulator module is placed over the pressure points at the top of the shoulder blade or directly to the upper side of the shoulder blade.

FIGS. 7A and 35A show variations of configurations targeting the arm. The neurostimulator module should be placed directly over the pressure point at the front of the arm about ⅓ of the way down from the shoulder and the back.

FIGS. 36A-36D show variations of foot configurations.

Microneurographic Recordings of Muscle Sympathetic Nerve Activity to Assess TES Effect and Optimize TES Protocols Sympathetic nervous system activity can only be directly assessed through neurophysiological recordings from sympathetic nerve fibers or from plasma measurements of norepinephrine spillover. Of the two, recording of muscle sympathetic nerve activity has higher temporal resolution and is both easier technically and provides real-time data. Accordingly, direct microneurographic recordings of muscle sympathetic nerve activity (MSNA) are considered the gold standard for assaying sympathetic outflow or tone. The method of performing intra-nerve bundle recordings of sympathetic nerve activity is well-established and has been used for decades to study autonomic function.

Microneurographic recordings of MSNA are most typically made from the peroneal nerve near the knee involving a mostly painless technique. MSNA is known to correlate with cardiovascular function, plasma norepinephrine concentrations and sleep/wake cycles, and anesthetic state. For example, depending on the conditions and physiological variables, general anesthetics reduce MSNA by as much as 50-80%.

In general, a TES system may incorporate an MSNA recording to assess the effectiveness of neuromodulation. In general, methods for assessing TES for modulating sympathetic nervous system activity are also described herein. For example, MSNA recordings were made from a subject before, during, and after receiving transdermal electrical stimulation using an anode location on the temple/forehead and a cathode electrode on the neck. The TES waveform was 10 minutes in duration with an asymmetric biphasic pulsed waveform at a frequency of 500 Hz and a peak current greater than 2 mA with capacitive discharge during each cycle. (Though other waveform parameters for enhancing a state of calm as described herein that suppress sympathetic nervous system activity would likely suppress MSNA in a similar fashion.)

Figure 42A:
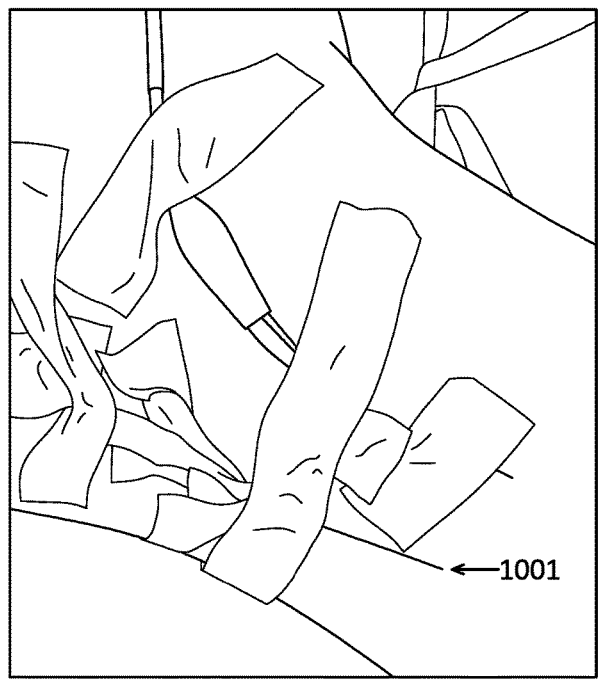
FIG. 42A is an image of a subject's knee showing the electrode position for microneurographic recordings of muscle sympathetic nerve activity (MSNA).
Figure 42B:
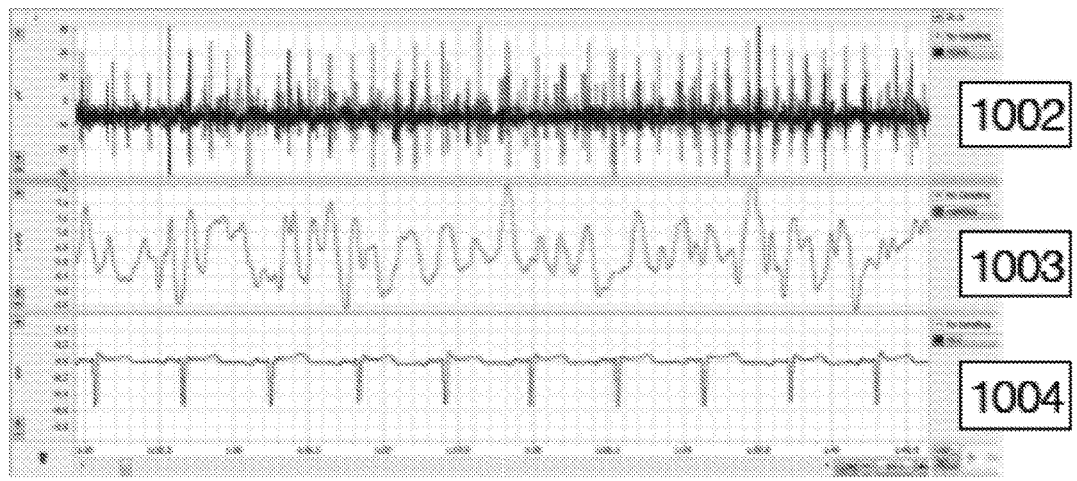
FIG. 42B shows sample electrophysiological MSNA recording.

Intra-nerve bundle recordings of sympathetic nerve activity were made from a subject's leg with a standard electrophysiology rig. FIG. 42A is an image of a subject's knee showing the electrode position for microneurographic recordings of muscle sympathetic nerve activity (MSNA)

with electrode position indicated by arrow 1001. FIG. 42B shows a sample electrophysiological MSNA recording from this subject, including raw MSNA spiking activity (top, 1002), smoothed inter-spike intervals (middle, 1003), and ECG (bottom, 1004).

Figure 43A:
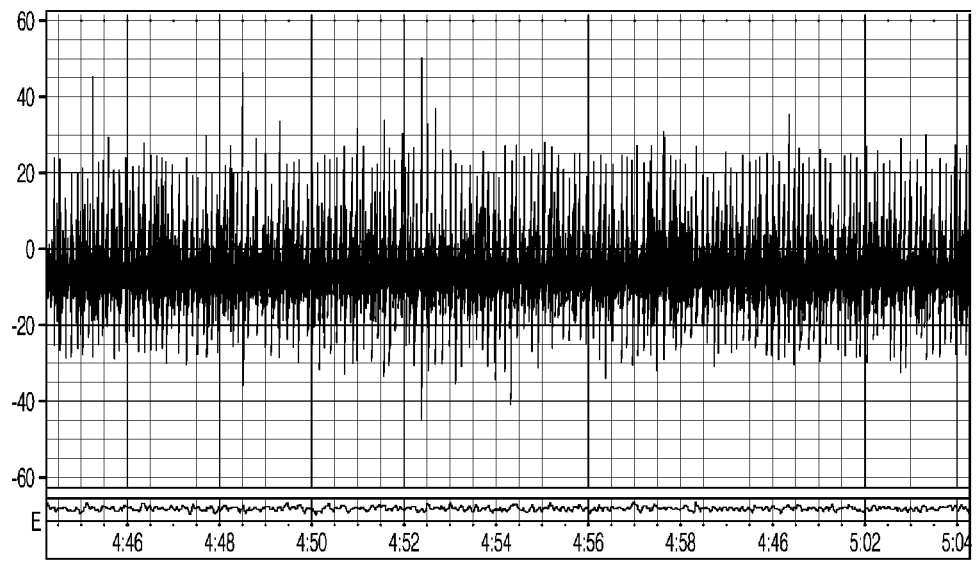
FIGS. 43A and 43B show sample baseline MSNA recording at two different temporal scales.
Figure 43B:
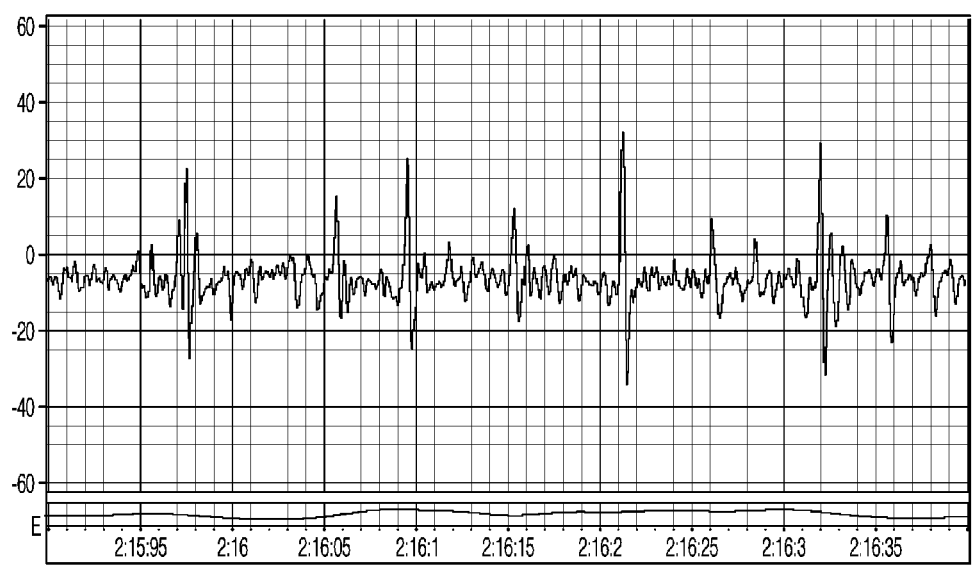
Figure 44A:
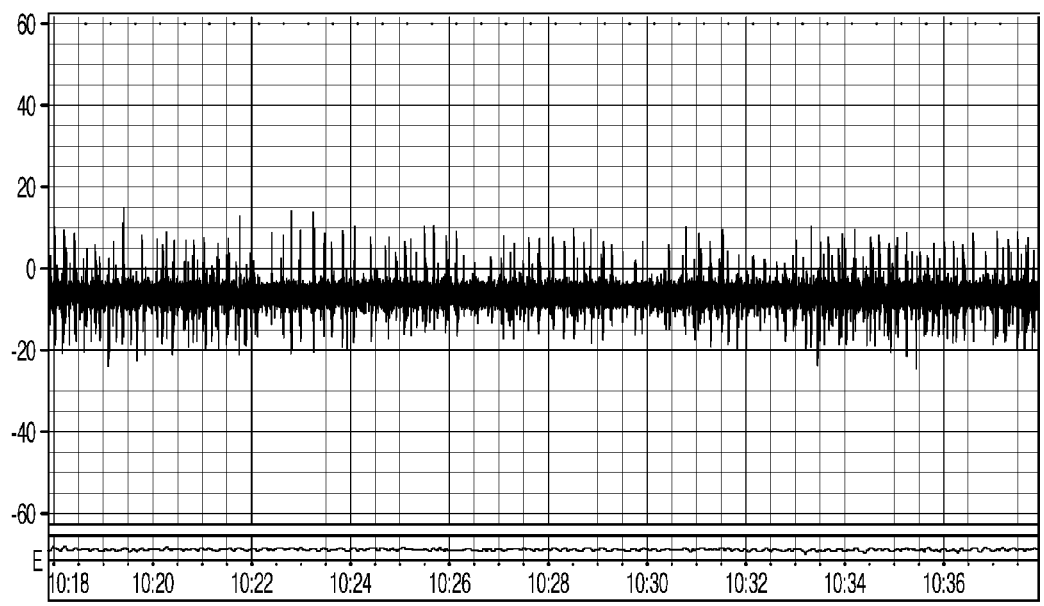
FIGS. 44A and 44B show sample MSNA recording at two different temporal scales during a TES session.
Figure 44B:
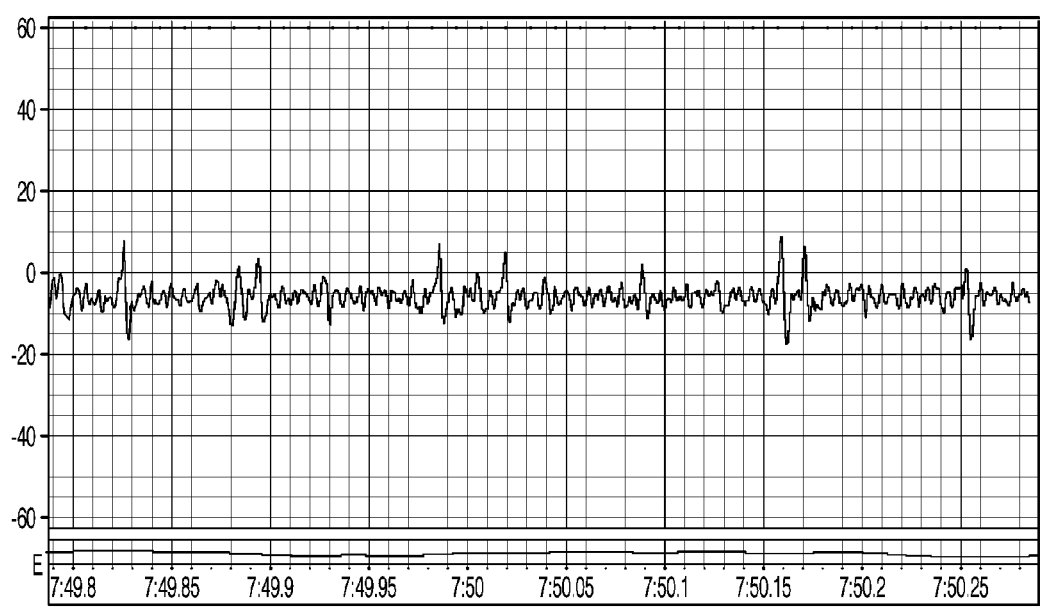

FIGS. 43A and 43B show sample baseline MSNA recording at two different temporal scales. The individual spikes are easily resolvable and can be analyzed for amplitude and other parameters during and after a TES session. During a TES session configured to inhibit sympathetic activity and induce a state of enhanced calmness, the size of spontaneous MSNA spikes is reduced. FIGS. 44A and 44B show sample MSNA recording at two different temporal scales during a TES session.

Figure 45A:
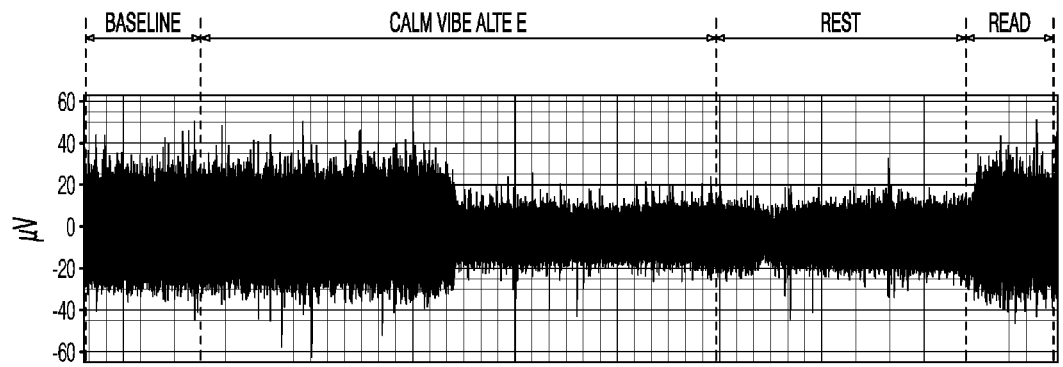
FIGS. 45A and 45B show long timescale (10 s of minutes) MSNA before, during, and after a TES session.
Figure 45B:
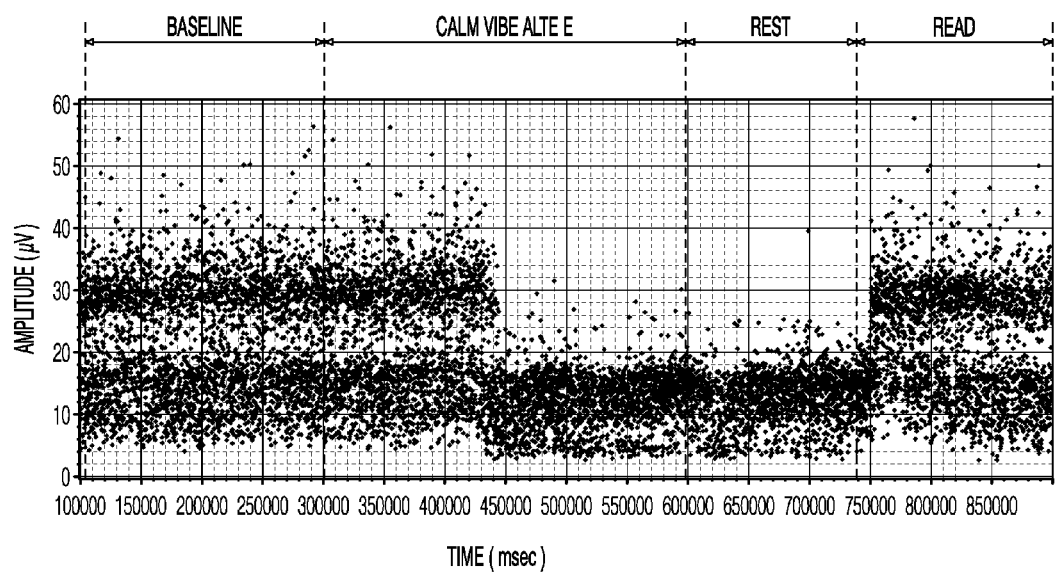

FIGS. 45A and 45B show long timescale (10 s of minutes) MSNA before, during, and after a TES session. The reduction in spontaneous MSNA activity is large, indicating substantial inhibition of sympathetic activity. With a latency of several minutes after the onset of stimulation, a 28% reduction in MSNA peak amplitude was observed relative to baseline (baseline MSNA spike average peak=14.87 microvolts; during a TES session for enhanced calmness that inhibits sympathetic nervous system activity MSNA spike average peak=10.64 microvolts).

Figure 46:
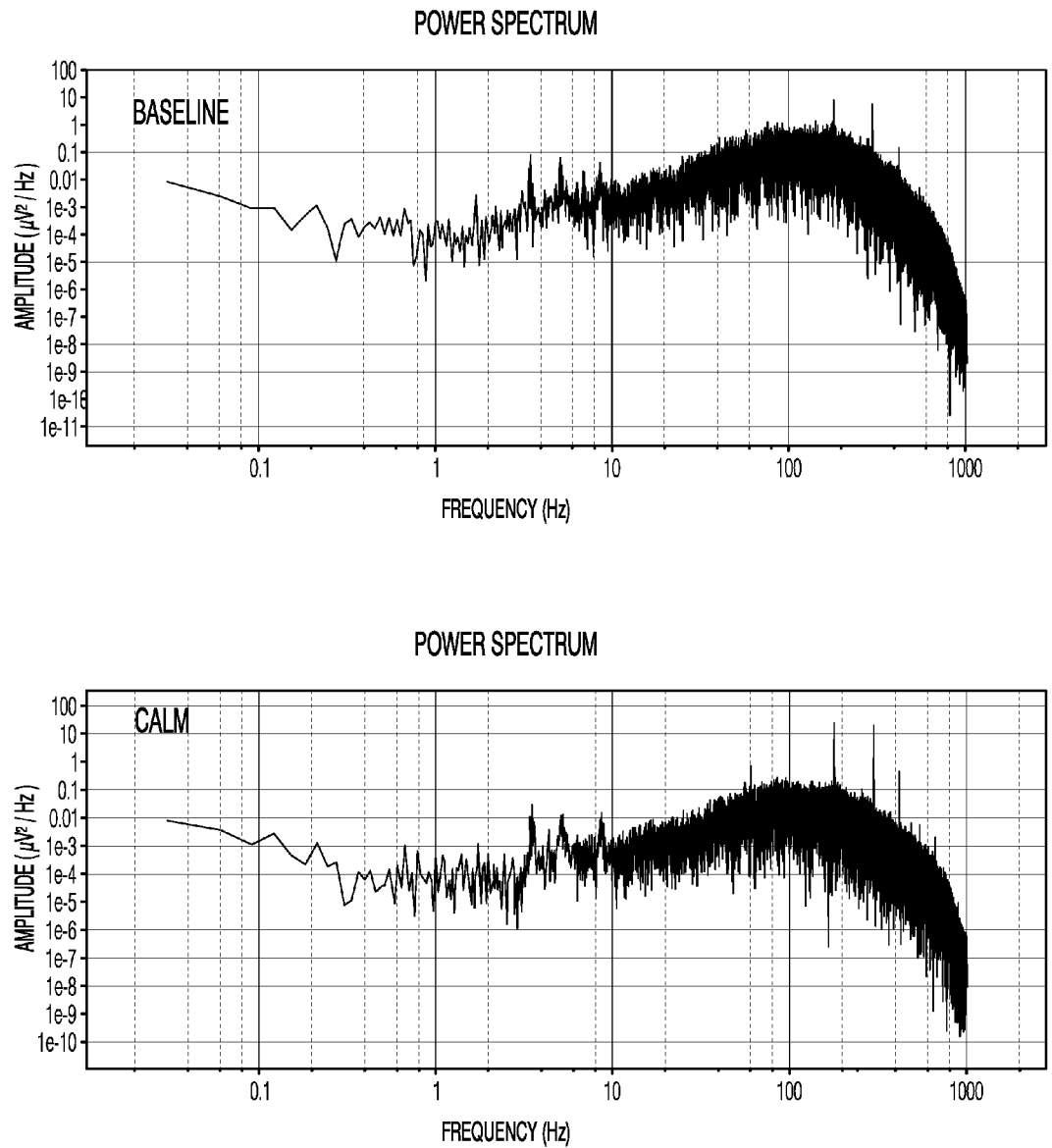
FIGS. 46 and 47 show power spectrum plots of MSNA recordings before ('baseline') and during ('calm') a TES session.
Figure 47:
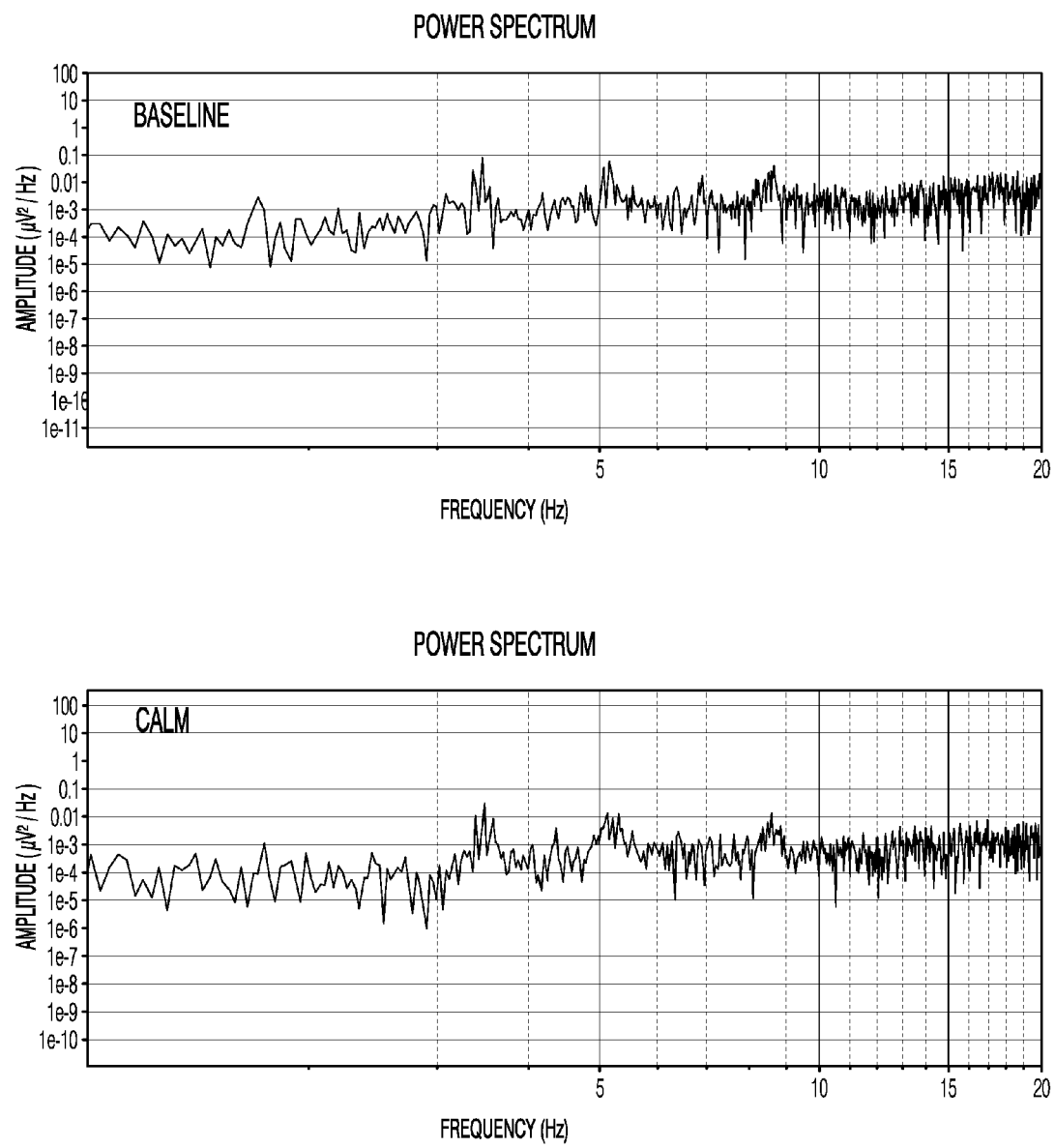
Figure 48A:
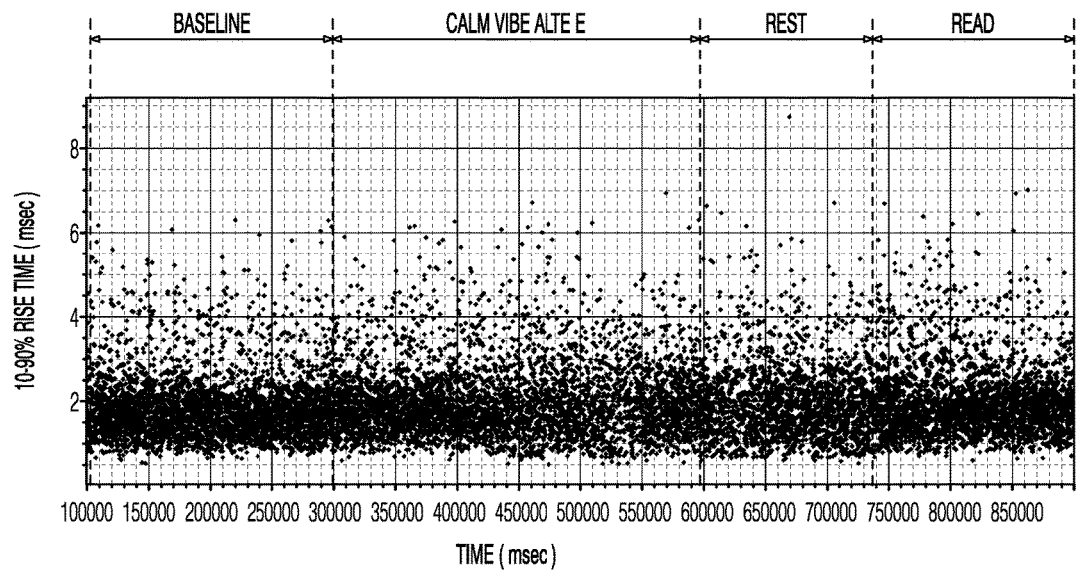
FIGS. 48A-48C are plots showing parameters of MSNA spikes before, during, and after a TES session.
Figure 48B:
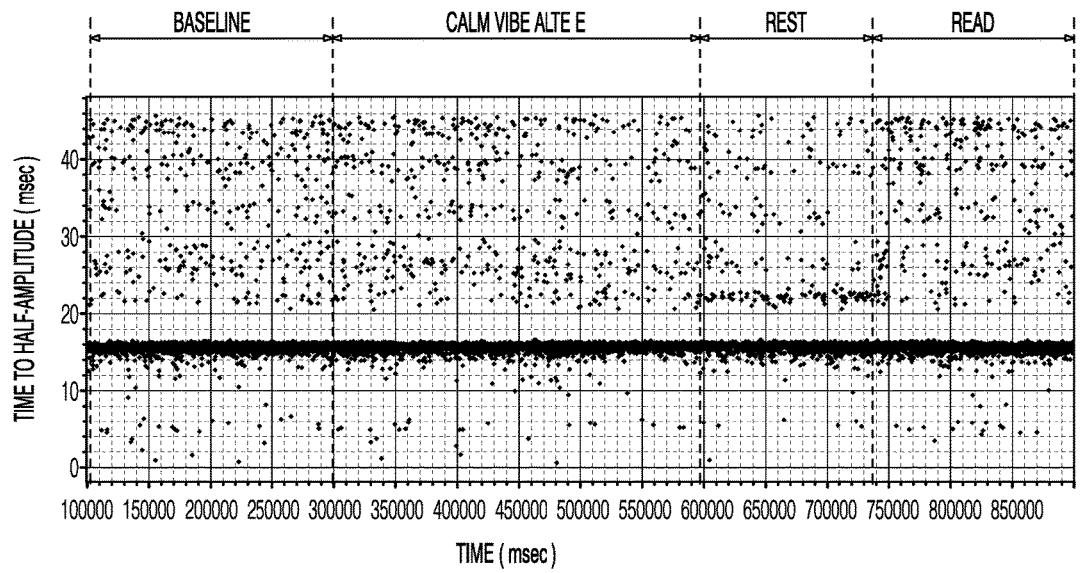
Figure 48C:
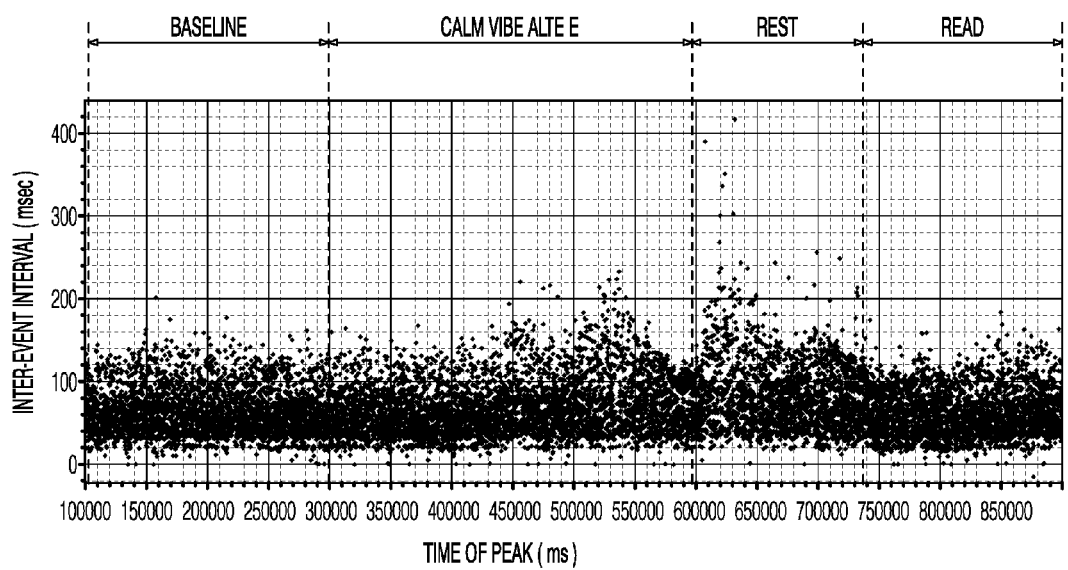

This reduction was not associated with an alteration in spike kinetics (10-90% rise time (FIG. 48A); time to half-amplitude (FIG. 48B)) or the power spectrum of spontaneous MSNA events (FIGS. 46 and 47). A slight reduction in the frequency of spontaneous MSN discharges was observed by plotting the inter-event intervals before during and after the TES session (FIG. 48C). In summary, these results show clear, direct physiological evidence that this TES configuration and waveform inhibit sympathetic nervous system activity.

System configurations that permit MSNA activity for optimizing electrode positions, waveform parameters, or other features of a TES session would be beneficial for enhancing the extent of sympathetic modulation—and include closed-loop systems that iterate through electrode locations (e.g. via an array) and/or waveform parameters while monitoring MSNA from a subject in real-time to identify optimal TES protocols.

Pulsing Strategies for Effective and Comfortable TES Waveforms

Some neurostimulators for TES described herein apply constant current, and effective waveforms with different parameters appear consistent with respect to pulsing when considering the voltage applied across the transdermal electrodes. For example, pilot studies suggest that voltage-defined waveforms may be most effective across a range of stimulation (pulsing) frequencies (i.e. 500 Hz (or lower) to 11 kHz (and higher) and amplitude modulation (bursting)) based on the pattern of applied voltage on the electrodes. Despite wide variation in current waveform parameters (pulse width, frequency, presence or absence of bursting), the voltage waveform is approximately conserved across effective calm waveforms.

Monopolar waveforms (or predominately monopolar; i.e. highly asymmetric waveforms) are most effective for inducing a state of calmness. Low duty cycle waveforms can be effective so long as the pulses delivered fit criteria as described below. In these embodiments, each pulse should rapidly rise to the highest voltage the neurostimulator can produce and then drop to zero volts as quickly as possible. If high voltage is not reached during a pulse, only a weak cognitive effect of enhanced calmness (i.e. reduced sympathetic nervous system activation) occurs. As soon as the rate of change of voltage slows (i.e. due to approaching voltage limits of the neurostimulator system), optimal calm-inducing waveforms end the stimulation pulse.

Once voltage has stopped increasing at a significant rate, little benefit follows from continued stimulation (further extending the duration of a pulse) at the approximately constant voltage. Rather, staying at that fixed higher voltage may cause discomfort and increased sympathetic activation, thus working at cross purpose to the sympathetic-inhibiting 'calm' waveforms. Thus, the optimal pulse-shaping strategy for calm waveforms is to end the pulse quickly, which can be achieved most immediately with a capacitive discharge (or other electrical circuit mechanism that reverses charge, including capacitive charge built up in the body and electrode, rapidly). The voltage plateau is an indication that the system is no longer capable of ramping to higher currents (voltages) quickly and short circuiting (i.e. capacitive discharge) should commence. This feature of the waveform motivates why personalization of calm waveforms benefits from instructions, guidance, and practice to find the 'sweet spot' current intensity at which maximum voltage is achieved (without discomfort). Across individuals, electrode impedance varies (and may also vary across sessions for an individual—for example if lotion or makeup is present on the subject's skin for one session but not another). Thus, the optimal 'sweet spot' current level may vary between individuals and sessions as impedance varies for constant current neurostimulators (in order to deliver voltage waveforms similar to FIG. 49A).

For example, at low frequency the voltage rise time is slower but the overall positive pulse duration is longer. In contrast, effective high-frequency waveforms have a faster voltage rise time but short positive pulse duration (i.e. >5 kHz as high frequency and greater, though one skilled in the art of waveform design recognize a gradual transition between 'low-frequency' and 'high-frequency' properties). The shape of the individual pulses is the key factor in this paradigm, rather than their frequency of repetition or whether there is bursting (i.e. an additional modulation of the waveform at a lower frequency).

In general, temporal gaps between pulses are not a bad thing and may in fact lead to increased comfort (for example due to less average current delivered) without diminishing the effectiveness of the waveform for inducing a state of calmness and reduced sympathetic activation.

With the electrical circuit and control firmware of the neurostimulator as described herein and in related filings referenced above, effective waveforms as described above can be achieved at low-frequency by reducing the duty cycle for decreasing pulsing frequency (for example one adjustment scheme may maintain similar pulse durations though nonlinear or sublinear duty cycle adjustment schemes as a function of decreasing frequency).

In contrast, high-frequency stimulation regimes (i.e. 5 kHz+, especially waveforms in the 7 kHz to 20 kHz range and higher) require bursting in order to make stimulation comfortable while still delivering pulses (bursting improves comfort because fewer pulses are delivered per second yet the pulses that are delivered are shaped appropriately for effectively activating peripheral nerves (i.e. cranial and cervical spinal nerves) to induced a state of enhanced calmness.

In summary, short, high-voltage pulses are key. At high stimulation frequencies (i.e. kHz), the nerve cannot follow these frequencies so bursting is equally effective for nerve modulation while minimizing total charge transfer, thus reducing discomfort (which can induce counter-productive sympathetic nervous system activation), reducing power requirements, and increasing the usable life of pH-buffering electrodes with consumable electrochemistry.

In summary, the relevant constraint is whether the waveform reaches peak voltage (~50V for the current puck). The time for ramp up to peak voltage is dependent on current. At higher frequencies, such as 10 kHz, high currents (e.g. 20 mA) allow this to occur in about 40-50 microseconds. At low frequencies, such as 500 Hz, low currents (e.g. 5 mA) can take several hundred microseconds for this to occur. Once peak voltage is reached, it is best to immediately turn on capacitive discharge (i.e. big negative current) to bring voltage back to zero and thus ensure comfort. Peak voltage requires a certain amount of charge transfer (time defined by current level) to charge up capacitance and reach high voltage, at least for our constant current system. Neurostimulator systems that operate at higher voltage (i.e. 80V or 100V or higher) may modulate targeted peripheral nerves more strongly to enhance calmness more effectively.

Another potential advantage of effective waveforms is the potential to generate them with a simplified, more power-efficient circuit. The waveforms as described above can be generated by an "inductor based direct pulsing" circuit idea proposal with a fraction of the cost, and a fraction of the circuit board area of the actual product. This circuit could not generate a wide range of different waves, but exactly the shark fin shape described, followed by a short-circuit, with any kind of burst modulation patterns. The exact shape of the waveform would depend on the user impedance. The peak voltage can be controlled by the circuit on demand. This circuit would not need any power converter and would be more efficient.

Figure 49A:
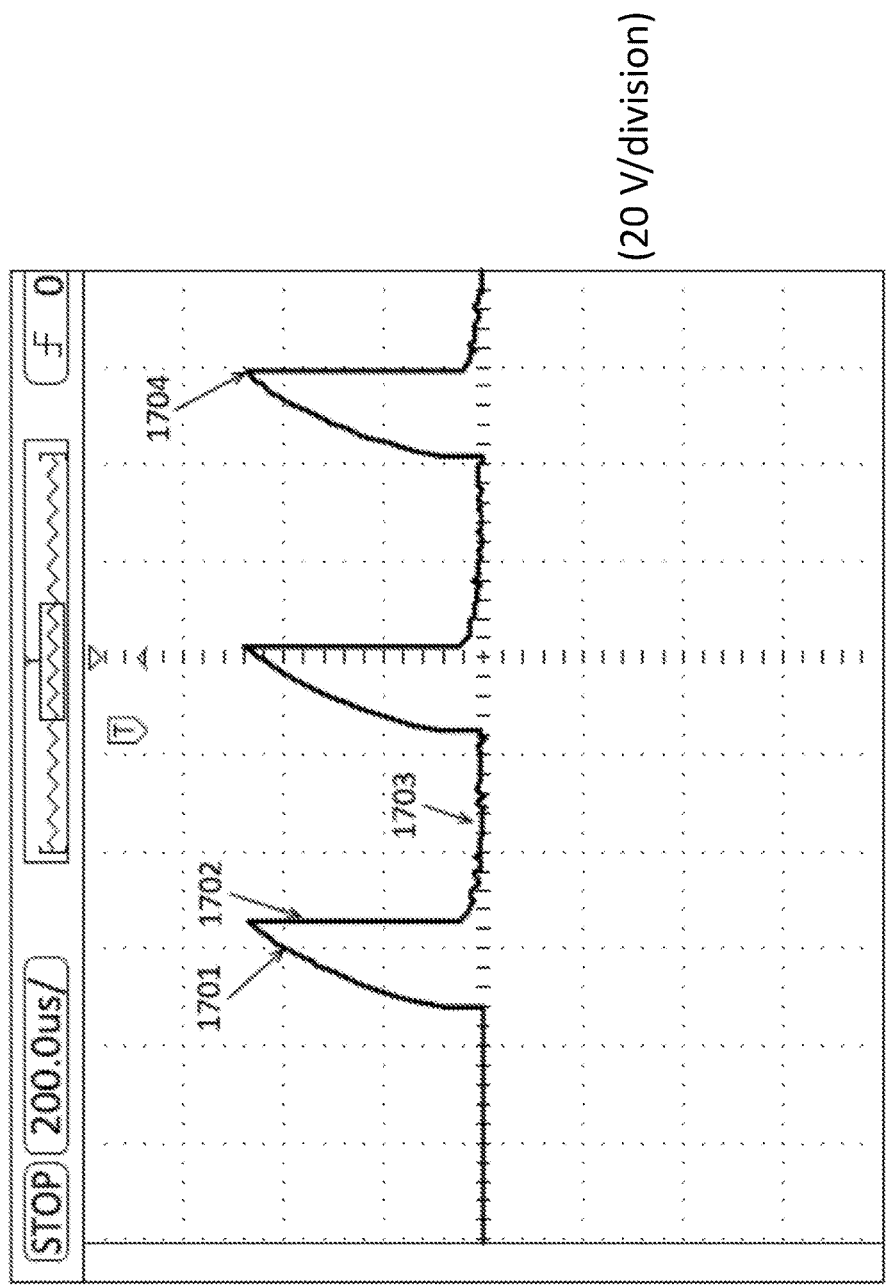
FIGS. 49A-49E show exemplar (FIG. 49A) and schematic representations (FIGS. 49B-49E) of effective pulsing regimes for inducing cognitive effects via the neurostimulator and electrode apparatus systems as described herein.
Figure 49B:
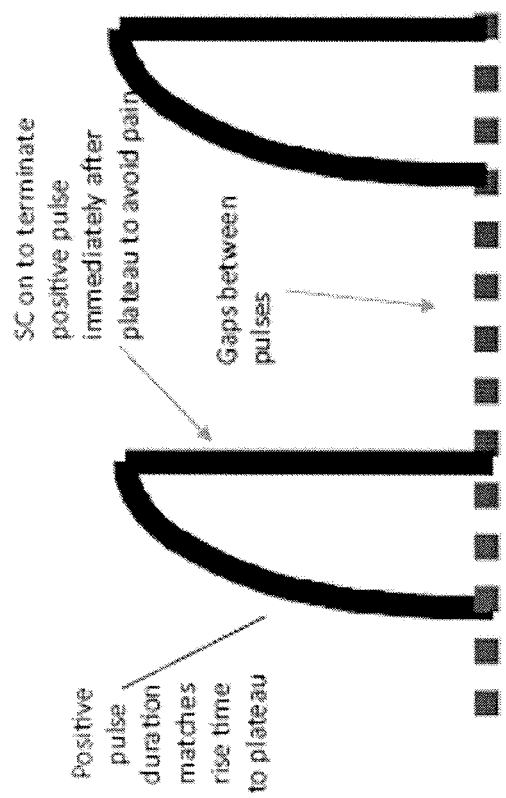
Figure 49C:
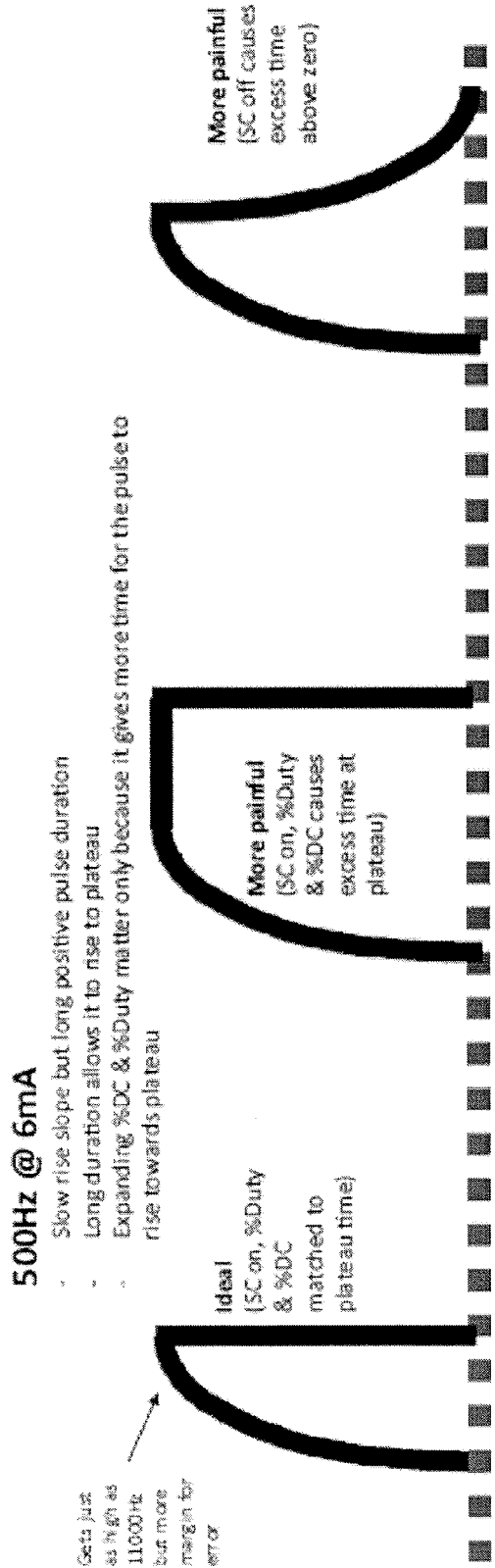
Figures 49D, 49E:
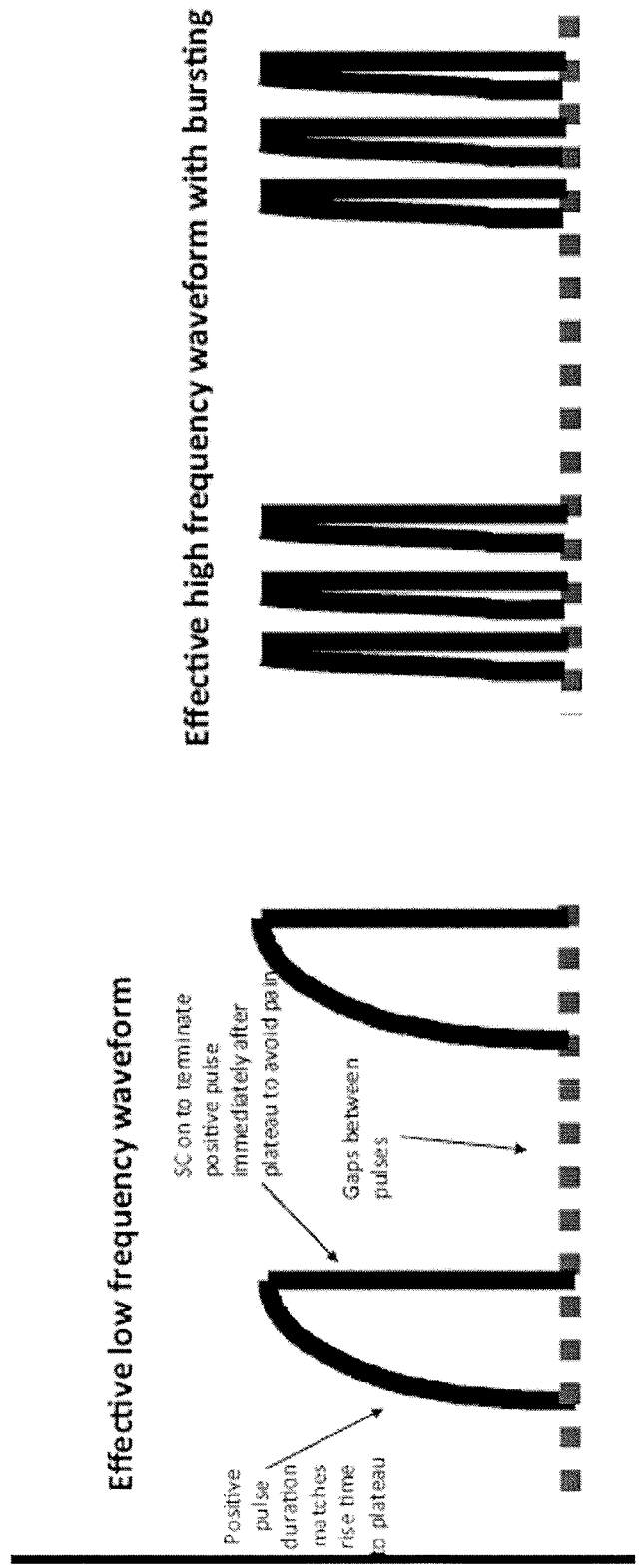

A voltage waveform of pulses for effectively suppressing sympathetic nervous system activity and inducing a state of enhanced calmness in a subject is shown in FIG. 49A. Waveform component 1701 shows how the pulse length is selected to be sufficiently long so that sufficient time elapses for the pulse to reach high voltage. Waveform component 1702 shows rapid offset of pulse facilitated by activating capacitive discharge circuit immediately after voltage starts to plateau at the end of the pulse. For a TES waveform to approximately reach the peak voltage of the neurostimulator system requires a certain amount of charge transfer (amount of time defined by current level) to charge up capacitance in body (i.e. skin) and reach high voltage, at least for systems designed to deliver constant current, including those described herein. Waveform component 1703 identifies the pause between pulses. For at least some effective TES waveforms for suppressing sympathetic nervous system activity, no negative pulse needed and gaps between pulses (i.e. bursting and/or low duty cycle) does not limit the effectiveness of the TES waveforms. Waveform component 1704 shows that, for this TES waveform effective for suppressing sympathetic nervous system activity through an anode electrode on the temple/forehead and a cathode electrode on the neck, the peak voltage reached is about 50 V, which is near the peak electrode supply voltage of the system. FIGS. 49B-49C indicate waveform features for effectively modulating sympathetic nervous system activity via TES. The schematics of TES pulses shown in FIGS. 49D-49E illustrate how waveforms with gaps (i.e. pauses) between pulses are effective for TES to suppress sympathetic nervous system activity through an anode electrode on the temple/forehead and a cathode electrode on the neck.
Effective TES Waveforms for Modulating Cognitive State, Including Suppressing Sympathetic Nervous System Activity, Using Pulsing at 150 to 750 Hz In general, a TES waveform having a pulsing frequency between 150 to 750 Hz may be effective for inducing a shift in cognitive state, including TES waveforms for modulating the activity of the autonomic nervous system.

Figure 50B:
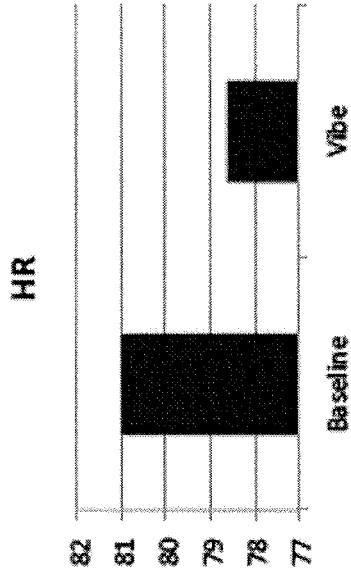
FIGS. 50A-50D show heart rate and heart rate variability for a baseline condition and a TES waveform having a pulsing frequency of 500 Hz.
Figure 50D:
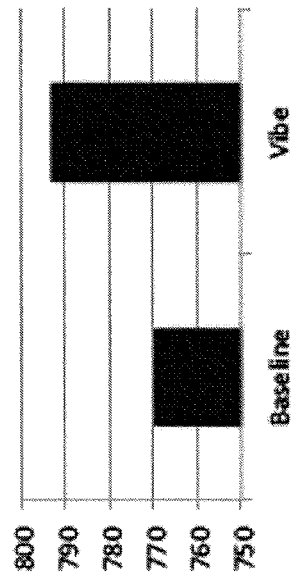
Figure 50A:
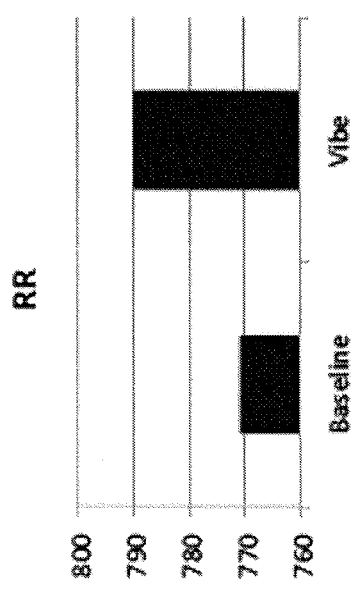
Figure 50C:
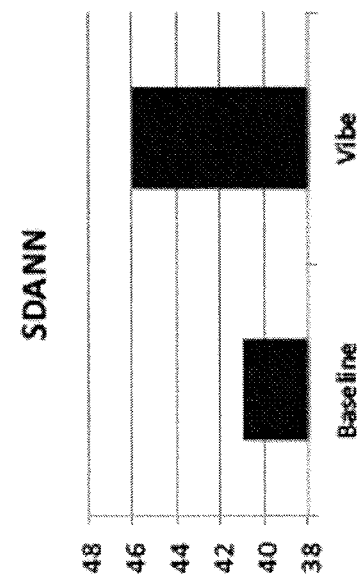

For example, a waveform with a peak current of 2-3.5 mA (intensity controlled by the subject), 500 Hz pulsing frequency, 35-45% duty cycle, 3% charge imbalance, and capacitive discharge during each stimulation cycle is effective for increasing RR intervals (FIG. 50A), reducing heart rate (FIG. 50B), and increasing heart variability (SDANN and SDNN, FIGS. 50C-50D). Moreover, these waveforms, when applied through electrodes on the forehead/temple and neck, may induce a significant enhancement of relaxation, including an induction of sleep (or drowsiness).

General Description of a Transdermal Neurostimulator, Electrode Apparatus, Waveforms, and Methods of Using the System In general, a user may wear a neuromodulation device and apply one or more waveforms using the neuromodulation device to induce a cognitive effect. In general, the user may control the wearable neuromodulation device through a user device. A user device may be used to control the applied waveforms ("ensemble waveforms") for use in a transdermal electrical stimulation protocol. A system may include the wearable neuromodulation device, and the user computing device for control of the transdermal electrical stimulation (TES) waveforms.

A time-varying pattern of electrical stimulation delivered transdermally (and, optionally, to some extent, transcranially) to induce neuromodulation may be referred to as a transdermal electrical stimulation waveform ('TES waveform'). A stimulation protocol may define the temporal pattern of current delivered to an anode-cathode set and can incorporate one or more waveform components including but not limited to: direct current, alternating current, pulsed current, linear current ramp, nonlinear current ramp, exponential current ramp, modulation of current (e.g., amplitude modulation at one or more frequencies), pulsed current (e.g., amplitude modulation where part of the modulated cycle is at zero intensity), and more complex time-varying patterns of electrical stimulation (including repeated, random, pseudo-random, and chaotic patterns). In operation, the device may provide current flow at target areas (e.g., in the brain, facial nerves (cranial nerves, brachial plexus nerve(s), and/or cervical spinal nerves), vagal nerve, or other neuronal targets) to induce neuromodulation when appropriate electrode configurations and stimulation protocols are delivered.

TES waveform parameters that may be used to invoke, enhance, or modify a variety of cognitive states may be considered compound waveforms including a number of different sub-portions that are temporally connected together and delivered to a user in sequence. In some variations, more complex waveforms are used for TES, and additional components may be included, such as transient capacitive discharges, multiple pulses per cycle, phase relationships of two or more pulses per cycle, complex pulse shapes, non-sinusoidal alternating current, etc. In some variations, an ensemble waveform (or portion of an ensemble waveform) may be modulated by an envelope of slower-frequency amplitude modulation (e.g., modulation of the current amplitude parameter). For example different types of amplitude modulation may be applied (e.g., amplitude modulation at frequencies between 0.5 Hz and 1000 Hz may be applied on top of the ensemble waveform. In some variations the amplitude modulation is applied as a sinusoidal (e.g., pure sinusoid, sawtooth, square pulses, etc.); in some variations the amplitude modulation is bursting, and results in an amplitude modulation duty cycle, in which stimulation intensity is decreased or turned off for a pre-determined period and switched on for a pre-determined period (where the amplitude modulation duty cycle can be calculated as the on period duration divided by the sum of the on period duration and off period duration).

The TES waveform components described herein may generally be formed of a basic unit comprising a plurality of biphasic pulses that may be asymmetric with respect to positive and negative going phases and may be charge imbalanced (although one or more capacitive discharging pulses may also be included within each repeating pulse to offset a charge imbalance as described herein). The component waveforms described herein may be defined by a duration and a set of waveform parameters including: a peak current amplitude (in mA), a frequency (in Hz or kHz), a percent charge imbalance, and a duty cycle. FIG. 5A schematically illustrates a basic waveform unit. This example shows the basic unit as a combination of square-waves (steps), however, rounded (including sinusoid), sawtoothed, triangular, and other shapes may be used. The waveform parameters for this basic unit waveform are defined by a duty cycle (or percent duty cycle), percent charge imbalance (also referred to as percent direct current, or percent DC), ramping or other amplitude modulation, one or more multiple frequency components, phase relationship of biphasic current, flat or structured noise, wave shapes (i.e., sawtooth, triangular, sine wave, square wave, exponential, or other wave shape), capacitance compensation features, or other parameters as discussed in U.S. patent application Ser. No. 14/091,121, filed Nov. 26, 2013, titled "Wearable Transdermal Electrical Stimulation Devices and Methods of Using Them", which is herein incorporated by reference in its entirety.

In FIG. 5A, the biphasic waveform includes a positive-going pulse having an amplitude $I_{peak}$, and a duration $t_p$ (time spent in the positive direction, relative to baseline), a negative-going pulse having an amplitude (in this example, $I_{peak}$ but in the negative direction) and a duration $t_n$ (time spent in the negative direction, relative to baseline). The total time of the base unit is $t_c$ (time for one period of a cycle).

As used herein, 'percent duty cycle' may refer to the proportion of a cycle of a waveform that causes non-zero (or nominally non-zero) current to be delivered transdermally (though for waveforms incorporating capacitive discharge, the nominally non-zero portion of the duty cycle may not include the non-zero portions of the cycle caused by capacitive discharge). For example, the duty cycle in FIG. 5A is the sum of $t_p$ and $t_n$ divided by $t_c$. Further, the percent charge imbalance (or 'percent direct current') refers to the non-zero portion of a waveform cycle that is positive-going or negative-going (again, excluding capacitive discharges, if present). In FIG. 5A, the percent charge imbalance is the ratio of the difference of $t_p$ and $t_n$ and the sum of $t_p$ plus $t_n$.

Inducing significant, robust, and/or reliable cognitive effects typically requires an appropriate ensemble waveform defined by a set of parameters for each component waveform. A stimulation protocol typically includes a composite waveform that defines the temporal pattern of current delivered to an anode-cathode set and can incorporate one or more waveform components including but not limited to: direct current, alternating current, pulsed current, linear current ramp, nonlinear current ramp, exponential current ramp, modulation of current, and more complex patterns (including repeated, random, pseudo-random, and chaotic patterns). In operation, the device may provide current flow at target areas (e.g., in facial nerves, cranial nerves, vagal nerve, in the brain, etc.) to induce neuromodulation when appropriate electrode configurations and stimulation protocols are delivered.

Although the apparatuses and methods described herein may be used to provide TES to induce and/or modify a variety of cognitive states, two particular examples are described in detail herein: (1) enhancing attention, alertness, or mental focus and (2) inducing a calm or relaxed mental state. Configurations of apparatuses and methods for causing neuromodulation that specifically achieve enhanced attention, alertness, or mental focus as opposed to an increased calm or relaxed mental state are described in particular detail.

Thus, a generic neurostimulator for modifying a cognitive state may include a pair of electrodes (or two sets of electrodes), referred to herein for convenience as an anode and a cathode (where the anode and cathode may loosely refer to their function as primarily anode and primarily cathode for biphasic waveform components), that can be applied to specific regions of the subject's body and used to provide TES stimulation within the relatively high-intensity, high-frequency ranges described as effective herein. Current is typically applied between the anode and cathode electrodes (or groups of anode and cathode electrodes). Without being bound by a particular theory of operation, the current may be passed through the body between the anode and cathode electrodes (or groups of anode and cathode electrodes), potentially applying energy in an appropriate treatment regime to underlying neural tissue (nerves, e.g., cranial, cervical spinal, vagal, etc., brain, etc.) in a particular neural pathway to result in the desired target effect (e.g., attention, alertness, or mental focus; inducing a calm or relaxed mental state). Thus, the placement locations of the electrodes on the subject's body are important to provide the desired cognitive effect. The placement positions for the pairs of electrodes (anodal and cathodal electrodes) specific to a desired cognitive effect may be referred to as a placement regime or configuration. For example, a first placement configuration for inducing a cognitive state of attention, alertness, or mental focus may include a first electrode applied to the subject near the temple and/or forehead area (e.g., laterally to the eye, such as slightly above and to the right of the right eye or above and to the left of the left eye) and a second electrode positioned behind the ear on the same side as the first electrode in the mastoid region (e.g., on or near the mastoid). High-intensity stimulation (as described in greater detail below) of this region may result in enhanced attention, alertness, or mental focus.

Another configuration of electrode positions may include an electrode positioned on the subject's skin near the subject's temple and/or forehead area (e.g., above and to the right of the right eye) and a second electrode on the subject's neck (e.g., on a superior portion of the neck centered at or near the midline and at least partially overlapping the midline). Appropriate TES stimulation of this region may result in enhancing a calm or relaxed mental state. Either of these configurations may also be used with an appropriate TES stimulation regime (waveform) to induce phosphenes by noninvasive transdermal electrical stimulation using the apparatuses described herein.

Generally speaking, peak stimulation intensities above at least 3 mA (e.g., greater than 5 mA, e.g., between 5 mA and 25 mA, etc.) may be advantageous for transdermal electrical stimulation that causes neuromodulation by targeting the brain, nerves (e.g., cranial nerves, vagal nerve, peripheral nerves, spinal nerves), and/or spinal cord. To achieve these peak intensities without causing significant pain, irritation, or discomfort in a subject may require appropriate electrodes and appropriate ensemble waveforms as described herein. Beneficial electrodes may have pH buffering properties and may contain components for uniformly (or more uniformly) delivering current across the dermal-facing portion of the electrode.

The TES waveforms for use with any of the configurations described herein may be a pattern of currents delivered into tissue of a user (e.g., transdermally). Although there may be variations (optimizations) of these waveforms and electrical protocols for each configuration (electrode placement) and each target cognitive state, in general, the patterns may be within the same range of values to provide biphasic, high-intensity, high-frequency and asymmetric with regard to the positive-going and negative-going phases of the waveform (in some cases not charge balanced) signals that are applied to robustly evoke a response in most individuals while causing at most a low level (e.g., minimal or none) of discomfort and/or pain.

These waveforms may be ensemble waveforms including a plurality (e.g., 3 or more) of component waveforms having a predetermined value for each of: current amplitude ("intensity"), frequency, percent charge imbalance, duty cycle, and in some variations capacitive discharge. These component waveforms may each have a duration (time), and may be connected together in a sequence to evoke the desired cognitive effect. Some of these component waveforms forming the ensemble waveform are ramps, in which one or more waveform parameter (current amplitude, frequency, duty cycle, percent charge imbalance) of the waveform is ramped up to the target/peak value of the waveform components from the previous value of the waveform components after transitioning to the new component waveform when delivering the ensemble waveform.

The ensemble waveforms described herein may reduce irritation, pain, and burning sensations in the dermis, muscles, and other tissues of users receiving TES. These embodiments permit higher current intensities to be transmitted comfortably so that desirable changes in a subject's cognitive function, cognitive state, mood, and/or energy levels can be attained. In addition to the high current amplitudes, high frequency (e.g., repeating the base waveform of FIG. 5A between about 250 Hz and about 50 kHz (e.g., between about 500 Hz and about 40 kHz, between about 1 kHz and about 35 kHz, etc.) may provide biphasic pulsed and/or alternating current stimulation that minimally activates sensory pathways and minimizes pH changes in tissue due to stimulation.

In addition to the waveform parameters described herein, it may be helpful to achieve higher transdermal currents while minimizing pain and irritation by using electrodes that distribute current evenly across the electrode and/or mitigate pH changes known to occur in tissue due to direct current stimulation or other charge imbalanced stimulation waveforms. Embodiments include TES systems and methods that use appropriate electrodes configured to reduce pain, irritation, itching, and burning sensations in a subject due to one or more of: mitigation of pH changes in tissue due to direct current stimulation or charge imbalanced stimulation; hydrogels or other electrically conductive media for more effectively coupling an electrode to a user's skin with low impedance; and components of an electrode assembly that achieve a more even distribution of current across the face of the dermally coupled electrode. Examples of electrode designs that may be used are provided herein, but additional examples may include Axelgaard Manufacturing Co., LTD., Axelgaard Little PALS (neonatal pediatric ECG electrodes) and PALS Platinum Blue (conductive cloth neurostimulation electrodes designed for peripheral transcutaneous electrical nerve stimulation (TENS) and muscle stimulation), which are particularly effective for delivering higher tDCS currents while minimizing pain, irritation, and tissue damage. Electrodes configured to spread current evenly across the face of the electrode and mitigate pH changes due to direct current stimulation and/or charge imbalanced stimulation are advantageous for safely and comfortably delivering higher current intensities (e.g., direct currents above about 1.5 mA) that would otherwise be painful, irritating, or damaging to a subject. One skilled in the art will recognize that other commercially available and custom-designed electrodes that mitigate pH changes in tissue and/or spread current evenly across the electrode surface in dermal contact are advantageous for high current TES.

As an illustrative example, a TES system configured for applying an ensemble waveform according to a protocol to minimize pain and irritation while evoking a robust response in a subject is illustrated in FIG. 5H. In this example, there are ten waveform components shown (time is on the x-axis, not shown to scale). The first component waveform has a zero current amplitude 2014, but a first frequency (e.g., 10 kHz), and duty cycle (e.g., 40%), and percent charge imbalance (e.g., 80%). Thus, once the ensemble waveform is applied, there is initially no current (since current is 0 mA). After a few seconds duration, the second component waveform starts 2015. The second component waveform has a value for the peak current amplitude (e.g., 5 mA), a frequency (e.g., 10 kHz, in this example, the same as the first component waveform), a percent charge imbalance (e.g., 80%, in this example, the same as the first component waveform), and a percent duty cycle (e.g., 40%, in this example, also the same as the first component waveform). This second component waveform also has a predetermined duration (e.g., 1 min), and ramping is on, so that the parameter that changes from the first component waveform (amplitude) is ramped over the 1 minute duration to the peak value. In some variations the waveform components may indicate which parameters (amplitude, frequency, etc.) are to be ramped and/or a separate duration and/or a method of ramping for each of the waveform components that has changed. The third component waveform 2016 has all of the same waveform parameters as the second, but with ramping off (or ramping time set to zero) and a duration of about 3 minutes. The fourth component waveform 2017 has ramping on again, a duration of one minute, and an increase in the peak current amplitude (e.g., 10 mA). The fifth component waveform 2018 has the same waveform parameter values as the fourth, but with ramping off, maintaining the waveform parameters for several minutes until the sixth component 2019, in which the frequency is increased (e.g., to 15 kHz) and ramping is on. The seventh component waveform 2020 increases the current value (e.g., to 12 mA), while keeping the frequency and other waveform parameters the same, with ramping on for the duration of the component (e.g., 5 min). The 8th component waveform 2020 has the same waveform parameters, but with ramping off for the duration (e.g., 2 min). The 9th component waveform has an increase in the frequency (e.g., to 17 kHz) and ramping on, while all other parameters stay the same. The 10th component waveform has all the same waveform parameters as the 9th, but with ramping off. Also not shown in this example, a capacitive discharge may be "on" during all of the component waveforms (or some of them).

This example shows primarily increasing current and frequency, however, any of the other components may be modified (e.g., duty cycle, percent current imbalance), or decreased as well as increased.

In any of the ensemble waveforms described herein, a capacitive discharge may be incorporated into any or all of the composite waveforms. As used herein, a capacitive discharge may be referred to as a controlled transient short circuiting of the electrodes at some point (or more than one point) during the pulsing waveform (e.g., every cycle, after every pulse, etc.). Capacitive discharge may be a beneficial feature for TES waveforms, because it may relieve capacitance built up in the subject's body (and electrodes coupled to the subject's skin) that can lead to pH changes and discomfort. Reducing capacitance in the subject's body also may improve the efficiency of stimulation by decreasing the voltage required for delivering a current (i.e., a high current such as one greater than 5 mA) transdermally. For example, FIGS. 33A and 33B illustrate two kinds or types of capacitive discharge that may be used. In FIG. 33A the basic waveform unit, such as the one shown and described above in FIG. 5A, includes a pair of capacitive discharges that occur following each positive-going or negative-going pulse. In some variations, e.g., the "calm" ensemble waveforms described herein, a capacitive discharge occurs at the end of the positive-going pulse and at the end of the negative-going pulse. The time constant for the return of the capacitive discharge may be sufficiently long so that the adjacent negative-going pulse rides on the return portion of the capacitive discharge, as shown in FIG. 33A. In some variations, such as the "energy" ensemble waveforms described herein, the capacitive discharge may occur at the start of a pulse. For example, in FIG. 33B, each base unit includes at least one capacitive pulse that occurs at the start of the negative-going pulse. These examples are not meant to be limiting with regard to the types of capacitive discharge that may be used in component waveforms for TES. Thus, in general, any of the ensemble waveforms may also include a parameter (e.g., an overall parameter and/or an individual parameter for each composite waveform) indicating if a capacitive pulse (or pulses) is included. In some variations, the capacitive pulse parameter may also indicate the type of capacitive pulse (e.g., positive-going, negative-going). The capacitive pulse parameter may also indicate the timing of a capacitive discharge during a cycle (i.e., relative to pulses or other features of the waveform, including after each positive-going pulse, after each negative-going pulse, before each positive-going pulse, before each negative-going pulse, etc.). The capacitive pulse parameter may also indicate the time constant for the capacitive pulse parameter and/or it may be set by the system. The capacitive pulse parameter may also indicate the number of capacitive discharges during a cycle (including values less than one, i.e., those that occur on every other cycle; every $3^{rd}$ cycle; every $4^{th}$ cycle; every $n^{th}$ cycle, etc.; and also including capacitive discharge that occurs on cycles selected randomly or pseudo-randomly). The capacitive pulse parameter may also indicate the maximum current (and/or maximum voltage) of the capacitive discharge, which is defined by elements of the electric circuit of the neurostimulator device configured for allowing the capacitive discharge to occur.

These ensemble waveforms may be delivered to the subject wearing the neurostimulator, or in some variations they may be modified (e.g., by scaling them down) as mentioned above. Scaling or otherwise modifying a waveform may be controlled in real-time or near-real-time by the user (subject) during a TES session, for instance as discomfort develops or to increase the strength of an intended cognitive effect. Scaling will typically change (e.g., by a percentage) one or more of the waveform parameters (e.g., current amplitude, frequency, duty cycle, charge imbalance, etc.). When a subject modifies a waveform to reduce discomfort (e.g., by one or more of: reducing current amplitude, increasing frequency, decreasing duty cycle, decreasing charge imbalance), the modified waveform may allow habituation to the current delivered so that the subject experiences reduced irritation or discomfort.

Biphasic transcranial alternating current stimulation (and biphasic pulsed current stimulation as shown in FIGS. 5A, 33A, and 33B) may yield stronger cognitive effects compared to transcranial direct current stimulation due to dramatically reducing discomfort in the skin under the electrodes (and, in at least some cases, enabling higher peak stimulation currents). Putative mechanisms for reduced irritation include: (1) reduced pH changes in tissue relative to pH changes occurring from direct current stimulation; and (2) reduced skin impedance at higher stimulation frequencies.

System Description

Figure 35P:
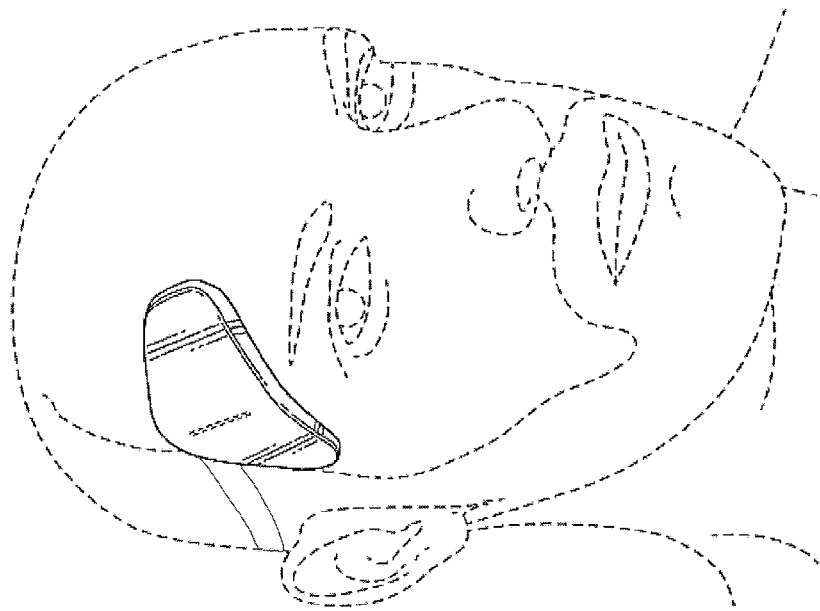
FIG. 35P illustrates the neurostimulator device worn on the subject's head.

In general, any appropriate neurostimulation system may use (and/or be configured to use or operate with) the ensemble waveforms as described herein. FIGS. 7A and 35A-35P describe and illustrate an example of a neurostimulation system (neurostimulator, electrodes, controller) that may be used. For example, a neurostimulation system may include a lightweight, wearable, neurostimulator device (neurostimulator) that is configured to be worn on the head and a consumable/disposable electrode assembly; in addition a device that may be worn and/or held by the user ("user device") which includes a processor and wireless communication module may be used to control the application of neurostimulation by the wearable neurostimulator. The neurostimulator and/or user device may be particularly adapted to deliver the ensemble waveforms as described herein. For example, the user device may present a list of ensemble waveforms and allow the user to select among them in order to select a desired cognitive effect. The ensemble waveforms may be ordered by the desired effect (e.g., calm, energy, etc.) and/or by time and/or by ranking, etc. Further, the user device may be adapted to communicate with the wearable neurostimulator and may transmit an identifier of the selected ensemble waveform, and/or waveform parameters that define all of a portion (e.g., component waveforms or portions of component waveforms) of the ensemble waveform, as well as any user adjustments such as user modification to the perceived intensity to be used to modify the actual waveforms delivered by, for example, attenuating the ensemble waveform parameters. Thus, for example, the user device maybe configured to send, and the neurostimulator to receive, the ensemble waveform parameters (duration, ramping parameter/ramping time, capacitive discharge parameters, current amplitude, frequency, percent duty cycle, percent charge imbalance, etc.).

The user device may also be referred to herein as a controller, and the controller (user device or user computing device) is typically separate from but communicates with the neurostimulator. For example, in some variations the controller may be a user device that wirelessly communicates with the neurostimulator. In some variations the controller is a mobile telecommunications device (e.g., smartphone or tablet) or wearable electronics (e.g., Google glass, smart watch, etc.), being controlled by an application that sends instructions and exchanges 2-way communication signals with the neurostimulator. Any of these embodiments may be referred to as handheld devices, as they may be held in a user's hand or worn on the user's person. However, non-handheld control user devices (e.g., desktop computers, etc.) may be used as well. The user device may be a general purpose device (e.g., smartphone) running application software that specifically configures it for use as a controller, or it may be a custom device that is configured specifically (and potentially exclusively) for use with the neurostimulators described herein. For example, the controller may be software, hardware, or firmware, and may include an application that can be downloaded by the user to run on a wireless-connectable (i.e., by Bluetooth) device (e.g., handheld device such as a smartphone or tablet) to allow the user to select the waveforms delivered by the neurostimulator, including allowing real-time modulation of the delivered neurostimulation to modify the user's cognitive state as described herein. The controller may be a component of the neurostimulator apparatus itself.

For example the system can be operated to induce either "calm" states of mind or "energetic" states of mind. Operating the system to induce a state of increased energy can be alternatively described as one or more of: enhancing focus and attention; enhancing alertness; increasing focus and/or attention; enhancing wakefulness; an increase psychophysiological arousal associated with changes in the activity of the hypothalamic-pituitary-adrenal axis and/or the reticular activating system; increasing subjective feeling of energy; increasing objective physiological energy levels; increasing motivation; increasing physiological arousal; and evoking a physical sensation of warmth in the subject's chest. Operating the system to induce a state of enhancing a calm or relaxed mental state can be alternatively described as one or more of: a state of calm within about 5 minutes of starting a TES session; a care-free state of mind; a mental state free of worry; induction of sleep; facilitating falling asleep; maintaining a state of sleep; a perception of slowing of a passage of time; muscular relaxation; enhanced concentration; inhibition of distractions; increased cognitive clarity; increased sensory clarity; a dissociated state; a mild intoxication; a euphoric state; a relaxed state; enhanced enjoyment of auditory and visual experiences; reduced physiological arousal; increased capacity to handle emotional or other stressors; a reduction in psychophysiological arousal associated with changes in the activity of the hypothalamic-pituitary-adrenal axis and/or the reticular activating system; a reduction in biomarkers of stress, anxiety, and mental dysfunction; anxiolysis; a state of mental clarity; enhanced physical performance; resilience to stress; a physical sensation of relaxation in the periphery; and a perception of feeling the heart beat.

For example, to induce energy, the electrode apparatus may be attached to the user's temple (and/or forehead) and behind the user's ear (e.g., mastoid region). To induce calm, the electrodes may be attached to the user's temple (and/or forehead) and the back of the user's neck. In both examples, the neurostimulator may apply an ensemble waveform for about 3-30 min (or longer) that is made up of different "blocks" having repeated waveform characteristics; the waveform ensemble may include transition regions between the different blocks. In general, at least some of the waveform blocks (and in some variations most or all of them) generally have a current amplitude of >3 mA (e.g., between 5 mA and 40 mA, between 5 mA and 30 mA, between 3 mA and 22 mA, etc.), and a frequency of >150 Hz (e.g., between 250 Hz and 25 kHz, between 500 Hz and 20 kHz, between 700 Hz and 15 kHz, etc.), the current is typically biphasic and is charge imbalanced, and has a duty cycle of between 10-99% (e.g., between 20-95%, between 30-80%, between 30-60%, etc.). One or more of these characteristics may be changed during stimulation over timescales of every few seconds to minutes as the ensemble waveform shifts between subsequent component waveforms.

When worn, the system may resemble the system shown in FIG. 35P, having an electrode assembly attached at two locations (points or regions) on the subject's head and/or neck) and a neurostimulator attached to the electrode assembly, as shown; in some variations a separate controller may be attached to coordinate the application of stimulation.

As will be described in greater detail herein, the neurostimulator may be lightweight (e.g., less than 30 g, less than 25 g, less than 20 g, less than 18 g, less than 15 g, etc.), and self-contained, e.g., enclosing the circuitry, power supply, and wireless communication components such as a rechargeable battery and charging circuit, Bluetooth chip and antenna, microcontroller, and current source configured to deliver waveforms with a duration of between 10 seconds and tens of minutes. A neurostimulator may also include safety circuitry. The neurostimulator may also include circuits to determine that the electrode is attached and what "kind" of electrode it is (i.e., for the calm or the energy mode; or indicating the batch and/or source of manufacture, etc.). FIGS. 7A and 35A-35F illustrate two variations of a neurostimulator.

For example, FIG. 7A illustrates a first example of a neurostimulator as described herein. In FIG. 7A, the neurostimulator is shown with a pair of electrodes attached. A first electrode 601 is coupled directly to the body 603 of the TES applicator 602, and a second electrode 606 is connected by a cable or wire 604 to the body 603 of the applicator 602. These electrodes are separate from each other, and may be replaceable/disposable. Different shaped electrodes 607 may be used with the same re-usable neurostimulator. The neurostimulator in this example includes a rigid outer body, to which the pair of electrodes is attachable, making electrical contact via one or more plug-type connectors.

FIGS. 35A-35F illustrate another, preferred embodiment of a neurostimulator as described herein. In this variation the neurostimulator is also a lightweight, wearable neurostimulator that attaches to an electrode, and includes contacts for making an electrical connection with two (or potentially more) electrically active regions (e.g., anodic and cathodic regions) on the electrode(s). However, in this example, the neurostimulator is configured to operate with a cantilevered electrode apparatus, and to attach both mechanically and electrically to the electrode apparatus at a region that is off-center on the bottom (underside or skin-facing side) of the neurostimulator, allowing one end region to be held securely to the skin while the other edge region is not pinned in this way. The "floating" end may therefore adjust slightly to different curvatures of the head, even while the electrode assembly (which may be flexible) is securely held to the skin. Thus, this cantilevered attachment mechanism may enhance comfort and adjustability of the device. In addition, the neurostimulator device may be configured specifically so that it can be comfortably worn at the user's temple, even in users wearing glasses. For example, the apparatus may be configured so that the skin-facing side (which connects to the electrode assembly via one or more connectors) is curved with a slightly concave surface having a slight twist angle. This curve shape may help the apparatus fit more snugly (more uniformly) to the surface of the temple. In addition, one end of the device (the end to be positioned in-line with the edge of the user's eye and the user's ear) may be thinner (e.g., less than 2 cm, less than 1.5 cm, less than 1 cm, less than 0.8 cm, etc.) than the opposite end, which may be worn higher up on the temple.

For example, FIGS. 35A-35F illustrate front, back, left side, right side, top and bottom perspective views, respectively of a variation of a neurostimulation device (neurostimulator or electrical stimulator) that may be used with cantilever electrode apparatuses. The overall shape of the neurostimulator may be triangular, and particularly the surface of the neurostimulator (though curved/concave and twisted) adapted to connect to the electrode apparatus and face the patient may be three-sided (e.g., roughly triangular). This roughly triangular shape may include rounded edges, and the thickness of the stimulator (in the direction perpendicular to the surface contacting the cantilever electrode apparatus) may vary, e.g., be thinner along one side, and particularly the side (the portion between the orbital edge and the auricular edge) that will extend laterally from the edge of the eye in the direction of the ear. This shape may also be beneficial when helping to fit/be worn on most people in a region of the face/head that tends to not have hair. Both adhesive and conductive hydrogel that may cover an active electrode region function more effectively on skin with little or no hair. This thin lower corner (the orbital/auricular corner) may fit between the eyebrow and hairline, while the wider portion is positioned up in the forehead area where there is less likely to be hair.

In FIGS. 35A-35F the various edges of the neurostimulator are labeled, based on where the apparatus will be worn by the subject, as is illustrated in FIG. 35P. In general, the side of the unit worn toward the ear is the auricular edge, the side worn highest on the forehead is the superior edge, and the side worn nearest the eye/eyebrow is the orbital edge. The overall shape of the neurostimulator is triangular (including rounded edges). As used herein triangular includes shapes having rounded/smooth transitions between the three sides, as illustrated. The subject-facing surface is specifically contoured to fit in the predefined orientation, making it difficult or impossible for a subject to misapply, and risk placing the active region of the attached cantilever electrode apparatus in the wrong place. When attaching the cantilever electrode apparatus to the neurostimulator, the cantilever electrode apparatus may flex or bend so that it is contoured to match the curved and twisted surface. This surface is a section of a saddle shape, in which there is an axis of curvature around which the surface is concavely curved, and an axis of twisting, which may distort the curved surface (the two axes may be different or the same).

Within the housing, any of the neurostimulators described herein may include a processor (e.g., microprocessor) or controller, a wireless communication module that is connected to the processor, and a power source (e.g., battery, etc.). The power source may be configured to provide power to the internal circuitry and/or the circuitry driving current between anodic and cathodic regions of the electrodes when worn by the user. The power supply may be a high-voltage power supply, e.g., able to provide up to 60 V across these electrode terminals. In general, the apparatus may also include circuitry that is configured to regulate the energy (e.g., current) delivered as required by the processor, which may in turn receive instructions via the wireless communications module from a controller. The controller may also communicate information, and in particular information about the electrodes, including confirming that the electrode assembly is connected and/or what type (e.g., calm, energy, make/model, batch, etc.) of electrode assembly is attached, and an indicator of the contact with the user's skin (e.g., conductance, a parameter proportional to conductance, or a value from which an estimate of the conductance of the electrode(s) may be derived).

The electrode assembly may mechanically and/or electrically connect to the neurostimulator, e.g., by snapping to the underside of the neurostimulator at one or more (e.g., two) connectors such as snap receivers. Thus in some variations the neurostimulator may be held onto the subject's (user's) head by the electrode assembly; the electrode assembly may be adhesively connected to the user's head and/or neck to form an electrical contact with the desired regions on the user, and the neurostimulator may be connected e.g., adhesively and/or electrically, to the electrode assembly. As described below, the connectors between the neurostimulator and the electrode assembly may be positioned in a particular and predetermined location that allows the neurostimulator to be robustly connected to the electrode assembly and therefore the user's head/neck without disrupting the connection, and while permitting the system to be worn on a variety of different body shapes.

Electrode assemblies are generally described in detail below, along with specific examples and variations. In particular, described herein are electrode assemblies that are thin (e.g., generally less than 4 mm, less than 3 mm, less than 2 mm, less than 1 mm, etc. thick, which may not include the thickness of the connectors that may extend proud from the thin electrode assembly), and flexible, and may be flat (e.g., formed in a plane). For example, they may be printed on a flex material, such as the material used to print a flex circuit. In use, they can be wrapped around the head to contact it in at least two locations (e.g., at the temple and the back of the neck and/or behind the ear). The electrode assembly may include a connector (electrical and/or mechanical) that extends proud of the otherwise flat/planar surface to connect the active regions of the electrode assembly to the neurostimulator. For example, the neurostimulator may be mechanically and electrically connected by one or more snaps extending from the front of the electrode assembly. In some examples, one snap connects to a first active electrode region (anodic or cathodic region) that is surrounded by an adhesive to adhere the active region to the user's head. A second electrode region (anodic or cathodic) on a separate part of the electrode assembly may be electrically connected to the other connector. For example, the second electrode region may be adapted to fit either on the region over the mastoid bone, behind the subject's ear (energy electrode configuration) or a region across the user's neck at the base of the hairline, e.g., near the midline of the neck (calm electrode configuration).

The electrode apparatus may be printed (e.g., by flexographic printing, laser printing with conductive ink, silk-screening, etc.) on a flexible (e.g., plastic) substrate (flex substrate) and may also include a pair of connectors (snaps) on the side opposite the skin-facing electrodes. The electrode active regions on the back of the assembly may include a layer of conductor (e.g., silver), a layer of a higher resistance conductor than silver (e.g. a conductive carbon), over which a layer of Ag/AgCl is placed that is sacrificial and acts as a pH buffer. A next layer of hydrogel overlays the Ag/AgCl electrode so that it can uniformly transfer charge across the active region into the skin. A portion of the electrode assembly around the active electrode area may have an adhesive that permits good contact with a user's skin.

There may be multiple configurations (e.g., shapes) of the electrode assembly, and, as described in greater detail herein, the electrode assembly may generally be formed on a flexible material ('flex circuit' material) and mechanically and electrically connected to the neurostimulator.

FIGS. 35G-35J illustrate one variation of a cantilever electrode apparatus ("electrode apparatus") that may be used with a neurostimulator and may be worn on a subject's head. This variation may be referred to as a "calm" configuration, as it is adapted to connect to a user's temple or forehead and the back of a user's neck. In this example, the cantilever electrode apparatus 400 includes a plurality of electrode portions (two are shown) 403, 405. In FIG. 35G, a front perspective view is shown. The front side is the side that will face away from the subject when worn. The cantilever electrode apparatus is thin, so that the electrode portions include a front side (visible in FIGS. 35G and 35H) and a back side (visible in FIG. 35J). As shown in the side view of FIG. 35i, the device has a thin body that includes the electrode portions 403, 405 as well as an elongate body region 407 extending between the two electrode portions. The elongate body is also thin (having a much larger diameter and height than thickness). The thickness is shown in FIG. 35i.

In this example, two connectors 415, 417 (electrical and mechanical connectors, shown in this example as snaps) extend from the front of the cantilever electrode apparatus. The front of the first electrical portion 403 may also include an optional foam and/or adhesive material 421 through which the snaps extend proud of the first electrical portion. The first electrical portion is shaped and sized so that the snaps will connect to plugs (ports, holders, opening, female mating, etc.) on the electrical stimulator. As described above, the connectors may be separated by between about 0.6 and about 0.9 inches (e.g., between about 0.7 and about 0.8 inches, etc., shown in FIGS. 35G-35J as about 0.72 inches). The second electrode portion may also include a foam or backing portion 423. This foam/backing region may be optional. In some variations the separation between the connectors is not limited to 0.7 to 0.8, but may be larger (e.g., between 0.7 and 1.2 inches, 0.7 and 1.1 inches, 0.7 and 1.0 inches, 0.7 and 0.9 inches, etc.) or smaller (e.g., between 0.2 and 0.7, 0.3 and 0.7, 0.4 and 0.7, 0.5 and 0.7, 0.6 and 0.7 inches, etc.).

FIG. 35J shows a back view of this first example of a cantilever electrode apparatus. In this example, the first 403 and second 405 electrode portions are also shown and include active regions 433, 435. The active regions are bordered by adhesive 440. The first 403 electrode portion includes, on the back (patient-contacting) side, a first active region 433, which is bounded, e.g., around its entire circumference, or at least on, by an adhesive 440. The active region may include a conductive material (e.g., electrically conductive gel). Similarly, the back of the second electrode portion 405 includes the second active region 435 surrounded on two sides by an adhesive material 440 that extends to the edge of the electrode region. The adhesive may be any biocompatible adhesive that can releasably hold the material to the skin.

FIGS. 35K-35N illustrate another example of a cantilever electrode apparatus. This example is very similar to the variation shown in FIGS. 35G-35J, but may be referred to as an "energy" configuration as it is configured to contact both the user's temple or forehead and a region behind the user's ear, over the mastoid region. The connectors (snaps 417, 415) are in the same position as shown in FIGS. 35G-35J, as are the shape of the first electrode portion 403 and foam/backing material 421 (which may also or alternatively be an adhesive material). An advantage of having multiple electrode apparatuses with the same shape is that they can be used interchangeably with a single neurostimulator device. However, the example shown in FIGS. 35K-35N includes a different overall shape, and may be used to connect, for example, to different regions of the patient's head. In particular, the portion of the substrate forming the elongate body region 407 extending between the two electrode portions 403, 405 is shaped slightly differently. In this example, the cantilever electrode apparatus may be configured to connect, for example, to the subject's temple with the first electrode portion (to which the neurostimulator may be connected) and the elongate body region may be bent around the subject's head so that the second electrode portion may be in electrical contact with a region behind the subject's ear (e.g., at or near the mastoid). By placing the first active region 433 of the first electrode portion 405 in electrical contact with the skin at the temple or forehead and using the adhesive material 440 surrounding the electrically active region 433 to hold the electrically active region (and the attached neurostimulator) securely in position on the subject's skin, the second electrically active region may also be adhesively 441 held to skin so that the second electrically active region 435 is in contact with the mastoid region.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc.). The elongate body region may also be bent or curved, as illustrated in both the variations of FIGS. 35G-35J and 35K-35N. The bend or curve, in which the elongate body may even double back on itself, may allow the material to flex or bend to allow it to be adjustably positioned over and/or around the subject's head, as shown in FIGS. 35o and 35P, for example.

Figure 35O:
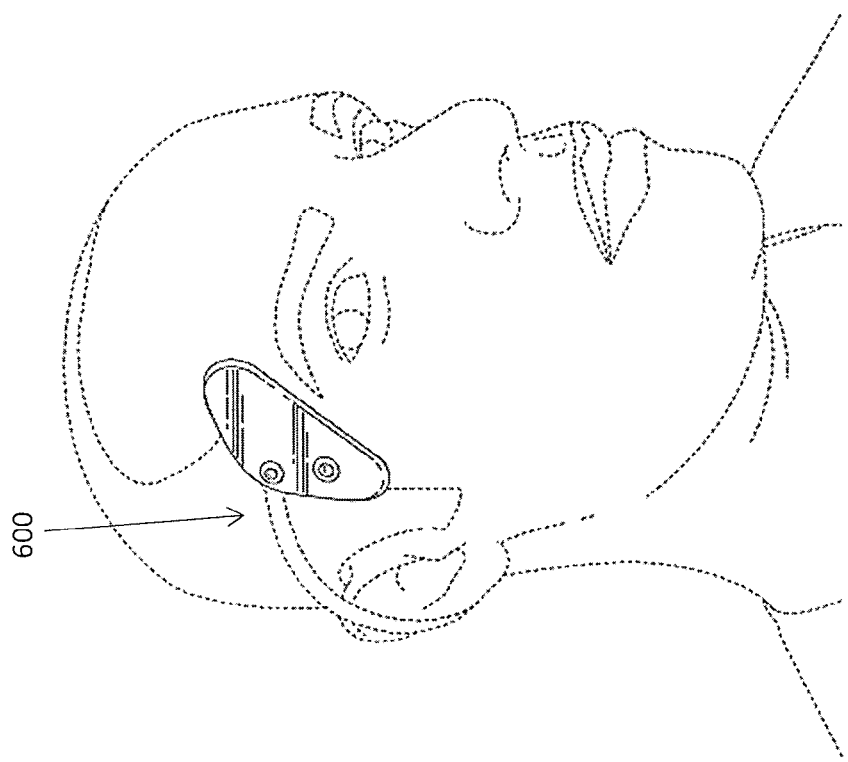
FIG. 35o illustrates the application of an electrode assembly that may be worn on the subject's head, and/or head and neck to induce a cognitive effect.

FIG. 35o illustrates a cantilever electrode apparatus (similar to those shown in FIGS. 5A and 36A) worn on a subject's head. As illustrated, the apparatus is positioned with the first electrode portion adhesively attached at the temple or forehead and a second electrode portion attached to a region behind the head (e.g., behind the ear or neck region, not shown). A neurostimulator (not shown in FIG. 35o) may be attached to the cantilever electrode apparatus either before or after it is applied to the subject. As shown in FIG. 35P the neurostimulator may be attached to the front side of the cantilever electrode apparatus by snapping onto the proud connectors, while the elongate body region 407 is bent to extend behind the subject's head and down to a portion on the midline of the back of the patient's neck. Both the first electrode portion and the second electrode portion may be adhesively held with the electrically active regions against the skin, allowing the neurostimulator to apply energy, and in particular the waveforms as described in U.S. patent application Ser. No. 14/320,443, now U.S. Pat. No. 9,014,811, filed Jun. 30, 2014, titled "TRANSDERMAL ELECTRICAL STIMULATION METHODS FOR MODIFYING OR INDUCING COGNITIVE STATE", and herein incorporated by reference in its entirety.

In use, a user may interact with a controller (e.g., a smartphone controlled by application software/firmware) that pairs with the neurostimulator (e.g., i.e., by Bluetooth). The user may operate the controller to select the operational mode, e.g., the type of cognitive effect to be induced, such as an energy mode or calm mode, and/or the device could automatically detect based on the configuration of an electrode to which the apparatus is attached. The user may select, for example, from a set of ensemble waveforms which ensemble waveform to execute. There may be separate waveforms to evoke a desired experience/effect (e.g., "calm" or "energy" ensemble waveforms). An ensemble waveform may generally be between about 3-90 min (e.g., between about 3-60 min, between about 5-60 min, between about 5-40 min, etc., between about 3-25 minutes, etc.) long, or longer (e.g., greater than 3 min, greater than 5 min, greater than 10 min, greater than 12 min, etc.). In general, an ensemble waveform may be broken up into segments with specific pulsing parameters, i.e., current amplitude, frequency, duty cycle, charge imbalance, shorting/capacitive discharge, etc., and these parameters may change at pre-specified times for subsequent component waveforms. Once the user selects an ensemble waveform, the user can start the neurostimulation and the user can control or change the perceived intensity (e.g., by dialing the perceived intensity up or down), pause, or stop the session using the phone (app). In general, the perceived intensity can be scaled by the user between 0-100% of a target perceived intensity (e.g., a target current, frequency, duty cycle, charge imbalance, and/or shorting/capacitive discharge), using a control such as one or more buttons, sliders, dials, toggles, etc., that may be present on the controller (e.g., smartphone) in communication with the neurostimulator. The controller may also allow a user to activate ("on demand") a waveform configuration that is designed to evoke a predetermined response. For example, the control device could be adapted to display one or more icons to trigger phosphenes or an intensification of the perceived cognitive effect or skin sensation intensity. In addition, the controller may be configured to allow the user to press an icon to help in applying the electrode apparatus and/or neurostimulator. For example, activating this control may cause the smartphone to activate a front-facing camera on the phone to help the user to attach the apparatus to the head. During or after a session, a user can access help screens, a profile page, social sharing interfaces (i.e., tweet your experience), feedback about a session, and analysis and history of previous use. In general, the system may also be configured to pass data to and from the controller and/or the neurostimulator and to/from a remote server via the Internet. These data may include user information, waveform data, information about the function or state of the hardware device or electrode assembly, etc.

In general, described herein are general TES waveforms parameters that may be used to invoke, enhance, or modify a variety of cognitive states. Although the apparatuses and methods described herein may be used to provide TES to induce and/or modify a variety of cognitive states, two particular examples are described in detail herein, including enhancing attention, alertness, or mental focus and inducing a calm or relaxed mental state. Configurations of apparatuses and methods specific to enhancing attention, alertness, or mental focus and inducing a calm or relaxed mental state, including specific configurations for causing neuromodulation that achieves one of these particular cognitive effects in a subject are described in particular detail.

Waveform Controller

Figure 34B:
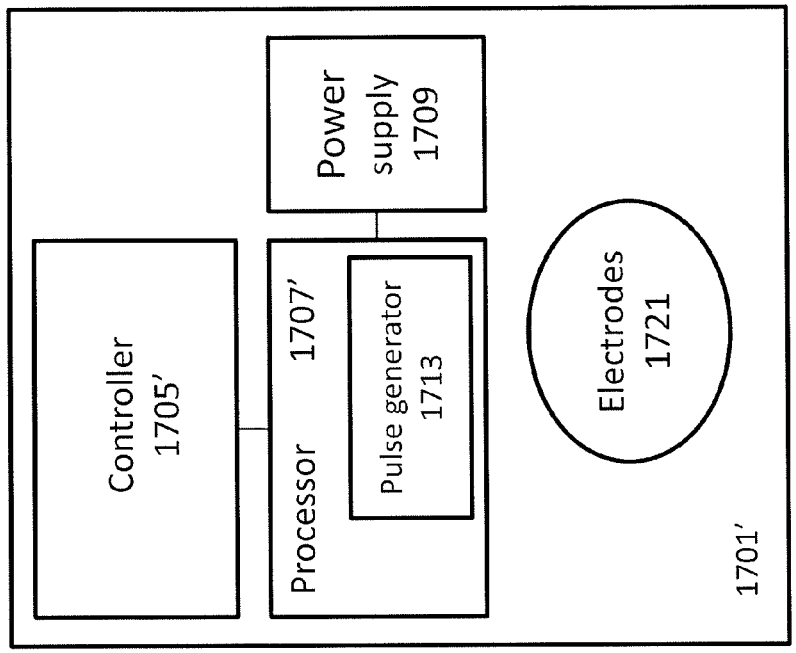
FIG. 34B is a schematic illustration of another example of a system in which the controller and processor are directly connected, rather than wirelessly connected.
Figure 34A:
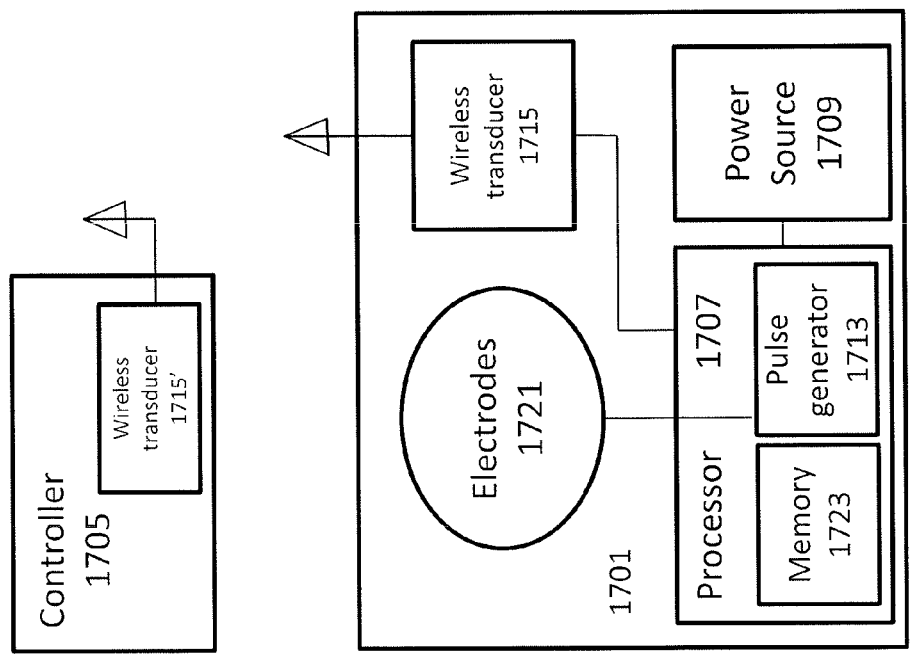
FIG. 34A is a schematic illustration of one example of an apparatus (e.g., system) including a wireless controller that sends command instructions, including ensemble waveform information, to a wearable neurostimulator having a processor adapted to receive and interpret this information, which may be sent in an abbreviated and efficient message encoding system.

Also described herein are method for efficient, compact and rapid communication of ensemble waveform control information from a controller (waveform controller) to a wearable neurostimulator. The controller may be remotely located relative to the wearable neurostimulator. FIG. 34A is a schematic illustration of a wearable neurostimulator 1701 such as the ones described herein (e.g., FIGS. 7A and 35A-35P), which may wirelessly receive control information (e.g., ensemble waveform information and/or command controls from a waveform controller 1705). In this example, the wearable neurostimulator includes at least two electrodes 1721 that are integral with or connectable to the neurostimulator 1701, and a processor 1707 that connects to wireless communication circuitry 1715 (e.g., wireless transducer), a power source 1709, and a pulse generator 1713 to apply the waveforms via the electrodes 1721. The processor may also include a memory 1723 having one or more registers for storing waveform information, including one or more of a: a current and/or next component waveform. The waveform controller 1705 may also include wireless communication circuitry 1715' for transmitting (and/or receiving) control information, including component waveform control information.

The processor 1707 is generally configured to receive and handle waveform information. Specifically, the processor described herein is configured to operate in real-time to communicate with and receive information from the waveform controller. The waveform controller may transmit (e.g., in real-time or near-real time) sequential component waveforms from the series of waveforms forming an ensemble waveform; to achieve this, the controller and processor share a specific communication architecture that allows the rapid and reliable transmission of component waveforms to the wearable apparatus, allowing the wearable apparatus to deliver the potentially complex ensemble waveform in an energy-efficient and reliable manner.

Specifically, the controller may transmit one or more control codes that may be received by the processor. A variety of control codes may be transmitted, for controlling any of the functions of the wearable neurostimulator, including self-reporting codes (instructing the device to run and/or return diagnostic information including power charge status), LED controls, pairing controls, power-down controls, and the like. In particular, the controller may transmit control codes instructing the neurostimulator to receive waveform information and in particular component waveform information. A command control may tell the processor to prepare to receive and/or deliver a new component waveform, or it may tell the processor to edit or modify an existing component waveform; the command control may also specific the number of segments to expect for the new component waveform or which segments in a stored (including currently running) component waveform to modify.

In general, any of the apparatuses described herein (e.g., within the processor of the neurostimulator) may include firmware and communication protocols for receiving and responding to the command messages. Any of the processors (neurostimulators) described herein may also be configured to transmit error codes back to the controller. For example, the processor may, during communication (e.g., via a communication circuit) check whether received waveform parameters comply with limitations of hardware and safety standards. Examples of error codes that may be safety conditions (e.g., current requested too high, electrode contact lost or poor connection, DC limit reached, communication lost), error codes related to the received command messages/communication (e.g., too many wave segments, fewer segments received than expected, received segments too short, received segments too long, etc.)

Any of the apparatuses for neurostimulation described herein may be configured to receive a plurality of neurostimulation command messages, including in particular the new waveform message and subsequent segment messages, which may include parameters from a controller such as a computing device (e.g., smartphone, etc.) and apply them as stimulation. The neurostimulator may also adjust them and/ or send one or more response error messages back to the controller if the parameters contained in the messages do not comply with hardware limitations and/or safety limits which may be included in the neurostimulator.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method comprising:
    activating a transdermal electrical stimulation (TES) applicator to deliver a pulsed, asymmetric, biphasic transdermal electrical stimulation having a frequency of 250 Hz or greater and an intensity of greater than 3 mA between an anode positioned on the subject's skin at a first location and a cathode on the subject's skin at a second location; and
    applying the biphasic transdermal electrical stimulation between the anode and cathode until the subject's sympathetic nervous system is suppressed;
    wherein the first location is on the back of the subject's neck at a medial portion of the neck and the second location is on the back of the subject's neck at a medial location above or below the first location.

2. The method of claim 1, wherein modifying the subject's sympathetic nervous system by applying the biphasic transdermal electrical stimulation for 10 seconds or longer comprises applying intervals of the biphasic transdermal stimulation having a frequency of 250 Hz or greater and an intensity of greater than 3 mA during the 10 seconds or longer.

3. The method of claim 1, wherein activating the TES applicator to deliver the pulsed, asymmetric, biphasic transdermal electrical stimulation further comprises, applying a capacitive discharge current to the anode and cathode to oppose any capacitance built-up during the delivery of the biphasic transdermal electrical stimulation.

4. The method of claim 1, wherein activating the TES applicator to deliver the pulsed, asymmetric, biphasic transdermal electrical stimulation further comprises, applying a capacitive discharge current periodically within each cycle of the biphasic transdermal electrical stimulation to oppose any capacitance built-up during the delivery of the biphasic transdermal electrical stimulation.

5. The method of claim 1, wherein activating the TES applicator comprises activating the TES applicator to deliver the biphasic transdermal electrical stimulation having a duty cycle of greater than 10 percent.

6. The method of claim 1, wherein activating the TES applicator comprises wirelessly triggering activation of the TES applicator.

7. The method of claim 1, further comprising varying the applied biphasic transdermal electrical stimulation while the biphasic transdermal stimulation is applied.

8. The method of claim 1, further comprising varying the applied biphasic transdermal electrical stimulation while keeping the biphasic transdermal electrical stimulation within a duty cycle of greater than 10 percent, the frequency of 750 Hz or greater, and the intensity of greater than 3 mA.

9. The method of claim 1, further comprising ramping the biphasic transdermal electrical stimulation during the application by modifying one or more of the intensity, frequency and duty cycle from an initial state and then restoring the one or more of the intensity, frequency and duty cycle back to the initial state.

10. A method of modifying a subject's sympathetic nervous system, the method comprising:
    positioning an anode on a medial portion of the subject's neck and a cathode on the medial portion of the subject's neck below or above the anode, wherein the anode is smaller than the cathode;
    activating a wearable transdermal electrical stimulation (TES) applicator to deliver a pulsed, asymmetric, biphasic transdermal electrical stimulation having a frequency of 250 Hz or greater and an intensity of greater than 3 mA between the anode and the cathode; and
    applying the biphasic transdermal electrical stimulation between the anode and the cathode until the subject's sympathetic nervous system is suppressed.

11. A method of modifying a subject's sympathetic nervous system, the method comprising:
    positioning an anode on a medial portion of the subject's neck and a cathode on the medial portion of the subject's neck below or above the anode, wherein the cathode is smaller than the anode;
    activating a wearable transdermal electrical stimulation (TES) applicator to deliver a pulsed, asymmetric, biphasic transdermal electrical stimulation having a frequency of 250 Hz or greater and an intensity of greater than 3 mA between the anode and the cathode; and
    applying the biphasic transdermal electrical stimulation between the anode and the cathode until the subject's sympathetic nervous system is suppressed.

* * * * *